United States Patent [19]

Smith et al.

[11] Patent Number: 5,276,159
[45] Date of Patent: Jan. 4, 1994

[54] DYNEMICIN ANALOGS: SYNTHESES, METHODS OF PREPARATION AND USE

[75] Inventors: Adrian L. Smith, Bishops Stortford, England; Chan-Kou Hwang, San Diego, Calif.; Sebastian V. Wendeborn, La Jolla, Calif.; Kyriacos C. Nicolaou, La Jolla, Calif.; Erwin P. Schreiner, Vienna, Austria; Wilhelm Stahl, Frankfurt am Main, Fed. Rep. of Germany; Wei-Min Dai, San Diego; Peter E. Maligres, La Jolla, both of Calif.; Toshio Suzuki, Niigata, Japan

[73] Assignee: The Scripps Research Institute, La Jolla, Calif.

[21] Appl. No.: 886,984

[22] Filed: May 21, 1992

Related U.S. Application Data

[63] Continuation-in-part of Ser. No. 788,225, Nov. 5, 1991, which is a continuation-in-part of Ser. No. 734,613, Jul. 23, 1991, abandoned, which is a continuation-in-part of Ser. No. 673,199, Mar. 21, 1991, abandoned, which is a continuation-in-part of Ser. No. 562,269, Aug. 1, 1990, abandoned.

[51] Int. Cl.$^5$ .......................... C07D 277/60
[52] U.S. Cl. ...................... 548/147; 546/43; 549/415
[58] Field of Search ........................ 548/147

[56] References Cited

PUBLICATIONS

Cabal et al. J.A.C.S. 112-3253 (1990).
Schoenen et al. Tetrahedron Lett. 30—3765-3768 (1989).
Kende et al, Tetrahedron Lett. 29—4217-4220 (1988).
Nicolaou et al. J.A.C.S. 114(23) 8908-21 (1992).
Konishi et al, J. Am. Chem. Soc. 112—3715-3716 (1990).
Konishi et al. J. Antibiot. 42:1449-1452 (1989).
Golik et al, J.A.C.S. 109:3461-3462 (1987).
Golik et al J.A.C.S. 109:3462-3464 (1987).
Lee et al J.A.C.S. 109:3464-3466 (1987).
Ellestad et al, J.A.C.S. 109:3466-3468 (1987).

*Primary Examiner*—Cecilia Tsang
*Attorney, Agent, or Firm*—Dressler, Goldsmith, Shore, Sutker & Milnamow, Ltd.

[57] ABSTRACT

A fused ring system compound is disclosed that contains an epoxide group on one side of the fused rings and an enediyne macrocyclic ring on the other side of the fused rings. The compounds have DNA-cleaving, antimicrobial and tumor growth-inhibiting properties. Chimeric compounds having the fused ring system compound as an aglycone bonded to (i) a sugar moiety as the oligosaccharide portion or (ii) a monoclonal antibody or antibody combining site portion thereof that immunoreacts with target tumor cells are also disclosed. Compositions containing a compound or a chimer are disclosed, as are methods of preparing a compound.

1 Claim, 8 Drawing Sheets

DYNEMICIN ANALOGS: SYNTHESES, METHODS OF PREPARATION AND USE

This invention was made with government support under Contract CA 46446 awarded by the National Institutes of Health. The government has certain rights in the invention.

CROSS-REFERENCE TO RELATED APPLICATIONS

This is a continuation-in-part of application Ser. No. 788,225, filed Nov. 5, 1991, which is a continuation-in-part of application Ser. No. 734,613, filed Jul. 23, 1991, now abandoned which is a continuation-in-part of application Ser. No. 673,199, filed Mar. 21, 1991, now abandoned, which is a continuation-in-part of application Ser. No. 562,269, filed on Aug. 1, 1990, now abandoned, whose disclosures are incorporated by reference.

TECHNICAL FIELD

The present invention relates to novel DNA-cleaving, cytotoxic and anti-tumor compounds, and particularly to fused ring systems that contain an enediyne macrocyclic ring and also an epoxide ring, as well as chimeras that contain such a fused ring system.

BACKGROUND ART

Dynemicin A (Compound 1 shown below),

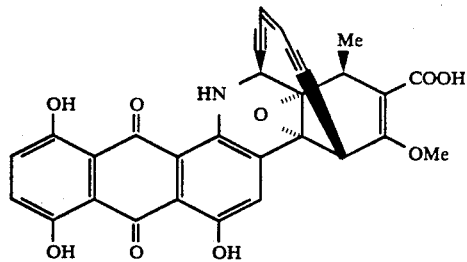

1 where Me is methyl, is a potent antibacterial and anticancer agent recently isolated from *Micromonospora chersina* [(a) Konishi et. al, *J. Am. Chem. Soc.,* 112:3715–3716 (1990); (b) Konishi et al., *J. Antibiot.,* 42:1449–1452 (1989)]. Its striking molecular structure combines characteristics of both the enediyne [Golik et al., *J. Am. Chem. Soc.,* 109:3461–3462 (1987); Golik et al., *J. Am. Chem. Soc.,* 109:3462–2464 (1987); Lee et al., *J. Am. Chem. Soc.,* 109:3464–3466 (1987); Ellestad et al., *J. Am. Chem. Soc.,* 109:3466–3468 (1987)] and the anthracycline ["Anthracycline Antibiotics", H. S. El Khadem, ed., Academic Press, New York (1982) and "Recent Aspects in Anthracyclinone Chemistry", Tetrahedron Symposia-in-Print No. 17, T. R. Kelly, ed., *Tetrahedron;* 40:4537–4794 (1984)] classes of antibiotics, and presents a considerable challenge to organic synthesis as well as a unique opportunity for the development of new synthetic technology and therapeutic agents.

The calicheamicin and esperamicin derivatives are perhaps the best known of the enediyne compounds. For a key paper describing the first synthesis of calicheamicinone, see: (a) Cabal et al., *J. Am. Chem. Soc.,* 112:3253 (1990). For other selected studies of model systems in the area of calicheamicins-esperamicins, see: (b) Nicolaou et al, *J. Am. Chem., Soc.,* 110:4866–4868 (1988); (c) Nicolaou et al., *J. Am. Chem. Soc.,* 110:7247–7248 (1988); (d) Schoenen et al., *Tetrahedron Lett.,* 30:3765–3768 (1989); (e) Magnus et al., *J. Am. Chem. Soc.,* 110:6921–6923 (1988); (f) Kende et al., *Tetrahedron Lett.,* 29:4217–4220 (1988).

BRIEF SUMMARY OF THE INVENTION

The present invention relates to novel fused ring systems that contain an epoxide ring and an enediyne macrocyclic ring, and thus have structural features similar to dynemicin A. The compounds have DNA-cleaving, antibiotic and antitumor activities. Compositions and methods of making and using the compounds are disclosed.

A fused ring compound of the invention has a structure that corresponds to the formula

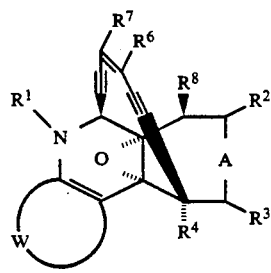

wherein A is a double or single bond;

$R^1$ is selected from the group consisting of H, $C_1$–$C_6$ alkyl, phenoxycarbonyl, benzyloxycarbonyl, $C_1$–$C_6$ alkoxycarbonyl, substituted $C_1$–$C_6$ alkoxycarbonyl (particularly substituted ethoxycarbonyl where the substituent is phenylsulfonyl or naphthylsulfonyl, with phenylsulfonyl most particularly preferred), o-nitrobenzyloxycarbonyl and 9-fluorenylmethyloxycarbonyl;

$R^2$ is selected from the group consisting of H, carboxyl, hydroxylmethyl and carbonyloxy $C_1$–$C_6$ alkyl;

$R^3$ is selected from the group consisting of H and $C_1$–$C_6$ alkoxy;

$R^4$ is selected from the group consisting of H, hydroxyl, $C_1$–$C_6$ alkoxy, oxyacetic acid, oxyacetic $C_1$–$C_6$ hydrocarbyl or benzyl ester, oxyacetic amide, oxyimidazilthiocarbonyl and $C_1$–$C_6$ acyloxy;

$R^6$ and $R^7$ are each H or together with the unsaturated carbon atoms of the intervening vinylene group form a one, two or three fused aromatic six-membered ring system;

W together with the carbon atoms of the depicted, intervening vinylene group forms an aromatic hydrocarbyl ring system containing 1, 2 or 3 six-membered rings such that the fused ring compound contains 3, 4 or 5 fused rings, all but two of which are aromatic, and in which that aromatic hydrocarbyl ring system, W, is joined [a, b] to the structure shown (i.e., W is joined [a,b] to the nitrogen-containing rings of the structure shown); and $R^8$ is hydrogen or methyl, with the proviso that $R^8$ is hydrogen when W, together with the carbon atoms of the intervening vinylene group is 9,10-dioxoanthra.

In preferred practice, W together with the intervening vinylidene group forms a benzo ring so that a compound has the structural formula shown below.

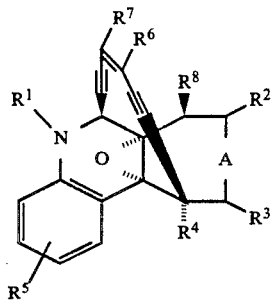

wherein $R^5$ is selected from the group consisting of hydrogen, $C_1$-$C_6$ alkoxy, hydroxyl, $C_1$-$C_6$ acyloxy, oxyethanol, oxyacetic acid, oxyacetic acid amide, oxyacetic $C_1$-$C_6$ hydrocarbyl ester, oxyethanol tertiary amino- or quaternary ammonium-substituted $C_2$-$C_3$ alkyl carboxylate, 3-hydroxyprop-1-ynyl, o-nitrobenzyloxy and halo, and A and the remaining R groups are as before described.

More particularly, in one embodiment, $R^2$, $R^3$, $R^5$, $R^7$ and $R^8$ are hydrogen so that a compound of the invention corresponds to the structural formula shown below, where $R^1$ and $R^4$ are as previously defined.

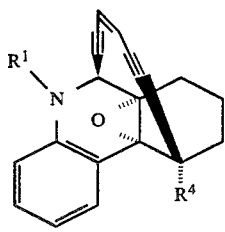

More preferably, $R^5$ is $C_1$-$C_6$ alkoxy, hydroxyl, $C_1$-$C_6$ acyloxy, carboxyl, $C_1$-$C_6$ hydrocarbyl or benzyl carboxylate, oxyethanol, oxyacetic acid, oxyacetic acid amide, oxyethanol tertiary amino- or quaternary ammonium-substituted $C_2$-$C_3$ alkyl carboxylate or 3-hydroxyprop-1-ynyl and $R^4$ is hydrogen (H) or hydroxyl so that a fused ring compound has the structural formula shown below.

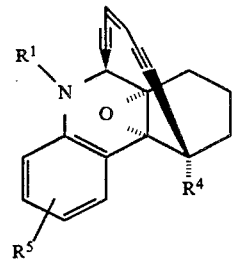

Also contemplated is a chimeric compound (also referred to as a chimer or chimera) that is comprised of a before-described fused ring compound as an aglycone portion bonded to (i) an oligosaccharide portion or (ii) a monoclonal antibody or antibody combining site portion thereof that immunoreacts with target tumor cells.

The oligosaccharide portion comprises a sugar moiety selected from the group consisting of ribosyl, deoxyribosyl, fucosyl, glucosyl, galactosyl, N-acetylglucosaminyl, N-acetylgalactasaminyl, a saccharide whose structure is shown below, wherein a wavy line adjacent a bond indicates the position of linkage.

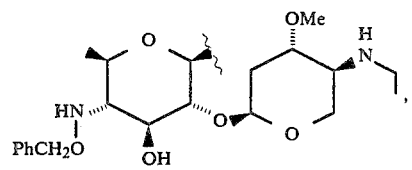

A

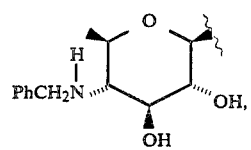

B

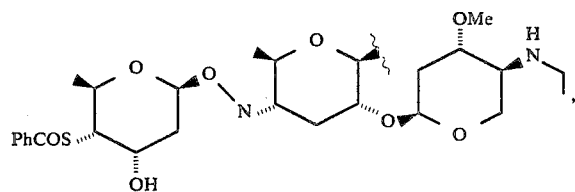

C

-continued
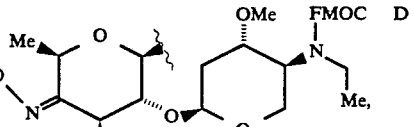
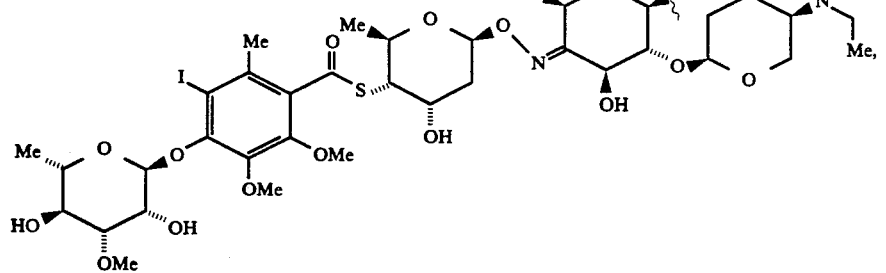
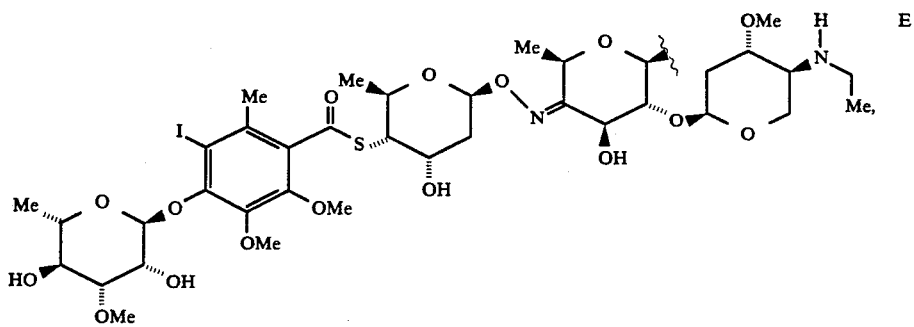
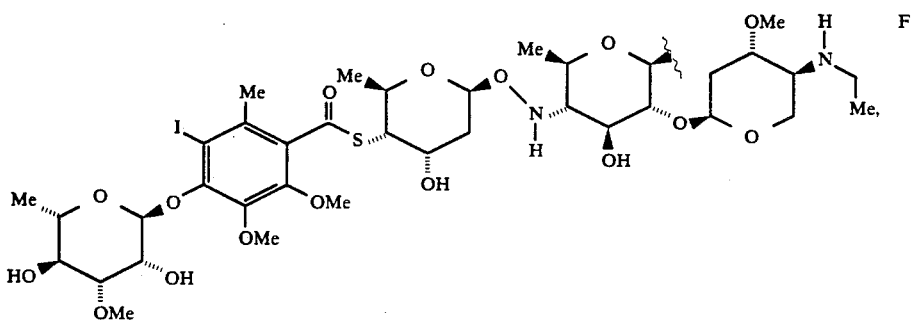
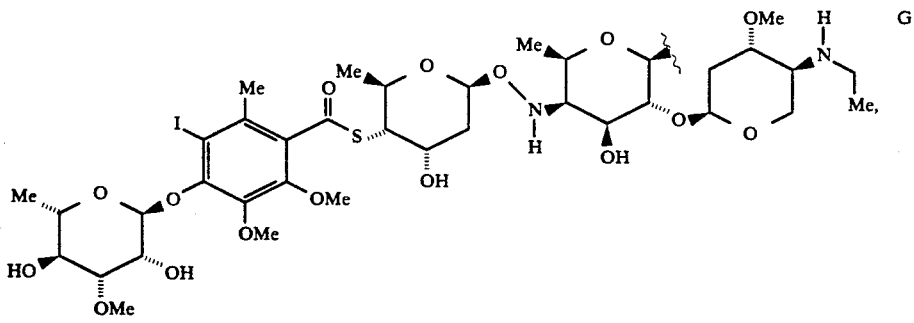
and
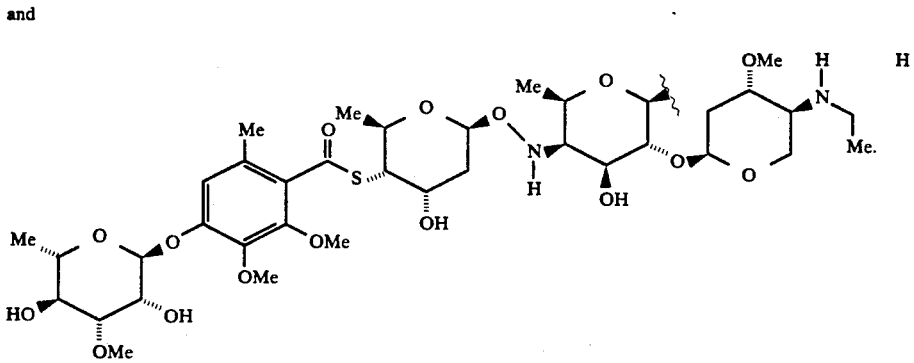

A monoclonal antibody or binding site portion thereof is bonded to the fused ring compound aglycone portion through an $R^4$ oxyacetic acid amide or ester bond, an oxyacetic acid amide or ester bond or oxyethanol ester bond from W. An oligosaccharide portion is glycosidically bonded to the aglycone portion through the hydroxyl of an $R^4$ oxyethanol group or the hydroxyl of an oxyethanol-substituent of W.

A pharmaceutical composition is also contemplated. That pharmaceutical composition contains a DNA cleaving, antibiotic or tumor cell growth-inhibiting amount of a before-defined compound or chimera as active agent dissolved or dispersed in a physiologically tolerable diluent.

A compound, chimera or a pharmaceutical composition of either is also useful in a method for cleaving DNA, for inhibiting tumor growth and as an antimicrobial. In accordance with such a method, the DNA to be cleaved, target tumor cells whose growth is to be inhibited or target microbial cells is (are) contacted with a composition of the invention. That contact is maintained for a time period sufficient for the desired result to occur. Multiple administrations of a pharmaceutical composition can be made to provide the desired contact.

BRIEF DESCRIPTION OF THE DRAWINGS

In the drawings forming a portion of this disclosure.

Lane 8 shows the result obtained with 0.1 mM Compound 40, and lane 9 shows the result obtained with 1.0 mM Compound 45. The designations Form I, II and III are as in FIG. 1.

Figure 7A:
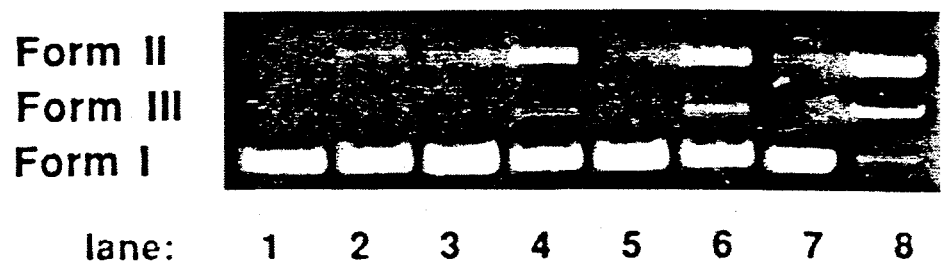

FIG. 7 is shown in two panels. FIG. 7a is a photograph of an ethidium bromide stained 1 percent agarose gel that illustrates the cleavage of ΦX174 Form I DNA by Compound 153 after 24 hours at 37° C. in various buffer solutions. Lanes 1, 3, 5, and 7 show the DNA alone in buffers with pH values of 6.0, 7.0, 7.4, and 8.5, respectively. Lanes 2, 4, 6 and 8 show the results obtained with 1.0 mM Compound 153 in buffers with pH values of 6.0, 7.0, 7.4, and 8.5, respectively.

Figure 7B:
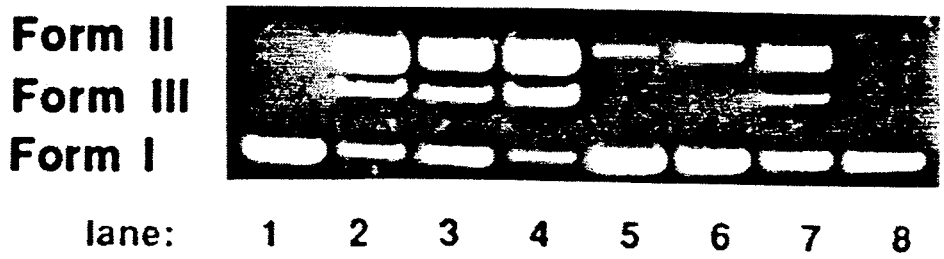

FIG. 7b is a photograph of an ethidium bromide stained 1 percent agarose gel that illustrates the cleavage of ΦX174 Form I DNA by Compounds 40, 45, 153, 47, 80, 171 and 76b for 24 or 48 hours at 37° C. in pH 8.5 Tris-HCl buffer. Lane 1 is the DNA alone as a control with the remaining lanes showing the results obtained with the following Compounds: lane 2 is 1 mM Compound 40 for 24 hours; lane 3 is 1 mM Compound 45 for 24 hours; lane 4 is 1 mM Compound 153 for 24 hours; lane 5 is 5 mM Compound 47 for 48 hours; lane 6 is 5 mM Compound 90 for 48 hours; lane 7 is 5 mM Compound 171 for 48 hours; lane 8 is 5 mM Compound 76b for 48 hours. The designations Form I, II and III are as in FIG. 1.

Figure 8:
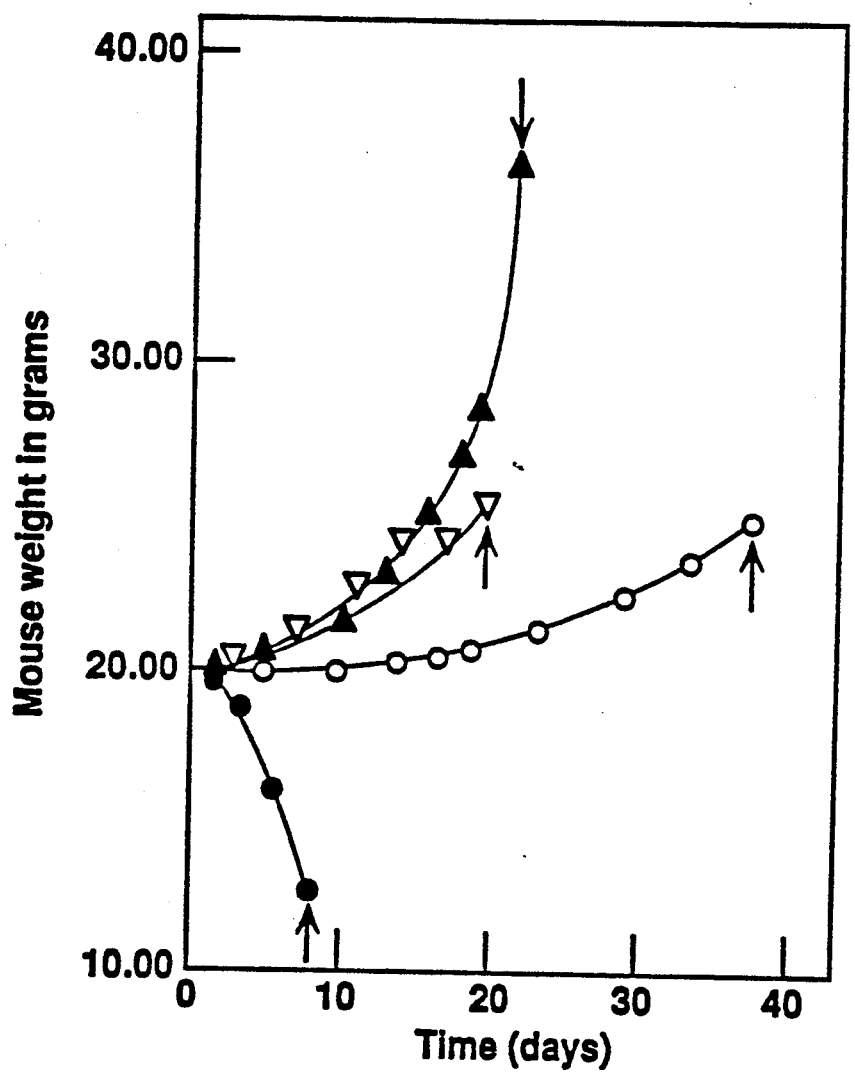

FIG. 8 shows a graph of the in vivo activity of Compound 45 in Balb/c mice injected with P-388 mouse leukemia cells as a function of mouse average weight change over a time period of almost 40 days. Control P-388 cell-containing mouse weights are shown as open triangles. Treated mice received 12 mg/kg, 25 mg/kg, or 50 mg/kg and their weights are shown by closed triangles, open circles, or closed circles, respectively. Arrows indicate death.

Figure 9:
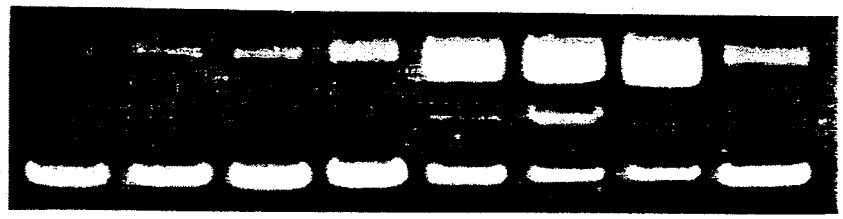

FIG. 9 is a photograph of an ethidium bromide stained 1 percent agarose gel that illustrates the effect on ΦX174 Form I DNA by the following compounds at 5.0 mM in 50 mM Tris-HCl buffer, pH 8.5 after 36 hours at 37° C. Lane 1 is the DNA control; lane 2 is DNA plus Compound 59a; lane 3 is DNA plus Compound 59b; lane 4 is DNA plus Compound 43; lane 5 is DNA plus Compound 42; lane 6 is DNA plus Compound 54; lane 7 is DNA plus Compound 201; and lane 8 is DNA plus Compound 202. Form 1 is supercoiled DNA; Form II is nicked DNA; Form 3 is linear DNA.

Figure 10:
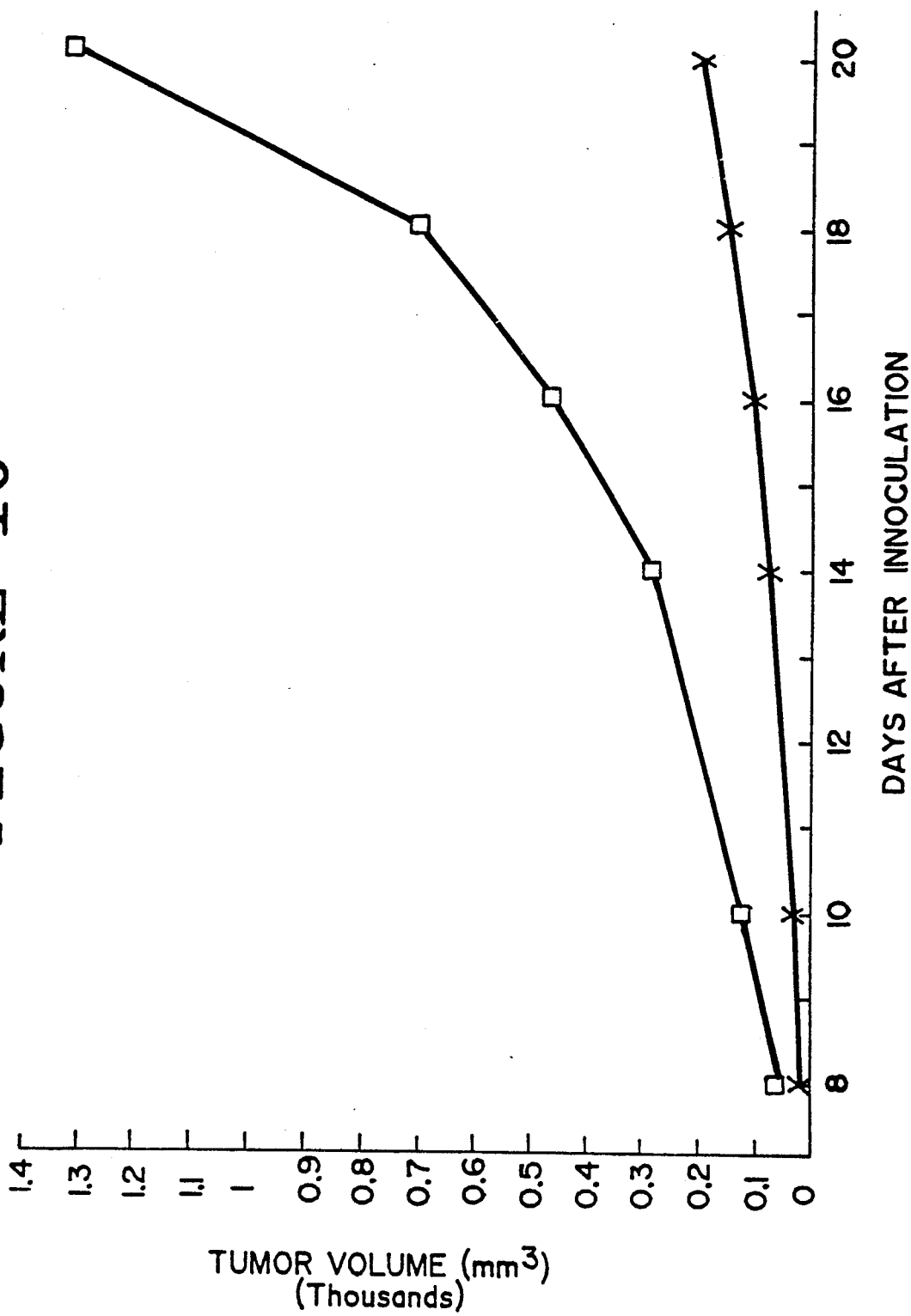

FIG. 10 is a graph showing the average tumor size in 6-10 week old female Balb/c BYJ mice inoculated with EMT-6 mammary tumor cells. Control mice (open squares) were treated with normal saline on days 1, 5 and 9 after inoculation. Study mice (X's) were treated with an equal volume of normal saline containing 10 mg/kg of Compound 153 on those same days post inoculation with the tumor cells.

DETAILED DESCRIPTION OF THE INVENTION

I. The Compounds

A compound of the invention contains an enediyne macrocycle linked to a fused ring that corresponds to structural Formula I

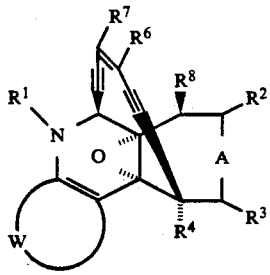

wherein A is a double or single bond;

$R^1$ is selected from the group consisting of H, $C_1$-$C_6$ alkyl, phenoxycarbonyl, benzyloxycarbonyl, $C_1$-$C_6$ alkoxycarbonyl, substituted $C_1$-$C_6$ alkoxycarbonyl (particularly a substituted ethoxycarbonyl where the substituent is phenylsulfonyl or naphthylsulfonyl with phenylsulfonyl most particularly preferred), o-nitrobenzyloxycarbonyl and 9-fluorenylmethyloxycarbonyl;

$R^2$ is selected from the group consisting of H, carboxyl, hydroxylmethyl and carbonyloxy-$C_1$-$C_6$ alkyl;

$R^3$ is selected from the group consisting of H and $C_1$-$C_6$ alkoxy;

$R^4$ is selected from the group consisting of H, hydroxyl, $C_1$-$C_6$ alkoxy, oxyacetic acid (—$OCH_2CO_2H$), $C_1$-$C_6$ hydrocarbyl or benzyl oxyacetic acid ester, oxyacetic amide, oxyethanol (—$OCH_2CH_2OH$), oxyimidazylthiocarbonyl and $C_1$-$C_6$ acyloxy;

$R^6$ and $R^7$ are each H or together with the intervening vinylene group form a one, two or three fused aromatic six-membered ring system;

W together with the bonded, intervening, vinylene group (i.e., the unsaturated carbon atoms bonded to W) forms a substituted aromatic hydrocarbyl ring system containing 1, 2 or 3 six-membered rings such that said fused ring compound contains 3, 4 or 5 fused 6-membered rings all but two of which rings are aromatic, and in which that aromatic hydrocarbyl ring system, W, is joined [a, b] to the structure shown; and $R^8$ is hydrogen or methyl with the proviso that $R^8$ is hydrogen when W together with the intervening vinylidene group is 9,10-dioxoanthra.

Exemplary $R^6$ and $R^7$ groups are shown in Scheme III and are discussed in relation thereto, and thereafter.

As noted above, the bond, A, between the $R^2$ and $R^3$ substituents can be a double or single bond. The bond A is preferably a single bond.

A $C_1$-$C_6$ alkyl group, as can be present in $R^1$ is exemplified by methyl, ethyl, propyl, isopropyl, butyl, sec-butyl, pentyl, 2-methylpentyl, hexyl, cyclohexyl, cyclopentyl and the like. A substituted $C_1$-$C_6$ alkyl group is also contemplated as an $R^1$ group. Such substituted alkyl groups include hydroxyalkyl groups such as 2-hydroxyethyl, 4-hydroxyhexyl and 3-hydroxypropyl, haloalkyl groups such as 2-chlorobutyl, 3-halopentyl such as 3-fluoropentyl, and the like. The above $C_1$-$C_6$ alkyl and substituted $C_1$-$C_6$ alkyl groups are further contemplated as the $C_1$-$C_6$ alkyl portion of a carbonyloxy $C_1$-$C_6$ alkyl group of $R^2$; i.e., a $C_1$-$C_6$ alkyl ester of a $R^2$ carboxyl group, and of a $R^1$ urethane group. Those same alkyl groups can constitute the alkyl portion of a $C_1$-$C_6$ alkoxy group of $R^3$ or $R^4$. A $C_1$-$C_6$ acyloxy group as is present in $R^4$ or $R^5$ (discussed hereinafter) is a carboxylic acid derivative of an appropriate alkyl group, above, except for, for example, cyclohexyl and iso-propyl, and is limited to a cyclopentylcarboxy group for the cyclopentane derivatives. Examples of such $C_1$-$C_6$ acyloxy groups include formyloxy, acetoxy, propionoxy, butyryloxy, isobutyryloxy, pentanoyloxy, 2-methylbutyryloxy, pivaloyloxy, hexanoyloxy, and the like.

The alcohol-carbonyl portion of a urethane $R^1$ is typically formed by the reaction of a corresponding halo formate derivative, such as a chloroformate like phenylchloroformate, with the secondary amine nitrogen atom that is formed by addition of an acetylenic group-containing moiety to the 6-position or a correspondingly numbered position of a fused ring system such as that shown in Scheme II hereinafter. Such groups can also be prepared by base-catalyzed exchange from a formed carbamate using the substituted ethyl alcohol as is illustrated hereinafter.

Exemplary $C_1$-$C_6$ alkoxycarbonyl groups and substituted $C_1$-$C_6$ alkoxycarbonyl groups contain a before-described $C_1$-$C_6$ alkoxy group or substituted $C_1$-$C_6$ alkoxy group linked to the carbonyl group and can be formed by reaction of a $C_1$-$C_6$ alkylchloroformate. Exemplary substituted ethoxycarbonyl groups that are a particularly preferred group of substituted $C_1$-$C_6$ alkoxycarbonyl group have a substituent other than hydrogen at the 2-position of the ethoxy group, and include 2-trimethylsilylethoxycarbonyl, 2-phenylsulfonylethoxycarbonyl, α- or β-2-naphthylsulfonylethoxycarbonyl, α- or β-2-anthracylsulfonylethoxycarbonyl, 2-propenoxycarbonyl, 2-hydroxyethoxycarbonyl, 2-triphenylphosphoniumethoxycarbonyl halide (e.g., chloride, bromide or iodide) and 2-trimethylammoniumethoxycarbonyl halide (as before).

It is particularly preferred that $R^1$ be a group that can be enzymatically or otherwise removed intracellularly to provide the resulting secondary amine free of a substituent group. A compound where $R^1$ contains a 2-substituted-ethoxycarbonyl group such as a 2-phenylsulfonyl-, 2-naphthylsulfonyl- and 2-anthracylsulfonyl- as are shown in Scheme III (shown as $R_1$ therein) can form the free secondary amine compound via a β-elimination under relatively mild conditions. An ethoxy carbonyl group can also be named an ethylene oxycarbonyl group. Phenylsulfonylethoxycarbonyl, α-naphthyl- and β-naphthylsulfonylethoxycarbonyl (collectively referred to as naphthylsulfonylethoxycarbonyl) are particularly preferred $R^1$ groups, with phenoxycarboxyl being a preferred $R^1$ group. When an $R^1$ group is o-nitrobenzyloxycarbonyl, UV light-irradiation (about 290-400 nm) provides cleavage of that group from a fused ring system, thereby providing a free amine group.

An $R^8$ group can be methyl or hydrogen with the proviso that $R^8$ is hydrogen when W along with the intervening vinylene group carbon atoms forms a 9,10-dioxoanthra ring. It is particularly preferred that $R^8$ be methyl when W forms a benzo ring.

$R^4$ groups that are hydrogen, hydroxyl, oxyethanol (—$OCH_2CH_2OH$), oxyacetic acid (—$OCH_2CO_2H$), oxyacetic $C_1$-$C_6$ hydrocarbyl esters such as the before-discussed $C_1$-$C_6$ alkyl groups such as ethyl oxyacetate (—$OCH_2CO_2CH_2CH_3$), as well as $C_1$-$C_6$ unsaturated esters such as the allyl, propargyl, 2-butenyl and the like, as well as the benzyl ester and oxyacetic amides constitute particularly preferred embodiments of the invention. Exemplary $C_1$-$C_6$ and benzyl esters that have been prepared; i.e., Compounds 24a-g exhibited activity against MIA PaCa-2 tumor cells.

A pharmaceutically acceptable non-toxic salt of the oxyacetic acid such as sodium, potassium, ammonium, calcium and magnesium is also contemplated. An oxyacetic acid amide corresponds to the chemical formula —$OCH_2CONR^{13}R^{14}$ wherein $R^{13}$ is hydrogen (H) or $C_1$-$C_6$ alkyl (as before) and $R^{14}$ is independently hydrogen, $C_1$-$C_6$ alkyl, phenyl, 1- or 2-naphthyl, 1- or 2-anthryl, or a peptide having 1 to about six amino acid residues; or $R^{13}$ and $R^{14}$ together with the nitrogen atom form a 5-or 6-membered ring as is present in pyrrolidine, piperidine, morpholine, imidazole or pyrrole.

A particularly contemplated peptide is distamycin, or a derivative thereof as discussed in Taylor et al., *Tetrahedron*, 40:457 (1984) and Baker et al., *J. Am. Chem. Soc.*, 111:2700 (1989). Distamycin derivatives are themselves known DNA-cleaving agents. Indeed, a N-bromoacetyldistamycin adduct of Compound 2 has been prepared.

Another particularly preferred peptide is -Ala-Ala-Ala-, [(-Ala-)$_3$] which sequence is recognized and cleaved by an intracellular lysosomal enzyme. Further suitable peptide linkers that are cleaved enzymatically in vivo are well known to skilled workers. See, for example, Reisfeld et al., *Human Cancer Immunology II*, 11(2):341 (1991) and the citations therein. So-called acid-cleavable linkers such as cis-aconitate and the like as are also well known can also be used along or in conjunction with a cleavable peptide linker. See for example, Reisfeld et al., *Human Cancer Immunology II*, 11(2): 341 (1991) and Mueller et al., *Bioconjugate Chem.*, 2:325 (1990), and the citations therein.

Appropriate diamine and dicarboxylic acid groups can be added at the carboxy- and amino-termini of the peptides or acid labile linkers, respectively, to join the fused ring enediyne to the Mab, as is discussed below. Exemplary diamines are the $\alpha,\omega$-$C_2$-$C_6$ alkylene diamines such as ethylene diamine, 1,3-propylene diamines and 1,6-hexylene diamine. Exemplary $\alpha,\omega$-$C_4$-$C_6$ dicarboxylic acids include succinic, maleic, glutaric and adipic acids.

An $R^4$ group that contains a derivatized oxyacetic acid amide or ester can also include a peptidyl spacer containing zero to about 6 residues such as (-Ala-)$_3$ that links the compound to a monoclonal antibody or an antibody binding site portion thereof, collectively referred to herein as a "Mab", as is illustrated in relation to Scheme III hereinafter (R or $R_3$). An $R^5$ group as discussed in detail hereinafter as a substituent of W as in a compound of Formula XIb can also constitute a useful spacer for bonding to a Mab.

The Mab utilized immunoreacts substantially only with target tumor cells; i.e., is tumor cell specific, and thereby provides further specificity to the drug molecules. Such a Mab-linked fused ring enediyne is one type of chimeric molecule of the invention.

The spacer portion of the compound-Mab construct serves to link the two portions of the molecule together. When there are zero peptide residues present, a lysine epsilon-amino group of the Mab forms the amido bond shown in Scheme III bonded to an $R_3$ group as spacer. The spacer peptide chain, when present, is typically comprised of amino acid residues having small side chains such as glycine or alanine, or relatively hydrophilic side chains such as serine, glutamine and aspartic acid. A peptide spacer is typically free of cysteine residues, but can contain cystine residues and otherwise can have substantially any structure that does not interfere with bonding between the two portions of the chimeric compound. A peptide can be prepared by an one of several synthetic methods as are well known. A particularly preferred peptide spacer includes an amine acid residue sequence that is recognized and cleaved by an enzyme such as lysosomal or other proteolytic enzyme present within a target neoplastic cell so that the fused ring enediyne can be freed from the Mab after endocytosis, as is well known.

The Mab portion of the above chimeric construct can constitute an intact antibody molecule of IgG or IgM isotype, in which case, a plurality of compounds can be present per antibody molecule. The binding site portions of an antibody can also be utilized, in which case, at least one compound is linked to the proteinaceous antibody binding site portion.

An antibody binding site portion is that part of an antibody molecule that immunoreacts with an antigen, and is also sometimes referred to as a paratope. Exemplary antibody binding site portions include F(ab), F(ab'), F(ab')$_2$ and F$_v$ portions of an intact antibody molecule, and can be prepared by well known methods. An intact monoclonal antibody and a portion that includes its antibody combining site portion can be collectively referred to as a paratope-containing molecule.

Exemplary anti-tumor Mabs are noted in the table below, listed by the name utilized in a publication, along with its deposit accession number at the American Type Culture Collection (ATCC), 12301 Parklawn Drive, Rockville, Md. 20852 U.S.A., and the tumor antigen with which the Mab paratope is reported to react. A citation to a discussion of each Mab and its immunoreactivity is provided by the footnote under the antigen listing.

| Exemplary Anti-Tumor Mabs | | |
| --- | --- | --- |
| Mab | ATCC No. | Antigen |
| B 3.6 | HB 8890 | GD3[1] |
| 14.8 | HB 9118 | GD2[2] |
| 11C64 | — | GD3[3] |
| 9.2.27 | — | Condritin sulfate proteoglycan[4] |
| R24 | — | GD3[5] |
| HT29/26 | HB 8247 | colon cancer glycoprotein gp 29[6] |
| HT29/36 | HB 8248 | colon cancer glycoprotein gp29[6] |
| CLT85 | HB 8240 | colon cancer[6] |
| F64.5 | — | mammary carcinoma[7] |
| R38.1 | — | pan carcinoma 70Kd protein[7] |
| F36/22 | HB 8215 | human breast carcinoma[8] |
| T16 | HB 8279 | human bladder tumor, glycoprotein gp48[9] |
| T43 | HB 8275 | human bladder tumor[9] |
| T101 | HB 8273 | human bladder tumor[9] |
| 116-NS-19-1 | HB 8059 | colorectal carcinoma monosialoganglioside[10] |
| 126 | HB 8568 | GD2[11] |
| CLH 6 | HB 8532 | colon cancer[12] |
| CLG 479 | HB 8241 | colon cancer[12] |
| 19.9 | CRL 8019 | CEA[13] |
| CLNH5 | — | lung carcinoma[14] |
| 16-88 | — | colon carcinoma[15] |
| KS1/4 | — | lung adenocarcinoma[16] |
| LM609 | — | vitronectin receptor[17] |

-continued

| | Exemplary Anti-Tumor Mabs | |
|---|---|---|
| Mab | ATCC No. | Antigen |

[1]Cheresch et al., Proc. Natl. Acad. Sci., U.S.A., 82:5155-5159 (1985); Proc. Natl. Acad. Sci., U.S.A., 81:5767-5771 (1984)
[2]Cheresch et al. Cancer Res. 44:5112-5118 (1986)
[3]Cheresch et al., J. Cell. Biol., 102:688 (1986)
[4]Bumol et al., Proc. Natl. Acad. Sci., U.S.A., 79:1245 (1982); Harper et al., J. Immunol., 132:2096 (1984)
[5]U.S. Pat. No. 4,507,391
[6]U.S. Pat. No. 4,579,827
[7]U.S. Pat. No. 4,522,918
[8]European Patent Application No. 84400420.0, publication No. 0 118 365, published September 12, 1984
[9]European Patent Application No. 84102517.4, publication No. 0 118 891, published September 19, 1984
[10]U.S. Pat. No. 4,471,057
[11]Cheresch et al., J. Cell. Biol., 102:688 (1986); U.S. Pat. No. 4,675,287
[12]U.S. Pat. No. 4,579,827
[13]U.S. Pat. No. 4,349,528
[14]Patent Application PCT/US83/00781, WO 83/04313
[15]European Patent Application No. 85300610.4, publication No. 0 151 030, published August 7, 1985
[16]Varki et al., Cancer Res., 44:681 (1984); Bumol et al., Hybridoma, 7:407 (1988)
[17]Cheresch et al., J. Biol. Chem., 262:17703 (1987); Smith et al., J. Biol. Chem., 265:2168 (1990)

A fused ring enediyne compound of the invention can also be glycosidically linked to a sugar moiety to form a second type chimeric molecule. In such a chimer, the fused ring enediyne compound takes the place of the aglycone as in an antibiotic molecule such as doxorubicin, calicheamicin or esperamicin, with the sugar moiety taking the place of the oligosaccharide portion. Bonding between the fused ring enediyne compound aglycone and oligosaccharide is typically via a hydroxyl group of a spacer group that is itself linked to the fused ring enediyne through a reacted hydroxyl group. A preferred spacer group is an oxyethanol group that can be an $R^4$ group or can be an $R^5$ substituent of W as is discussed and illustrated hereinafter. The glycosidically bonded saccharide thus forms an ether bond via the hydroxyl group of the oxyethanol group.

The oligosaccharide portion of the molecule is typically added after the synthesis of the fused ring enediyne compound (aglycone) portion is complete, except for any blocking groups on otherwise reactive functionalities of the aglycone that are typically removed after addition of the oligosaccharide portion. A sugar moiety is added by standard techniques as are discussed hereinafter.

A glycosidically-linked sugar moiety can be a monosaccharide such as ribosyl, deoxyribosyl, fucosyl, glucosyl, galactosyl, N-acetylglucosaminyl, N-acetylgalactosaminyl moiety or the more preferred saccharides whose structures are shown below, wherein a wavy line adjacent a bond indicates the position of linkage.

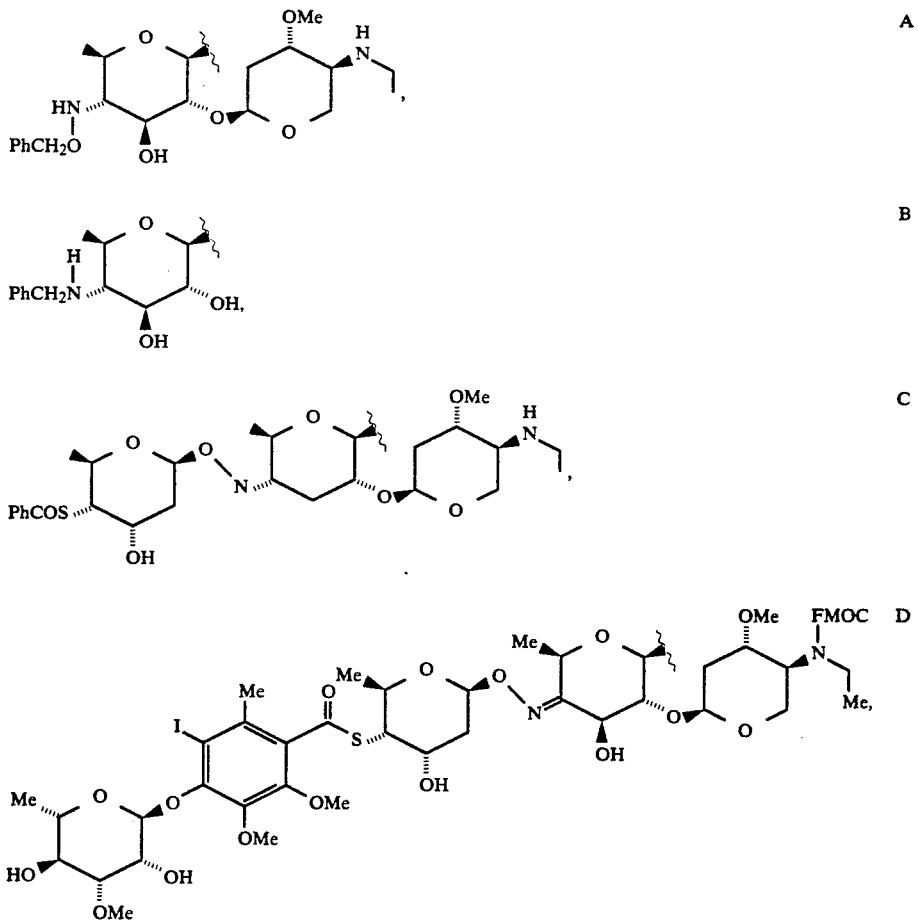

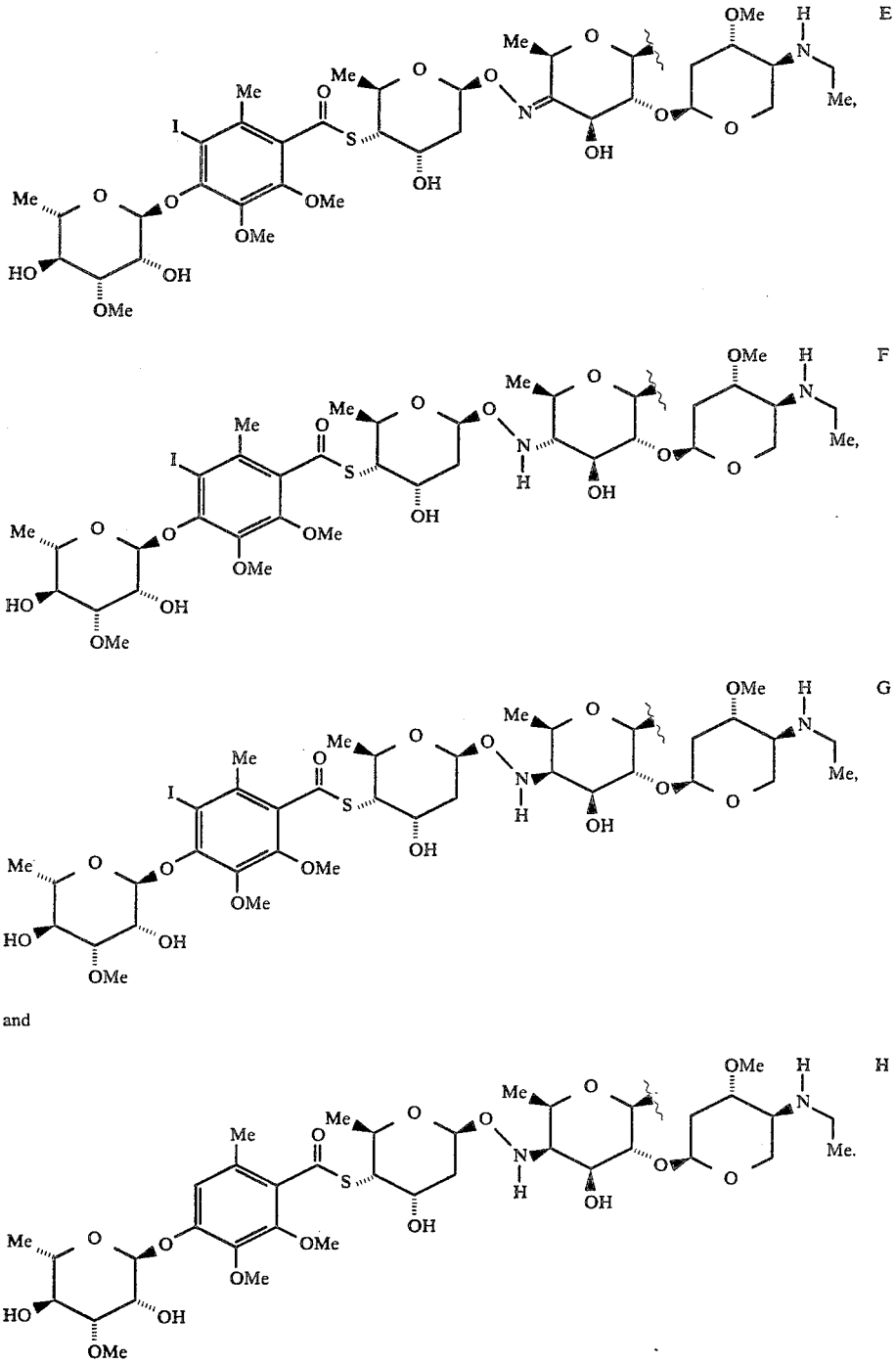

The position of the glycosyl bond to be formed in the sugar moiety used for forming a chimeric compound is typically activated prior to linkage to the fused ring enediyne compound. For example, the 1-position hydroxyl group of an otherwise protected sugar (as with $^t$BuMe$_2$Si or Et$_3$Si groups) is reacted with diethylaminosulfur trifluoride (DAST) in THF and in the presence of 4 Å molecular sieves at −78° C. to form the 1-fluoroderivative. The enediyne having a free hydroxyl group is then reacted with the 1-fluro-protected saccharide in the presence of silver perchlorate and stannous chloride to provide a protected desired, typically blocked, chimer molecule.

Similarly, treatment of 1-position hydroxyl of an otherwise protected saccharide with sodium hydride and trichloroacetonitrile [Grandler et al., *Carbohydr. res.*, 135:203 (1985); Schmidt, *Angew. Chem. Int. Ed., Engl.*, 25:212 (1986)] in methylene chloride at about room temperature provides a 1-α-trichloroacetimidate group to activate the saccharide for coupling with the fused ring enediyne (aglycon) hydroxyl. Coupling is then carried out in boron trifluoride-etherate in methylene chloride to provide the protected desired chimer compound.

Once the aglycone and oligosaccharide are coupled, the protecting groups that are present are removed to provide the desired compound, which is then recovered using standard techniques. Exemplary syntheses are discussed hereinafter.

The 1, 2 or 3 six-membered ring fused rings that along with the depicted vinylene group constitute the structure W are aromatic hydrocarbyl rings. Such rings can thus be benzo, naphtho and anthra rings, using fused ring nomenclature. The anthra (anthracene) derivative rings contemplated here contain 9,10-dioxo groups (are derivatives of anthraquinone) and are therefore referred to as 9,10-dioxoanthra rings.

Where a benzo, naphtho or 9,10-dioxoanthra ring forms part of the fused ring system, those fused rings are bonded to the remaining fused ring system through the carbon atoms of the 1- and 2-positions or are (a, b). A benzo, naphtho or 9,10-dioxoanthra fused ring portion can also contain one or more substituents at the ring positions remaining for substitution. Those substituent groups are selected from the group consisting of hydroxyl, $C_1$–$C_6$ alkoxy, oxo, $C_1$–$C_6$ acyloxy and halo (chloro, bromo or iodo).

For a benzo ring, one or two substituents can be present at one or two of the remaining positions of the radical. Symmetrical substitution by the same substituent is preferred because of the lessened possibility for isomer formation. When a single substituent is present on a benzo ring, that substituent is referred to as $R^5$, which designation for convenience includes hydrogen. $R^5$ is thus selected from the group consisting of hydrogen (no substituent), $C_1$–$C_6$ alkoxy, carboxyl, $C_1$–$C_6$ hydrocarbyl or benzyl carboxylate, benzyloxy, o-nitrobenzyloxy, hydroxy, $C_1$–$C_6$ acyloxy, oxyethanol, oxyethanol tertiary amino or quaternary ammonium $C_2$–$C_6$ alkyl carboxylic acid ester, oxyacetic acid, oxyacetic acid $C_1$–$C_6$ hydrocarbyl ester, oxyacetic acid amide, 3-hydroxyprop-1-ynyl and halo.

It is preferred that a hydroxyl group or a group that can form a hydroxyl group intracellularly be present, such that a hydroxyl group be present intracellularly at a position meta to the nitrogen in the adjacent ring. When two substituents are present on a benzo ring, they are referred to as $R^{10}$ and $R^{11}$ and are selected from the group consisting of $C_1$–$C_6$ alkoxy, benzyloxy, oxo, $C_1$–$C_6$ acyloxy, hydroxyl and halo.

W is more preferably a benzo group that contains a single substituent $R^5$. In one particularly preferred embodiment, $R^5$ is situated in the benzo ring meta or para to the nitrogen atom bonded to $R^1$. That $R^5$ group is more preferably selected from the group consisting of hydroxyl, $C_1$–$C_6$ alkoxy, benzyloxy, o-nitrobenzyloxy, $C_1$–$C_6$ acyloxy, carboxyl, $C_1$–$C_6$ hydrocarbyl or benzyl carboxylate, oxyethanol, oxyacetic acid, oxyacetic $C_1$–$C_6$ hydrocarbyl ester, oxyacetic acid amide, oxyethanol tertiary amine- or quaternary ammonium-substituted $C_2$–$C_6$ alkyl carboxylate or 3-hydroxyprop-1-ynyl. An $R^5$ oxyacetic acid or oxyethanol or 3-hydroxyprop-1-ynyl group is useful for linking the aglycone to an oligosaccharide or antibody combining site portion via an ether or ester group, as discussed previously for $R^4$.

When $R^5$ is meta to the above nitrogen atom, it is preferred that the $R^5$ group be an electron releasing group such as hydroxyl or a $C_1$–$C_6$ acyloxy group that can provide a hydroxyl group intracellularly. A $C_1$–$C_6$ acyloxy group is believed to be a pro-drug form of the hydroxyl group that is cleaved intracellularly by an endogenus esterase or the like to provide the hydroxyl group. The presence of such an electron releasing group appears to assist in enhancing the potency of the compound against target tumor cells. It is believed that the enhanced potency is due to enhanced triggering of the epoxide opening and cyclization reactions.

When $R^5$ is para to the above nitrogen atom, it is preferred that the $R^5$ group be an o-nitrobenzyloxy group, oxyethanol, carboxyl, $C_1$–$C_6$ hydrocarbyl or benzyl carboxylate, oxyacetic acid or oxyacetic acid $C_1$–$C_6$ hydrocarbyl ester. Those groups are particularly useful for the preparation of chimeras.

The presence of an $R^5$ substituent para to the nitrogen that is an oxyethanol, oxyacetic acid or oxyacetic acid amide as discussed for an $R^4$ group before, is also useful for providing enhanced water solubility to a fused ring enediyne compound discussed herein. One particularly preferred compound that contains an oxyethanol $R^5$ group para to the nitrogen atom is Compound 153, whose structure is illustrated hereinafter.

Another particularly preferred $R^5$ substituent that is para to the nitrogen atom is an oxyethanol ester of a tertiary or quaternary amine substituted $C_2$–$C_6$ alkyl carboxylic acid (carboxylate). These substituents provide still further enhancements to water solubility because of the formal charge of a quaternary ammonium group or the protonation of the tertiary amine at physiological pH values, e.g. pH 7.2-7.4.

Exemplary $C_2$–$C_6$ alkyl carboxylic acids are those discussed in conjunction with a $C_1$–$C_6$ acyloxy group. The amine substituent is preferably bonded to the carbon atom farthest down the alkyl chain from the carboxyl group and is therefore an ω-(omega) substituent. Thus, tertiary amine and quaternary ammonium derivatives of ω-amino acids such as glycine, β-alanine, γ-aminobutyric acid and 6-aminocaproic acid are preferred.

The amine portion of an oxyethanol tertiary amine- or quaternary ammonium-substituted $C_2$–$C_6$ alkyl carboxylic acid ester has the structure —$NR^{20}R^{21}$ or —$^+NR^{20}R^{21}R^{22}$ wherein $R^{20}$, $R^{21}$ and $R^{22}$ are each independently $C_1$–$C_6$ alkyl, or $R^{20}$ and $R^{21}$ together with the nitrogen atom form a 5- or 6-membered ring, or $R^{20}$, $R^{21}$ and $R^{22}$ ($R^{20-22}$) together with the nitrogen atom form a pyridinium or pyrazinium group. Exemplary $C_1$–$C_6$ alkyl groups have already been discussed, and methyl is preferred for each of $R^{20-22}$. Exemplary 5- and 6-membered ring compounds formed by $R^{20}$, $R^{21}$ and the nitrogen atom include piperidine, morpholine, pyrrolidine, imidazole, pyrrole and piperazine. Thus, exemplary —$NR^{20}R^{21}$ portions of tertiary amine groups include dimethylamino, diethylamino, hexylisopropylamino, di-sec-butylamino, N-morpholinyl, N-piperidyl and N-imidazyl. Exemplary quaternary ammonium groups include trimethylammonium, ethyldimethylammonium, ethyliso-propylhexylammonium, N-methylmorpholinium, N-butylpiperidinium, pyridinium and pyrazinium. A suitable anion for the quaternary group is of course contemplated and includes halide ions such as chloride and bromide, sulfate, acetate or another $C_1$–$C_6$ acyloxy group anion.

An N,N,N-trimethylglycine chloride ester of an oxyethanol substituent is particularly preferred. An exemplary compound utilizing such an $R^5$ substituent is Compound 250, whose structure is illustrated hereafter.

A particularly preferred compound has a structure corresponding to Formula XIb, hereinafter.

A naphtho ring can have three substituents. This ring can have a 4-position radical, $R^5$, selected from the group consisting of hydroxyl, $C_1$–$C_6$ alkoxy, benzyloxy, $C_1$–$C_6$ acyloxy, carboxyl, $C_1$–$C_6$ hydrocarbyl or benzyl carboxylate, and halo, and substituents at the 5-($R^{10}$) and 8-positions ($R^{11}$) that are selected from the group consisting of hydroxyl, $C_1$–$C_6$ alkoxy, benzyloxy, $C_1$–$C_6$ acyloxy, oxo and halo radicals. A 9,10-dioxoanthra ring can have three substituents at the 4-($R^5$), 5-($R^9$) and 8-positions ($R^{12}$) that are independently selected from the group consisting of hydroxyl, $C_1$–$C_6$ alkoxy, benzyloxy, $C_1$–$C_6$ acyloxy and halo. Thus, $R^5$, $R^9$ and $R^{12}$ can define the same groups, and all three groups can be written as either $R^5$, $R^9$ or $R^{12}$, but they are shown separately herein.

Exemplary structural formulas for such fused ring compounds are illustrated below by structural Formulas II–IX, wherein each of the R groups is as discussed before.

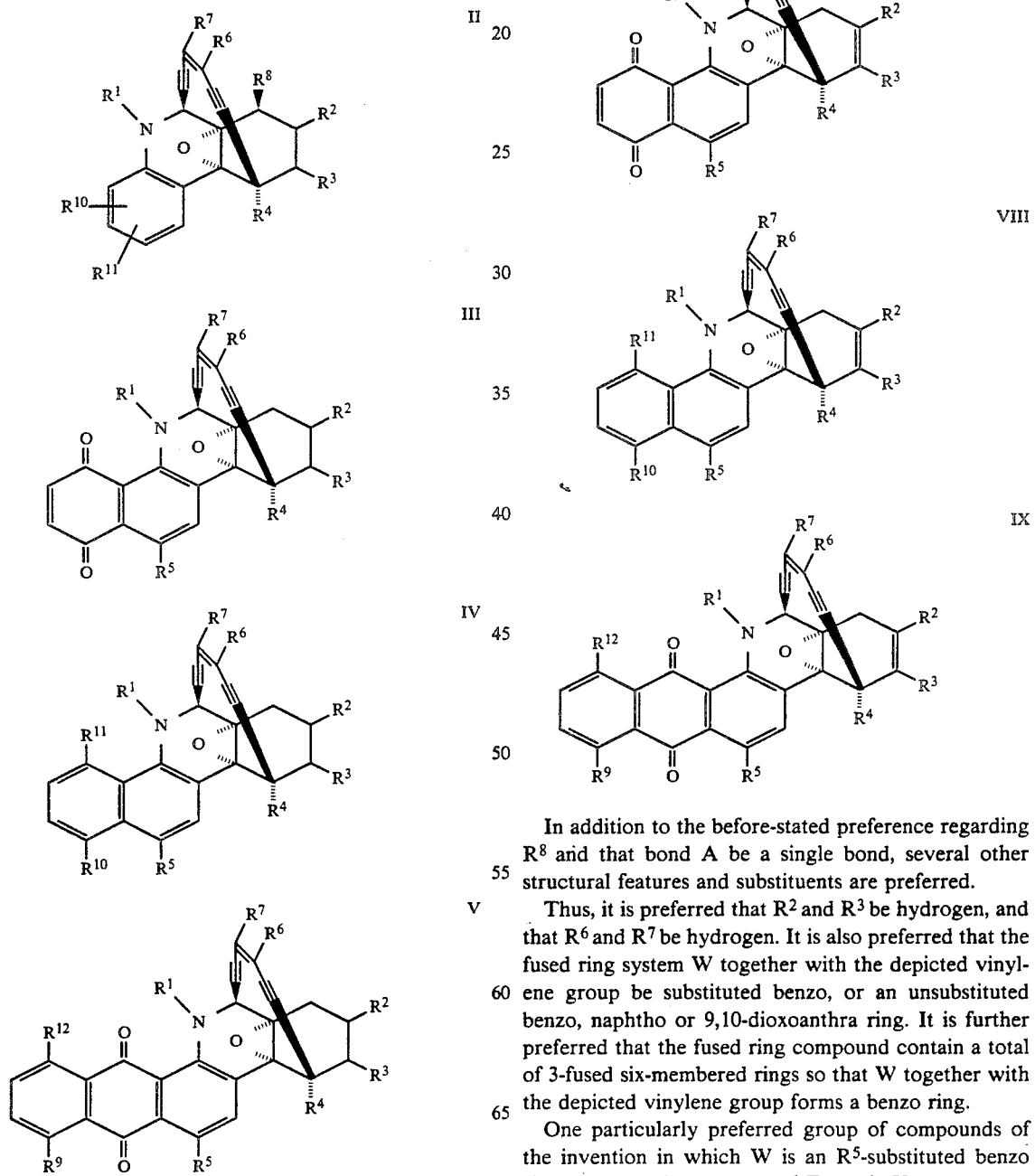

In addition to the before-stated preference regarding $R^8$ and that bond A be a single bond, several other structural features and substituents are preferred.

Thus, it is preferred that $R^2$ and $R^3$ be hydrogen, and that $R^6$ and $R^7$ be hydrogen. It is also preferred that the fused ring system W together with the depicted vinylene group be substituted benzo, or an unsubstituted benzo, naphtho or 9,10-dioxoanthra ring. It is further preferred that the fused ring compound contain a total of 3-fused six-membered rings so that W together with the depicted vinylene group forms a benzo ring.

One particularly preferred group of compounds of the invention in which W is an $R^5$-substituted benzo ring corresponds to structural Formula X.

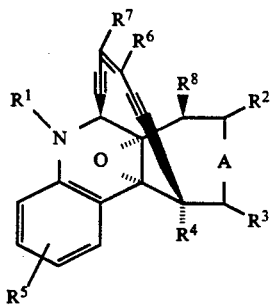

X wherein A is a double or single bond;

R$^1$ is selected from the group consisting of H, C$_1$–C$_6$ alkyl, phenoxycarbonyl, benzoxycarbonyl, C$_1$–C$_6$ alkoxycarbonyl, substituted C$_1$–C$_6$ alkoxycarbonyl (particularly substituted ethoxycarbonyl where the substituent is phenylsulfonyl or naphthylsulfonyl, with phenylsulfonyl most particularly preferred), o-nitrobenzyloxycarbonyl, and 9-fluorenylmethoyloxycarbonyl;

R$^2$ is selected from the group consisting of H, carboxyl, hydroxylmethyl and carbonyloxy C$_1$–C$_6$ alkyl;

R$^3$ is selected from the group consisting of H and C$_1$–C$_6$ alkoxy;

R$^4$ is selected from the group consisting of H, hydroxyl, oxyacetic acid (—OCH$_2$CO$_2$H), oxyacetic C$_1$–C$_6$ hydrocarbyl or benzyl ester, oxyacetic amide, oxyethanol, oxyimidazylthiocarbonyl and C$_1$–C$_6$ acyloxy;

R$^5$ is selected from the group consisting of hydrogen, C$_1$–C$_6$ alkoxy, benzyloxy, o-nitrobenzyloxy, hydroxyl, C$_1$–C$_6$ acyloxy, carboxyl, C$_1$–C$_6$ hydrocarbyl or benzyl carboxylate, oxyethanol, oxyacetic acid, oxyacetic acid C$_1$–C$_6$ hydrocarbyl ester, halo, oxyacetic acid amide, oxyethanol tertiary amino- or quaternary ammonium-substituted C$_2$–C$_6$ alkyl carboxylate and 3-hydroxyprop-1-ynyl; and R$^6$ and R$^7$ are each H or together form with the intervening vinylidene group form a one, two or three fused aromatic ring system, and R$^8$ is methyl or hydrogen.

A still more preferred group of compounds of the invention correspond to structural Formulas XI, XIa and XIb.

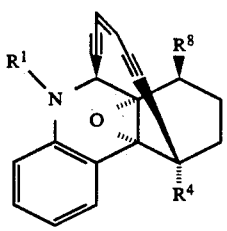

XI

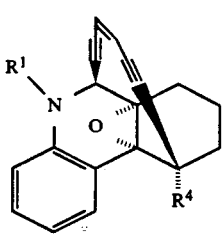

XIa

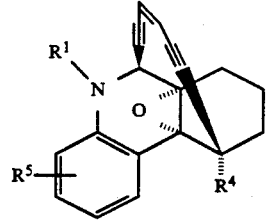

XIb wherein R$^1$, R$^4$, R$^5$ and R$^8$ are as previously defined.

Of the compounds corresponding to structural Formula XI, there are further preferences for R$^1$, R$^4$ and R$^5$. These preferences also relate to the previously discussed compounds.

Thus, R$^1$ is most preferably phenoxycarbonyl phenylsulfonylethoxycarbonyl, naphthylsulfonylethoxycarbonyl or hydrogen. R$^8$ is most preferably hydrogen (H) to provide a compound of Formulas XIa or XIb. R$^4$ is most preferably H, hydroxyl, imidazylthiocarbonyloxy, benzyl oxyacetate and C$_1$–C$_6$ hydrocarbyl oxyacetate such as ethyl oxyacetate. R$^5$ in Formulas XI and XIa is H, but is more preferably hydroxyl, C$_1$–C$_6$ alkoxy, benzyloxy, C$_1$–C$_6$ acyloxy, oxyethanol, oxyacetic acid, oxyacetic acid C$_1$–C$_6$ hydrocarbyl or benzyl ester and o-nitrobenzyloxy, oxyacetic acid amide, oxyethanol tertiary amino- or quaternary ammonium-substituted C$_2$–C$_6$ alkyl carboxylate or 3-hydroxyprop-1-ynyl as in Formula XIb. It is noted that an R$^5$ o-nitrobenzyloxy group is not usually used in a pharmaceutical composition discussed hereinafter.

The structural formulas of particularly preferred compounds are shown below, along with compound numbers as utilized herein. In the formulas below and elsewhere herein, Ph=phenyl, Me=methyl, NBnO-=o-nitrobenzyloxy and $^t$BuCO$_2$=pivaloyl.

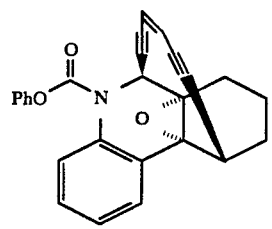

21

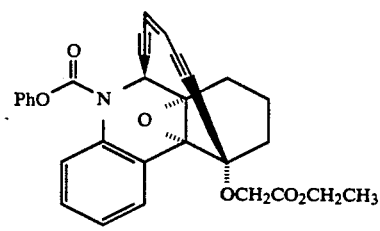

24c

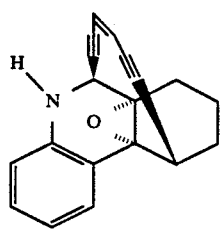

40

-continued
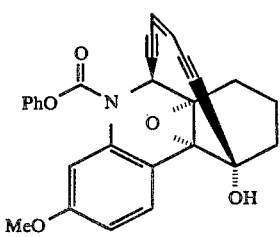
41
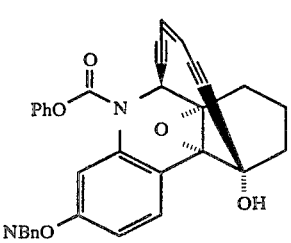
43
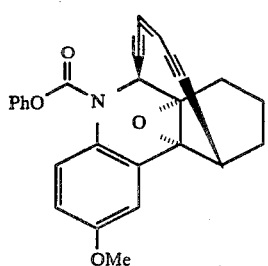
41a
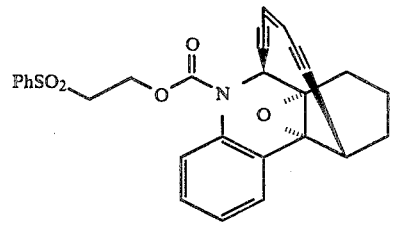
45
41b
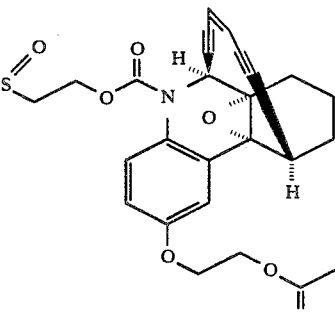
250
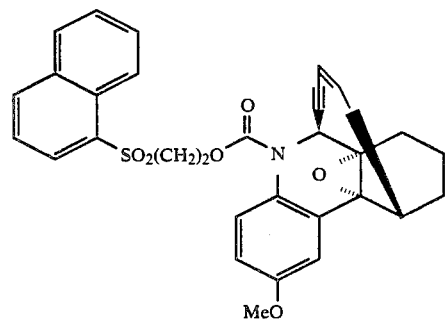
41c
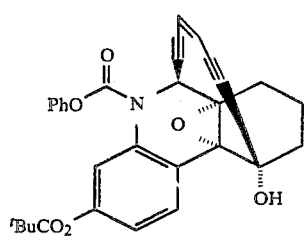
59a
42
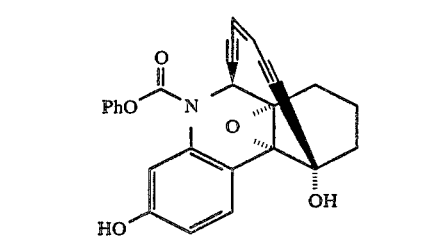
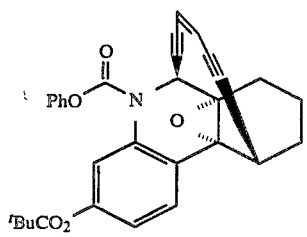
59b
41d
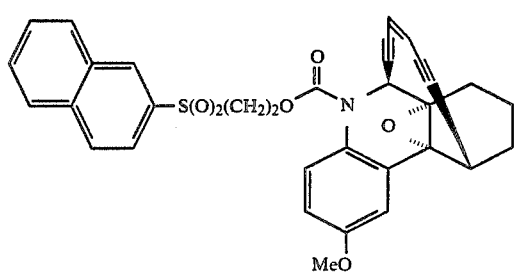
120

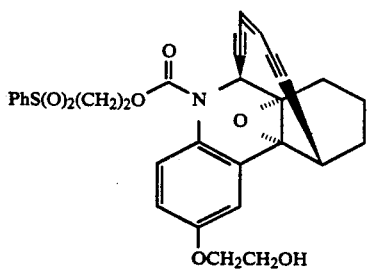

153

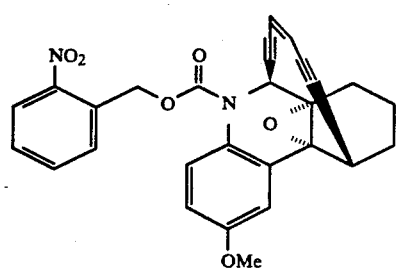

160

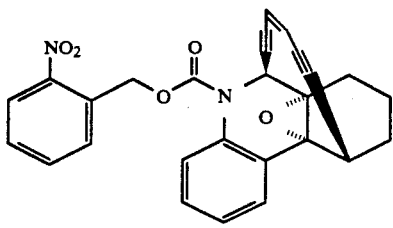

161

II. Pharmaceutical Compositions

A compound or chimera of the invention is useful as a DNA cleaving agent, and also as an antimicrobial and a cytoxic (antitumor) agent, as are dynemicin A, calicheamicin, esperamicin and neocarzinostatin. A compound of the invention can also therefore be referred to as an "active agent" or "active ingredient".

DNA cleavage can be assayed using the techniques described hereinafter as well as those described by Mantlo et al., *J. Org. Chem.*, 54:2781 (1989); Nicolaou et al., *J. Am. Chem. Soc.*, 110:7147 (1989); Nicolaou et al., *J. Am. Chem. Soc.*, 110:7247 (1988) or Zein et al., *Science*, 240:1198 (1988) and the citations therein.

A compound or chimer of the invention is useful against Gram-positive bacteria such as *S. aureus* and *epidermis*, *Micrococcus luteus* and *Bacillus subtillis* as is dynemicin A. Such a compound or chimer also exhibits antimicrobial activity against *E. coli*, *Pseudomonas aeruginos*, *Candida albucans* and *Aspergillis fumigatus*. Activity of a compound of the invention against the above microorganisms can be determined using various well known techniques. See, for example, Konishi et al., *J. Antibiotics*, XLII:1449 (1989). Antimicrobial and antitumor assays can also be carried out by techniques described in U.S. Pat. No. 4,837,206, whose disclosures are incorporated by reference, as well as by the procedures described hereinafter.

A before-described compound can also be shown to undergo a Bergman cycloaromatization reaction in the presence of benzyl mercaptan, triethylamine and 1,4-cyclohexadiene as discussed in Haseltine et al., *J. Am. Chem. Soc.*, 111:7638 (1989). This reaction forms a tetracyclic reaction as is formed during DNA cleavage, and can be used as a co-screen to select more active compounds.

A pharmaceutical composition is thus contemplated that contains a before-described compound or chimer of the invention as active agent. A pharmaceutical composition is prepared by any of the methods well known in the art of pharmacy all of which involve bringing into association the active compound and the carrier therefor. For therapeutic use, a compound or chimer of the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier.

A carrier or diluent is a material useful for administering the active compound and must be "pharmaceutically acceptable" in the sense of being compatible with the other ingredients of the composition and not deleterious to the recipient thereof. As used herein, the phrases "physiologically tolerable" and "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound or chimer of the invention (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds or chimers can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences*, Mack Publishing Co., Easton, Pa. (1980).

An active agent can also be administered in the form of liposomes. As is known in the art, liposomes are generally derived from phospholipids or other lipid substances. Liposomes are formed by mono-or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, Ed., *Methods in cell Biology*, Vol. XIV, Academic press, New York, N.Y. (1976), p. 33 et seq.

An active agent can also be used in compositions such as tablets or pills, preferably containing a unit dose of the compound or chimer. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

A previously noted preferred or particularly preferred compound or chimer is preferred or particularly preferred for use in a pharmaceutical composition.

A compound or chimer of the invention is present in such a pharmaceutical composition in an amount effective to achieve the desired result. For example, where in vitro DNA cleavage is the desired result, a compound or chimer of the invention can be utilized in an amount sufficient to provide a concentration of about 1.0 to about 5000 micromolar ($\mu$M) with a DNA concentration of about 0.02 $\mu$g/$\mu$L. As a cytotoxic (antitumor) agent, an effective amount of a compound or chimer of the invention is about 0.05 to about 50 mg per kilogram, and more preferably about 0.1 to about 15 mg per kilogram of body weight or an amount sufficient to provide a concentration of about 0.01 to about 50 $\mu$g/mL to the bloodstream. A compound or chimer of the invention exhibits antimicrobial activity in a concentration range of about 0.01 mg to about 50 $\mu$g/mL. The above concentrations and dosages vary with the particular compound of the invention utilized as well as with the target, e.g., DNA, tumor, microbe, as is well known. Lower dosages are preferred when multiple administration is utilized.

III. Methods

A compound or chimer of the invention is useful in cleaving DNA, as a cytotoxic agent and also in inhibiting the growth of neoplastic cells, and is utilized in a method for effecting such a result. A compound or chimer of the invention is typically utilized in a before-described composition.

In accordance with such a method, DNA to be cleaved or target cells to be killed or whose growth is to be inhibited are contacted with a composition that contains a compound or chimer of the invention (active ingredient) present in an amount effective or sufficient for such a purpose, as discussed before, dissolved or dispersed in a physiologically tolerable (pharmaceutically acceptable) diluent. That contact is maintained for a time sufficient for the desired result to be obtained; i.e., DNA cleaved, cells killed or neoplastic cell growth inhibited.

As is discussed hereinafter in particular regard to Compound 153, preliminary studies indicate that the principal mechanism of cytotoxicity exhibited by a fused ring enediyne disclosed herein is DNA cleavage within the contacted cells. Without being bound by theory, it is nevertheless believed that both DNA cleavage in vitro and cytotoxy or cell growth inhibition by contact with a disclosed fused ring enediyne operate substantially similarly.

Where the desired result is carried out in vitro, contact is maintained by simply admixing the DNA or target cells with the composition and maintaining them together under the appropriate conditions of temperature and for cell growth to occur, as for control, untreated cells. Thus, a single admixing and contacting is typically sufficient for in vitro purposes.

The above method is also useful in vivo, as where a mammal such as a rodent like a rat, mouse, or rabbit, a farm animal like a horse, cow or goat, or a primate like a monkey, ape or human is treated. Here, contact of a composition and the cells to be killed or whose growth is to be inhibited is achieved by administration of the composition to the mammal by oral, nasal or anal administration or by introduction intravenously, subcutaneously or intraperitoneally. Thus, contact in vivo is achieved via the blood or lymph systems.

Although a single administration (admixture) and its resulting contact is usually sufficient to maintain the required contact and obtain a desired result in vitro, multiple administrations are typically utilized in vivo. Thus, because of a body's breakdown and excreting pathways, contact between an active ingredient of a composition and the target cells is typically maintained by repeated administration of a compound of the invention over a period of time such as days, weeks or months, or more, depending upon the target cells.

Exemplary methods of the invention for DNA cleavage and inhibition of MIA PaCa-2 human pancreatic carcinoma (ATCC CRL 1420) and MB49 murine bladder carcinoma target cells (obtained from Dr. Lan Bo Chen of the Dana Farber Cancer Institute, Boston, Mass.) as well as several other neoplastic cell lines are discussed hereinafter, as are in vivo uses to inhibit the growth of neoplastic cells in mice.

As is shown and discussed in greater detail hereinafter, compounds that contain a phenylsulfonylethyleneoxycarbonyl group bonded to the nitrogen atom of the fused ring enediyne compound exhibit cytoxic selectivity betwen cancerous and normal cells, with the cancerous cells being killed at lower doses than the normal cells. A difference of about $10^{8-9}$ in concentration was noted for the cytotoxicities of Compound 153 and 250 between peripheral blood lymphocytes and Molt-4 leukemia cells.

Exemplary concentrations for in vitro cytoxicity studies vary with the cells to be killed, and can range from about $10^{-5}$M to about $10^{-15}$M, as is seen from the data in Tables 1-5 hereinafter. Exemplary concentrations and dosages for in vivo use can be those used for dynemicin A or calicheamicin $\gamma_1{}^I$. Typical in vivo dosages are about 1 to about 100 mg/kg body weight of the recipient mammal. Exemplary concentrations useful for in vitro cleavage of DNA range from about 0.1 to about 5 mM.

IV. Compound Syntheses

A compound of the invention can be prepared by a number of routes, several of which are illustrated in the schemes hereinafter. The retrosynthetic plan for these syntheses is illustrated below in Scheme I, with the general forward synthesis shown in Scheme II, thereafter.

formed as Compound 5. Introduction of that oxygen-containing substituent can be accomplished by oxidation as with m-chloroperbenzoic acid (mCPBA), followed by acylation and reflux to rearranged the formed acylated N-oxide to the 10-position (steps a and b) of Compound 5. The acetyl group is removed to form the alcohol (Compound 6, step c), which is then blocked with a t-butyldimethylsilyl group (Si$^t$BuMe$_2$; Compound 7, step d).

An appropriate acetylenic group-containing compound is added adjacent to the nitrogen atom (at the 6-position) as by reaction of an ethynyl Grignard reagent in the presence of an activating moiety that also functions to block the secondary amine so generated, such as phenyl chloroformate to form an R$^1$ substituent of Compound 8 (step e).

The epoxide ring is added next between the 6-and 10-positions by oxidation as with (mCPBA) as in Com-

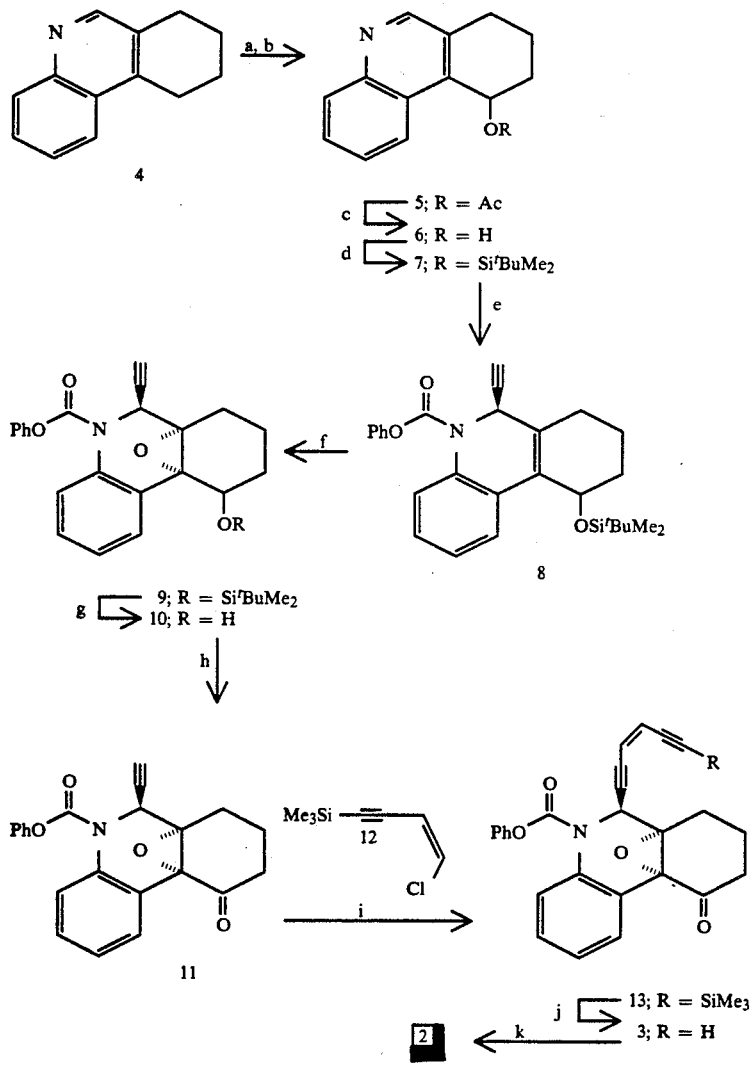

Briefly, the basic fused 3-, 4- or 5-fused six-membered ring system is first formed.

Following Scheme II for a general synthesis, using the tetrahydro-phenanthridine fused ring system of Compound 4 (W is benzo) as exemplary, an oxygen-containing substituent R$^4$ having an oxygen atom of that group bonding to the 10-position ring carbon atom is pound 9 (step f). The formed epoxide ring is on the opposite side of the ring plane from the 6-position acetylenic group, and preferably, the epoxide is in an α-configuration, whereas the acetylenic group is β.

The oxygen-linked $R^4$ group $Si^tBuMe_2$ is replaced with a hydrogen (step g) and the alcohol so formed is next converted to a ketone, Compound 11 (see also step h, Scheme III). The vinyl acetylene portion of the enediyne-containing ring is added as in Compound 13, when necessary. This step can be carried out by reacting (Z) 1-chloro-4-trimethylsilyl-but-1-en-3-yne (Compound 12) with the ketone Compound 11 in the presence of butylamine, triphenylphosphine and palladium$^{II}$ acetate (step i).

Scheme III illustrates that the entire enediyne carbon skeleton can be bonded to the 6-position in a single step, as is discussed hereinafter. Scheme III also illustrates formation of a benzo ring W by reaction of an aniline compound with ethyl cyclohexanone-2-carboxylate. Compound 41 was prepared starting with m-anisidine ($R^5$=m-methoxy), whereas a meta-pivaloyl ester ($R^5$=meta-$C_5$ acyloxy) was prepared from a meta-benzyl ether in preparing Compounds 59a and 59b. Where a $R^8$ methyl group is desired, ethyl 3-methylcyclohexanone-2-carboxylate is utilized.

A derivative of a compound such as Compounds 2 or 21 having a hydroxyl group ($R^5$, or $R_4$ of Scheme III) can be prepared following the synthetic route illustrated in Scheme III ($R_2$=H,H) through step j and then Scheme VII, by utilizing meta-(2-nitrobenzyloxy)aniline for preparation of a tri-cyclic compound analogous to that formed in step a of Scheme III. The meta-2-nitrobenzyloxy (NBnO) group can be removed after step j of Scheme III to form the meta-hydroxyl-substituted derivative of a compound such as Compounds 2 or 21 by irradiation with ultraviolet light. A meta-hydroxyl-substituted derivative of Compound 2, Compound 42, has been so prepared via Compound 43, irradiated, and shown to cause cleavage of double stranded DNA at a 2 mM concentration.

After removal of the trimethylsilyl group from the otherwise free (unlinked) acetylenic group (Scheme II, step j), the acetylenic group is inserted into the carbonyl group at position-10 by reaction with a base such as lithium diisopropylamide (LDA) to form a fused ring compound of the invention where $R^4$ is hydroxyl (OH) (step k). The $R^4$ group can later be replaced with a hydrogen or derivatized as discussed hereinafter.

As noted before, $R^6$ and $R^7$ are preferably hydrogen (H). However, $R^6$ and $R^7$ along with the intervening vinylidene group can together form an aromatic mono-, di- or tri-cyclic ring system that can be hydrocarbyl or heterocyclic. When such a ring system is present, the ethylenic bond of the enediyne-containing ring is also one of the unsaturated carbon-to-carbon bonds of aromatic ring system, and the entire enediyne carbon skeleton is typically bonded at the 6-position (see Scheme III, $R_2$) as a single unit, as is shown in Scheme XI.

Scheme III

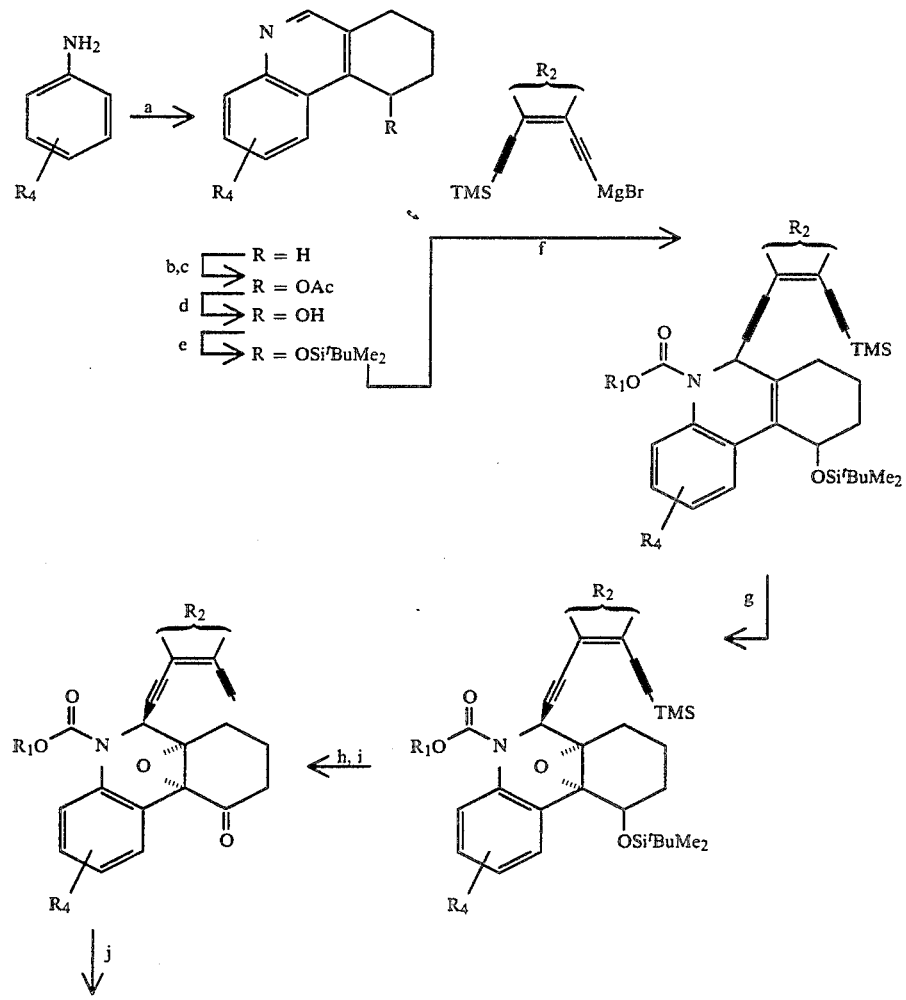

Scheme III

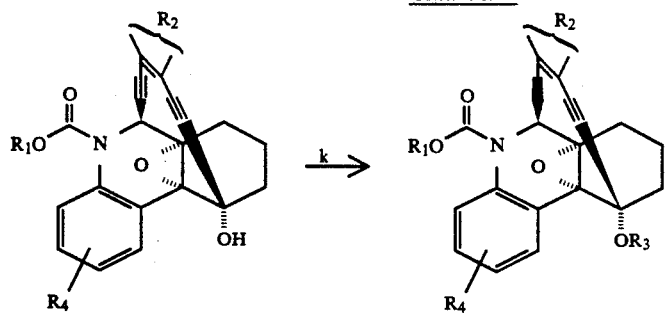

Turning more specifically to Scheme III, 2-ethoxycarbonylcyclohexanone is reacted with the aniline ($R_4$ as shown hereinafter), and the reaction product cyclized by treatment with $H_2SO_4$. The cyclized material is reduced with lithium aluminum hydride and then air oxidized (step a) to form the tricyclic compound. That compound is oxidized, acetylated and rearranged (steps b and c) to form the acetoxy compound (R=OAc) whose acetyl group is removed to form the alcohol (step d, R=OH) that is then reacted with t-butyldimethylsilyl trifluoromethanesulfonate in the presence of 2,6-lutidine in step e (R=OSi$^t$BuMe$_2$).

The product of step e is reacted first with a chloroformate whose $R_1$ group is shown hereinafter, and then with diacetylide or an aromatic diacetylide ring system compound ($R_2$ as shown hereinafter) blocked with a tirmethylsilyl group (TMS) and containing a mono-Grignard reagent in step f to form the partially linked macrocyclic ring precursor.

The epoxide ring is formed in step g by reaction with mCPBA. The Si$^t$BuMe$_2$ group is removed in step h by reaction with $^n$BuNF, and the resulting alcohol is oxidized with pyridinium chlorochromate in the presence of molecular sieves in step i to form the ketone.

The macrocyclic ring is closed in step j by reaction with lithium diisopropylamide (LDA). The hydroxyl group formed in step j is reacted in step k with an appropriate 2-haloacetic acid derivative ($R_3$ as shown hereinbelow) to form the final product.

```
R3 = CH2COOH
     CH2CONH-peptide
     CO(CH2)2COOMe
     CH2CONH-Phenyl
     CH2CONH-Naphthyl
     CH2CONH-Anthracyl
     CH2CO2-spacer-Mab
     spacer-Saccharide R4 = OMe
     OH
     OCOMe
     OCO'Bu
     ONBn
     H
```

Subscripted R groups are used in this scheme to distinguish R groups therein from the superscripted R groups defined elsewhere herein.

The "spacer" noted for $R_3$ is a peptide that typically contains zero to about six amino acid residues that links a monoclonal antibody, "Mab", to the compound. The $R_3$ "spacer" linked to an oligosaccharide is typically an oxyethanol or oxyacetic acid group used to form the glycosidic bond to the saccharide, or bond to a paratope-containing molecule.

A vicinal diyne aromatic compound suitable for introduction at the 6-position (based on Compound 4) of a 3-, 4- or 5-fused six-membered ring system can be prepared by alkylation of a vicinal dihalide with trimethylsilylacetylene in the presence of diisopropylamine, dicyanophenylpalladium chloride, triphenylphosphene and cuprous iodide to form the vicinal bis-trimethylsilylacetylene derivative.

Exemplary vicinal dihalo aromatic compounds commercially available from Aldrich Chemical Co. of Milwaukee, Wis. include 1,2-diiodobenzene, 1,2-dibromobenzene and 1,2-dichlorobenzene. 2,3-Dibromonaphthalene, 2,3-dibromoanthracene and 6,7-dichloroquinoxaline have the following Chemical Abstracts Registry Numbers (R.N.) 13214-70-5, 117820-97-0, and 19853-64-6.

After preparation of the vicinal bis-trimethylsilylacetylene derivative, one of the trimethylsilyl groups (TMS) is replaced with a hydrogen atom by reaction with silver nitrate and potassium cyanide. The resulting aromatic diacetylide is then reacted with the fused ring system as described previously.

An appropriate vicinal diacetylide can also be prepared via a vicinal, dihydroxymethyl compound. In one exemplary synthesis, 1,4-dimethoxy-6,7-dimethylnaphthalene (R.N. 73661-12-2) is reacted with N-bromosuccinimide (NBS) and azobisisobutyronitrile (AIBN) in a halogenated solvent such as carbon tetrachloride to form the corresponding vicinal dibromomethyl derivative. Reaction of that dibromo compound with hydroxide ion forms the vicinal dihydroxymethyl derivative. Mild oxidation of the dihydroxymethyl compound with pyridinium chlorochromate (PCC) provides the corresponding vicinal dialdehyde. Reaction of the dialdehyde with triphenylphosphine and carbon tetrabromide, followed by reaction with butyl lithium and then with trimethylsilyl chloride provides the vicinal di-TMS acetylene derivative. Following replacement of one TMS group with hydrogen as discussed before, the aromatic diacetylide is reacted with the fused ring system as was also discussed before.

The above method of synthesis can also be applied to unsubstituted aromatic compounds, such as vicinal dicarboxylic acids, anhydrides or esters. For example, phthalic acid and naphthalene-2,3-dicarboxylic acid are both available from Aldrich Chemical Co. Either or both can be used to form the corresponding dimethyl esters by reaction with diazomethane. Reduction of the diesters to vicinal dihydroxymethyl derivatives can be accomplished by reduction using diisobutylaluminum hydride (DIBAL). The resulting dihydroxymethyl compounds are thereafter reacted as described above to form a desired compound.

It is preferred that an aromatic diacetylide contain its two vicinal acetylenic groups symmetrically bonded to the ring system so as to minimize isomer formation. Thus, 2,3-disubstituted-naphthalene, anthracene or quinoxaline compounds are utilized, or a 6,7-disubstituted-quinoxaline, or the like.

An exemplary synthesis for compounds corresponding to structural Formula V is illustrated in Scheme IV, shown below.

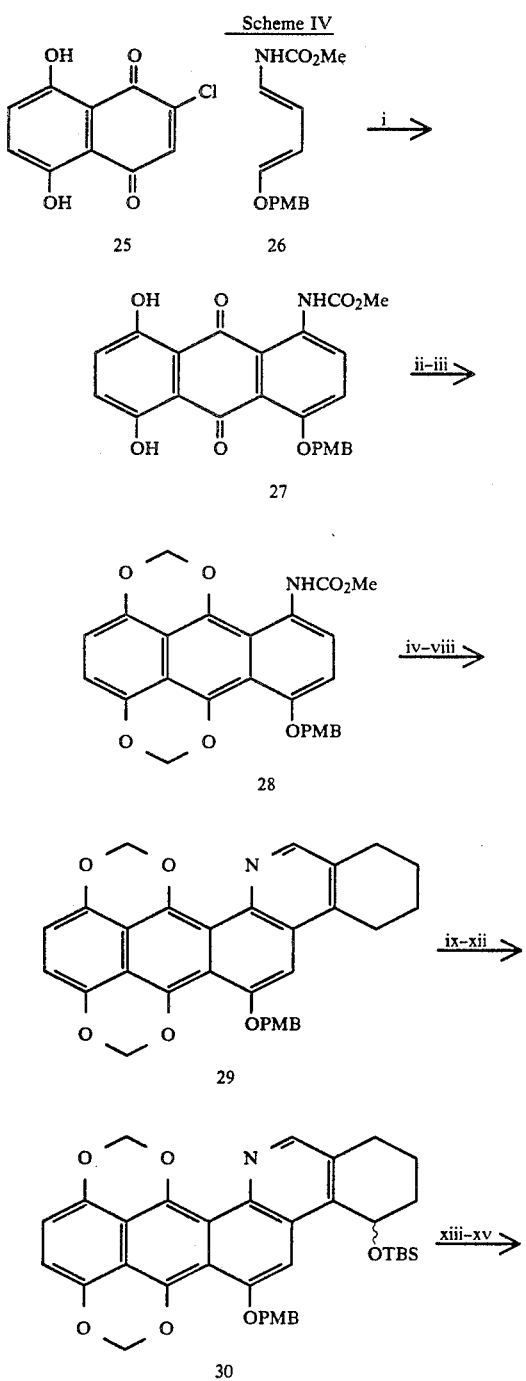

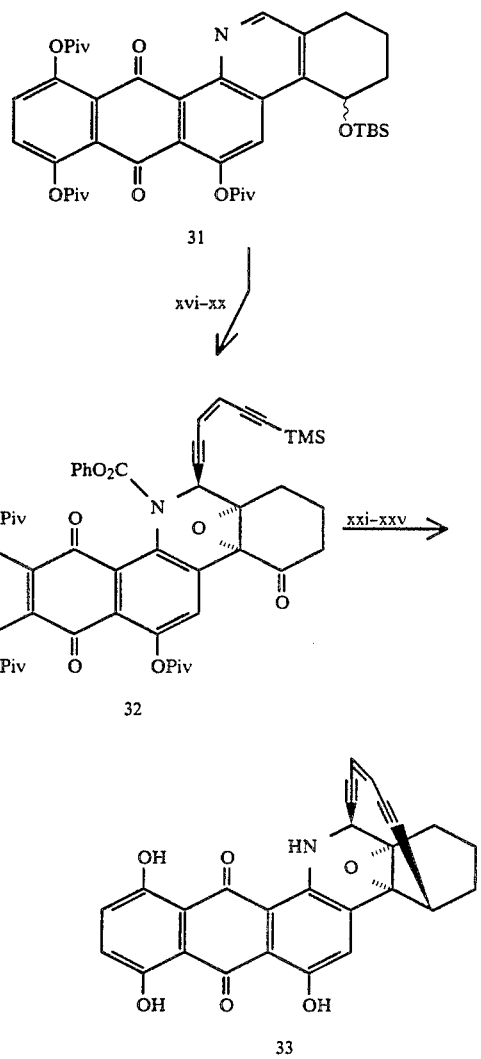

Thus, chloronaphthazarin, Compound 25, [Banville et al., Can J. Chem., 52:80 (1974); Savard et al., Tetrahedron, 40:3455 (1984); and Echavarren et al., J. Chem. Res. (3), 364 (1986)] is reacted in step i with diene Compound 26 [Schmidt et al., Synthesis, 958 (1982)] in A Diels-Alder reaction to form the aminoanthraquinone, Compound 27. Reduction of the quinone as with DIBAL in step ii, followed by alkylation with methylene bromide in the presence of cesium fluoride in DMF as step iii provides the O-blocked Compound 28.

Removal of the urethane group with base in step iv, annellation and subsequent reaction as illustrated in Scheme III provides Compounds 29 (steps v-viii) and 30 (steps ix and xii). Compound 30 is then reacted with lithium iodide in pyrazine, oxidized with 2,3-dichloro-5,6-dicyanobenzoquinone (DDQ), and reacted with pivaloyl chloride (Piv) to form Compound 31 (steps xiii-xv).

Ethylmagnesium bromide is reacted with Compound 31 in the presence of phenyl chloroformate (step xvi). The resulting compound is reacted with mCPBA to form the epoxide (step xvii). The TBS group is removed with $^n$Bu$_4$NF to form the alcohol (step xviii) that is then oxidized with Jones reagent (step xix) to form the corresponding ketone. That ketone is reacted with (Z)-1-chloro-4-trimethylsilylbut-1-en-3-yne, palladium°, CuI and butylamine to form Compound 32 (step xx). Compound 32 is reacted with silver nitrate and potassium cyanide (step xxi), LDA (step xxii), thiocarbonyldiimidazole (step xxiii), tri-n-butylstannane and AIBN (step xxiv), and then hydroxide ion (step xxv) to form Compound 33.

For preparation of a compound corresponding to structural Formula IX, 1-aminoanthraquinone (Aldrich Chemical Co.) can be used as a starting material. Here, the amino group is blocked as with a t-Boc group, the quinone function is reduced as with DIBAL and the resulting phenolic hydroxyl groups are blocked with pivaloyl chloride.

The t-Boc group is then removed as by reaction with trifluoroacetic acid (TFA) and the aromatic ring is annelated with ethyl cyclohexanone-2-carboxylate, followed by cyclization with sulfuric acid, reduction with lithium aluminum hydride and then air oxidation to reform the quinoid structure as the pivaloyl groups are lost during the prior reactions.

The above reactions form the fused ring system. The enediyne macrocycle portion is thereafter added as discussed before.

Where a double bond is desired in the otherwise saturated six-membered ring as is shown in structure Formulas VI, VII, VIII and IX, that functionality can be added as follows. The fused ring system and epoxide are formed, one of the acetylenic linkages is made, the amine blocked and the ketone is formed, all as discussed previously. Exemplary compounds of the required structure are Compounds 13 and 32 shown in Scheme II and IV. The compound is then oxidized to introduce hydroxyl group α (position 9 of Compound 13) to the ketone at position 10 of Compound 13. That hydroxyl group is then blocked as with triethylsilyl (TES or Et₃Si) chloride and the macrocyclic enediyne ring is closed. The hydroxyl group resulting from the ring closure is either removed as discussed before or blocked with a group that is not removed by removal of the TES group.

The TES group is removed and the resulting hydroxyl group is oxidized to a ketone as by Swern oxidation. That ketone is then reacted with LDA and methyl chloroformate to form a carboxy enol whose hydroxyl group can be methylated with diazomethane. Subsequent reaction with hydroxide ion and neutralization provides the unsaturated methoxy carboxylic shown in structural Formulas VI, VII, VIII and IX.

For a compound of structural Formula VI, where the $R^8$ methyl group is present, that methyl group is in the β-configuration. Here, the ketone formed by the above Swern oxidation is reacted with LDA, phenylselenylbromide and hydrogen peroxide to form an enone. That enone is reduced with copper hydride, which attacks from the α-face to provide the β-stereochemistry for the $R^8$ methyl group. The reduced enone is then reacted as above to provide the double bond and $R^2$ and $R^3$ groups.

A compound of the general formula of Compound 24

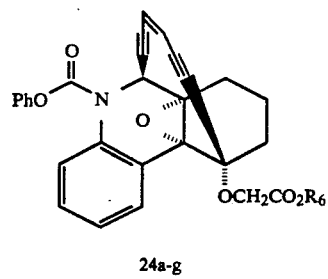

$R_6$ = a) H;
b) Methyl;
c) Ethyl;
d) Iso-propyl;
e) Allyl;
f) Propargyl;
g) Benzyl.

24a-g can be prepared by reaction of an appropriate 2-haloacetic acid (Compound 24a) or 2-haloacetate ester (Compounds 24b-g) with Compound 2 in the presence of a base such as cesium carbonate ($Cs_2CO_3$) and a crown ether such as 18-crown-6. Exemplary syntheses of Compounds 24a, 24c and 262, and similarly substituted compounds having a phenylsulfonylethylene oxycarbonyl group replacing the phenyl oxycarbonyl group, e.g. Compound 120, are provided hereinafter. A compound wherein $R^4$ is a $C_1$-$C_6$ alkoxy group can be similarly prepared from Compound 2 by alkylation with a $C_1$-$C_6$ halo derivative such as iodo or triflate derivative in the presence of $Cs_2CO_3$.

Removal of the carbamate group from the nitrogen atom of a compound such as Compound 2 to form a free amine-containing compound such as Compound 40 is achieved by reaction with lithium aluminum hydride reduction. Variants in the alcohol portion of a carbamate derivative of a dynemicin analog can be prepared from a phenoxycarbonyl derivative such as Compound 2 by reaction with the replacing alcohol in the presence of the sodium salt of the alcohol as is shown schematically in Scheme VIII, and discussed thereafter and elsewhere herein.

V. Results

The key retrosynthetic step that led to the present synthetic strategy is shown in Scheme I, as noted previously. Scheme II outlined the construction of Compound 2 starting from the quinoline derivative Compound 4 [(a) Masamune et al., *J. Org. Chem.*, 29:681-685 (1964); (b) Curran et al., *J. Org. Chem.*, 49:2063-2065 (1984); (c) Hollingsworth et al., *J. Org. Chem.*, 1537-1541 (1948)]. Thus, treatment of Compound 4 with m-chloroperbenzoic acid (mCPBA) in dichloromethane gave the corresponding N-oxide (step a) which underwent regiospecific rearrangement [Boekelheide et al., *J. Am. Chem. Soc.*, 76:1286-1291 (1954)] upon heating in acetic anhydride (step b) to give the acetoxy derivative Compound 5 (62 percent overall yield).

Compound 5 was converted to the corresponding silyl ether Compound 7 in 92 percent overall yield by standard methods via hydroxy Compound 6 (steps c and d). Addition of phenyl chloroformate [Comins et al., *J. Org. Chem.*, 55:292-298 (1990)] to a mixture of Compound 7 and ethynylmagnesium bromide at −78° C. led to the formation of Compound 8 in 92 percent yield (step e).

Treatment of Compound 8 with mCPBA led to epoxide Compound 9 (85 percent) (step f), which was converted to ketone Compound 11 via alcohol Compound 10 by desilylation(step g) followed by oxidation (step h). Coupling Compound 11 with the vinyl chloride derivative Compound 12 via Pd(OAc)₂-CuI catalysis (step i) followed by AgNO₃/KCN treatment (step j) resulted in the formation of the requisite precursor Compound 3 via coupling product Compound 13 (79 percent overall yield). Finally, treatment of Compound 3 with LDA in toluene at −78° C. (step k) gave the targeted dynemicin A model Compound 2 (80 percent based on 25 percent recovery of starting material). Compound 2 is also referred to as DY-1 in FIGS. 10 and 11.

Compound 2 crystallized from ether in colorless prisms, mp 232°-235° C. dec. X-ray crystallographic analysis (this X-ray crystallographic analysis was carried out by Dr. Raj Chandha, Department of Chemistry, University of California, San Diego) confirmed its structure (ORTEP drawing Oakridge Thermal Ellipsoid Plotter) and revealed some interesting structural features.

The acetylenic moieties are bent from linearity with the following angles: C14, 160.4°; C15, 170.8°; C18, 171.6° and C19, 162.0°. The distance between carbons C14 and C19 (cd distance) [Nicolaou et al., *J. Am. Chem. Soc.*, 110:4866–4868 (1988)] was found to be 3.63 Å, a value that agrees well with the calculated one for the MMX minimized structure of Compound 2 (3.63 Å) and that of the experimentally derived [(a) Konishi et al, *J. Am. Chem. Soc.*, 112:3715-3716 (1990); (b) Konishi et al., *J. Antibiot.*, 42:1449-1452 (1989)] distance in dynemicin A (3.54 Å). The calculated distance for these acetylenic carbons was found to be 3.40 Å. See: Semmelhack et al., *Tetrahedron Lett.*, 31:1521-1522 (1990). [The MMX87 force field in computer programs MMX and PCMODEL from Serena Software, P.O. Box 3076, Bloomington, Ind. 47402-3076 was used.]

Scheme V outlines a cascade of novel transformations of model system Compound 2.

to Compound 17 in 82 percent yield, presumably via intermediates 14 and 15. This transformation (2→17) was also carried out using 1.0 equivalent of TsOH.H$_2$O and 50 equivalents of Et$_3$SiH in benzene at 25° C. (24 hours, 85 percent).

For a study using Et$_3$SiH and a number of other hydrogen donors to trap C-centered radicals, see: Newcomb et al., *J. Am. Chem. Soc.*, 108, 4132-4134 (1986). Compound 17 derived from this reaction with Et$_3$SiH was contaminated with about 5 percent of an, as yet, unidentified product (detected by $^1$H NMR spectroscopy).

Thus, protonation of the epoxide group in Compound 2 initiates formation of triol Compound 14 which undergoes spontaneous Bergman cyclization [(a) Bergman, *Acc. Chem. Res.*, 6:25-31 (1973); Jones et al., *J. Am. Chem. Soc.*, 94:660–661 (1972); Lockhart et al., *J. Am. Chem. Soc.*, 103:4091–4096; (b) Darby et al., *J. Chem. Soc. Chem. Commun.*, 1516-1517 (1971); (c) Wong et al., *Tetrahedron Lett.*, 21:217-220 (1980)] to form a benzenoid diradical which is, in turn, rapidly trapped by the hydrogen donor present to furnish cyclized product Compounds 15, 15a, or 15b. Under the reaction conditions, triol Compound 15 apparently undergoes a pinacol-type rearrangement leading to the observed final product Compound 17. The structure of Compound 17 was supported by its spectroscopic data and was confirmed by X-ray crystallographic analysis.

Furthermore, it was found that trimethylsilyl trifluoromethylsulfonate (TMSOTf) in the presence of Et$_3$SiH induces the same transformation (2→17), (Scheme V) at −78° C. in less than 5 minutes (78 percent yield), suggesting a very low energy of activation Scheme V

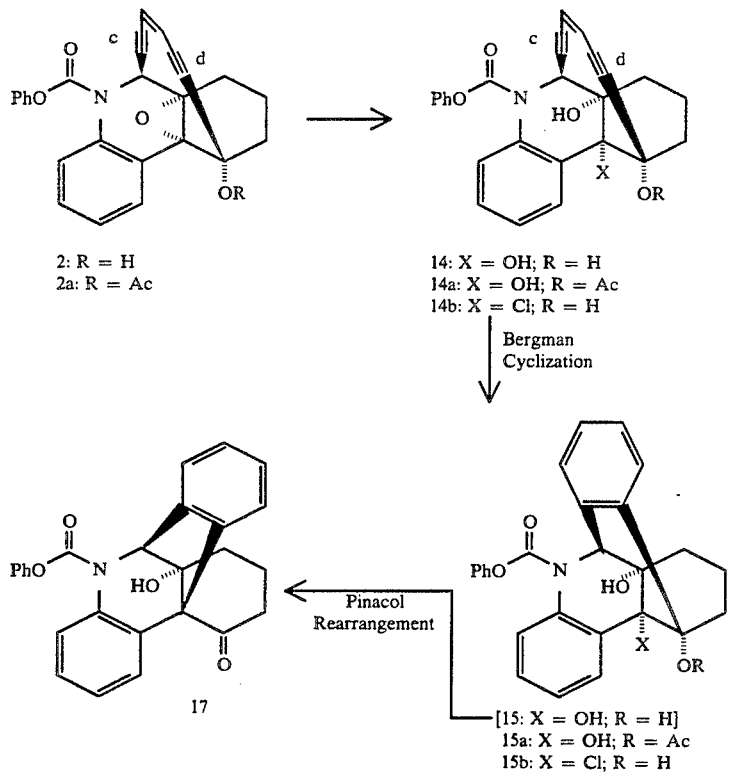

Thus, upon treatment with p-toluenesulfonic acid (TsOH.H$_2$O) in benzene-1,4-cyclohexadiene (3:1, 0.05 M) at 25° C. for 24 hours, Compound 2 was converted for the cyclization process. The rather dramatic shortening of the cd distance in going from epoxide Compound 2 (cd=3.63 Å, X-ray and MMX) to triol compound 14a (cd=3.19 Å, MMX) is noteworthy. For comparison with other similar enediyne cyclizations and calculations, see: (1) Nicolaou et al, *J. Am. Chem. Soc.*, 110:4866-4868 (1988); (b) Nicolaou et al., *J. Am. Chem. Soc.*, 110:7247-7248 (1988); (c) Hazeltine et al., *J. Am. Chem. Soc.*, 111:7638-7640 (1989); (d) for similar stabilization of enediynes via cobalt complexation, see: Magnus et al., *J. Am. Chem. Soc.*, 110:1626-1628 (1988) and Magnus et al., *J. Am. Chem. Soc.*, 110:6921-6923 (1988); (e) Semmelhack et al., *Tetrahedron Lett.*, 32:1521-1522 (1990); (f) Snyder et al *J. Am. Chem. Soc.*, 111:7630-7632 (1989); (g) Magnus et al., *Tetrahedron Lett.*, 30:1905-1906 (1989).

In an attempt to prevent the pinacol rearrangement of triol Compound 15, the acetate derivative Compound 2a was prepared from Compound 2 [acetic anhydride, 4-dimethylaminopyridine (DMAP), 84 percent], and was subjected to the epoxide opening and cyclization reaction conditions as described above. Indeed, the acetate diol Compound 15a was obtained (84 percent yield) as the final product of this cascade starting with Compound 2a and using TsOH.H$_2$O as the initiator (presumably via intermediate Compound 14a).

The use of anhydrous HCl in CH$_2$Cl$_2$ in the presence of Et$_3$SiH (Scheme V hereinbefore) also resulted in triggering of the cyclization cascade leading from Compound 2 to Compound 15b (85 percent yield) presumably via the intermediacy of Compound 14b (cd=3.145 Å, MMX). The same conversion (2→15b) was also effected by the use of 3.0 equivalents of MgCl$_2$ and 50 equivalents of Et$_3$SiH in CH$_2$Cl$_2$ at 25° C. (12 hours, 87 percent) or 1.2 equivalent of TiCl$_4$ and 50 equivalents of Et$_3$SiH in CH$_2$Cl$_2$ at −78° C. (0.5 hour, 60 percent).

Thus, only Compound 15 underwent the further pinacol-type rearrangement to form Compound 17.

These cyclizations are analogous to those observed for dynemicin A. [(a) Konishi et al., *J. Am.Chem. Soc.*, 112:3715-3716 (1990); (b) Konishi et al., *J. Antibiot.*, 42:1449-1452 (1989); (c) Sugiura et al., *Proc. Natl. Acad. Sci. USA*, 87:3831-3835 (1990)].

An alternate mode of triggering the cyclization of Compound 2 based on cobalt complexation of the acetylenes was devised. This triggering cyclization is illustrated in Scheme VI, below. This pathway was designed so as to prevent the acetylenes from spontaneously cyclizing upon epoxide opening and thus allow the isolation of the postulated intermediate cis-diol.

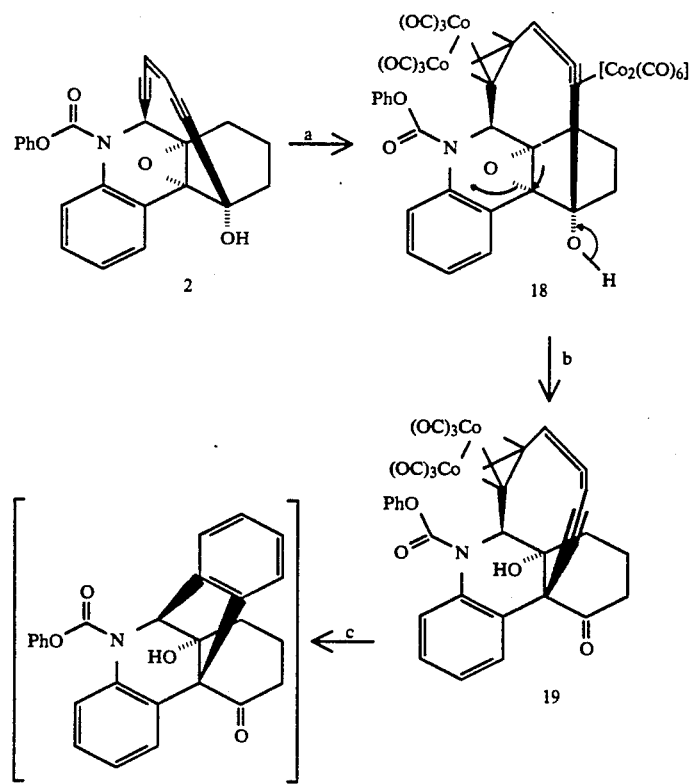

Scheme VI

Scheme VI

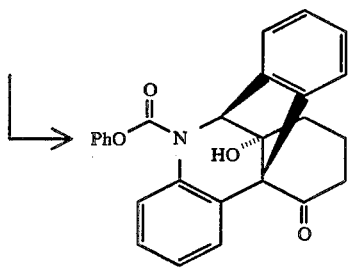

17

Thus, reaction of Compound 2 with $Co_2(CO)_8$ (2.2 equivalents) resulted in the formation of the dicobalt complex Compound 18 (step a) in 96 percent yield. Use of one equivalent of $Co_2(CO)_8$ resulted in the formation of a monocobalt complex in addition to dicobalt derivative Compound 18 and starting material Compound 2. [For similar stabilization of enediynes via cobalt complexation, see: Magnus et a., *J. Am. Chem. Soc.*, 110:1626-1628 (1988); and Magnux et al., *J. Am. Chem. Soc.*, 110:6921-6923 (1988)].

Treatment of Compound 18 with trifluoroacetic acid in $CH_2Cl_2$ (zero degrees C) followed by aqueous workup led to the formation of the stable cis opening product Compound 19 (step b; 92 percent yield). Upon exposure of Compound 19 to ferric nitrate, or trimethylamine N-oxide in $CH_2Cl_2$ in the presence, or absence, of $Et_3SiH$ at 25° C., the cyclized product Compound 17 was obtained in 85-92 percent yield via liberation of the acetylenic groups to afford Compound 14 followed by spontaneous and sequential generation of Compounds 15 and 17 as shown in Schemes V and VI. The same study [reaction with $Fe(NO_3)_3$] carried out in $CD_2Cl_2$ resulted in the incorporation of two deuterium atoms in Compound 17 confirming methylene chloride as an effective hydrogen atom donor in these aromatization studies.

To obtain a closer model to dynemicin A, the tertiary hydroxy group in Compound 2 was removed to form Compound 21 as shown in Scheme VII below.

Scheme VII

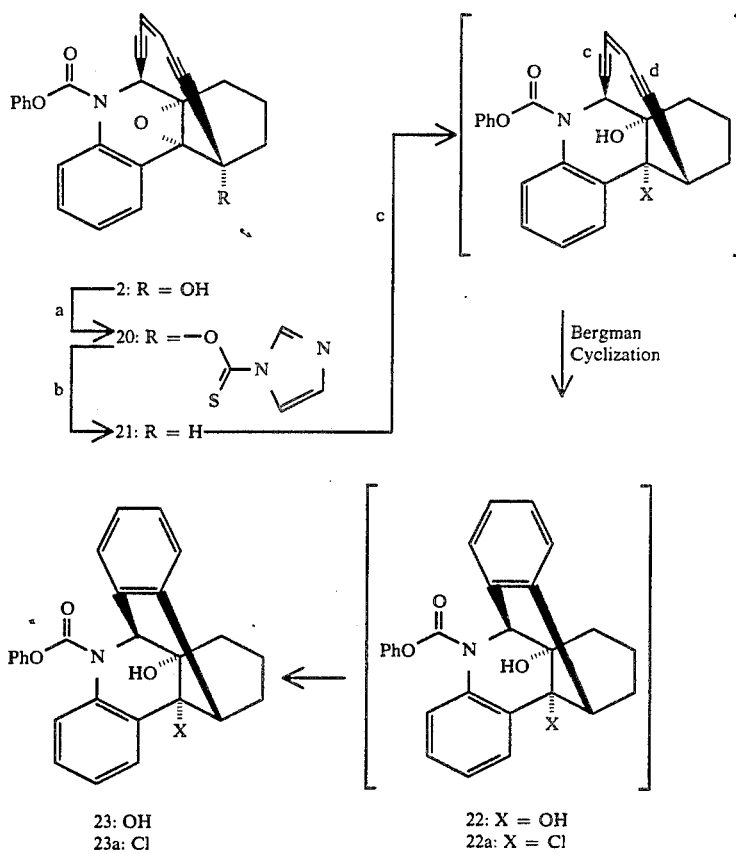

23: OH
23a: Cl

22: X = OH
22a: X = Cl

Thus, reaction of Compound 2 with thiocarbonyldiimidazole in the presence of DMAP resulted in the formation of Compound 20 in 95 percent yield (step a). Compound 20, upon treatment with $^nBu_3SnH$ in the presence of a catalytic amount of AIBN (toluene, 75° C.), led to the desired Compound 21 (step b; 72 percent yield). This model system Compound 21 also underwent smooth cyclization to polycycles Compounds 23 (86 percent) and 23a (82 percent) upon suitable triggering, (as summarized in Scheme VII).

An ORTEP drawing of dynemicin A model Compound 21 (mp 251.2 52° C. dec, from ether - petroleum ether) as determined by X-ray crystallographic analysis was prepared. The following angles revealed considerable deviation of the acetylenic groupings from their preferred linear arrangement: C17-C18-C19=170.2°; C9-C19-C18=162.0°; C14-C15-C16=170.1°; and C13-C14-C15=163.7°. The distance between carbons C14 and C19 (cd distance) was found to be 3.59 Å, which agrees well with the values derived for the MMX minimized structure of Compound 21 (3.59 Å) and from the X-ray crystallographic analysis of dynemicin A (3.54 Å). [Konishi et al., *J. Am. Chem. Soc.*, 112:3715-3716 (199)]. Again, the considerable shortening of the cd distance is noted in going from 9 to the cis diols 10 (cd=3.21 Å, MMX) and 10a (cd=3.19 Å, MMX).

In order to allow for the generation of the parent enediyne system Compound 40, Compound 45 was designed and synthesized from Compound 21 as shown in Scheme VIII, below.

with one equivalent of mCBPA, the corresponding sulfoxides, Compounds 21b and 46b are prepared.

To prepare Compound 40 that was too labile for isolation, Compound 45 was reacted with an excess of $Cs_2CO_3$ and 0.5 equivalents of 18-crown-6 in a dioxane:1,4-cyclohexadiene (4:1) solution for one hour at 25° C. as step c. Compound 47 was reacted with 1.2 equivalents of 1,8-diazabicyclo[5.4.0]undec-7-ene (DBU) in benzene at 5° C. for one hour to provide a 97 percent yield of Compound 48 as step c.

Freshly prepared Compound 40 was reacted with either phenol (i, PhOH) or thiophenol (ii, PhSH) using two equivalents of either nucleophile at 25° C. for two hours to provide Compounds 49 (25 percent yield) or 50 (33 percent yield, respectively, as step d. The reactivity of Compound 40 and its ability to cleave DNA add credibility to the notion of a pathway including epoxide ring opening and the intermediacy of an iminoquinone methide species in the mode of action of dynemicin A, at least as a partial mechanism.

Interestingly, the methoxy derivative, Compound 48 proved to be quite stable under basic or neutral conditions. Treatment of Compound 48 with 0.5 equivalents of p-toluenesulfonic acid-$H_2O$ (step d iii, TSOH) in dioxane:water:1,4-cyclohexadiene (4:1:1) at 60° C. for ten minutes provided Compound 51 (20 percent yield).

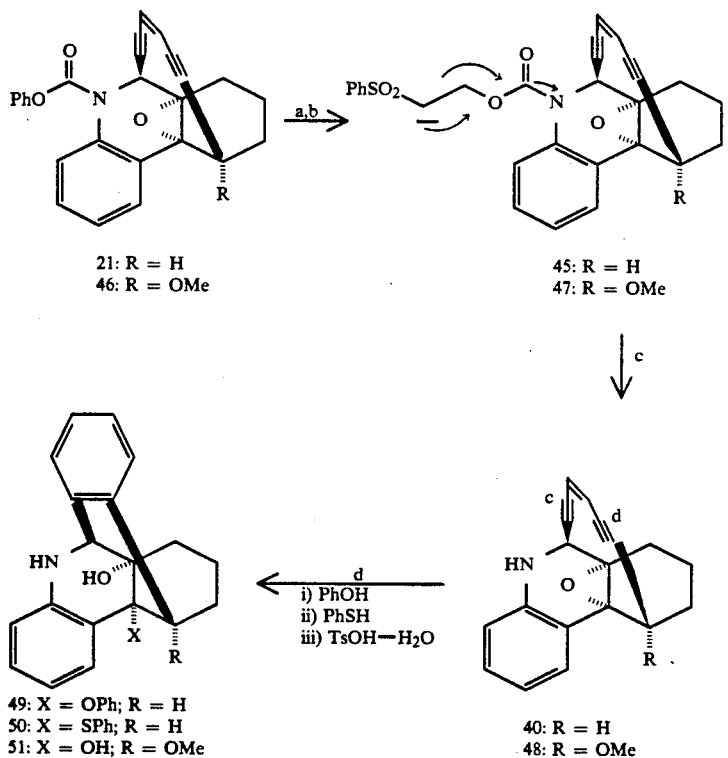

Scheme VIII

Thus, Compounds 21 and 46 were separately reacted with ten equivalents of 2-phenylthioethanol [PhS(CH$_2$)$_2$OH] in acetonitrile for 12 hours in the presence of three equivalents of $Cs_2CO_3$ and 0.5 equivalents 18-crown-6 in step a to form the corresponding phenylthioethoxy Compounds 21a and 46a, respectively. The products of that reaction were then individually reacted with 2.5 equivalents of mCBPA in $CH_2Cl_2$ at 0°-25° C. to provide Compounds 45 (85 percent overall) and 47 (82 percent overall) as step b. When step b is carried out An X-ray crystallographic analysis of Compound 48 confirmed its molecular structure and revealed a number of interesting parameters including a cd distance of 3.63 Å [Calcd. cd=3.61 Å, MMX] and the non-linearity of the acetylenic groupings [angles at acetylenic carbons: C-14, 163.3°; C-15, 173.0°; C-18, 169.3°; C-19, 160.5°].

Enediyne model system Compound 43 (Scheme IX) was designed for its potential to generate species 42 under photolytic, neutral conditions. Following the strategy developed earlier for the synthesis of Compound 21, Compound 43 was constructed in good overall yield. Reactions of Compound 43 are shown in Scheme IX.

Scheme IX

44a: R = PhO; Nu = EtO
44b: R = PhO; Nu = EtS
44c: R = Nu = NHn-Pr

+ 54: R = PhO

Irradiation in step a of Compound 43 in THF-H$_2$O (10:1) for 40 minutes [Hanover mercury lamp, pyrex filter] at ice-cooling temperature resulted in clean conversion to Compound 42 as observed by TLC and $^1$H NMR spectroscopy (THF-d$_8$: D$_2$O 10:1, 300 MHz). Attempted isolation of Compound 42 led to decomposition, whereas treatment of crude Compound 42 in a pH 8.0 buffer-THF solution containing either ethanol (EtOH), mercaptoenthanol (EtSH) or n-propylamine ($^n$PrNH$_2$) as nucleophiles (Nu) at 25° C. under argon atmosphere for 1.5 hours provided a mixture of Compounds 44a and 54 (31 percent yield), 44b (34 percent yield), or 44c (46 percent yield), respectively, as step b.

In another set of reactions of Compound 42 that are shown in Scheme IXa, the hydroxyl group was acetylated (step a; acetic anhydride/pyridine with a catalytic amount of DMAP at 25° C. for two hours 77 percent yield) to provide Compound 200. Photolytic cleavage [step b; THF-H$_2$O (10:1), under argon at zero degrees C. for 40 minutes] of Compound 200 provided Compound 201. Acetylation of Compound 201 provided Compound 202 (step c; acetic anhydride/pyridine, 25° C., 30 minutes; 92 percent yield).

Reaction of Compound 201 in ethanol-THF-phosphate buffer (pH 8.0 (1:1:1) under argon at 25° C. for a period of ten hours provided a mixture Compounds 203 and 204 in 20 percent yield.

Scheme IXa

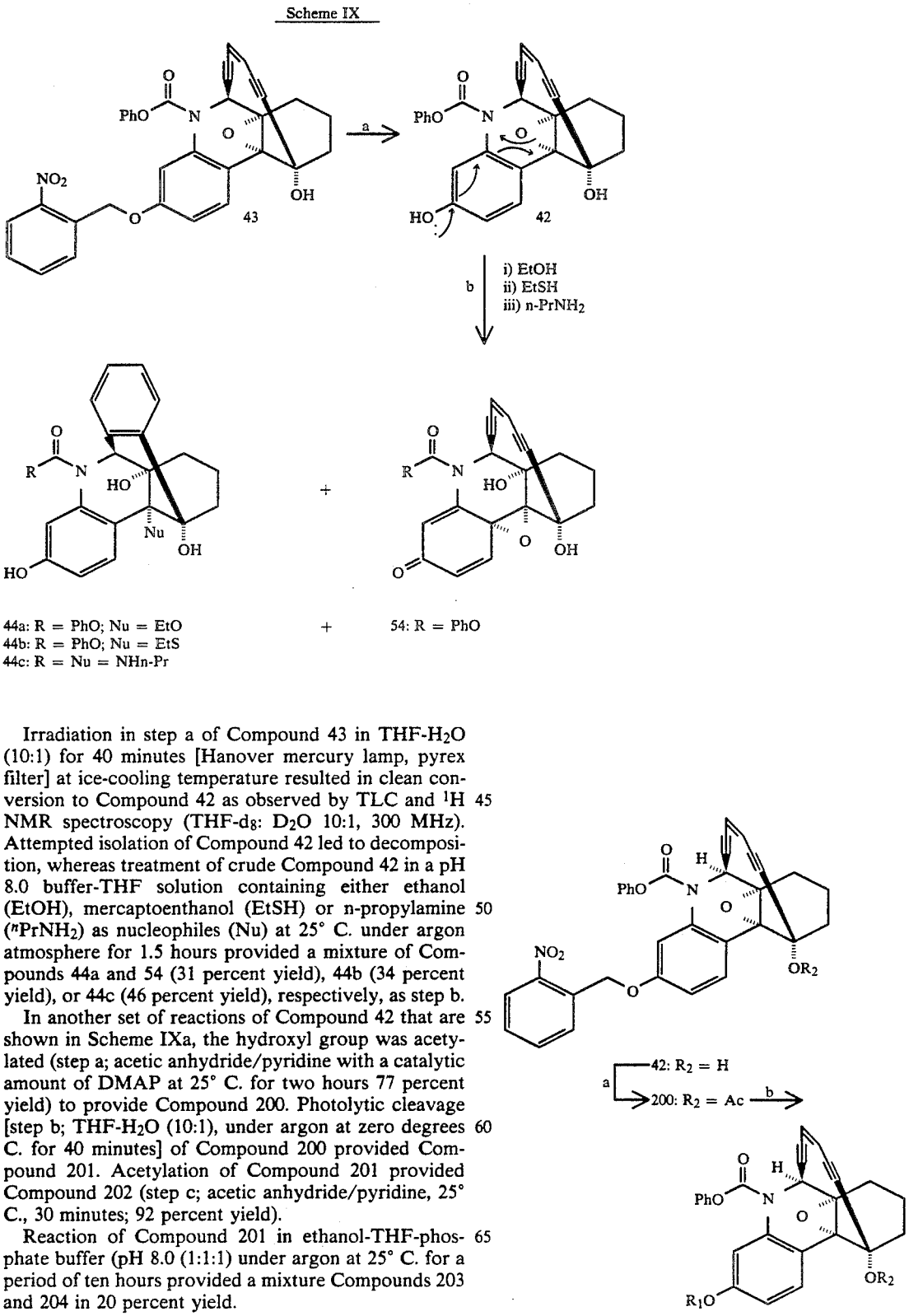

-continued
Scheme IXa

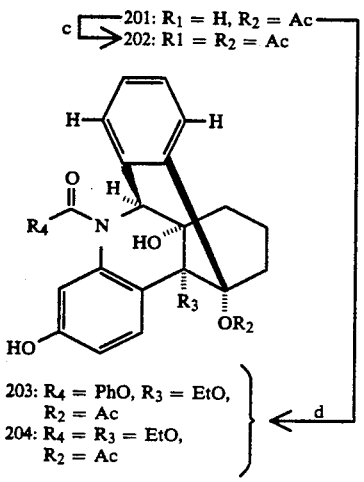

203: R₄ = PhO, R₃ = EtO, R₂ = Ac
204: R₄ = R₃ = EtO, R₂ = Ac

Photoactivation can also occur via photodeprotection of the amine group. For example, irradiation of Compounds 160 and 161, shown below, provided the free amine.

160

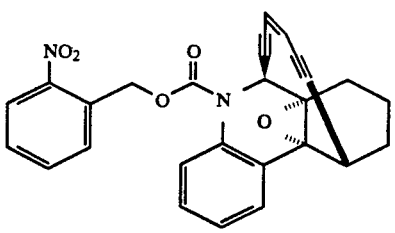

161

-continued

Noteworthy in Scheme IX was the isolation of Compound 54 in about 5-10 percent yield from the reaction of 42 with ethanol, in air, along with Compound 44a (33 percent yield), as a sensitive but stable molecule under neutral conditions. The isolation of Compound 54 provides strong evidence for the intermediacy of quinone methide Compound 52, [A) Dyall et al., *J. Am. Chem. Soc.*, 94:2196 (1972); b) Zanarotti, *Tetrahedron Lett.*, 23:3815 (1982); c) Zanarotti, *J. Org. Chem.*, 50:941 (1985); d) Angle et al., *J. Am. Chem. Soc.* 111:1136 (1989); e) Angle et al., *Tetrahedron Lett.*, 301193 (1989); f) Crescenzi et al., ibid 31:6095 (1990); g) Barton et al., ibid 31:8043 (1990); h) Angle et al., ibid 112:4524 (1990)], trapping of which with molecular oxygen would provide Compound 54 as is shown in Scheme X, below. Compound 54 also exhibited DNA cleaving activity.

Scheme X

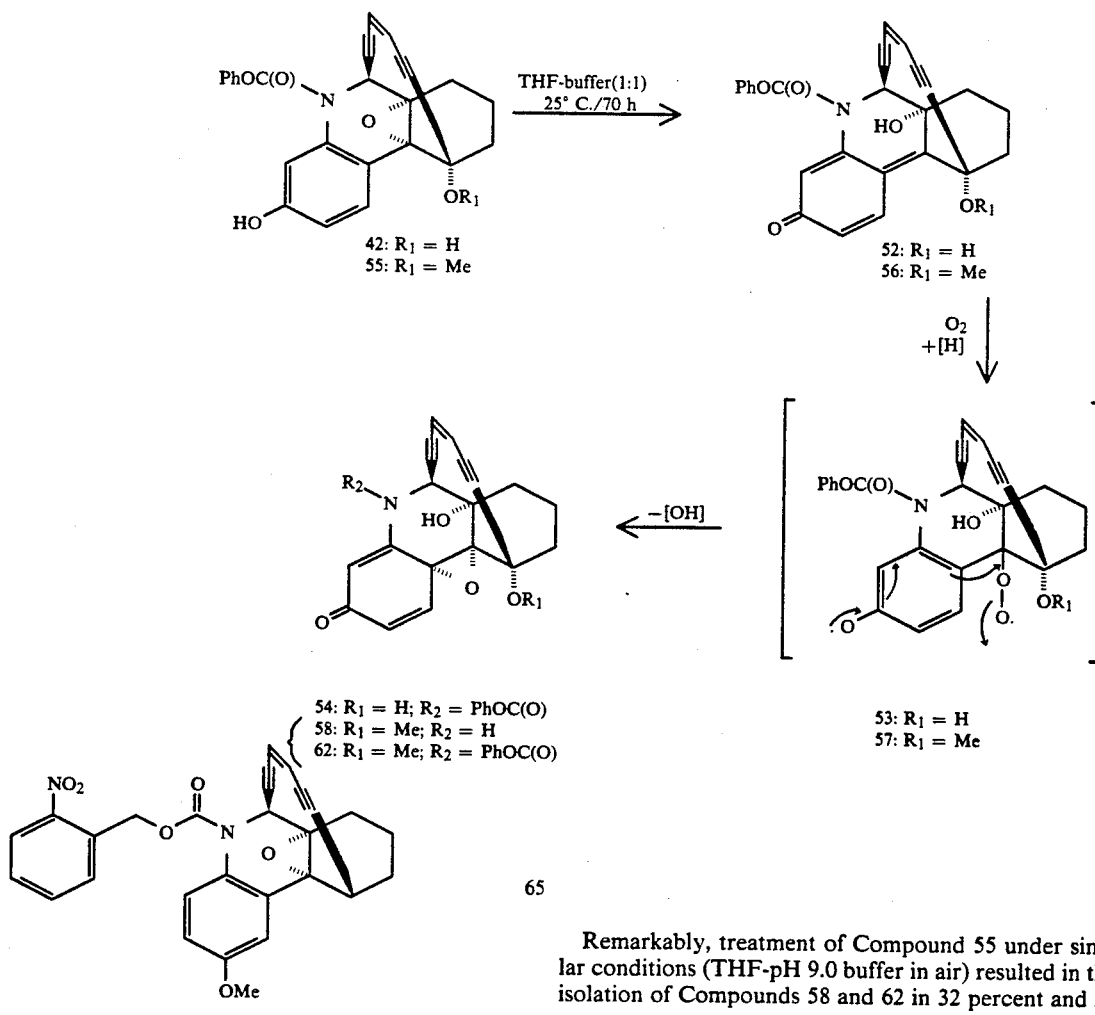

Remarkably, treatment of Compound 55 under similar conditions (THF-pH 9.0 buffer in air) resulted in the isolation of Compounds 58 and 62 in 32 percent and 25 percent yields, respectively, as stable molecules. Quinone methide intermediates have been implicated in the mode of action of anthracycline antibiotics [for recent postulated quinone methide intermediates in the area of anthracycline antibiotics, see:
   a) Boldt et al., *J. Org. Chem.*, 52:2146 (1987);
   b) Gaudiano et al., *J. Org. Chem.*, 54:5090 (1989);
   c) Egholm et al., *J. Am. Chem. Soc.*, 111:8291 (1989);
   d) Ramakrishnan et al., *J. Med. Chem.*, 29:1215 (1986);
   e) Boldt et al., *J. Am. Chem. Soc.*, 111:2283 (1989);
   f) Gaudiano et al., *J. Am. Chem. Soc.*, 112:9423 (1990);
   g) Karabelas et al., *J. Am. Chem. Soc.*, 112:5372 (1990);
   h) Gaudiano et al., *J. Am. Chem. Soc.*, 112:6704 (1990)
   ] and dynemicin A.

The pivaloate ester Compounds 59a and 59b were also synthesized according to the previously discussed general strategy shown in Scheme II (shown in detail hereinafter in Scheme XVIII) for their potential to liberate phenolic species of type of Compound 42 (Scheme IX), thus presenting yet another triggering mechanism to initiate the dynemicin A-type cascade. Indeed, upon exposure to four equivalents of LiOH in ethanol:water (3:1) at 25° c. for 4-6 hours, Compounds 59a and 59b were smoothly converted to products 60a (56 percent) and 60b (42 percent), respectively, presumably via a sequence involving concomitant carbamate exchange [EtO- for PhO-].

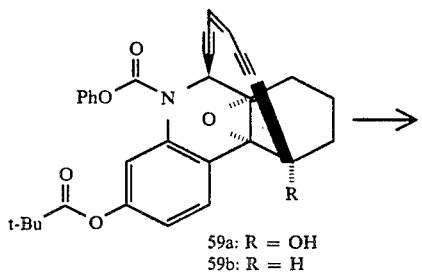

59a: R = OH
59b: R = H

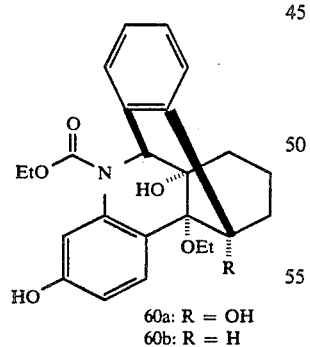

60a: R = OH
60b: R = H

The methoxy compound 41 was also synthesized following the procedures outlined in Scheme III starting with m-anisidine, and exhibited reasonable stability under neutral and basic conditions. As expected, however, this compound cyclized rapidly under acidic conditions. For example, upon treatment with TsOH.H₂O in benzene:1,4-cyclohexadiene (1:1) at 25° C. for one hour, Compound 41 afforded the aromatized product Compound 61 (32 percent yield).

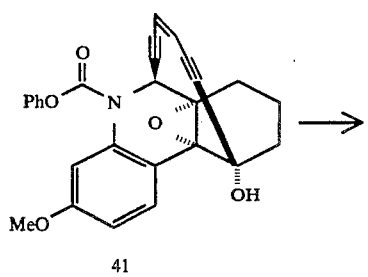

41

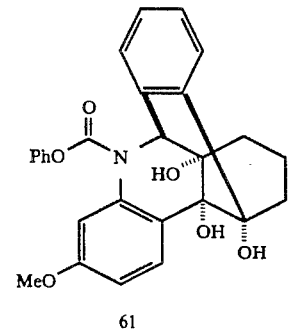

61

Compound 41-1 was similarly prepared using p-anisidine as starting material. Treatment of Compound 41-1 as per steps a and b of Scheme V yields the corresponding methoxyphenyl derivative Compound 41a having a hydrogen in place of the hydroxyl of Compound 41. Treatment of Compound 41a with 2-phenylthioethanol, 2-α-naphthylthioethanol or 2-β-naphthylthioethanol under basic conditions as discussed in regard to Scheme VIII, followed by oxidation led to Compounds 41b, 41c and 41d, respectively.

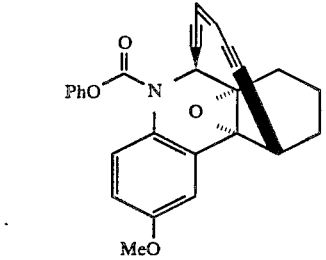

41a

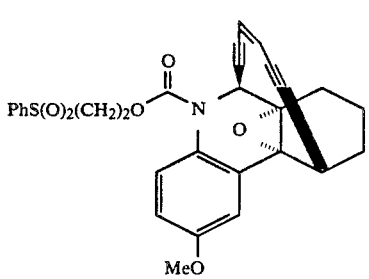

41b

53
-continued
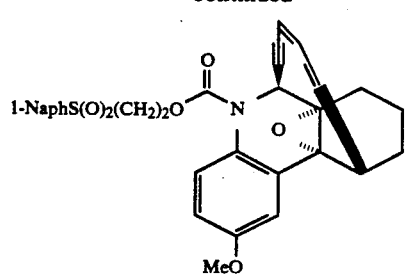
41c
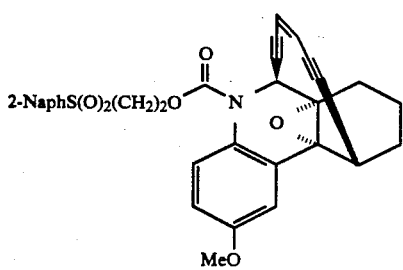
41d
54
Compound 171 is prepared in a reaction similar to that for Compound 59a. For the synthesis of Compound 171, the pivolate group is removed from the ring, and an acetate group is added to the bridgehead hydroxyl.
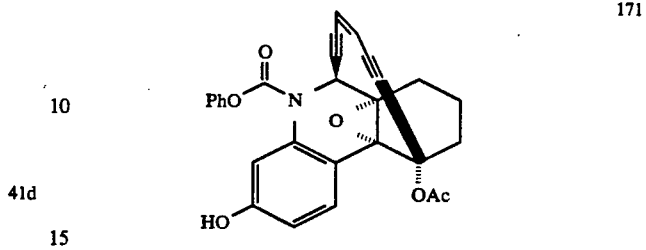
171
The synthesis of Compounds 70 and 80 (Scheme III, $R_2$=benzo or naphto) proceeded as summarized in Scheme XI, shown below.
SCHEME XI
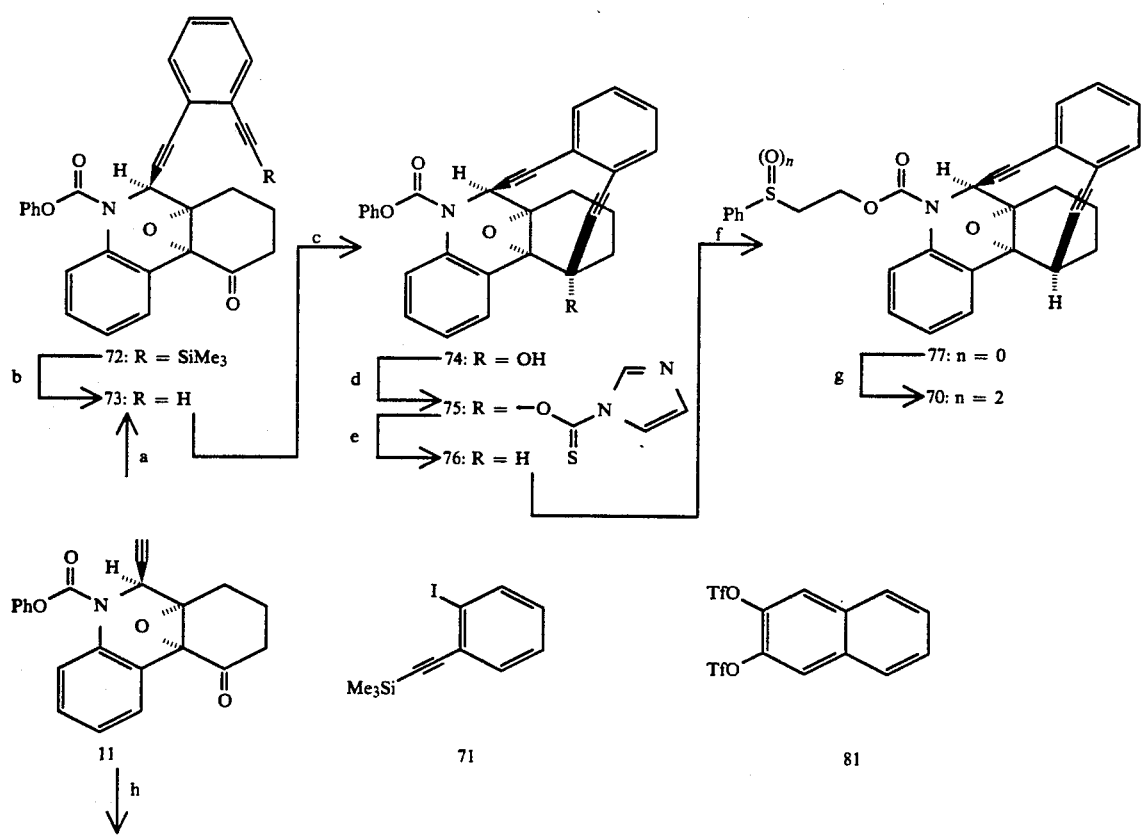

-continued
SCHEME XI

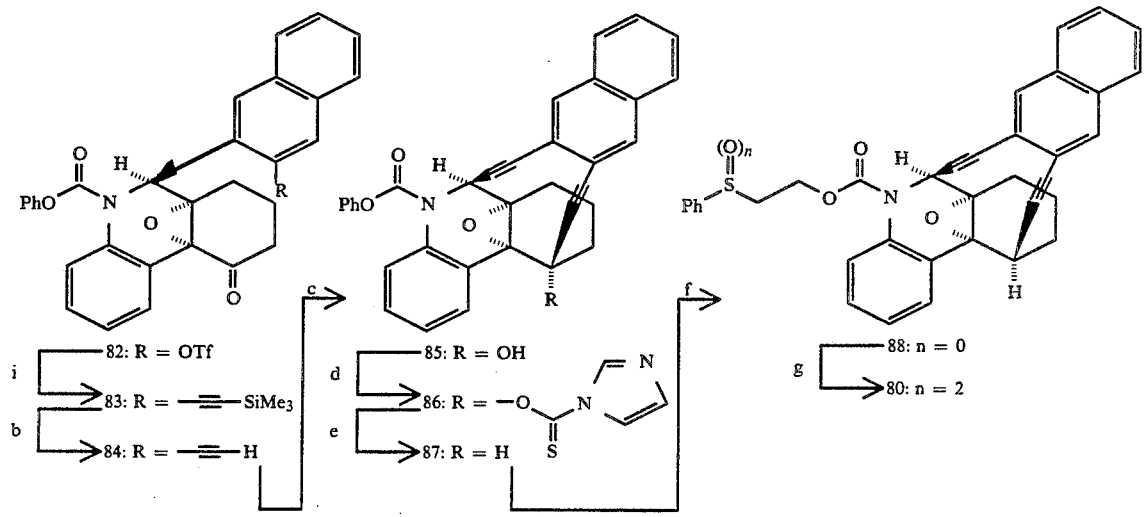

Thus, coupling of the readily available Compounds 11 [Nicolaou et al., *J. Am. Chem. Soc.*, 112:7416 (1990); Nicolaou et al., *J. Am. Chem. Soc.*, 113:3106 (1991)] and 71 using palladium (O)-copper(1) catalysis afforded product Compound 72 (55 percent yield) as step a. Desilylation of Compound 72 with lithium hydroxide in step b followed by base-induced (lithium diisopropylamide; LDA) ring closure led to Compound 74 via 73 (75 percent overall yield) in step c. Conversion of Compound 74 to the thionoimidazolide Compound 75 (84 percent based on 67 percent conversion of staring material) as discussed elsewhere herein, followed by deoxygenation with tri-n-butylstannane ($^n$Bu$_3$SnH) in step e resulted in the formation of 76 (94 percent). Exchange of the phenoxy (PhO) group of Compound 76 with 2-phenylthioethoxy (PhSCH$_2$CH$_2$O) took place smoothly under basic conditions (two equivalents of PhSCH$_2$CH$_2$ONa, THF) leading to Compound 77 (92 percent yield) in step f, from which the sulfone Compound 70 was generated by oxidation using 2.5 equivalents mCPBA (81 percent yield) in step g.

Similar chemistry employing the naphthalene ditriflate Compound 81 led from Compound 11 to arenediyne Compounds 85-80 via intermediate Compounds 82-84 in comparable yields as depicted in Scheme XI. Step h utilized acetonitrile as a solvent and a one hour reaction time as compared with step ad of the scheme that used benzene as solvent and 3.5 hours of reaction to obtain yields of 55 and 56 percent, respectively. Step i utilized five equivalents of trimethylsilylacetylene, 0.05 equivalents of Pd(PPh$_3$)$_4$, 0.2 equivalents of CuI and two equivalents of triethylamine in acetonitrile (as were present in steps a and b) with a reaction time of 20 hours at 25° C. to provide Compound 82 in 76 percent yield. Steps c-g of both reactions were identical. Reaction of Compounds 77 or 88 with one equivalent each of mCPBA leads to preparation of the corresponding sulfoxides, Compounds 77a and 88a.

The free amine Compounds, 76a and 87a, shown below, corresponding to Compounds 76 and 87 were prepared from their corresponding phenylsulfonylethyl carbamates 70 and 80 under basic conditions. Those compounds were both stable at 25° C., whereas Compound 40 decomposed at that temperature.

Treatment of Compounds 76a and 87a with silica gel in benzene initiated epoxide opening to form the corresponding diols 76b and 87b, respectively. Diol Compound 76b cyclized spontaneously at 25° C. in the presence of 1,4-cyclohexadiene to form the cycloaromatized diol, Compound 76c. In contrast to Compound 76b, diol Compound 87b was stable in the presence of 1,4-cyclohexadiene, but cycloaromatized at elevated temperature (65° C., two hours) to form Compound 87c.

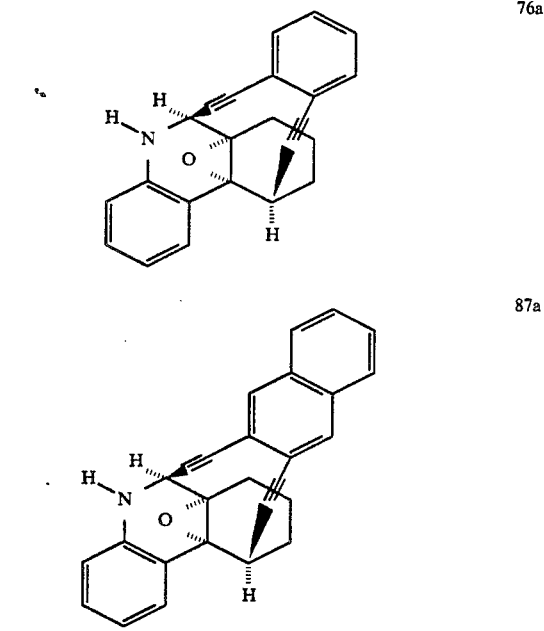

The cycloaromatization of enediyne Compounds 76, 70, 87 and 80 was then studied in order to determine the precise structural and spectroscopic changes taking place. Thus, whereas cycloaromatization of Compound 76 (about 0.02 M solution) under acid conditions [1.2 equivalents of TsOH.H$_2$O, benzene-cyclohexdiene (4:1), 25° C., four hours] produced smoothly the corresponding naphthalene derivative (78 percent) no dramatic changes in the UV and fluorescent spectra were observed for the starting arenediyne and cycloaromatized product.

In contrast, however, similar acid-induced Bergman cycloaromatization of the naphthalene enediyne Compound 87 furnished the epoxy-containing anthracene derivative Compound 89 (49 percent) that exhibited, as expected, strong and characteristic UV and fluorescence profiles that were distinct from those of the starting arenediyne Compound 87 [UV (EtOH), 87; $\lambda_{max}$ (log $\epsilon$) 304 (3.47), 294 (4.01), 284 (4.26), 267-240 (4.53-4.55), 214 (4.50) nm; 89;$\lambda_{max}$ (log $\epsilon$)390 (3.74), 369 (3.78), 351 (3.66), 333 (3.45), 318 (3.20), 267-244 (4.43-4.46), 215 (4.43) nm. Fluorescence (EtOH, 1 $\mu$M, excitation at 260 nm, Compound 87:$\lambda_{max}$ 435, 412, 393, 374, 357 nm; 89:$\lambda_{max}$ 520, 466, 442, 413, 392 nm].

Attempted cycloaromatization of Compounds 70 and 80 under a variety of basic conditions led to decomposition, presumably via the in situ generated free amines and diradical species, whereas acid treatment resulted in the formation of epoxy-opened (dihydroxy) Compounds 78 and 89a albeit in low yields (20 percent and 15 percent, respectively). Interestingly, both Compounds 70 and 80 exhibited DNA cleaving properties under basic conditions (supercoiled $\phi$X174 DNA, pH 9.0) and potent anticancer activity against a variety of cell lines as discussed hereinafter.

Generally, o-nitrobenzyl (ONBn) carbamate derivatives can be prepared from the phenoxyurethanes by reacting 2 equivalents of 2-nitrobenzyl alcohol with 2 equivalents of sodium hydride (NaH) in THF at 25° C. for 2 hours in the presence of the phenoxyurethane. Specifically, Compound 160 was produced in 45 percent yield when Compound 41a was used as the starting material. Compound 161 was produced in 40 percent yield when the same reaction was performed using Compound 21 as the starting material.

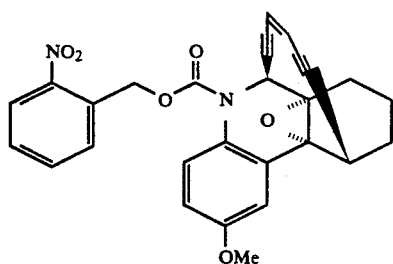
160

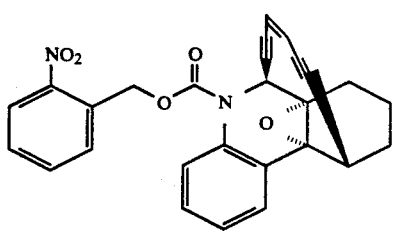
161

Saccharide-Containing Chimeras

Chimeric compounds that include both a fused ring enediyne as the aglycone and a before-discussed mono- or oligosaccharide as the oligosaccharide portion is also contemplated, as noted earlier. The previously depicted saccharides are related to the calicheamicin oligosaccharide.

The before-depicted saccharides correspond to the calicheamicin oligosaccharide (Structures F and G), the oxime precursor thereto (Structures D and E), and fragments thereof (Structures A-C). More specifically, the disaccharide Structure A corresponds to the calicheamicin A and E rings with the hydroxylamine link to a B ring analog. The monosaccharide Structure B corresponds to the A ring alone with the hydroxylamine-linked B ring analog. The trisaccharide thiobenzoate Structure C corresponds to rings A, E and B, and a C ring analog. The 5-ring Structure D corresponds to the FMOC-blocked oxime precursor to the complete calicheamicin oligosaccharide, whereas 5-ring Structure E is the FMOC-deblocked version thereof. Structures F and G are the complete calicheamicin oligosaccharides that are epimeric about the 4-position of the A ring hydroxylamine linkage, with Structure F having the native calicheamicin oligosaccharide stereochemistry. Structure H has the same native configuration as Structure F, but lacks the iodide group on the aromatic ring. These saccharides are discussed in more detail hereinafter.

Inasmuch as the previously depicted saccharides of the calicheamicin oligosaccharide are derivatives of known compounds, as rae their suitably protected precursors, their complete syntheses need not be discussed in complete detail herein. Those syntheses are described in Nicolaou et al., *J. Am. Chem. Soc.*, 112:4085-4086 (1990); Nicolaou et al., *Ibid.*, 112:8193-8195 (1990); Nicolaou et al., *J. Chem. Soc., Chem. Commun.*, 1275-1277 (1990) as well as in U.S. patent application Ser. No. 07/520,245 filed May 7, 1990 and Ser. No. 07/695,251 filed May 3,1991, all of whose disclosures are incorporated by reference herein. Nevertheless, the saccharides used herein differ somewhat from the reported saccharides, so their syntheses will be discussed, at least in pertinent part herein below.

The disaccharide-linked hydroxylamine compound is prepared in a manner analogous to that of Compound 12 of Nicolaou et al., *J. Am. Chem. Soc.*, 112:8193-8195 (1990), except that an o-nitrobenzyl (shown as NBnO or ONBn in the schemes) glycoside is utilized instead of the methyl glycoside precursor, Compound 9 of that paper. The synthesis for the disaccharide is illustrated in Schemes XII and XIII, and is discussed below.

Scheme XII

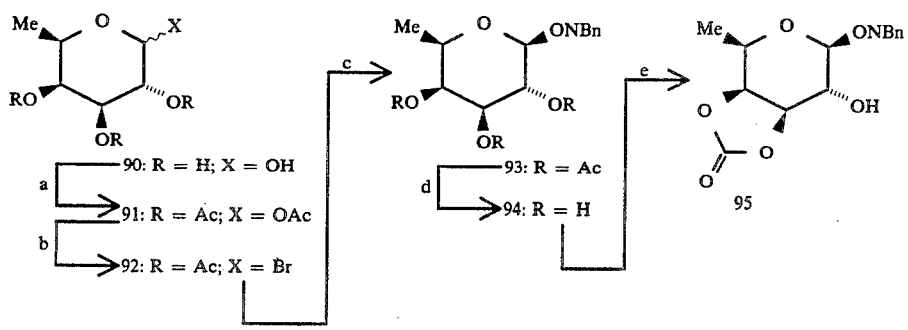

Thus, D-fucose Compound 90 was peracetylated in step a to form tetraacetate Compound 91 which was converted to the anomeric bromide Compound 92 in step b, and glycosylated with o-nitrobenzyl alcohol to afford Compound 93 in step c (63 percent overall yield).

Deacetylation of Compound 93 in step d led to Compound 94, which reacted selectively with carbonyl diimidazole in step e to afford the requisite ring A intermediate 95 in 86 percent overall yield.

Scheme XIII

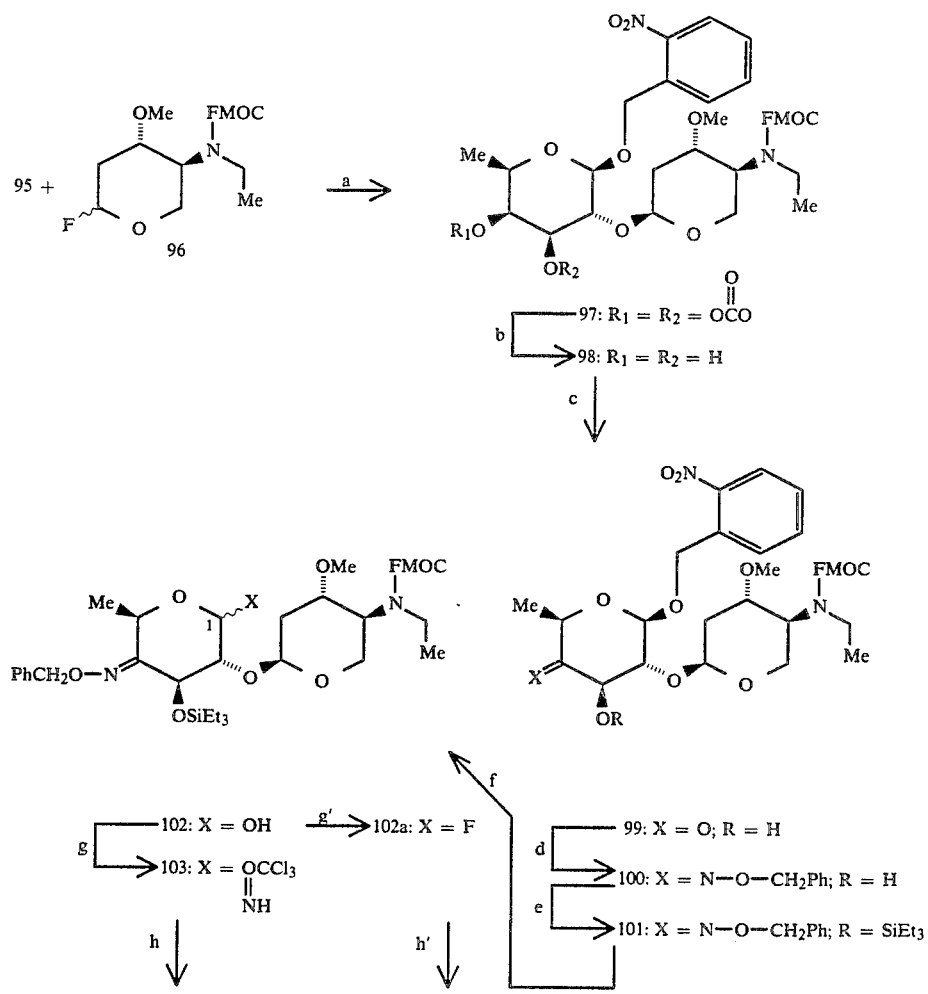

Scheme XIII -continued

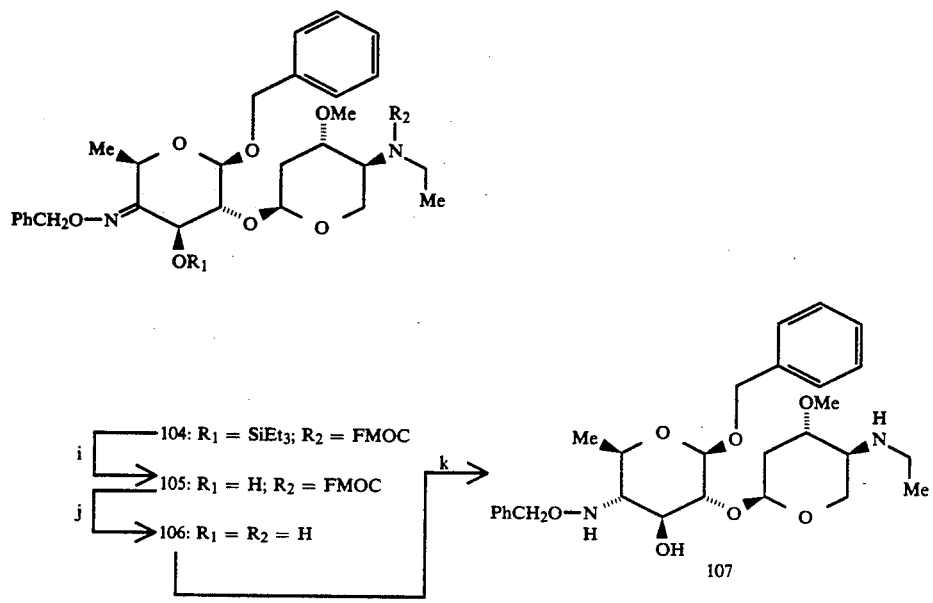

Turning to Scheme XIII, intermediate Compound 95 was then coupled [Mukaiyama et al., *Chem. Lett.*, 431 (1981); Nicolaou et al., *J. Am. Chem. Soc.*, 106:4159 (1984)] to glycosyl fluoride Compound 96 (Compound 8 of the above paper; Me=methyl with AgClO$_4$—SnCl$_2$ catalyst in step a, leading stereoselectively to disaccharide Compound 97 as the major anomer (80 percent yield, about 5:1 ratio of anomers). Chromatographic purification of Compound 97 with removal of the carbonate protecting group (NaH-HOCH$_2$CH$_2$OH, 90 percent) in step b to form Compound 98, and treatment in step c with $^n$Bu$_2$SnO—Br$_2$ [David et al., *J. Chem. Soc. Perkin Trans* 1. 1568 (1979)] led to hydroxyketone Compound 99 (65 percent yield plus 17 percent Compound 98) via intermediate Compound 98.

Oxime formation in step d with O-benzyl hydroxylamine under acid conditions led to Compound 100 (90 percent, single geometrical isomer of unassigned stereochemistry; Ph=phenyl) which was silylated in step e under standard conditions to furnish Compound 101 (90 percent). Photolytic cleavage [Zenhavi et al., *J. Org. Chem.*, 37:2281 (1972); Zenhavi et al., ibid, 37:2285 (1972); Ohtsuka et al., *J. Am. Chem. Soc.*, 100:8210 (1978); Pillai, *Synthesis*, 1 (1980)] of the o-nitrobenzyl group from Compound 101 (THF—H$_2$O, 15 minutes) produced lactol Compound 102 in 95 percent yield in step f. Treatment of Compound 102 with NaH-Cl$_3$CC≡N [Grandler et al., *Carbohydr. Res.* 135:203 (1985); Schmidt, *Angew Chem. Int. Ed., Engl.*, 25:212 (1986)] in CH$_2$Cl$_2$ for two hours at 25° C. in step g resulted in the formation of the α-trichloroacetimidate Compound 103 in 98 percent yield. Reaction of benzyl alcohol (2.0 equivalents) with trichloroacetimidate Compound 103 under the Schmidt conditions [Grandler et al., *Carbohydr. Res.*, 135:203 (1985); Schmidt, *Angew Chem. Int. Ed., Engl.*, 25:212 (1986)] [BF$_3$·Et$_2$O, CH$_2$Cl$_2$, −60 → −30° C.] resulted in stereoselective formation of the β-glycoside Compound 104 (79 percent yield) together with its anomer (16 percent, separated chromatographically) [$^1$H NMR, 500MHz, C$_6$D$_6$, 104: J$_{1,2}$=6.5 Hz, epi-Compound 104: J$_{1,2}$=2.4 Hz].

On the other hand, treatment of lactol Compound 102 with DAST in step g' led to the glycosyl fluoride Compound 102a in 90 percent yield (about 1:1 anomeric mixture). Reaction of Compound 102a with benzyl alcohol in step h' in the presence of silver silicate [Paulsen et al., *Chem. Ber.*, 114:3102 (1981)] —SnCl$_2$ resulted in the formation of the β-glycoside Compound 104 and its anomer in 85 percent (about 1:1 anomeric mixture).

Generation of intermediate Compound 106 via Compound 105 proceeded smoothly under standard deprotection conditions in steps i and j. Finally, exposure of Compound 106 to Ph$_2$SiH$_2$ in the presence of Ti(O$^i$Pr)$_4$ in step k resulted in the formation of the desired target Compound 107 as the only detectable product (92 percent yield). Interestingly, reduction of Compound 106 with NaCNBH$_3$—H⊕ led predominantly to the 4-epimer of Compound 107 (90 percent yield). the stereochemical assignments of Compound 107 and epi-107 at C-4 were based on $^1$H NMR coupling constants [$^1$H NMR, 500MHz, C$_6$D$_6$, 107: J$_{3,4}$=9.5, J$_{4,5}$=9.5 Hz; epi-107: J$_{3,4}$=1.9 Hz, J$_{4,5}$=1.5 Hz].

The hydroxylamine linked A ring derivative (Structure B) can be prepared starting with Compound 9 of Nicolaou et al., *J. Am. Chem. Soc.*, 112:8193-8195 (1990). There, the 2-hydroxyl is blocked with a t-butyldimethylsilyl ($^t$BuMe$_2$Si) group as before, and the carbonate group removed by reaction of sodium hydride in ethylene glycol-THF at room temperature. The keto group can be prepared by oxidation with dibutylstannic oxide ($^n$Bu$_2$SnO) in methanol at 65°. The 3-position hydroxyl is similarly blocked with a $^t$BuMe$_2$Si group, and the oxime formed as above.

The trisaccharide plus C ring analog (Structure C) can be readily prepared from Compound 19 of Nicolaou et al., *J. Am. Chem. Soc.*, 112:8193-8195 (1990). Thus, that Compound 19 is reacted with benzoyl chloride in the presence of triethylamine and a catalytic amount of DMAP in methylene chloride to provide the blocked oxime-containing trisaccharide.

The use of Compounds 2 and 103 in preparing an exemplary chimera is illustrated in Scheme XIV, below, and discussed hereinafter.
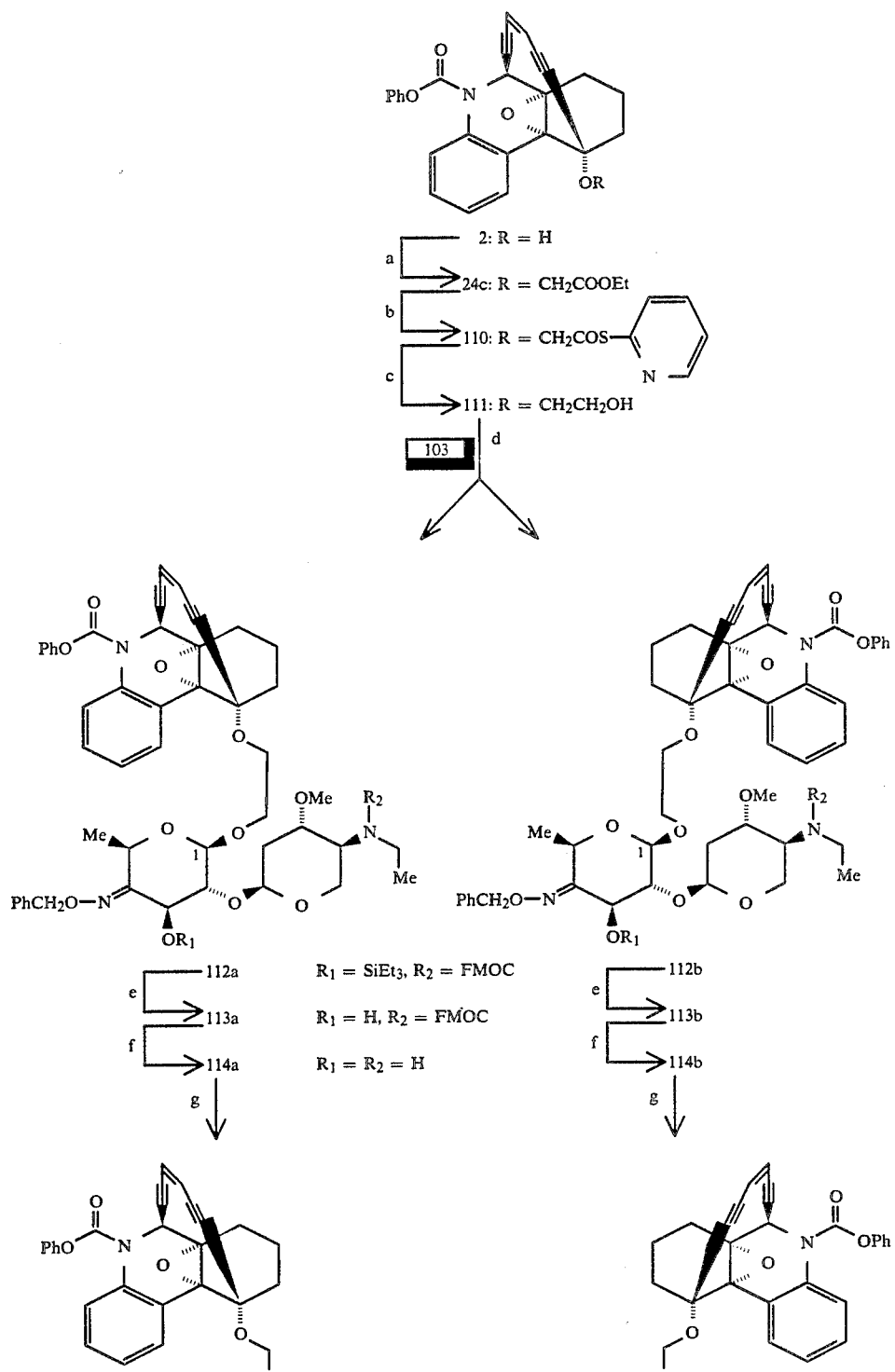
Scheme XIV

Scheme XIV

-continued

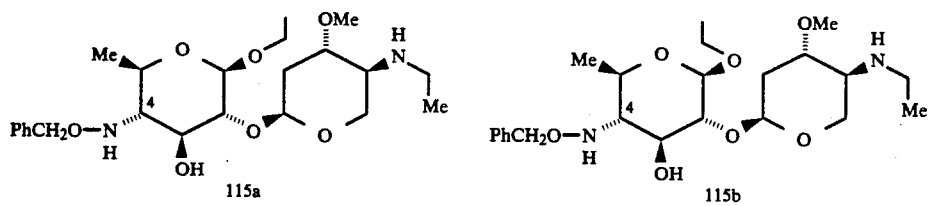

Thus, as shown in Scheme XIV, coupling of Compound 2 with ethyl bromoacetate under basic conditions led to derivative Compound 24c (60 percent yield), which was converted to primary alcohol Compound 111 (80 percent overall yield) by: (i) ester hydrolysis; (ii) 2-pyridyl thiolester formation (collectively step b) and (iii) reduction in step c. Coupling of Compound 111 (1.2 equivalent) with trichloracetimidate Compound 103 under the influence of $BF_3 \cdot Et_2O$ as described before led to the formation of two major products (70 percent, about 1:1 ratio) and two minor products (14 percent, about 1:1 ratio), which were chromatographically separated.

The major isomers were shown to be the diastereomeric β-glycoside Compounds 112a ($R_f$=0.12, silica, 20 percent ethyl acetate in petroleum ether) and 112b ($R_f$= 0.10, silica, 20 percent ethyl acetate in petroleum ether) [$^1$H NMR, 500 MHz, $C_6D_6$, 112a; $J_{1,2}$=6.5 Hz; 112b; $J_{1,2}$=6.5 Hz], whereas the minor isomers were shown to be the α-anomers of Compounds 112a and 112b at C-1 [$^1$H NMR, 500 MHz, $C_6D_6$, epi-112a, $J_{1,2}$=2.4 Hz: epi-112b, $J_{1,2}$=2.4 Hz]. Sequential deprotection of Compounds 112a and 112b as described above for Compound 104 led to oxime Compounds 114a and 114b via intermediate Compounds 113a and 113b, respectively.

Finally, reduction of Compounds 114a and 114b under the $Ph_2SiH_2$—$Ti(O^iPr)_4$ conditions led exclusively to the targeted Compounds 115a and 115b respectively (90 percent yield). The C-4 stereochemistry of Compounds 115a and 115b was again based on the coupling constants $J_{4,3}$=9.5 and $J_{4,5}$=9.5 Hz for then newly installed H-4. Structures 112a-115a and 112b-115b are interchangeable since the absolute stereochemistry of the aglycons has not been determined. Physical data for Compounds 115a and 115b are provided hereinafter.

Still further chimeras have been prepared that contain a fused-ring enediyne glycosidically-linked to the complete calicheamicin oligosaccharide or an analog thereof. Exemplary synthetic steps are outlined in Schemes XV and SVI, below.

Scheme XV

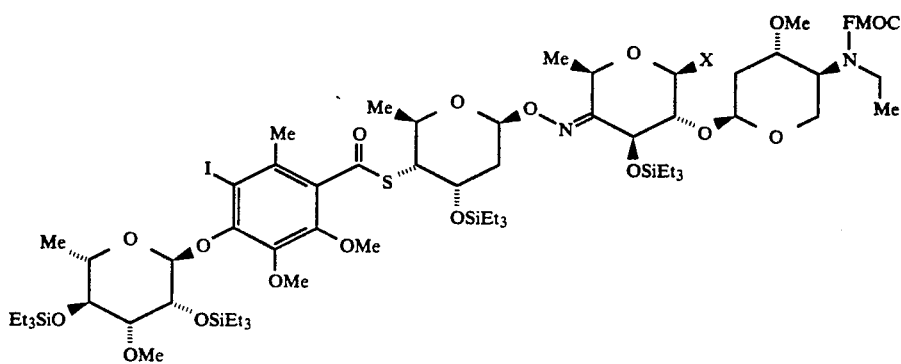

Scheme XV -continued

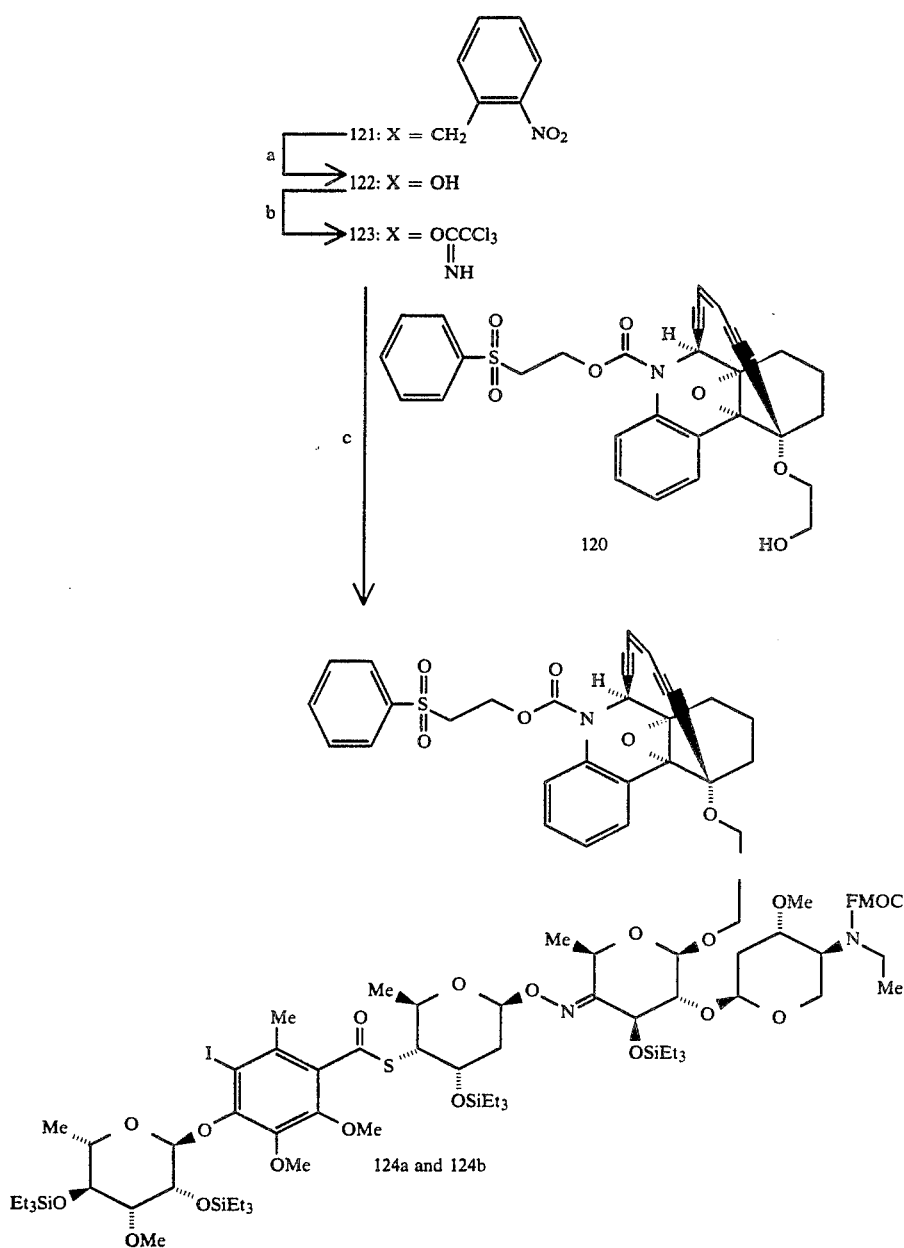

Thus, a compound such as Compound 111 of Scheme SIV was reacted with phenylthioethanol in the presence of a base as discussed elsewhere to exchange out the phenoxide moiety from the corresponding carbamate. That compound was then oxidized with m-chloroperbenzoic acid to form the corresponding 2-(phenylsulfonyl)ethyl carbamate, Compound 120.

Racemic compound 120 was reacted with Compound 123 as shown in Scheme XV. Compound 123 was prepared from Compound 121 via compound 122, and shown in the scheme and discussed in regard to Scheme XIII as to the preparation of Compound 103. Compound 121 was itself prepared in a manner analogous to that discussed in Nicolaou et al., *J. Am. Chem. Soc.*, 112:8193–8195 (1990), except that Compound 99 herein was utilized instead of Compound 12 of the published paper, and Et₃Si blocking groups were used instead of ᵗBuMe₂Si blocking groups that were used in the published paper.

Thus, Compound 121 was irradiated in THF—H₂O (9:1, v/v) at zero degrees C in step a to provide a 95 percent yield of Compound 122. That compound was reacted with a catalytic amount of NaH and trichloroacetonitrile in methylene chloride (1:12, v/v) at 25° C. to provide a 98 percent yield of Compound 123 in step b. Compounds 120 and 123 were coupled in step c in benzyl alcohol, BF₃.Et₂O in methylene chloride at −60°→−30° C. to provide Compound 124 as a mixture of diastereomeric anomers 124a and 124b present as a β- to α-anomer ratio of about 5:1, the β-anomer being shown as Compound 124a, and the α-anomer, Compound 124b, not being shown.

Reaction of Compounds 124a and 124b with ⁿBuNF using standard conditions removed the triethylsilyl groups. The oximem- and FMOC-containing, hydroxyl deblocked compound that resulted, Compounds 125a and 125b, thus contained the oligosaccharide portion discussed previously as oligosaccharide Structure D. Subsequent reaction with diethylamine under usual conditions removed the FMOC group to form Compounds 126a and 126b. The completely deblocked oxime-containing oligosaccharide portion of Compounds 126a and 126b is the oligosaccharide discussed previously as oligosaccharide Structure E.

meric at the 4-position of the A ring as indicated by the number 4 and the arrow. The epimeric portions of Compounds 127a and 127b provide the oligosaccharide portions previously identified as oligosaccharide Structures F and G, with only the epimer present in calicheamicin (Structure F) being shown in Scheme XVI.

As prepared, Compounds 125-127 were mixtures of diastereomers. Those diastereomers have been separated, but eh absolute configurations of the fused-ring enediyne portions are presently unknown, and only one

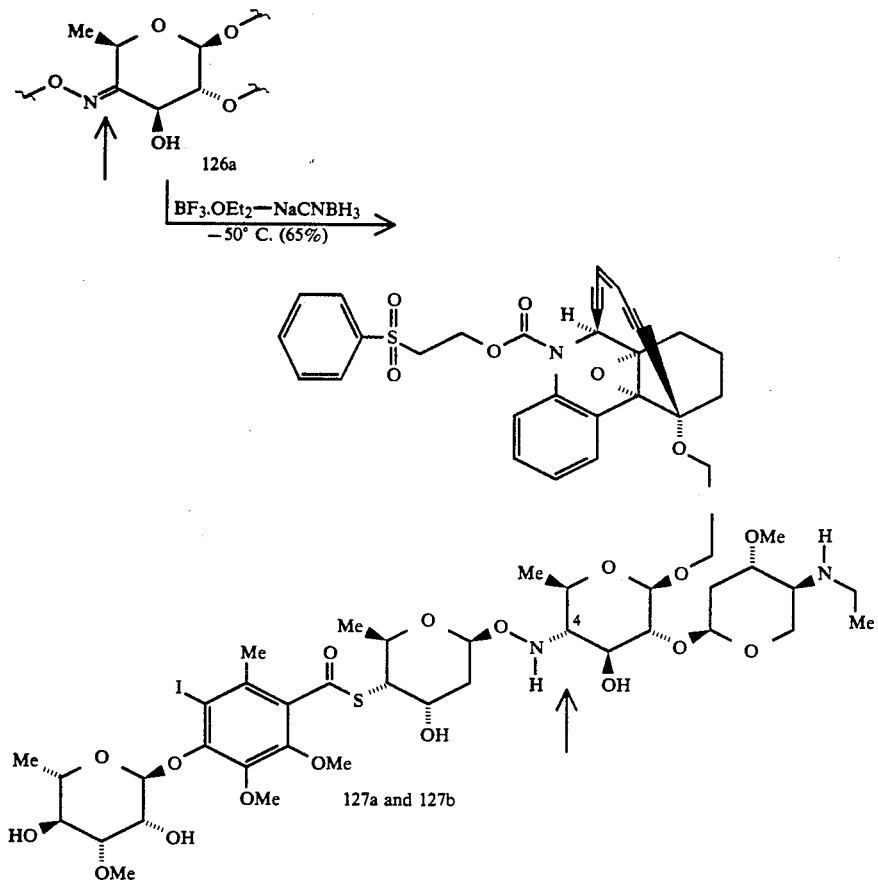

Scheme SVI shows only the oxime-containing ring of Compound 126a, with the remaining portions indicated by the wavy lines. As is shown in Scheme XVI, reduction of Compound 126a with sodium cyanoborohydride in BF$_3$.Et$_2$O at −50° C. provided a 65 percent yield of epimeric Compounds 127a and 127b, that were present in about equal amounts. Those compounds were epiis illutrated, whereas both were shown in Scheme XIV.

Chimeric Compounds 400 and 401 (shown below) can be preapred by following the chemistry outlined and discussed in relation to Schemes XV and XVI by replacing Compound 120 of Scheme XV with Compound 153.

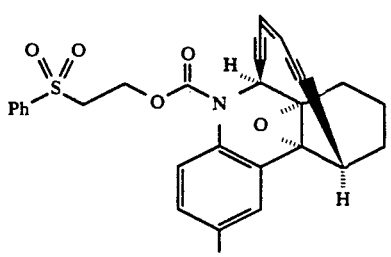

-continued

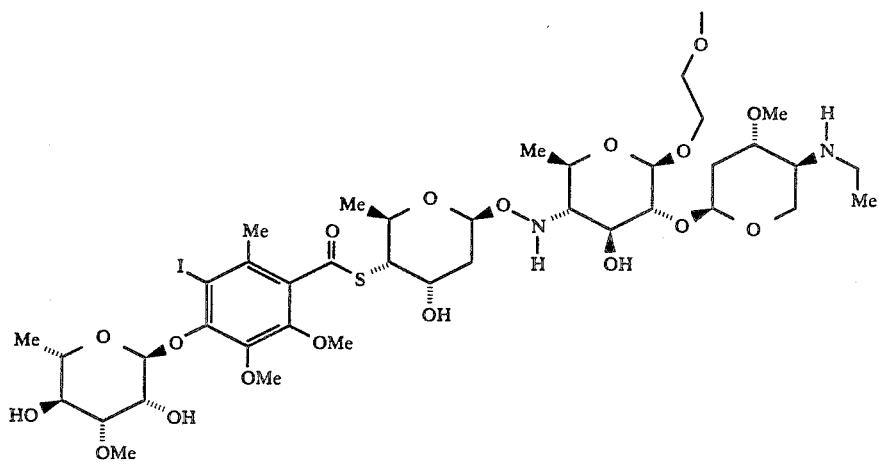

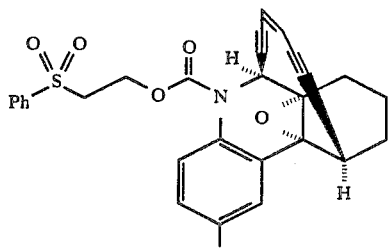

401

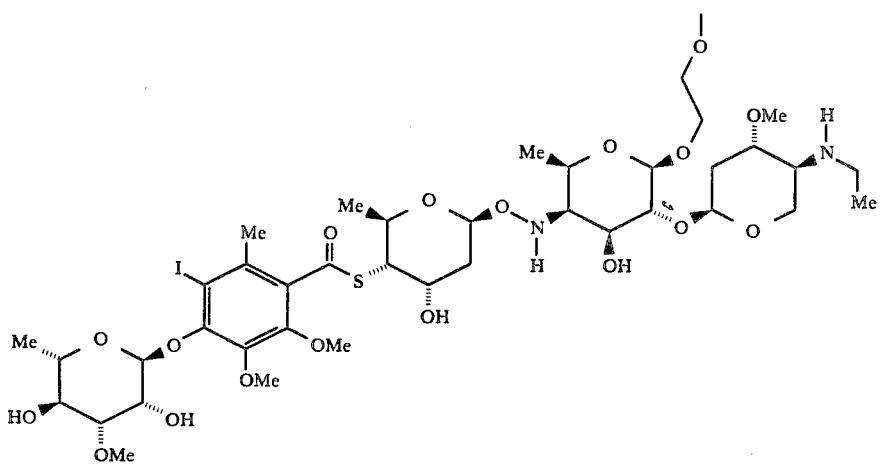

The data in Table 3, hereinafter, illustrates the effects of several chimeric compounds containing oligosaccharides on the killing of cancer cells. Compounds 127a and 127that contain the calicheamicin $\gamma_1^I$ oligosaccharide portion linked to an enediyne aglycone portion were found to be particularly effective. Compound 127a contained that oligosaccharide in the native configuration (saccharide F) whereas Compound 127b had the epimeric configuration (saccharide G).

Previous studies by the Ellestad [(a) Zein et al., Science, 240:1198 (1988); (b) Zein et al., Science, 244:697 (1989); (c) Ding et al., J. Am. Chem. Soc., 113:6617 (1991)], Schreiber [Hawley et al., Proc. Natl. Acad. Sci. U.S.A., 86:1105 (1989)]; Kahne [(a) Walker et al., J. Am. Chem. Soc., 112:6428 (1990); and (b) Walker et al., J. Am. Chem. Soc., 113:4716 (1991)]; and Danishefsky [Dark et al., Proc. Natl. Acad. Soc., 88:7464 (1991)] groups suggested selective interactions of the calicheamicin $\gamma_1^I$ oligosaccharide with duplex DNA along specific sequences within the minor groove. In particular, Schreiber et al. [Hawley et al., Proc. Natl. Acad. Sci. U.S.A., 86:1105 (1989)] proposed a binding model for this interaction based on both the stereochemistry of the oligosaccharide bonds and the potential of its iodine group to bind to the DNA's nitrogen atoms.

Footprinting studies the O-methyl glycosides of saccharides A, an analog of C, F, G and H, Compounds A-1, C'-1, F-1, G-1 and H-1, respecitvely, as shown below, were designed to probe these questions. Those studies demonstrated that although the calicheamicin oligosaccharide glycoside binds specifically to DNA, the preferred saccharide binding sites do not coincide precisely with those observed for intact calicheamicin.

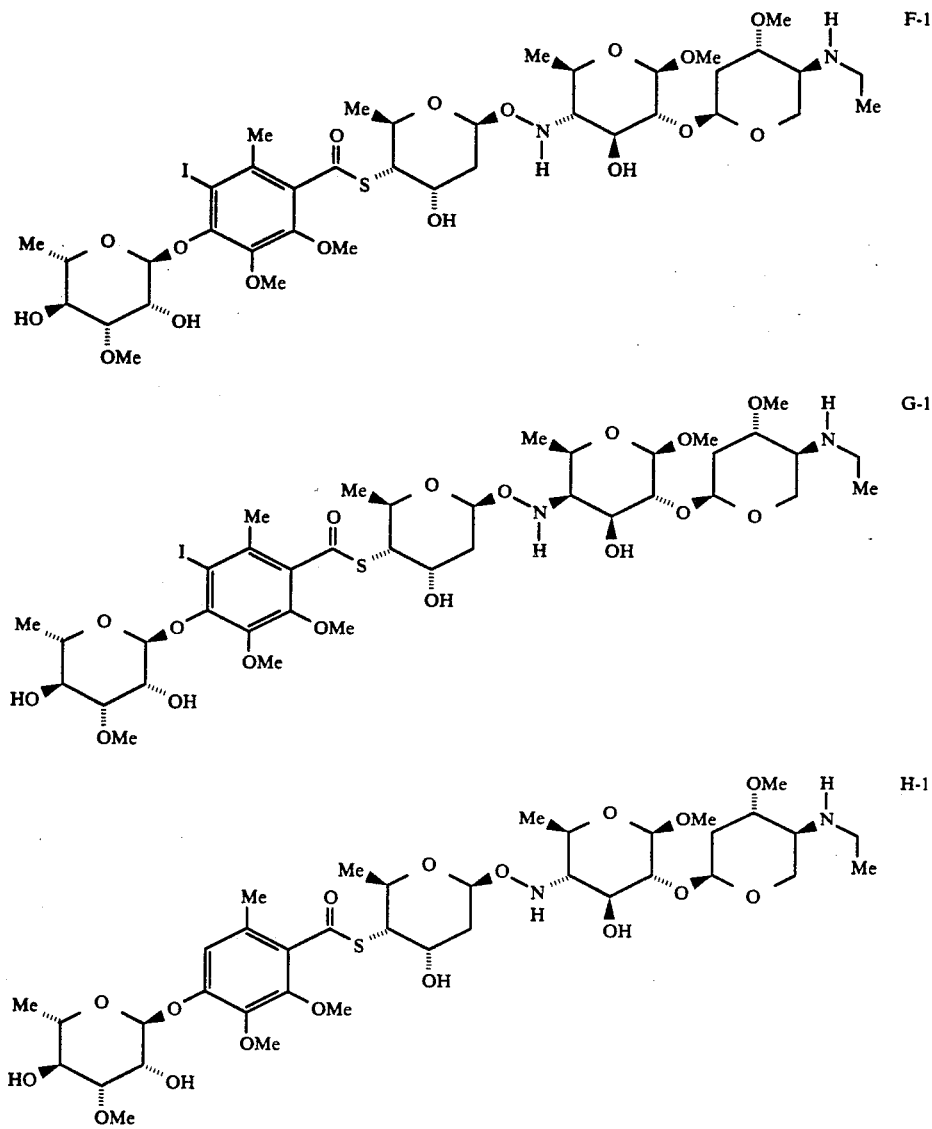

The oligosaccharides A-1, C'-1, F-1, G-1 and H-1 were obtained by chemical synthesis following procedures similar to those discussed before. The 93 base-pair Sal I - Sph I double-stranded DNA fragment of pBR322 was obtained enzymatically and was [5'-$^{32}$P]-labeled on one strand. pBR322 DNA was cleaved at the unique Sal I site, dephosphorylated using calf intestine phosphatase, [5'-$^{32}$P]-phosphorylated using T4 polynucletide kinase and [g-$^{32}$P] ATP (4.5 $^m$Ci/pmol), and cleaved again at the unique Sph I site. These precursors generated a 93 base-pair double-stranded fragment, [5'-$^{32}$P]-labeled at the Sal I end, which was purified by gel electrophosresis in a nondenaturing 10 percent polyacrylamide gel and subsequent column chromatography on Sephadex G-25. The oligosaccharides were pre-incubated with the DNA fragment at 37° C. for 30 minutes and DNase I was added to cleave the DNA and generate footprinting patterns by autoradiography.

The autoradiograms showed that the natural oligosaccharide F-1 provided concentration-dependent protection, presumably due to binding, in the region of three calicheamicin $\gamma_1{}^I$ binding sites: CTCT, TCCT and AGGA (reading 5'→3' along the labeled strand). The oligosaccharide G-1 with the unnatural stereochemistry at the hydroxylamine nitrogen-bearing C-4 position offered no protection at the same concentrations. A similar lack of protection under the same conditions was observed with the oligosaccharides H-1, in which the iodine atom was replaced by a hydrogen, A-1 and C'-1.

That the protection pattern did not coincide precisely with the observed calicheamicin cleavage sites prompted the carrying out of replicate footprinting studes over a 48 base-pair segment of the DNA fragment. The degree of protection against DNase I digestion offered by both the natural and unnatural stereoisomers was determined by comparing the amount of radioactivity in adjacent lanes along the electrophoresis gel. The protected regions coincided only roughly with calicheamicin $\gamma_1{}^I$ recognition sequences [(a) Zein et al., Science, 240:1198 (1988); (b) Zein et al., Science, 244:697 (1989); (c) Ding et al., J. Am. Chem. Soc., 113:6617 (1991)], Schreiber [Hawley et al., Proc. Natl. Acad. Sci. U.S.A., 86:1105 (1989)] and observed calicheamicin $\gamma_1{}^I$ cleavage sites. The disparity may be due to: (1) imprecise DNA recognition by the carbohydrate moiety alone; (2) impaired access of DNase I at sites adjacent to bound carbohydrate; and (3) distortion of the DNA duplex adjacent to bound carbohydrate which prevents functional recognition by DNase I. Nonetheless, these data demonstrate selective binding of oligosaccharide F-1 with specific base sequences of DNA and illustrate as crucial the natural stereochemistry at C-4 for calicheamicin $\gamma_1{}^I$.

These results show that some, but not all, of the binding specificity of calicheamicin $\gamma_1{}^I$ resides in its carbohydrate domain. This is consistent with Schreiber's hypothesis concerning the importance of the iodine and carbohydrate stereochemistry to this binding. However, it appears that the enediyne moiety confers added specificity to the calicheamicin/DNA interactions.

Although the above binding studies help to illustrate the binding specificity for calicheamicin $\gamma_1{}^I$ and to corroborate Schreiber's hypothesis as to the importance of the iodide group and stereochemistry, they do not completely explain the binding specificity of that agent nor do they explain efficacies in cancer cell killing exhibited by Compounds 127a and 127b shown in Table 3, hereinafter. Thus, although some binding specificity can be obtained for chimeras bound to saccharide F, chimeras that utilize other saccharides are also useful. This type of activity with and without saccharide binding and DNA cleaving specificities is also shown for calicheamicin $\gamma_1{}^I$ and esperimicin, respectively, whose aglycone portions are substantially the same, but whose saccharide portions differ, and which exhibit double DNA strand cuts at specific sequences (calicheamicin $\gamma_1{}^I$) and no strong sequence specificity in DNA cleaving (esperimicin). Zein et al., *Science*, 244:697 (1989).

Preparation of other chimeras using other appropriate fused ring enediyne aglycones and oligosaccharide portions can be carried out similarly.

As noted earlier, an $R^5$ group such as that shown in Formula X is preferably a hydroxyl group or a group convertible thereto intracellualarly. The presence of an $R^5$ hydroxyl group also provides an atom (oxygen) that can be used to link a hydroxyl-containing spacer group that itself can be glycosidically linked to a before-described saccharide. A generalized synthesis is illustrated in Scheme VI. A more specific partial synthesis is illustrated in Scheme XVII, below, that was used to prepare Compound 59.

Scheme XVII

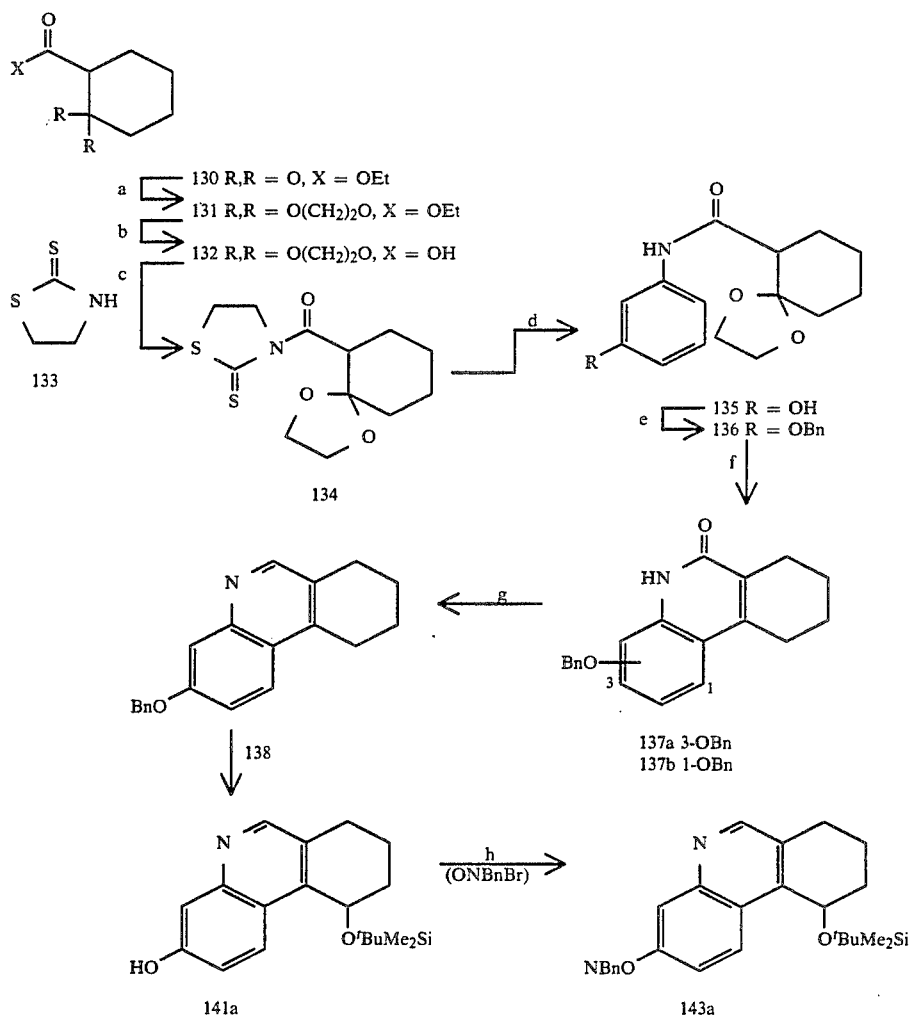

Scheme XVII

-continued

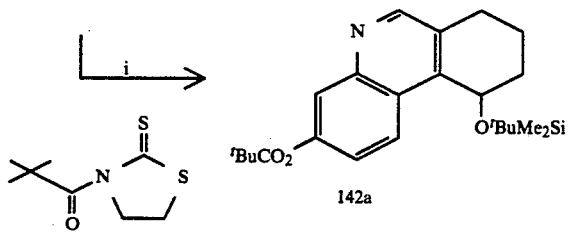

142a

Thus, in accordance with Scheme XVII, ethyl cyclohexanone-2-carboxylate, Compound 130, was reacted in step a with 1.2 equivalents of ethylene glycol and 0.1 equivalents of TsOH.H$_2$O in benzene at reflux for ten hours to form Compound 131. Compound 131 was reacted in step b with sodium methoxide-methanol at reflux for eight hours to form Compound 132 in 78 percent yield from Compound 130.

Compound 132 was then reacted in step c with Compound 133 in the presence of 1.2 equivalents of DCC and 0.1 equivalents of DMAP in methylene chloride at 25° C. for 14 hours to form Compound 134 in 96 percent yield. Compound 134 is a particularly useful intermediate for use in preparing a dynemycin analog of this invention, as is seen from Scheme XVII discussed here, and Scheme XVIIa discussed hereinafter.

Compound 134 was reacted with m-aminophenol in THF at reflux for 96 hours to provide Compound 135 in 87 percent yield in step d. Compound 135 was reacted with benzylbromide, 1.05 equivalents of NaH and 0.1 equivalents of $^n$Bu$_4$NI in THF at 25° C. in step e to form Compound 136 in 72 percent yield.

Compound 136 was cyclized in step f in 37 percent Hcl—THF (1:2.7) at reflux for three hours to provide a mixture of the cyclized product Compounds 137a and 137b in 100 percent yield. Compounds 137a and 137b were formed in about a 4:1 ratio in the order named. Compounds 137a and 137b as a mixture were treated with DIBAL and two equivalents of LiAlH$_4$ in THF at reflux for three hours and then with oxygen and SiO$_2$ at 25° C. for 24 hours to form Compound 138 in 50 percent yield.

A similar reaction sequence can be used with p-anisidine in place of the m-aminophenol to form the corresponding methoxy compound. That compound when treated with two equivalents of sodium ethylthiolate in DMF at 160° C., followed by acylation with acetic anhydride and then reaction with sodium methoxide provides the substituted phenol para to the nitrogen atom. That phenol, when treated as in step e forms the benzyl ether, Compound 139.

Another method of preparing Compound 139 is illustrated below in Scheme XVIIa. Here, Compound 134 was reacted directly with 4-aminophenol (step a; 1.0 equivalent, THF at reflux for 15 hours) to form Compound 205 in 86 percent yield. Compound 205 was then benzylated (step b; 1.05 equivalents of NaH, 1.0 equivalents benzyl bromide, 0.1 equivalents of $^n$Bu$_4$NI, THF at 25° C. for one hour) to produce Compound 139.

Compound 206 was prepared in 87 percent yield from Compound 134 by reaction with 5-aminosalicylic acid (step a; 1.0 equivalents, THF at reflux for seven days) Compound 207 was prepared in 77 percent yield from Compound 206 using an excess of benzyl bromide (3.0 equivalents NaH, 3.0 equivalents benzyl bromide, 0.2 equvialents $^n$Bu$_4$NI, THF at reflux for three hours.

Scheme XVIIa

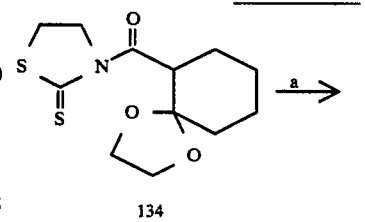

134

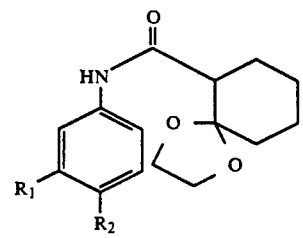

b ⎡ 205: R$_1$ = H, R$_2$ = OH
  ⎣→ 139: R$_1$ = H, R$_2$ = OBn
c ⎡ 206: R$_1$ = CO$_2$H, R$_2$ = OH
  ⎣→ 207: R$_1$ = CO$_2$Bn, R$_2$ = OBn

Either of Compounds 138 or 139, when treated as in steps a and b of Scheme II, or c-e of Scheme III provides the corresponding benzyloxy Compounds 140a or 140b. Hydrogenation of either of Compounds 140a or 140b using 10 percent Pd/C in ethanol at 25° C. provides the corresponding phenol derivatives Compounds 141a and 141b.

Reaction of either phenol with 1.05 equivalents of NaH and mercaptothiazolyl pivolate in THF provides the corresponding pivaloyl esters Compounds 142a and 142b. The pivaloyl ester Compound 142a was preapred as discussed above after a five minute reaction time at 25° C. in 99 percent yield (1.05 equivalents NaH, 1.0 equivalents of mercaptothiazolyl pivolate; THF).

Similarly, reaction of either of Compounds 141a and 141a with 1.05 equivalents of NaH and of o-nitrobenzyl bromide and 0.1 equivalents of $^n$Bu$_4$NI in THF provides the corresponding photolabile ONBn group and Compounds 143a and 143b. Compound 143a was prepared in 90 percent yield after a one hour reaction time.

Any of Compounds 142a, 142b, 143a or 143b can be used to form a fused-ring enediyne compound of the invention using the steps outlined in the prior reaction schemes, such as Scheme II. For example, following step e of Scheme II, yield of ethynyl group additions were between about 90 and 99 percent, with ratios of trans to cis additions being between about 2:1 and about 6:1. Results for this reaction are shown in the table, below for the examplary meta-substituted quinolines and ethynylation products shown with exemplary enediyne-epoxide product numbers also being illustrated.
TABLE
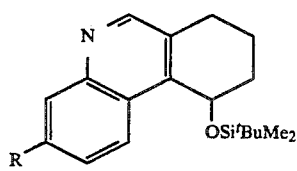
QUINOLINE
TABLE-continued
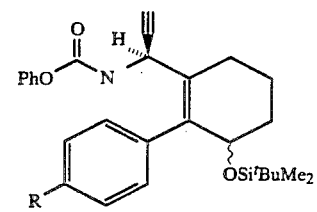
ADDUCT
| R | quinoline | adduct | ratio(trans:cis) | yield(%) |
|---|---|---|---|---|
| H | 7 | 8 | 3.5(78:22) | 95 |
| MeO | 208 | 226 | 5.3(84:16) | 99 |
| BnO | 140a | 140c | 3.8(79:21) | 90 |
| NBnO | 143a | 143b | 3.8(79:21) | 98 |
| $^t$BuCO$_2$ | 142a | 142b | 2.2(69:31) | 95 |
Scheme XVIII
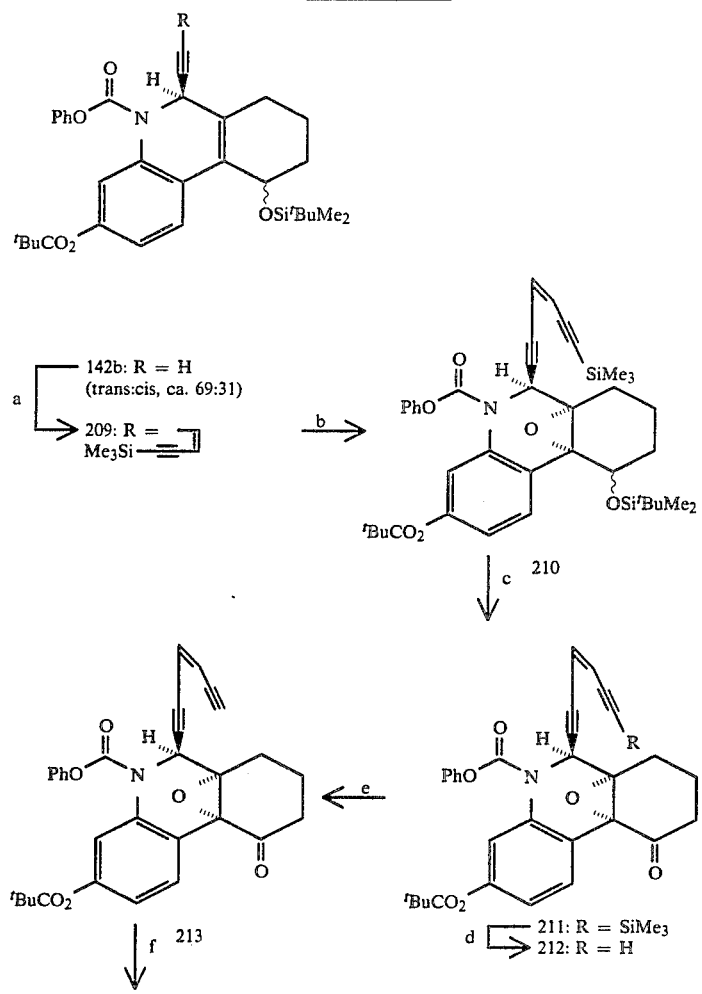

Scheme XVIII

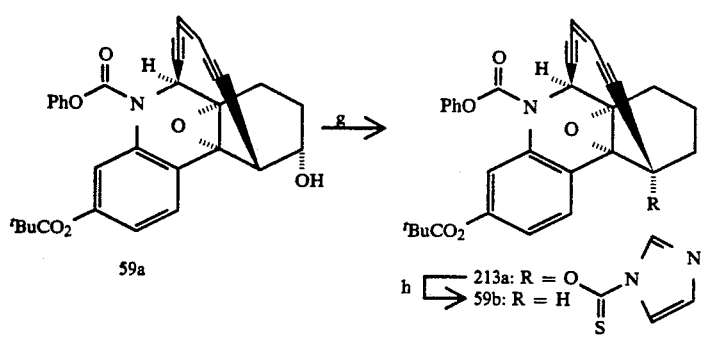

Scheme XVIII (above) presents an alternative preparation of Compounds 59a and 59b starting from Compound 142a. Thus, coupling of Compound 142a with 1-chloro-4(trimethylsilyl)-but-1-en-3-yne under the standard conditions (step a) gave Compound 209 in 67 percent yield. Epoxidation of Compound 209 with mCPBA in step b led to Compound 210 in 71 percent yield. Reaction of Compound 210 with BF$_3$.Et$_2$O followed by exposure to 48 percent aqueous HBr in THF in step c gave enones Compounds 211 (34 percent) and 212 (18 percent). Removal of the ttrimethylsilyl group from Compound 211 under standard conditions [4.0 equivlanets of AgNo$_3$, H$_2$O-ETOH-THF (1:1:1), 25° C. for one hour, followed by 7.0 equivalents of KCN at 25° C. for ten minutes] led to Compound 213 (90 percent) which was subjected to epoxidation using mCPBA under basic conditions to afford epoxide Compound 213 in 45 percent yield in step e. Cyclization of Compound 213 under the standard LDA conditions in step b (1.0 equivalents LDA, toluene, −78° C., 20 minutes) gave Compound 59a in 80 percent yield. Deoxygenation of Compound 59a proceeded as previously discussed for similar compounds via thionoimidazolide Compound 213a (58 percent yield, plus 33 percent recovered starting material) to afford the targeted Compound 59b (69 percent, plus 9 percent recovered Compound 59a.

The o-nitrobenzyl derivative, Compound 43 was synthesized similarly. This sequence, proceeded in good overall yield. Although quite stable for isolation and characterization purposes, this enediyne proved rather labile as compaed to the ester Compound 59a. Attempted deoxygenation via the thionoimidazolide was not successful due to extensive decomposition at the first stage of the two-step sequence.

The use of Compound 143b to prepare fused-ring enediyne compounds having a spacer portion in the benzo ring para to the carbamate nitrogen atom is illustrated in Scheme XIX, below.

Scheme XIX

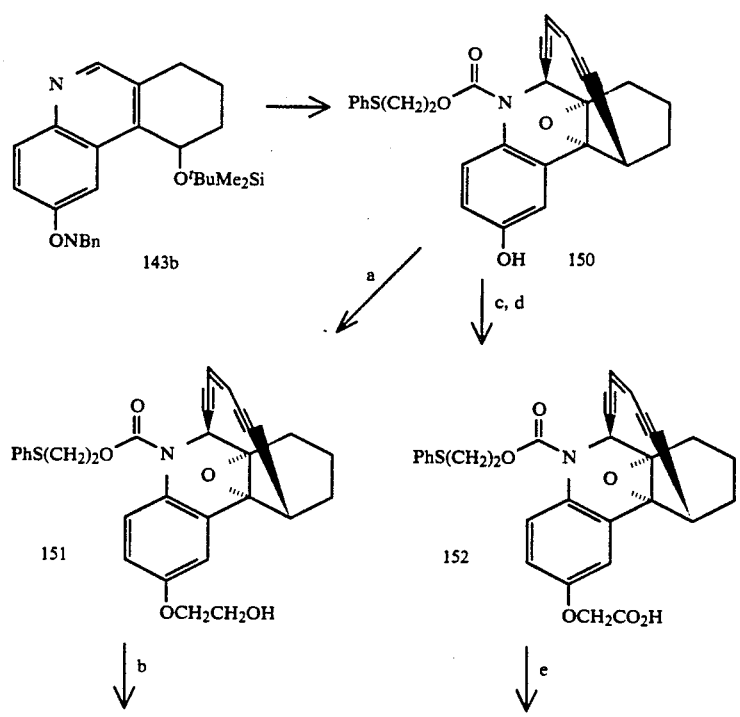

Scheme XIX

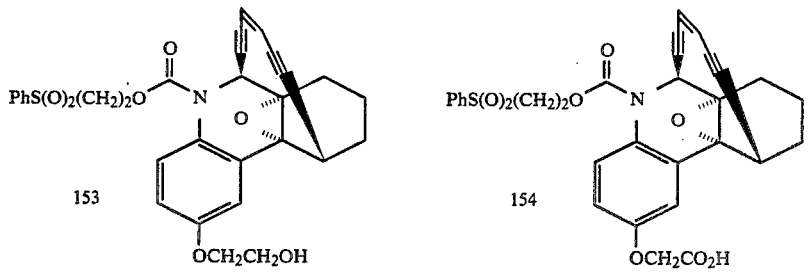

Thus, Compound 143b is reacted as discussed elsewhere herein to form fused-ring enediyne Compound 150. Those prior reactions are indicated schematically by the two arrows between Compounds 143b and 150. Compound 150 is a para-hydroxy analog of the compound formed in step b of Scheme VIII.

Compound 150 is then reacted in step a with 2-bromoethanol and NaH in the THF to form Compound 151. Compound 151 is oxidized in step b as with mCPBA to form Compound 153, whose ethoxyethanol hydroxyl group can be used to form a glysidic link to a saccharide as discussed previously.

In an alternative synthesis, Compound 153 was reacted with the chloride salt of 2-trimethylammonium acetyl chloride (N,N,N-trimethylglycal chloride chloride) to form Compound 250. Compound 250 exhibited enhanced water solubility as compared to Compound 153, and similar in vitro cytotoxicity against cancer cell lines and normal cells, as shown hereinafter in Table 5.

Compound 150 can also be reacted with ethyl bromoacetate and cesium carbonate in acetonitrile as in step c to form the corresponding ethyl carboxymethyl derivative. Hydrolysis of that ester with lithium hydroxide in THF-water and neutralization provides the free acid Compound 152 in step d. Oxidation of the free acid as in step b provides Compound 154. The carboxylic acid group of Compound 154 can be used to form a chimera via an ester link to a before-discussed saccharide, or an ester or amide link to a before-discussed monoclonal antibody.

An alternative synthesis for compounds substituted at C-2; i.e., those having a substitutent para- to the nitrogen atom began with p-anisidine (Compound 270) and ethyl cyclohexanone-2-carboxylate (Compound 130) as is shown in Scheme XX.

Scheme XX

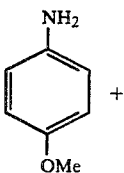

270

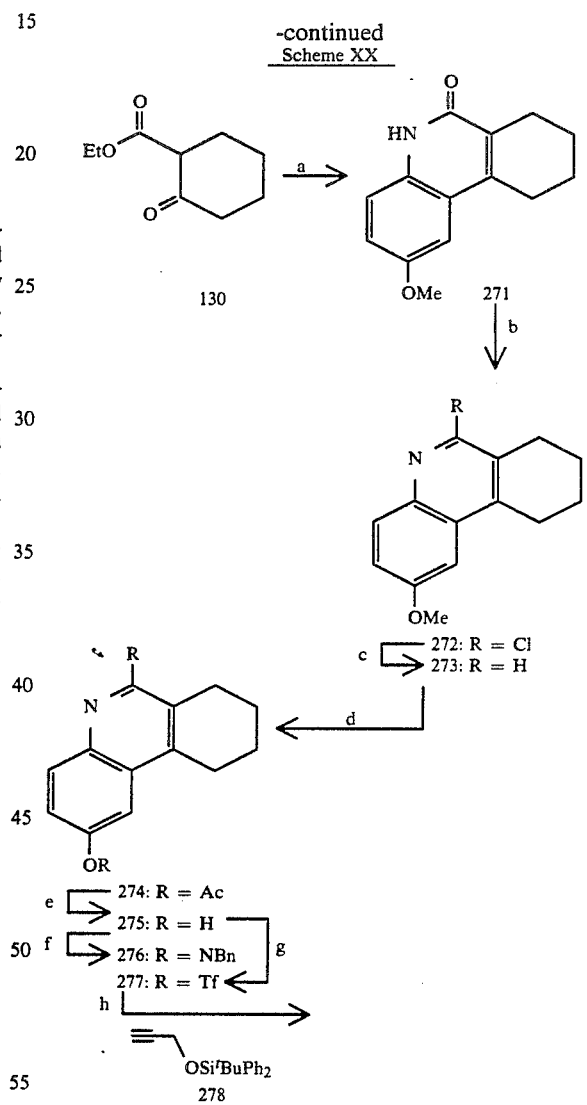

Thus, condensation of Compound 270 with Compound 130 under the influence of cnc. $H_2SO_4$ and heat

[Masamune et al., *J. Org. Chem.*, 29:681 (1964)] produced Compound 271 in 30 percent yield. Reaction of Compound 271 with POCl₃ at 100° C. furnished chloride Compound 272 (94 percent) which was subjected to catalytic hydrogenolysis to afford the requisite Compound 273 (94 percent) [Hollingsworth et al., *J. Chem. Soc.*, 1537 (1948)]. The latter compound served well as precursor to both of Compounds 276 and 279. Demethylation of Compound 273 with NaSEt at 160° C. followed by cooling and in situ acetylation (for isolationn purposes) produced Compound 274 (86 percent overall yield). The phenol Compound 275 was then conveniently generated from Compound 274 by exposure to NaOMe in MeOH at 60° C. (98 percent), and was smoothly converted to its o-nitrobenzyl ether (NBn) Compound 276 (94 percent) and triflate Compound 277 (78 percent) by standard chemistry. Coupling of triflate Compound 277 with acetylenic unit s-[(t-butyldiphenylsilyl)oxy]-prop-1-yne (Compound 278) under the catalytic action of PdCl₂(PPh₃)₂ and CuI furnished the desired target Compound 279 in 97 percent yield.

Functionalization of the C-10 position in these systems (Compounds 273, 276 and 279) was achieved according to Scheme XXI (below), with steps a–c being substantially similar to steps a–c of Scheme II. Oxidation with mCPBA led to N-oxides 280a–c (87–91 percent) which upon heating in acetic anhydride at 70° C. gave the corresponding acetates 281a–c in 56–91 percent yield. Deacetylation with NaOMe in MeOH then furnished the hydroxy compounds 282a–c in 69–89 percent yield.

Scheme XXI

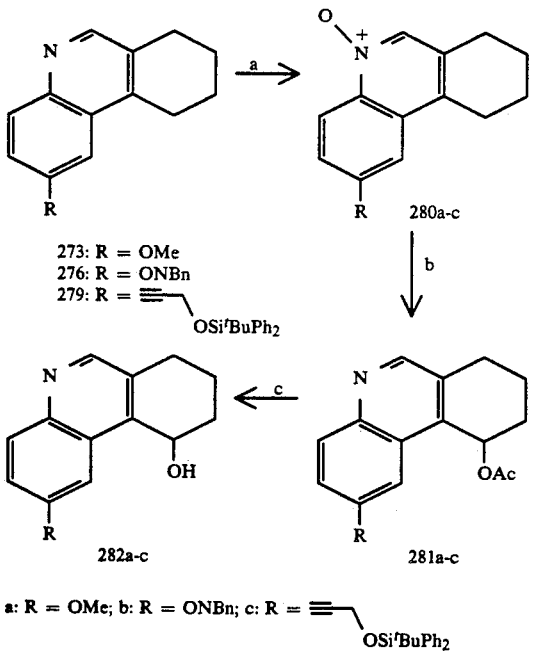

273: R = OMe
276: R = ONBn
279: R = ≡—\
OSi$^t$BuPh₂ a: R = OMe; b: R = ONBn; c: R = ≡—\
OSi$^t$BuPh₂

Compound 282a–c were then synthesized into endiyne compounds 41b–d, 153 and 300 following the general methods outlined in Schemes II, XI and IVII. Details of the sytneses are discussed hereinafter in the examples. It is noted, however, that use of the o-nitrobenzyl protecting group for the phenolic hydroxyl group led to highly crystalline intermediates and permitted photodeprotection.

Figure 1:
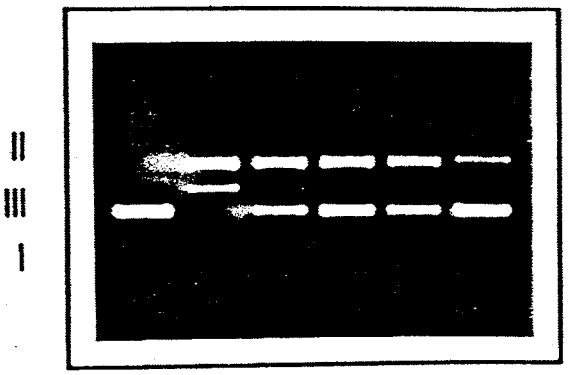
FIG. 1 is a photograph of an ethidium bromide stained 1 percent agarose gel that illustrates the cleavage of ΦX174 Form I DNA by Compound 40 after 24 hours in phosphate buffers (50 mM) containing 20 volume percent THF at pH 7.4. Lane 1 is the DNA alone as control, lanes 2-6 show the results obtained with 5000, 2000, 1000, 500 and 100 μM Compound 40, respectively. The designations I, II and III outside the gel indicate Forms I, II and III of the DNA, respectively.

The results of an exemplary DNA-cleaving study using Compound 40 in a method of the invention are illustrated in FIG. 1. Other compounds such as Compound 41 [Formula X wherein R¹ is phenoxycarbonyl, R²=R³=R⁶=R⁷=R⁸=H, A is a saturated bond, R⁴ is hydroxyl and R⁵ is methoxy at the "e" position of the benzo ring] also cleaved DNA. Compound 41 was utilized at a 2 mM concentration at pH 5.0

Figure 2:
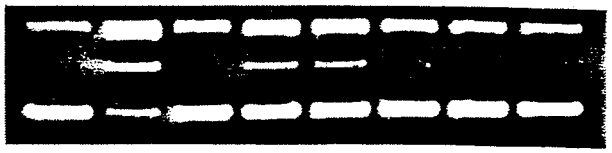
FIG. 2 is a photograph of an ethidium bromide stained 1 percent agarose gel that illustrates the cleavage of ΦX174 Form I DNA by Compounds 40, 47, 42, 54, 55, 58 and 62 after 24 hours in pH 8.0 50 mM Tris-HCl buffer. Lane 1 is the DNA alone as control, lanes 2, 3, 4, 5, 6, 7 and 8 show the results obtained with 5 mM of each of compounds 40, 47, 42, 54, 55, 58 and 62, respectively. The designations Form I, II and III are as in FIG. 1.

Compounds 40, 42 and 54 were further found to cause significant DNA cleavage when incubated at 5 mM with supercoiled φX174 DNA at pH 8.0 (FIG. 2). Noteworthy in these studies is the observation of double strand cuts as well as single strand cuts, as is the case with dynemicin A (Compound 1). The methoxy derivatives 47, 55, 58 and 62 exhibited diminished activity against DNA.

Figure 6:
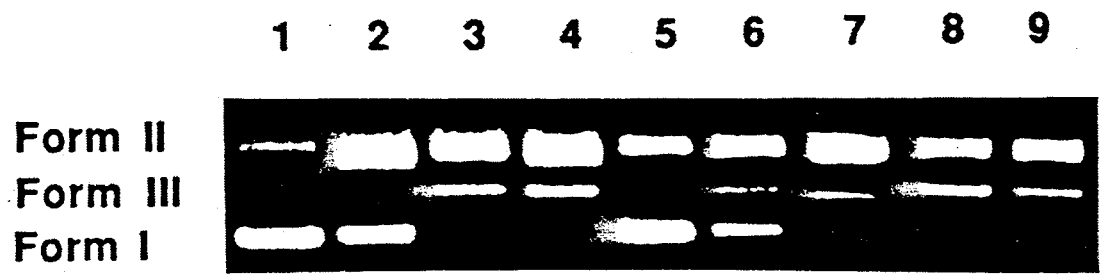
FIG. 6 is a photograph of an ethidium bromide stained 1 percent agarose gel that illustrates the cleavage of ΦX174 Form I DNA by Compounds 70, 76a, 76b, 87a, 87b, 40, and the N-protected 2-(phenysulfonyl)ethoxy carbamate of Compound 40, Compound 45, after 48 hours at 37° C. in pH 8.5 Tris-HCl buffer. Lane 1 is the DNA alone as a control, lanes 2, 3, 4, 5, 6, and 7 show the results obtained with 10 mM of each of Compounds 70, 76a, 76b, 80, 87a, and 87b, respectively.

The DNA cleaving activity of selected arenediynes is shown in FIG. 6. These compounds show diminished activity towards DNA relative to Compound 40, which is expected given their chemical and steric profiles.

FIG. 7a shows the DNA cleaving activity of 2-(phenylsulfonyl)ethoxycarbamate Compound 153. There was no DNA cleavage activity at acidic pH values, as expected, but Compound 153 did show some DNA cleavage activity at a pH value of 7.0 and higher. The potency of Compound 153 against a panel of tumor cells is shown in Table 4.

The DNA cleavage activity at a pH value of 8.5 of other compounds is shown in FIG. 7b. Again, as expected, the phenylsulfone-containing Compounds 45 and 153 exhbited strong DNA cleavage activity at that pH value. The free phenolic Compound 171 likewise showed strong activity.

Compounds 42 and 201 exhibited significant DNA cleaving action against φX174 supercoiled DNA (FIG. 9). Compound 54 also exhibited DNA cleaving capability (FIG. 9) although its triggering mechanism is not clear at present. As expected from their chemical profiles, Compounds 59a, 59b, 43 and 202 were found to be inert towards supercoiled DNA (FIG. 9).

Figure 3:
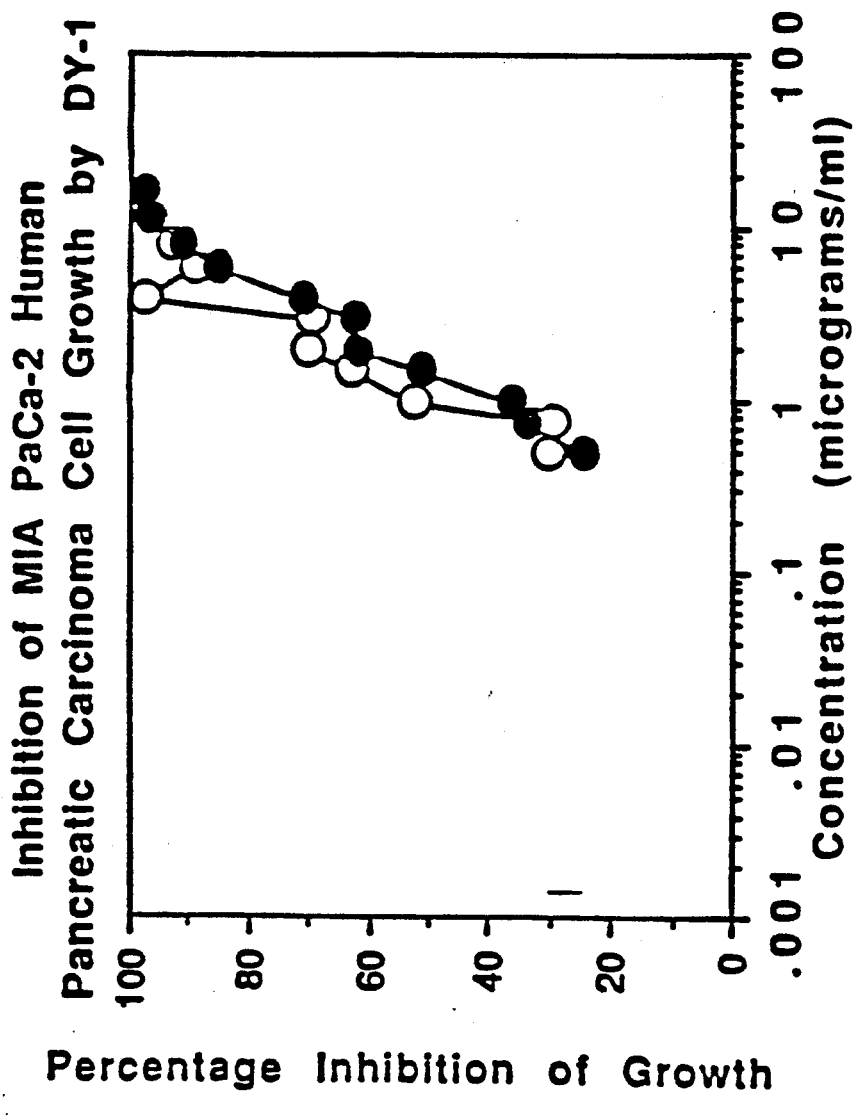
FIG. 3 is a graph showing results from two studies of the percent growth inhibition of MIA PaCa-2 human pancreatic carcinoma cells over a four-day time period by various concentrations of Compound 2 (DY-1).
Figure 4:
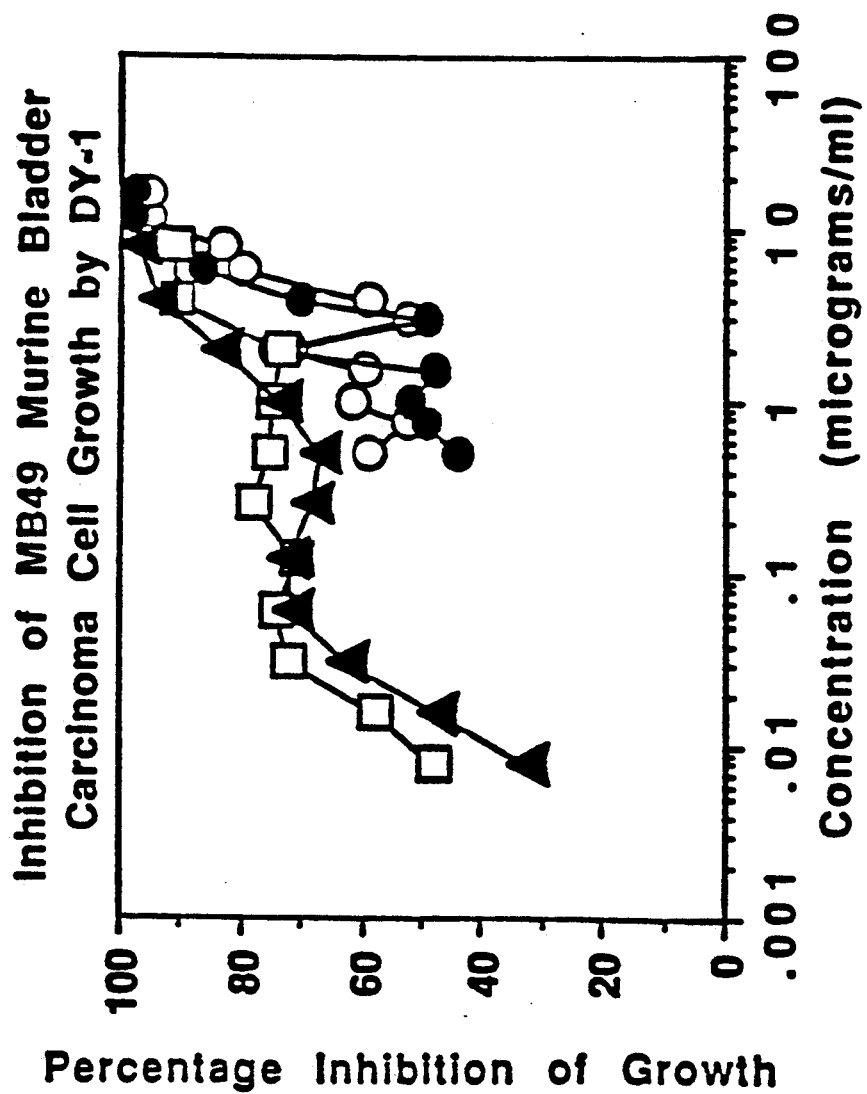
FIG. 4 is a graph showing the results from four studies of the percent growth inhibition over a four-day time period of MB49 murine bladder carcinoma cells by various concentrations of Compound 2 (DY-1). $IC_{50}$ values for two of the studies were 43 nM and 91 nM.
Figure 5:
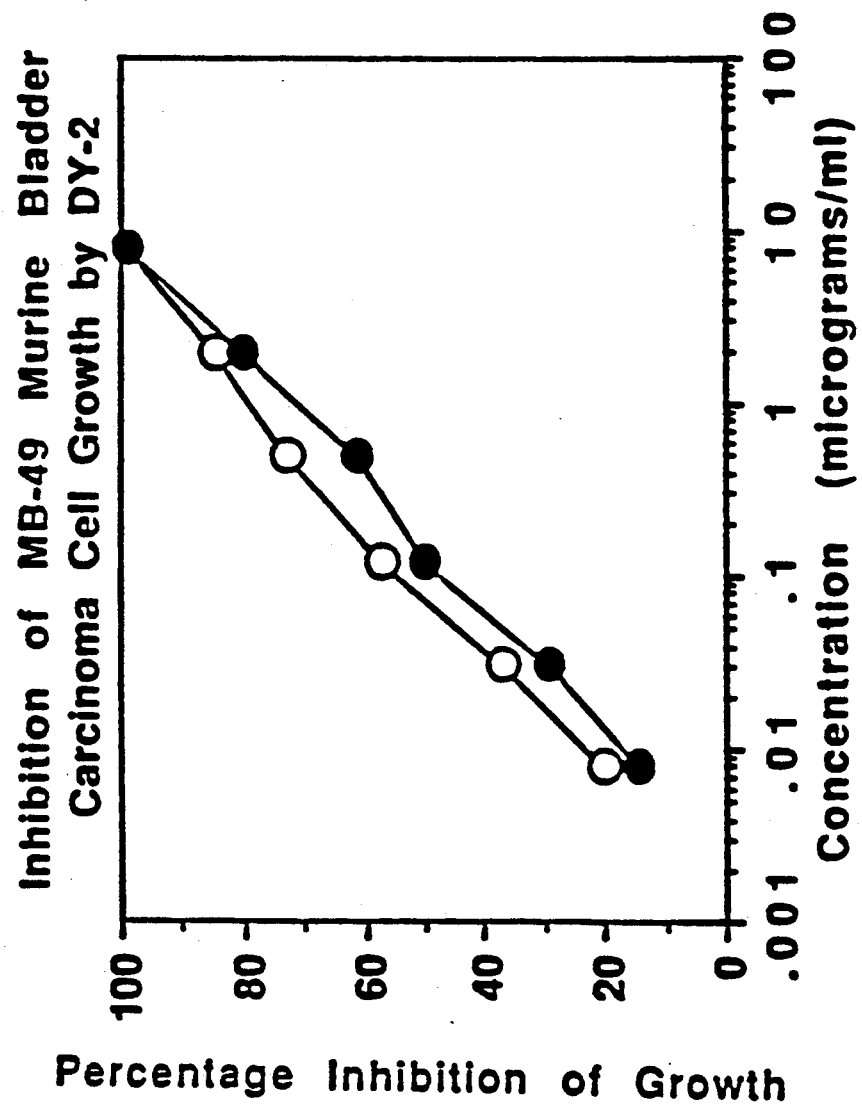
FIG. 5 is a graph showing the results from two studies of the percent growth inhibition over a four-day time period of MB49 murine bladder carcinoma cells by various concentrations of Compound 21 (DY-2).

The compounds also exhibit anti-microbial activity and all of those assayed exhibit some activity in vitro against tumor cells. A graph illustrating the inhibition of MIA PaCa-2 human pancreatic carcinoma cell growth using Compound 2 (DY-1) is shown in duplicate in FIG. 3. Graphs illustrating the inhibition of MB-49 murine bladder carcinoma cell growth for Compounds 2 and 20 (DY-2) are shown in FIGS. 4 and 5, in quadruplicate and duplicate respectively. Values of IC₅₀ obtained from the two wider range studies shown in FIG. 4 were 43 nM and 91 nM. In a comparative study, Compound 2 was also shown to be more active against the cancerous MB-49 cells than against non-transformed CV-1 African green monkey kidney cells (ATCC CCL 70) or WI-38 human lung cells (ATCC CCL 75).

The results of an in vivo assay using Compound 45 is shown in FIG. 8. Use of this compound in a dosage of 25 mg/kg in mice infected with a murine leukemia virus increased the life span 175 percent over untreated animals. Also, the toxicity of Compound 45 was significantly less than naturally occurring enediynes. The lethal dose, LD₅₀, of Compound 45 was in the range of 50 mg/kg, compared to an LD₅₀ of calichemicin γ₁1 of 5 μg/kg in mice.

Each of the dynemicin A analog Compounds 24a–g exhibited anti-tumor cell activity against MIA PaCa-2 cells, with the esters (Compounds 24b–g) being more potent than the free acid (Compound 24a). Compounds 24a-g were also active against MB-49 cells and inactive against CV-1 and WI-38 cells. Compounds 2b-d shown below each exhibited weaker anti-tumor activity against MB-49 cells than did Compound 2.

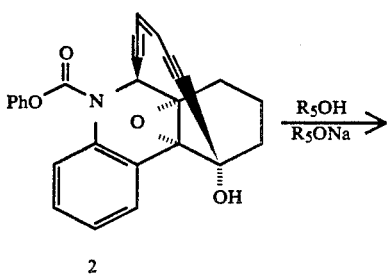

2

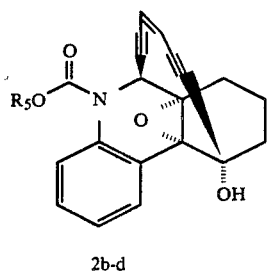

2b-d $R_5$ = —$CH_3$(2b);

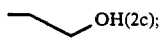

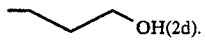

The described chemistry supports the viability of two paths as triggering mechanisms for the dynemicin A-type cascade by showing that a lone pair of electrons on a heteroatom (N or O) strategically positioned on the aromatic ring in relation to the epoxide moiety serves to initiate the cycloaromatization reaction. Such reactive species can be generated within the cell by enzymatic reactions, or as shown above, be released from suitable precursors under mild conditions in the laboratory. In addition, the relative stability and observation of Compounds 42, 54, 58 and 62 is interesting in that it allows for the scenario of bioreduction prior to intercalation as well as for the possibility of DNA interacting nucleophilically against quinone methide species. Thus the proposition that dynemicin A may be interacting with DNA by a dual mechanism (nucleophilic and radical) appears attractive, not only because of the observed preference for cleavage of adenine and quanine, but also in view of the chemistry of Compound 42.

Further biological evaluation data are provided hereinafter in Tables 1-5.

BEST MODE FOR CARRYING OUT THE INVENTION

Methods

DNA Cleavage Studies

The ethereal solution of Compound 40 produced by the LiAlH$_4$ reduction of Compound 21 (39 mg, 0.10 mmol) was evaporated in vacuo to dryness and the residue dissolved in THF (4 mL) to give a 25 mM solution of Compound 40, assuming complete conversion of Compound 21. Analysis of Compound 40-induced damage to supercoiled, covalently closed, circular (form I) $\phi$X174 DNA was performed by incubation at varying concentrations of Compound 40 (100 $\mu$M-5000 $\mu$M) in phosphate buffered aqueous solution at 37° C. for 12-24 hours followed by agarose gel electrophoresis to separate the various DNA products.

Thus, a vial containing a 50 micromolar per base pair solution of $\phi$X174 Form I double stranded DNA in 2.0 microliters of pH 7.4 phosphate (50 mM) buffers were added 6.0 microliters of the same buffer solution and 2.0 microliters of a 5.0 millimolar ethanol solution of Compound 40.

The vials were then placed in a 37° C. oven for 12-24 hours. A 2.0 microliter portion of glycerol loading buffer solution containing bromothymol blue indicator was added to each vial. A 10 microliter aliquot was then drawn from each. Gel electrophoresis analysis of the aliquots was performed using a 1.0 percent agarose gel with ethidium bromide run at 115 volts for 1 hour. DNA cleavage was indicated by the formation of nicked relaxed circular DNA (form II) or linearized DNA (form III), which was detected by visual inspection of the gel under 310 nanometer ultraviolet light using ethidium bromide.

Procedure for 6-Well Cytotoxicity Assay

MIA PaCa-2 cells, MB-49, CV-1 or WI-38 cells were loaded into each well of a 6-well plate at a density of 100,000 cells/well in 3 ml culture medium. They were incubated for 4 hours (37° C., 7 percent CO$_2$). Then 6 microliters of solution containing a compound to be assayed were added into 3 ml of medium (RPMI-1640, with 5 percent fetal bovine serum and 1 percent glutamine) in a 500X dilution so that in one well ethanol was added to make a 0.2 percent ethanol control. The plates were then incubated for 4 days (37° C., 7 percent CO$_2$). The medium was then drained, crystal violet dye (Hucker formula) was added to cover the well bottoms and then they were rinsed with tap water until rinses were clear. The stained cells were solubilized for quantitation with Sarkosyl solution (N-Lauryl sarcosine, 1 percent in water) at 3 ml/well. The absorbance of the solution was then read at 590-650 nm.

Large Scale Screening Against Cancerous Cell Lines

In addition to the screening already discussed, several of the before-described compounds and chimeras were screened against several or all of a panel of ten to twenty-five cancerous cell lines as target cells and seven "normal"cell preparations. This screening utilized a sulforhodamine B cytotoxidity assay as discussed below.

SULFORHODAMINE B CYTOTOXICITY ASSAY

1. Preparation of target cells in 96-well plates
    a. Drain media from T$_{75}$ flask of target cell lines(s) and carefully wash cell monolayer two times with sterile PBS (approximately 5 ml per wash)
    b. Add 5 mL trypsin/EDTA solution and wash monolayer for approximately 15 seconds
    c. Drain all but approximately 1 mL of trypsin-/EDTA from flask, cap flask tightly, and incubate at 37° C. for approximately two to five minutes until cells come loose.
    d. Add 10-15 mL tissue culture (T.C.) medium (RPMI 1640 plus 10 percent fetal calf serum and 2 mM L-glutathione) to flask and pipet gently up and down to wash cells.

e. Remove a ½ mL aliquot of the cell suspension and transfer to a glass 12×75 mm culture tube for counting.
f. Count cells on a hemacytometer using trypan blue, and determine percent viability.
g. Adjust volume of cell suspension with T.C. media to give a density of $1\times 10^5$ cells/mL.
h. Add 100 μL of T.C. medium to wells A1 and B1 of a 96-well plate for blanks.
i. Add 100 μL of cell suspension to the remaining wells of the 96-well plates.
j. Incubate plates for 24 hours at 37° C., 5-10 percent $CO_2$ in a humidified incubator.

2. Preparation of sample drugs and toxic control
   a. Stock drug solutions were prepared by dissolving drug in the appropriate solvent (determined during chemical characterization studies) and sterile filtering the drug-solvent solution through a sterile 0.2 μ filter unit. An aliquot was taken from each filtered drug solution and the O.D. was measured to determine the drug concentration.
   b. Dilute the stock drug solution prepared above with T.C. medium to the desired initial concentration ($10^{-2}$–$10^{-4}$M). A minimum volume of 220 μL of diluted drug is required per 96-well plate used in the assay.
   c. Prepare toxic control by diluting stock doxorubicin solution to $10^{-7}$ to $10^{-9}$M in T.C. medium. A minimum volume of 300 μL is required per 96-well plate.

3. Addition of Sample Drugs, Compounds, Chimeras and Controls to 96-well Plates
   1. Remove and discard 100 μL of T.C. medium from the wells in Column #2 of the 96-well plate using a multi-channel pipettor and sterile tips.
   b. Add 100 μL of the initial compound dilution to adjacent duplicate wells in Columns #2. (Four materials can be tested in duplicate per 96-well plate.)
   c. Remove 10 μL of diluted compound from the wells in Column #2 and transfer to the corresponding wells in Column #3. Mix by pipetting up and down gently approximately five times.
   d. Transfer 10 μL to the appropriate wells in Column #4 and continue to make 1:10 dilutions of compound across the plate through Column #12.
   e. Remove and discard 100 μL of medium from wells F1, G1, and H1. Add 100 μL of toxic control (Doxorubicin diluted in T.C. medium) to each of these wells.
   f. Incubate (37° C., 5-10 percent $CO_2$ in humidified incubator) plates for a total of 72 hours. Check plates at 24 hour intervals microscopically for signs of cytotoxicity.

4. Cell Fixation
   a. Adherent cell lines:
      1. Fix cells by gently layering 25 μL of cold (4° C.) 50 percent trichloroacetic acid (TCA) on top of the growth medium in each well to produce a final TCA concentration f 10 percent.
      2. Incubate plates at 4° C. for one hour.
   b. Suspension cell lines:
      1. Allow cells to settle out of solution.
      2. Fix cells by gently layering 25 μL of cold (4° C.) 80 percent TCA on top of the growth medium in each well.
      3. Allow cultures to sit undisturbed for five minutes.
      4. Place cultures in 4° C. refrigerator for one hour.
   c. Wash all plates five times with tap water.
   d. Air dry plates.

5. Staining Cells
   a. Add 100 μL of 0.4 percent (wt./vol.) Sulforhodamine B (SRB) dissolved in 1 percent acetic acid to each well of 96-well plates using multichannel pipettor.
   b. Incubate plates at room temperature for 30 minutes.
   c. After the 30 minute incubation, shake plates to remove SRB solution.
   d. Wash plates two times with tap water and 1> with 1 percent acetic acid, shaking out the solution after each wash. Blot plates on clean dry absorbent towels after last wash.
   e. Air dry plates until no standing moisture is visible.
   f. Add 100 μL of 10 mM unbuffered Tris base (ph 10.5) to each well of 96-well plates and incubate for five minutes on an orbital shaker.
   g. Read plates on a microtiter plate reader at 540 nM.

$IC_{50}$ values; i.e., the concentration of Compound required to kill one-half of the treated cells, were then calculated.

The cell lines assayed are listed below along with their respective sources:

| Cell Line | Source and Type |
|---|---|
| UCLA M-14 | Dr. R. Reisfeld of The Scripps Research |
| UCLA M-21 | Institute, and originally obtained from |
| UCLA P-3 | Dr. D. Morton, University of California, Los Angeles. M-14 and M-21 are human melanoma cell lines, whereas P-3 is a human non-small cell lung carcinoma cell line. |
| PBL | Human peripheral blood lymphocytes (R. W. Johnson Pharmaceutical Research Institute, La Jolla, CA) |
| HMEC | Human mammary epithelial cells |
| NHDF | Normal human dermal fibroblasts |
| NHEK | Normal human epidermal keratinocytes |
| NHEM | Normal human epidermal melanocytes (Clonetics Corporation, San Diego, CA) |
| HNBM | Human normal bone marrow (Dr. R. Handgretinger, University of Tubingen, Tubingen, Germany) |

All other cells or cell lines were obtained from the American Type Culture Collection (ATCC) (all except CHO cells are human or mouse cancer cell lines as described by the ATC).

Control studies were also carried out using the following well known anticancer drugs with the following $IC_{50}$ values for NHDF and cancer cells.

| | Range of Average $IC_{50}$ Values (Molarity) | |
|---|---|---|
| Drug | NHDF | Cancer Cells |
| Doxorubicin | — | $1.6\times 10^{-10}$–$9.8\times 10^{-8}$ |
| Dynemicin A | $10^{-8}$ | $1.6\times 10^{-8}$–$9.8\times 10^{-10}$* |
| Calicheamicin | $2.5\times 10^{-9}$ | $5\times 10^{-5}$–$10^{-12}$** |
| Morpholinodoxorubicin | — | $1.6\times 10^{-7}$–$9.8\times 10^{-9}$ |
| Taxol | $10^{-8}$ | $10^{-7}$–$10^{-9}$ |
| Methotrexate | $5\times 10^{-5}$ | $>10^{-4}$–$10^{-8}$ |
| Cis-Platin | $5\times 10^{-5}$ | $10^{-4}$–$10^{-6}$ |
| Melphelan | $10^{-4}$ | $10^{-4}$–$10^{-6}$ |

*UCLA-P3 cells were susceptible at $10^{-12}$M. All other cells were susceptible at $1.56\times 10^{-10}$M or higher concentrations.
**Molt-4 cells were susceptible at $10^{-12}$M. All other cells were susceptible at $3.9\times 10^{-9}$M or higher concentrations.

Tables 1 and 2 herein below provide average $IC_{50}$ data from five to all ten of the above cancer cells liens for fused ring enediyne compounds disclosed herein. Those tables provide a generic structure and a description of the R group of that generic structure for each compound. Compound numbers as noted hereinbefore are also provided. Table 3 contains data for two fused-ring enediyne compounds (Compounds 47 and 120) as well as data for six chimers. Table 4 contains cancer cell and normal cell cytotoxicity data for one select fused ring enediyne, Compound 153 against a number of "normal" cell preparations and tumor cell lines. Table 5 contains cancer cell and normal cell cytotoxicity data for another fused ring enediyne, Compound 250 against a similar panel of cells.

TABLE 1

Anticancer Activity ($IC_{50}$) Of Enediyne Compounds

| Structure | Number of Compound | $IC_{50}$ (M)* |
|---|---|---|
| 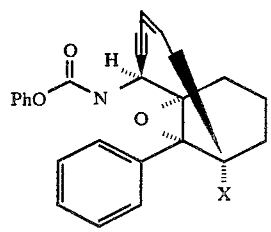 | 2: X = OH | $6.3 \times 10^{-6}$ |
|  | 46: X = OMe | $6.3 \times 10^{-5}$ |
|  | 24b: X = $OCH_2CO_2Me$ | $5.0 \times 10^{-6}$ |
|  | 24a: X = $OCH_2CO_2H$ | $6.3 \times 10^{-5}$ |
|  | 21: X = OH | $5.0 \times 10^{-6}$ |
| 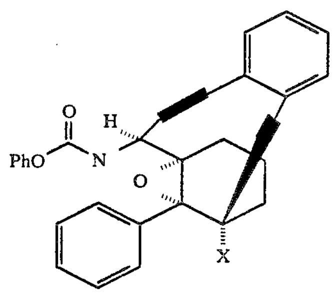 | 74: X = OH | $2.0 \times 10^{-5}$ |
|  | 76: X = H | $7.9 \times 10^{-6}$ |
| 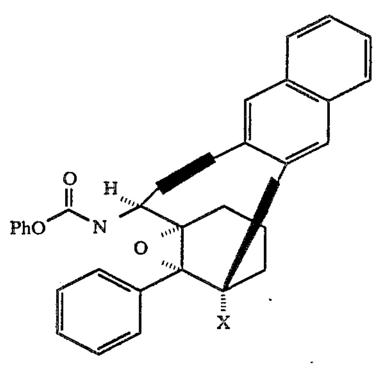 | 85: X = OH | $2.0 \times 10^{-5}$ |
|  | 87: X = H | $3.2 \times 10^{-6}$ |
| 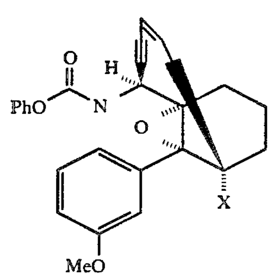 | 41-1: X = OH | $2.0 \times 10^{-5}$ |
|  | 41a: X = H | $2.0 \times 10^{-5}$ |

TABLE 1-continued

Anticancer Activity (IC$_{50}$) Of Enediyne Compounds

| Structure | Number of Compound | IC$_{50}$ (M)* |
|---|---|---|
| | 59a: X = OH | $7.9 \times 10^{-7}$ |
| | 59b: X = H | $(9.8 \times 10^{-8})**$ |
| | | $2.0 \times 10^{-7}$ |
| | | $(1.0 \times 10^{-11})**$ |

*Average data obtained from 5~10 cell lines.

**Data obtained from MOLT-4 (Leukemia) cell line.

TABLE 2

Anticancer Activity (IC$_{50}$) Of Enediyne Compounds

| Structure | Number of Compound | IC$_{50}$ (M)* |
|---|---|---|
| | 21: R = Ph | $5.0 \times 10^{-6}$ |
| | 21a: R = CH$_2$CH$_2$SPh | $6.3 \times 10^{-5}$ |
| | 21b: R = CH$_2$CH$_2$SOPh | $3.2 \times 10^{-5}$ |
| | 45: R = CH$_2$CH$_2$SO$_2$Ph | $2.0 \times 10^{-7}**$ |
| | 76: R = Ph | $7.9 \times 10^{-6}$ |
| | 77: R = CH$_2$CH$_2$SPh | $3.6 \times 10^{-5}$ |
| | 70: R = CH$_2$CH$_2$SO$_2$Ph | $3.2 \times 10^{-6}$ |
| | 87: R = Ph | $3.2 \times 10^{-6}$ |
| | 88: R = CH$_2$CH$_2$SPh | $5.0 \times 10^{-5}$ |
| | 80: R = CH$_2$CH$_2$SO$_2$Ph | $1.6 \times 10^{-6}$ |

TABLE 2-continued

Anticancer Activity (IC$_{50}$) Of Enediyne Compounds

| Structure | Number of Compound | IC$_{50}$ (M)* |
|---|---|---|
| | 41a: R = Ph | $2.0 \times 10^{-5}$ |
| | 41b: R = CH$_2$CH$_2$SO$_2$Ph | $2.5 \times 10^{-7}$** |
| | 41c: R = CH$_2$CH$_2$SO$_2$Ar$_a$ | $2.0 \times 10^{-7}$** |
| | 41d: R = CH$_2$CH$_2$SO$_2$Ar$_b$ | $1.3 \times 10^{-7}$** |

Ar$_a$ = 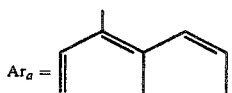

Ar$_b$ = 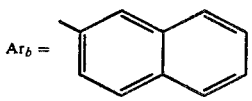

*Average data obtained from 5~10 cell lines.
**IC$_{50}$ ≅ $1.0 \times 10^{-11}$ obtained from MOLT-4 (Leukemia) cell line.

TABLE 3

Anticancer Activity (IC$_{50}$) Of Enediyne Compounds

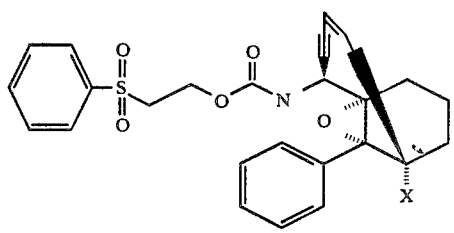

| Number of Compound | IC$_{50}$ (M)* |
|---|---|
| 47: X = OMe | $5.0 \times 10^{-6}$ |
| 120: X = OCH$_2$CH$_2$OH | $4.0 \times 10^{-5}$ |
| 125a: X = OCH$_2$CH$_2$OR$_1$ | $<10^{-4}$ |
| 126a: X = OCH$_2$CH$_2$OR$_2$ | $4.4 \times 10^{-5}$ |
| 125b: X = OCH$_2$CH$_2$OR$_1$ | $<10^{-4}$ |
| 126b: X = OCH$_2$CH$_2$OR$_2$ | $8.7 \times 10^{-6}$ |
| 127a: X = OCH$_2$CH$_2$OR$_3$ | $1.4 \times 10^{-7}$** |
| 127b: X = OCH$_2$CH$_2$OR$_4$ | $7.6 \times 10^{-6}$** |

R$_1$ = 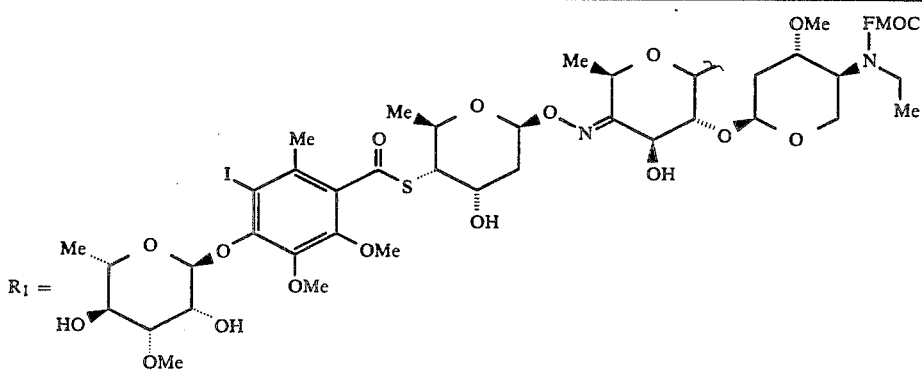

TABLE 3-continued
Anticancer Activity (IC$_{50}$) Of Enediyne Compounds
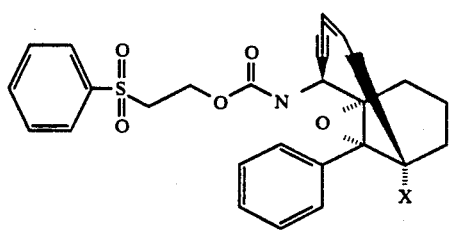
| Number of Compound | IC$_{50}$ (M)* |
|---|---|
R$_2$ = [structure]
R$_3$ = [structure]
R$_4$ = [structure]
*Average data obtained from 5~10 cell lines.
**IC$_{50}$ = 1.0 × 10$^{-9}$ for 127a and 1.0 × 10$^{-10}$ for 127b obtained from MOLT-4 (Leukemia) cell line.

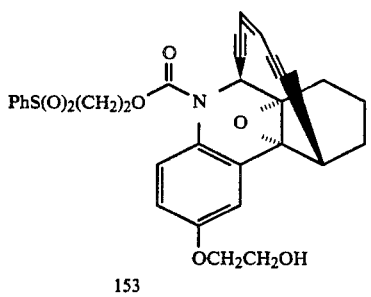

153

TABLE 4

Cytotoxicites of Enediyne 153 Against a Panel of Cells and Tumor Cell Lines

| Cell type | Cell Line | IC$_{50}$[M] |
|---|---|---|
| Normal Cell Lines | | |
| Peripheral Blood Lymphocytes | PBL | $1.8 \times 10^{-5}$ |
| Bone Marrow | HNBM | $5.0 \times 10^{-5}$ |
| Human Mammary Epithelial Cells | HMEC | $6.3 \times 10^{-6}$ |
| Normal Human Dermal Fibroblast | NHDF | $5.0 \times 10^{-6}$ |
| Normal Human Epidermal Keratinocytes | NHEK | $3.1 \times 10^{-6}$ |
| Normal Human Epidermal Melanocytes | NHEM | $3.1 \times 10^{-6}$ |
| Chinese Hamster Ovary | CHO | $3.1 \times 10^{-6}$ |
| Cancer Cell Lines | | |
| Melanoma | SK-Mel-28 | $3.1 \times 10^{-5}$ |
| Melanoma | M-14 | $1.6 \times 10^{-6}$ |
| Melanoma | M-21 | $1.6 \times 10^{-6}$ |
| Ovarian Carcinoma | Ovcar-3 | $7.8 \times 10^{-7}$ |
| Ovarian Carcinoma | Ovcar-4 | $7.8 \times 10^{-7}$ |
| Astrocytoma | U-87 UG | $7.8 \times 10^{-7}$ |
| Glioblastoma | U-251 MG | $3.9 \times 10^{-7}$ |
| Cervical Carcinoma | SIHA | $3.9 \times 10^{-7}$ |
| Breast Carcinoma | MCF-7 | $7.8 \times 10^{-7}$ |
| Breast Carcinoma | MCF-7 (ADR) | $2.0 \times 10^{-7}$ |
| Renal Carcinoma | 786-0 | $1.9 \times 10^{-7}$ |
| Prostate Carcinoma | PC-3 | $3.9 \times 10^{-7}$ |
| Lung Carcinoma | H-322 | $3.9 \times 10^{-7}$ |
| Lung Carcinoma | H-358 | $2.0 \times 10^{-7}$ |
| Lung Carcinoma | H-522 | $9.8 \times 10^{-8}$ |
| Lung Carcinoma | UCLA P-3 | $9.8 \times 10^{-8}$ |
| Colon Carcinoma | HT-29 | $9.8 \times 10^{-8}$ |
| Pancreatic Carcinoma | Capan-1 | $3.1 \times 10^{-9}$ |
| T-Cell Leukemia | TCAF | $1.1 \times 10^{-9}$ |
| T-Cell Leukemia[a] | TCAF-DAX | $1.7 \times 10^{-9}$ |
| Myeloma | RPMI-8226 | $7.7 \times 10^{-9}$ |
| Mouse Leukemia | P-388 | $4.6 \times 10^{-9}$ |
| Mouse Leukemia | L-1210 | $1.3 \times 10^{-9}$ |
| Promyeocytic Leukemia | HL-60 | $3.6 \times 10^{-11}$ |
| T-Cell Leukemia | Molt-4 | $2.0 \times 10^{-14}$ |

[a]Multiple drug resistant cell line.

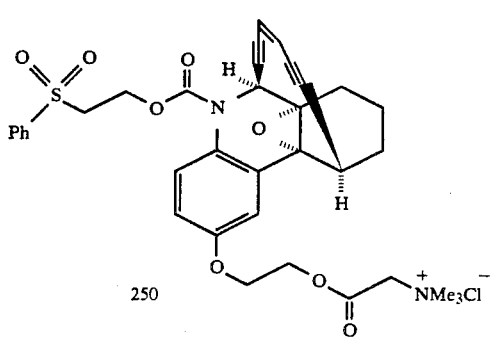

250

TABLE 5

Cytotoxicities of enediyne 250 against a panel of 11 tumor cell lines and 4 nomral cell lines.

| Cell type | Cell line | IC$_{50}$[M] |
|---|---|---|
| Cancer cell lines | | |
| Melanoma | SK-Mel-28* | $3.1 \times 10^{-6}$ |
| Colon carcinoma | HT-29 | $1.9 \times 10^{-7}$ |
| Ovarian carcinoma | Ovcar-3 | $>9.8 \times 10^{-8}$ |
| Breast carcinoma | MCF-7 | $>9.8 \times 10^{-8}$ |
| Breast carcinoma | MCF-7(ADR)** | $1.9 \times 10^{-7}$ |
| Lung carcinoma | H-322 | $1.3 \times 10^{-5}$ |
| Pancreatic carcinoma | Capan-1 | $>9.8 \times 10^{-8}$ |
| Promyeocytic leukemia | HL-60 | $>9.8 \times 10^{-8}$ |
| T-cell leukemia | Molt-4 | $\sim 10^{-4}$ |
| Prostate carcinoma | PC-3 | $1.6 \times 10^{-6}$ |
| Cervical carcinoma | SIHA | $>9.8 \times 10^{-8}$ |
| Normal cell lines | | |
| Normal human epidermal keratinocytes | NHEK | $1.6 \times 10^{-6}$ |
| Human mammary epithelial cells | HMEC | $3.1 \times 10^{-6}$ |
| Normal human dermal fibroblast | NHDF | $6.3 \times 10^{-6}$ |
| Chinese hamster ovary | CHO | $9.8 \times 10^{-8}$ |

*Multiple drug resistant cell line.
**(ADR) = Adriamycin resistance.

As will be seen from the data of the tables, the compounds and chimeras had activities similar to those of the well known anticancer drugs.

Compounds having an R$^4$ hydrogen tended to be more active than those having an R$^4$ hydroxyl or other oxygen-containing group. Compounds whose carbamate portion contained a phenylsulfonylethoxy or naphthylsulfonylethoxy group were about 10 to 100 times more active than similar compounds having a phenoxy group as part of the carbamate. Compounds having an electron releasing group relative to hydrogen para to the carbamate nitrogen atom tended to be equal to less active than those with hydrogen, whereas compounds with an intracellular-formed electron releasing group (e.g. Compounds 59a and 59b) relative to hydrogen meta to that nitrogen atom tended to be more active than compounds having hydrogen at that position.

Turning to the chimeras, the data Table 3 indicate that the chimeras are effective. Those data also indicate that the presence of the FMOC group inhibits activity, but that presence of the oxime does not. Those data also indicate that chimeras having the stereochemistry of the calicheamicin oligosaccharide are more active than those having the epimeric stereochemistry at C-4 of the A ring.

The data of the tables also show compounds and chimeras described herein to be particularly active against Molt-4 leukemia cells. Thus, for those cells, Compounds 59b, 41b, 41c and 41d exhibited IC$_{50}$ values 10,000 times more potent than the potency observed against the other cell lines. The activity of chimeric Compound 127a against Molt-4 cells was about 100-times that of the average of the other cell lines examined. Those IC$_{50}$ values against Molt-4 cells were also 10,000–100,000 times smaller than the IC$_{50}$ values for those compounds against NHDF cells.

That data in Table 4 focus exclusively on the activity of Compound 153 against a panel of twenty-five different cancer cell lines and seven "normal" cell preparations. There are significant differences in the cytotoxities of these cells lines, with IC$_{50}$ values ranging from $1.6 \times 10^{-6}$ M to an extremely low value of $2.0 \times 10^{-14}$ M against the Molt-4 leukemia cell line. This high potency may be due to the increased solubility of Compound 153 in water compared to the other enediyne compounds.

More significantly, Compound 153 showed a relative selectivity for tumor cell lines as opposed to normal, untransformed cells. For example, at a concentration of $10^{-8}$ M Compound 153, only 20 percent of Molt-4 tumor cells exhibited viability. In contrast, 100 percent of normal human mammary epithelial cells (HMEC) were viable at the same concentration. At concentrations between $10^{-6}$ and $10^{-7}$M, tumor cell lines showed a range of sensitivities, with cell viabilities ranging from 0 to 80 percent, whereas the normal HMEC were 100 percent viable at these concentrations of Compound 153. These data indicate that Compound 153 not only shows selectivity between normal and cancerous cells, but displays tumor cell selectivity as well.

The data in Table 4 also show that except for the three melanoma cell lines, Compound 153 was about one to eight orders of magnitude ($10^1$–$10^8$ times) more active against tumor cells than against "normal" cells. Another striking effect shown in Table 4 is the activity of Compound 153 against the multiple-drug resistant TCAF-DAX cell line, with an IC$_{50}$ value of $1.7 \times 10^{-9}$M compared to $1.1 \times 10^{-9}$M for TCAF.

In another study, Molt-4 leukemia cells were treated with ethidium bromide, which led to uptake by DNA through intercalcation and consequent fluorescence. Exposure of those cells to Compound 153 (10 $\mu$M at $10^7$ cells/ml) led to rapid DNA strand breakage as determined by fluorimetry, resulting in 95 percent destruction after four hours at 37° C. Cell death showed about a two-hour delay relative to DNA strand breakage. These observations implicate DNA strand cleavage as the direct cause of cell destruction in these studies.

In separate studies, Compound 153 was also shown to severely impair the ability of M-21 melanoma cells to synthesize DNA (by inhibition of [$^3$H]thymidine uptake), and protein (inhibition of [$^3$H]leucine uptake). These determinations were made by standard tissue growth procedures using RPMI tissue culture medium supplemented with 10 percent fetal bovine serum plated at $10^4$ cells in 100 $\mu$l of medium in 96-well tissue culture plates. The cells were permitted to adhere for 24 hours, and the dilutions of Compound 153 were added in 10 $\mu$l volumes and incubated for 72 hours at 37° C. in a humidified atmosphere containing five percent CO$_2$. The plates were then washed three times with tissue culture medium and again incubated for 24 hours, as above. Each well received 1 $\mu$Ci of $^3$H-labeled substrate, and after an additional 16 hours of incubation, cells were collected on glass fiber filters with a Skatron cell harvester. Finally, the filters were placed in Ecolume scintillation cocktail (ICN, Irvine, CA), and radioactivity was measured with a Beckeman scintillation counter. Incorporation of the $^3$H label was calculated as a percentage of untreated controls.

In other studies, IC$_{50}$ values were determined for the anti-tumor agents dynemicin A, calicheamicin $\gamma_1^I$, taxol, vinblastine/vincristine, doxorubicin, actinomycin D and bleomycin sulfate against the SK-Mel-28, M-14, M-21, Capan-1, Ovcar-3, Ovcar-4, UCLA-P-3, U-87, U-251 and Molt-4 cell lines. The respective IC$_{50}$ values obtained were: $10^{-7}$–$10^{-11}$, $10^{-8}$–$10^{-12}$, $10^{-7}$–$10^{-9}$, $10^{-7}$–$10^{-9}$, $10^{-6}$–$10^{-9}$, $10^{-7}$–$10^{-9}$ and $10^{-4}$–$10^{-5}$M. Those values can be compared with the Compound 153 IC$_{50}$ values for those cell lines of $10^{-6}$–$10^{-14}$M Compound 153 exhibited the highest potency amongst all of the agents assayed against the Molt-4 leukemia cell line and was comparable to most of the other agents against the other cell lines. A notable exception to that finding was bleomycin sulfate, which was considerably less active against all the cell lines. Bleomycin sulfate also acts by DNA cleavage, as do dynemicin A and calicheamicin $\gamma_1^I$.

Compound 153 was found to remain intact for 1.5 hours in a pH 7.0 phosphate buffer (100 mM) at 37° C. At higher pH values, Compound 153 was found to decompose cleanly to form phenyl vinyl sulfone and the corresponding free amine enediyne Compound 153a both of which could be detected by $^1$H NMR spectroscopy and mass spectrocopy.

The data in Table 5 for the more water soluble derivative of Compound 153, Compound 250, show similar results to those of Table 4, with a few more exceptions to the general rule.

In an in vivo study whose results are shown in FIG. 8, Balb/c mice were injected intra-peritoneally with $10^6$ P-388 leukemia cells per mouse (the cells were suspended in 100 $\mu$l RPMI medium) on day zero. Therapy was started on day 1 by injecting each group of four animals with the indicated dose of Compound 45, which was administered only once in this assay. The course of therapy was followed by tumor-induced weight change in the animals and by recording death incidents (arrows). The control mice exhibited a rapid exponential weight gain and were euthanized on day 20 due to excessive weight. Animals treated with 12 mg/kg Compound 45 showed a similar but slower weight increase, and on day 20 three of the four animals died. Animals treated with 50 mg/kg Compound 45 showed a rapid weight loss followed by death within 8 days. At the dose of 25 mg/kg Compound 45, the increase in life span over the control group was 175 percent (therapeutic group/control group). Normal mice (non-leukemic mice) exhibit a negligible weight gain over the time period of this study.

The data of FIG. 10 illustrate a further in vivo study using Compound 153. Here, groups of 6–10 week old, female Balb/c BYJ mice (obtained from The Scripps Research Institute breeding colony, La Jolla, CA) 8 per group) were inoculated with $5 \times 10^5$ cells of the EMT6 tumor cell line, a mammary tumor. The mice were then treated with normal saline (control) or normal saline containing 10 mg/kg of Compound 153 (study) on days 1, 5 and 9 after the inoculation.

The average tumor volume was then calculated for each group of mice. As can be seen from the graph of FIG. 10, by day 8 post inoculation, there was a slight difference in the average volume of the tumors, with the study group having a lower tumor burden. By day 20 post inoculation, the control group's average tumor volume was about seven times that of the study group. The data of FIG. 10 also show that by the end of the study period, the untreated, control tumors were growing rapdily, whereas tumor growth of the treated, study tumors was much slower, and almost linear.

An exemplary study was carried out to illustrate that a synthesized endiyne could be linked to a monoclonal antibody (Mab) to form a stable chimer without starting the Bergman cyclization cascade. Compound 153 was used for these studies and was first reacted with glutaric anhydride to form the corresponding glutarate half-ester, Comnpound 402. The free carboxyl group was then converted into an N-hydroxyl succinimidyl ester, Compound 403. Compound 403 was thereafter reacted with Mab KS1/4. Mab KS1/4 binds to the surface of a number of neoplastic cell lines. [Varki et al., *Cancer Res.*, 44:681 (1984); Bumol et al., *Hybridoma*, 7:407 (1988)] These steps are outlines in Scheme XXII, below.

Based on a presumed molecular weight of 150,000 for the Mab and using optical density measurements to determine the relative amounts of Mab (280 nm) and enediyne (302 nm) present, the chimer Compound 404 was determined to contain an average of about eleven enediyne molecules per Mab molecule.

Scheme XXII

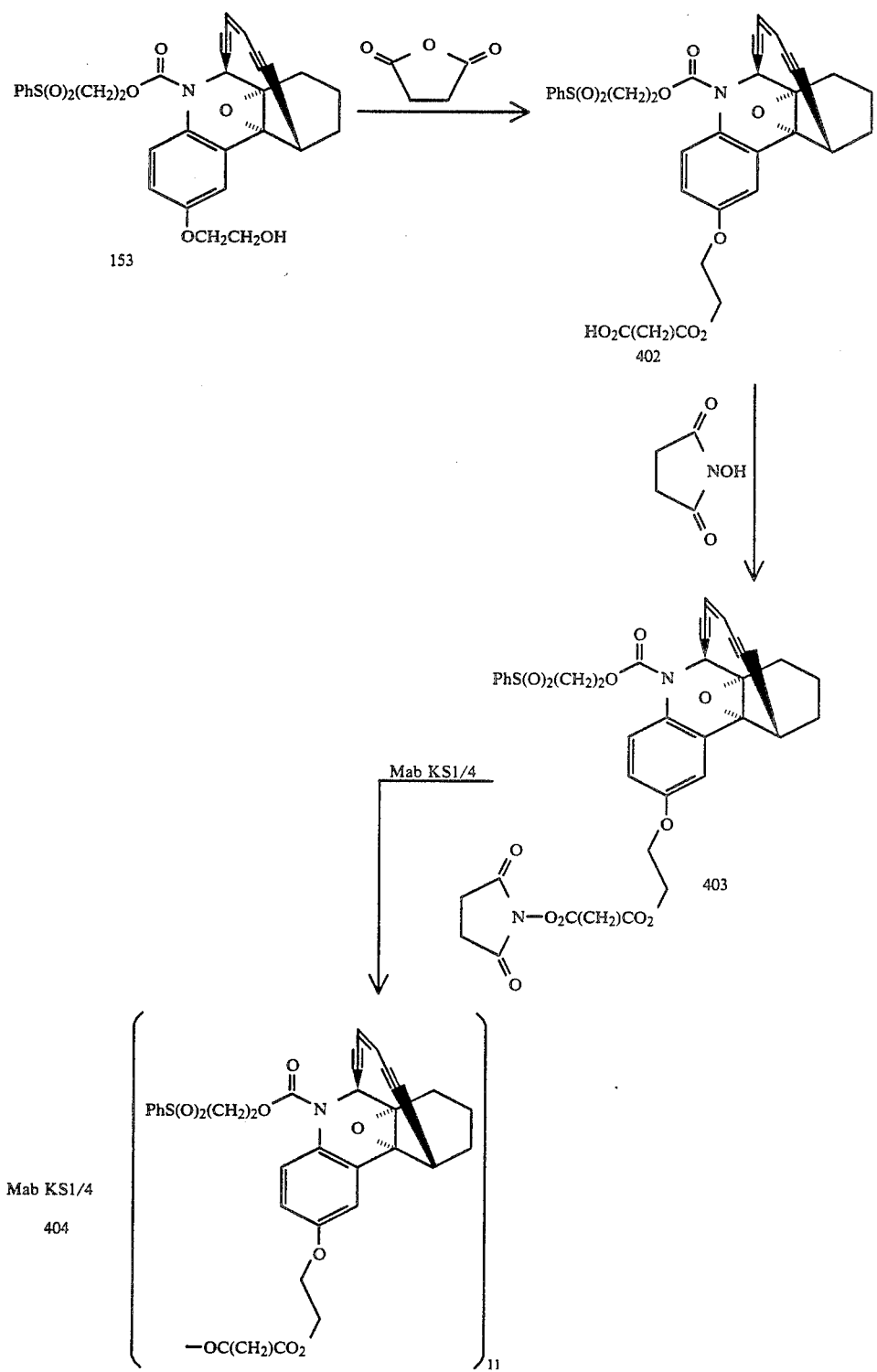

The resulting chimer, Compound 404, was separated from the reaction mixture by gel chromatography.

Chimer Compound 404 was then assayed for its ability to bind to target neoplastic cells using cells of the UCLA-P3 cell line, to which Mab Ks-1/4 is known to bind [Bumol et al., Hybridoma, 7:407 (1988)]. The results of that binding study showed that the chimer bound to the neoplastic cells in a manner similar to that of the free Mab at concentrations of about $10^{-12}$–$10^{-9}$ molar, and more tightly up to about $10^{-6}$ molar. Similar findings were made with Ocvar 3 cells.

Compound Preparation and Data

General Techniques: Melting points were recorded on a METTLER FP62 apparatus and are not corrected. NMR spectra were recorded on a Bruker AM-300 or AMX-500 instrument. IR spectra were recorded on a Nicolet 205 FT-IR spectrophotometer. Low-resolution mass spectra (MS) or high-resolution mass spectra (HRMS) were recorded on a VG ZAB-ZSE mass spectrometer under positive fast atom bombardment (FAB+) conditions. Elemental analyses were performed by Robertson Microlit Laboratories, Inc., Madison, NJ.

All reactions were monitored by thin-layer chromotagraphy carried out on 0.25 mm E. Merck silica gel plates (60F-254) using UV light, 7 percent ethanolic phosphomolybdic acid and heat as developing agent. Preparative thin-layer chromatography (preparative TLC) was performed on 0.5 mm×20 cm×20 cm E. Merck silica gel plates (60F-254). E. Merck silica gel (60, particle size 0.040–0.063 mm) was used for flash column chromatography.

All reactions were carried out under an argon atmosphere with dry, freshly distilled solvents under anhydrous conditions unless otherwise noted. Yields refer to chromatographically and spectroscopically ($^1$H NMR) homogeneous materials, unless otherwise stated.

EXAMPLE 1:

7,8,9,10-Tetrahydrophenanthridine N-oxide (Compound 4a)

A solution of 4 (1.42 g, 7.76 mmol) in dichloromethane (50 mL) was treated at 25° C. with mCPBA (1.58 g of an 85 percent sample, 7.76 mmol) and stirred for 1 hour. The solution was poured into saturated sodium bicarbonate solution (50 mL) and extracted. The aqueous layer was extracted with further dichloromethane (2×50 mL), the combined organic layers were dried (Na$_2$SO$_4$), evaporated in vacuo, and the residue was purified by flash chromatography on silica eluting with 25 percent MeOH in EtOAc to give the pure N-oxide Compound 4a (1.24 g, 80 percent) as an off-white crystalline solid: R$_f$=0.34 (25 percent MeOH in EtOAc); mp 131.7° C. (from EtOAc); IR (CDCl$_3$) $\nu_{max}$ 2950, 1580, 1390, 1300, 1210, 1140 cm$^{-1}$; $^1$H NMR (500 MHz, CDCl$_3$): δ8.72 (d, J=8.3 Hz, 1 H, H-4), 8.31 (s, 1 H, H-6), 7.91 (d, J=8.3 Hz, 1 H, H-1), 7.68 (t, J=8.3 Hz, 1 H, H-2 or H-3), 7.61 (t, J=8.3 Hz, 1 H, H-2 or H-3, 3.02 (t, J=6.3 Hz, 2 H, H-10), 2.79 (t, J=6.3 Hz, 2 H, H-7), 1.98–1.84 (m, 4 H); MS (FAB+) m/e (relative intensity) 200 (M+H, 100), 184 (12); HRMS calcd for C$_{13}$H$_{14}$NO (M+H) 200.1075, found 200.1055.

EXAMPLE 2

Compound 2

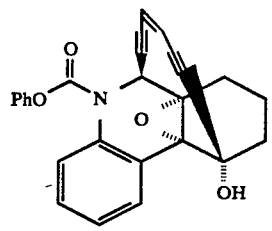

A solution of enediyne 3 (205 mg, 0.50 mmol) in dry THF (10 mL) was cooled to −78° C. and treated with lithium diisopropylamide (0.37 mL of a 1.5 M solution in cyclohexane, 0.56 mmol). After stirring 1 hour at −78° C., the reaction was quenched with saturated ammonium chloride solution (2 mL), allowed to warm to room temperature, poured into saturated sodium bicarbonate solution (30 mL), and extracted with dichloromethane (3×50 mL). The combined organic extracts were dried (Na$_2$SO$_4$), evaporated in vacuo, and purified by flash chromatography on silica eluting with 50 percent ether in petroleum ether to give recovered 3 (48 mg, 23 percent), followed by the ten-membered enediyne Compound 2 (120 mg, 59 percent) as a white crystalline solid: R$_f$=0.42 (50 percent ether in petroleum ether); mp=228°–230° C. dec. (from ether); IR (CDCl$_3$) $\nu_{max}$ 3420, 2360, 2330, 1720 cm$^{-1}$; $^1$H NMR (500 MHz, CDCl$_3$): δ8.60 (dd, J=8.1, 1.3 Hz, 1 H, aromatic), 7.47–7.10 (series of multiplets, 8 H, aromatic), 5.83 (d, J=01.1 Hz, 1 H, olefinic), 5.67 (dd, J=10.1, 1.6 Hz, 1 H, olefinic), 5.53 (d, J=1.6 Hz, 1 H, C H-N), 2.35–1.71 (series of multiplets, 6 H, C H$_2$); $^{13}$C NMR (125 MHz, CDCl$_3$): δ151.0, 135.8, 131.3, 129.3, 128.0, 127.8, 126.3, 125.8, 125.3, 124.0, 122.2, 121.6, 100.4, 94.3, 93.9, 88.8, 74.1, 73.2, 64.4, 50.5, 35.4, 23.2, 19.1; MS: m/e (relative intensity) 409 (26, M+), 368 (18), 236 (11), 162 (13), 131 (100); HRMS: calcd. for C$_{26}$H$_{19}$NO$_4$: 409.1314, found: 409.1314; Anal. calcd. for C$_{26}$H$_{19}$NO$_4$·H$_2$O: C, 73.06; H, 4.95; N, 3.28. found: C, 73.44; H, 5.04; N, 3.26.

Compounds 2b-d were prepared from Compound 2 by reaction of Compound 2 with a mixture of the appropriate alcohol and its sodium salt.

EXAMPLE 3

N-Phenyloxycarbonyl-6-(3(Z)-hexene-1,5-diynyl)-6a:1-0a-epoxy-10-oxo-5,6,6a,7,8,9,10,10a octahydrophenanthridine (Compound 3)

Silver nitrate (5.28 g, 31.2 mmol) was added to solution of the silyl acetylene Compound 13 (4.50 g, 9.36 mmol) in 100 mL of a H 20-EtOH-THF mixture (1:1:1) at 25° C., and the mixture was stirred until TLC analysis (30 percent ether in petroleum ether) indicated the consumption of 13 (approximately 1 hour). Potassium cyanide (4.32 g, 57.6 mmol) was then added and the mixture was stirred for 10 minutes. The mixture was poured into saturated sodium bicarbonate solution (100 mL) and extrated with dichloromethane (3×100 mL). The combined organic layers were dried (Na$_2$SO$_4$), evaporated in vacuo, and purified by flash chromatography on silica eluting with 30 percent ether in petroleum ether to give enediyne Compound 3 (2.30 g, 60 percent) as a colorless gum: R$_f$=0.38 (30 percent ether in petroleum ether); IR (CDCl$_3$) $\nu_{max}$ 3304, 2940, 2240, 1720, 1492, 1378, 1321, 1206 cm$^{-1}$; $^1$H NMR (500 MHz, CDCl$_3$): δ8.87 (dd, J=7.8, 1.4 Hz, 1 H, H-4), 7.53-7.09 (m, 8 H, aromatic), 5.93 (d, J=1.2 Nz, 1 H, H-6), 5.78 and 5.79 (AB quartet, J=10.1 Hz, 2 H, olefinic), 3.16 (d, J=1.2 Hz, 1 H, C≡C—H), 2.79-2.66 (m, 2 H, H-9), 2.38-2.29 (m, 2 H, H7), 2.04-1.89 (m, 2 H, H-8); $^{13}$C NMR (125 MHz, CDCl$_3$): δ150.9, 135.9, 130.0, 129.3, 128.8, 127.6, 125.9, 125.8, 123.0, 121.4, 120.4, 120.2, 90.6, 85.1, 82.8, 80.1, 75.1, 57.4, 48.1, 38.9, 23.9, 18.3; MS m/e (relative intensity) 409 (2, M+), 262(15), 212(18), 162(59), 58(100); HRMS: calcd. for C$_{26}$H$_{19}$NO$_4$: 409.1314, found: 409.1308.

EXAMPLE 4

10-Acetoxy-7,8,9,10-tetrahydrophenanthridine (Compound 5)

A solution of 7,8,9,10-tetrahydrophenanthridine N-oxide (Compound 4a) 1.23 g, 6.18 mmol) in acetic anhydride (50 mL) was heated to 100° C. for 20 hours, evaporated to dryness, dissolved in dichloromethane (50 mL) and washed with saturated sodium bicarbonate solution (50 mL). The aqueous layer was extracted with dichloromethane (2×50 mL), the combined organic layers were dried (Na$_2$SO$_4$), evaporated in vacuo, and the residue was purified by flash chromatography on silica eluting with Et$_2$O to give pure Compound 5 (1.15 g, 77 percent ) as a white crystalline solid: R$_f$=0.33 (ether); mp=128°-129° c. (from ether); IR (CDCl$_3$) $\nu_{max}$ 2970, 1728, 1241 cm$^{-1}$; $^1$H NMR (500 MHz, CDCl$_3$): δ8.70 (s, 1 H, H-6), 8.08 (d, J=9.5 Hz, 1 H, H-4), 7.76 (d, J=9.5 Hz, 1 H, H-1), 7.63 (t, J=7.2 Hz, 1 H, H-2 or H-3), 7.52 (t, J=7.2 Hz, 1 H, H-2 or H-3), 6.57 (bs, 1 H, CH—OAc), 3.02 (bd, J=17.5 Hz, 1 H, H-7), 2.88-2.80 (m, 1 H, H-7), 2.27 (bd, J=13.8 Hz, 1 H, H-9), 2.05 (s, 3 H, OAc), 2.01-1.88 (m, 3 H); $^{13}$C NMR (125 MHz, CDCl$_3$): δ1702.2, 152.3, 147.5, 137.8, 131.8, 130.1, 127.9, 127.0, 126.8, 122.2, 64.5, 29.1, 27.8, 21.7, 18.4; MS (FAB+) m/e (relative intensity) 242 (M+H, 100), 182 (23); HRMS calcd. for C$_{15}$H$_{16}$NO$_2$ (M+H) 242.1181, found 242.1181; Anal. calcd. for C$_{15}$H$_{15}$NO$_2$; C, 74.67; H, 6.27; N, 5.80. Found: C, 74.59; H, 6.31; N, 5.82.

EXAMPLE 5

10-Hydroxy-7,8,9,10-tetrahydrophenanthridine (Compound 6)

A solution of Compound 5 (1.15 g, 4.77 mmol) in methanol (50 mL) was treated with potassium carbonate (200 mg, catalytic) and stirred for 1 hour. The solution was poured into saturated sodium bicarbonate solution (100 mL) and extracted with dichloromethane (1×100 mL, 2×50 mL). The combined organic layers were dried (MgSO$_4$), evaporated in vacuo, and the residue was purified by flash chromatography on silica eluting with ethyl acetate to give alcohol Compound 6 (0.95 g, 100 percent) as a white crystalline solid: R$_f$=0.20 (ether); mp=176°-177° C. (from ether); IR (CDCl$_3$) $\nu_{max}$ 3600, 2950, 1510 cm$^{-1}$; $^1$H NMR (500 MHz, CDCl$_3$): δ8.51 (s, 1 H, H-6), 8.20 (d, J=9.1 Hz, 1 H, H-4), 8.00 (d, J=9.1 Hz, 1 H, H-1), 7.61 (t, J=6.8 Hz, 1 H, H-2 or H-3), 7.55 (t, J=6.8 Hz, 1 H, H-2 or H-3), 5.39 k (bs, 1 H, CH—OH), 2.89 (bd, J=16.1 Hz, 1 H, H-7), 2.80-2.72 (m, 1 H, H-7), 2.80-2.60 (bs, 1 H, OH), 2.24 (bd, J=12.5 Hz, 1 H, H-8 or H-9), 2.07-1.88 (m, 3 H); MS (FAB+) m/e (relative intensity) 200 (M+H, 100), 154 (41), 136 (37), 109 (24); HRMS calcd. for C$_{13}$H$_{14}$NO (M+H) 200.1075, found 200.1085.

EXAMPLE 6

10-tert-Butyldimethylsilyloxy-7,8,9,10-tetrahydrophenanthridine (Compound 7)

A solution of Compound 6 (3.70 g, 18.6 mmol) in dry dichloromethane (100 mL) was treated with 2,6-lutidine (3.4 mL, 27.9 mmol) and tert-butyl-dimethylsily triflate (5.35 mL, 22.3 mmol). After stirring for 1 hour at 25° C., methanol (2 mL) was added, stirring was continued for a further 5 minutes, and then the solution was poured into saturated sodium bicarbonate solution (100 mL) and extracted. The aqueous layer was extracted with further dichloromethane (2×50 mL), the combined organic layers were dried (Na$_2$SO$_4$), evaporated in vacuo and the residue was purified by flash chromatography on silica eluting with 50 percent ether in petroleum ether to give pure silyl ether Compound 7 (5.38 g, 92 percent) as a white solid. 7: colorless oil; R$_f$=0.50 (70 percent ether in petroleum ether); IR (CDCl$_3$) $\nu_{max}$ 2970, 2930, 2860 cm$^{-1}$; $^1$H NMR (500 MHz, CDCl$_3$): δ8.68 (s, 1 H, H-6), 8.08 (d, J=4.7 Hz, 1 H, H-1 or H-4), 8.05 (d, J=4.7 Hz, 1 H, H-1 or H-4), 7.62 (t, J=4.7 Hz, 1 H, H-2 or H-3), 7.53 (t, J=4.7 Hz, 1 kH, H-2 or H-3), 5.45 (t, J=2.8 Hz, 1 H, H-10), 3.00 (dd, J=5.5, 16.6 Hz, 1 H, CH—Ar), 2.81 (m, 1 H, CH—Ar), 2.23-2.10 (m, 2 H, CH$_2$), 1.88-1.78 (m, 2 H, CH$_2$), 0.84 (s, 9 H, $^t$Bu), 0.22 (s, 6 H, SiME$_2$); $^{13}$C NMR (125 MHz, CDCl$_3$): δ152.8, 147.0, 141.2, 129.8, 129.3, 127.9, 126.9, 126.1, 123.6, 63.2, 31.8, 27.0, 25.8, 18.2, 16.4, −3.6, −4.5; MS (FAB+) m/e (relative intensity) 314 (M+H, 100), 256 (7), 182 (11); HRMS calcd. for C$_{19}$H$_{28}$NOSi (M+H) 314.1940, found 314.1951.

EXAMPLE 7

N-Phenyloxycarbonyl-10-tert-butyldimethylsilyloxy-6-ethyl-5,6,7,8,9,10-hexahydrophenanthridine (Compound 8)

A solution of quinoline Compound 7 (5.20 g, 16.6 mmol) in dry THF (166 mL) was cooled to −78° C. and treated with ethnylmagnesium bromide (36.5 mL of a 0.5 M solution in THF, 18.3 mmol) followed by phenyl chloroformate (2.3 mL, 18.3 mmol). The solution was allowed to warm up slowly to 25° C. over 1 hour, quenched with saturated ammonium chloride solution (10 mL), poured into saturated sodium bicarbonate solution (150 mL) and extracted. The aqueous layer was extracted with dichloromethane (2×100 mL), the combined organic layers were dried (Na$_2$SO$_4$), evaporated in vacuo, and purified by flash chromatography on silica eluting with 10 percent ether in petroleum ether to give pure carbamate Compound 8 (6.96 g, 92 percent) as a colorless oil (about 3:1 mixture of isomers as judged by NMR). R$_f$=0.85 (30 percent ether in petroleum ether); IR (CDCl$_3$) $\nu_{max}$ 3300, 2952, 2858, 2250, 1715, 1473, 1204 cm$^{-1}$; $^1$H NMR (500 MHz, CDCl$_3$): δ7.68 (d, J=7.5 Hz, 1 H, H4), 7.40-7.12 (m, 8 H), 5.68, 5.61 (2×s, 1 H, H-6), 5.00, 4.69 (2×bs, 1 H, H-10), 2.50-1.50 (m, 7 H), 0.80, 0.92 (2×s, 9 H, $^t$Bu), 0.28, 0.19, 0.10, 0.09 (singlets, 6 H, SiMe$_2$); $^{13}$C NMR (125 MHz, CDCl$_3$): δ151.1, 136.3, 132.9, 129.8, 129.3, 127.2, 126.0, 125.4, 125.1, 124.2, 124.1, 123.9, 122.0, 80.2, 72.3, 65.0 and 64.2, 48.7 and 48.2, 32.3 and 31.3, 28.0, 26.1, 18.4 and 16.3, −4.1 and −4.8; MS m/e (relative intensity) 459 (M+, 10), 402 (100), 366 (10), 308 (24), 206 (26), 151 (27), 75 (29); HRMS calcd. for C$_{28}$H$_{33}$O$_3$NSi (M+): 459.2230, found: 459.2233.

EXAMPLE 8

N-Phenyloxycarbonyl-10-tert-butyldimethylsilyloxy-6a:10a-epoxy-6-ethyl-5,6,6a,7,8,9,10,10a-octahydrophenanthridine (Compound 9)

A solution of Compound 8 (8.60 g, 18.8 mmol) in dichloromethane (120 mL) was treated with mCPBA (8.08 g of a 60 percent sample, 37.6 mmol) and stirred at 25° C. for 3 hours. The solution was poured into saturated sodium bicarbonate solution (100 mL), extracted, and the aqueous layer extracted with further dichloromethane (2×100 mL). The combined organic layers were dried ($Na_2SO_4$), evaporated in vacuo, and the residue was purified by flash chromatography on silica eluting with 10 percent ether in petroleum ether to give epoxide Compound 9 (8.20 g, 92 percent) as a white foam (mixture of two isomers, about 3:1 ratio); $R_f$=0.73 (30 percent ether in petroleum ether); IR ($CDCl_3$) $\nu_{max}$ 3307, 2953, 2250, 1721, 1494, 1384, 1322, 1250, 1207 cm$^{-1}$; $^1$H NMR (500 MHz, $CDCl_3$): δ7.88 (d, J=7.1 Hz, 1 H, H-4), 7.50–7.10 (M, 8 H), 5.58 (bs, 1 H, H-6), 4.82 (dd, J=10.0, 5.7 Hz, 1 H, H-10), 2.34 (dd, J=14.8, 5.6 Hz, 1 H), 2.09 (bs, 1 H), 1.95–1.85 (m, 2 H), 1.78–1.62 (m, 2 H), 1.40–1.30 (m, 1 H); $^{13}$C NMR (125 MHz, $CDCl_3$): δ153.9 and 151.1, 135.5, 129.2, 129.2, 129.1, 128.3, 128.1, 127.9, 127.1, 125.5, 121.6, 78.5, 73.8, 72.8, 69.9, 60.4, 48.0, 31.0 and 29.6, 26.0 and 25.8, 24.0, and 26.5, 18.2 and 20.3, −0.28, −0.28, −0.37; MS: m/e (relative intensity) 475(M+,2), 419 (100), 325 (28), 268 (10), 222 (14), 151 (18), 73 (42); HRMS: calcd. for $C_{28}H_{33}O_4NSi$ (M+): 475.2179, found: 475.2175.

EXAMPLE 9

N-Phenyloxycarbonyl-6a:10a-epoxy-6-ethyl-10-hydroxy-5,6,6a,7,8,9,10,10a-octahydrophenanthridine (Compound 10)

A solution of epoxide Compound 9 (8.20 g, 17.4 mmol) in THF (100 mL) was treated with TBAF (20.9 mL of a 1M solution in THF, 20.9 mmol) and heated to 42° C. for three hours. The solution was evaporated in vacuo and purified by flash chromatography on silica eluting with 50 percent $Et_2O$/petroleum ether to give pure alcohol Compound 10 (6.00 g, 100 percent) as a white crystalline solid (about 3:1 mixture of isomers as shown by NMR). $R_f$=0.31 (50 percent ether in petroleum ether); mp 78°–79° C. (from $Et_2O$); IR ($CDCl_3$) $\nu_{max}$ 3580, 3306, 2951, 2250, 1720, 1595, 1494, 1382, 1322, 1206 cm$^{-1}$; $^1$H NMR (500 MHz, $CDCl_3$): δ7.91 and 7.88 (d, J=8.0 Hz, 1 H, H-4), 7.50–7.08 (m, 8 H), 5.62 and 5.59 (d, J=1.0 Hz, 1 H, H-6), 4.89 and 4.70 (m, 1 H, H-10), 2.47–1.35 (m, 8 H); $^{13}$C NMR (125 MNz, $CDCl_3$): δ150.9, 135.5, 129.3, 128.7, 128.6, 128.4, 127.7, 127.3, 126.1, 125.8, 121.5, 78.7 and 78.2, 74.8 and 70.8, 73.2, 66.6, 65.9 and 64.4, 60.9 and 58.2, 47.8, 30.3 and 27.0, 24.1 and 19.0, 15.2 and 13.8; MS m/e (relative intensity) 361 (M+, 65) 224 (100), 196 (24), 180 (29), 167 (30), 94 (40), 77 (45); HRMS: calcd. for $C_{22}H_{19}NO_4$ (M+); 361.1314, found: 361.1317.

EXAMPLE 10

N-Phenyloxycarbonyl-6a:10a-epoxy-6-ethyl-10-oxo-5,6,6a,7,8,9,10,10a-octahydrophenanthridine (Compound 11)

Alcohol Compound 10 (6.009, 17.4 mmol) was dissolved in dry dichloromethane (180 mL) and treated with powdered, activated 5Å molecular sieves (1 g) and pyridinium chlorochromate (6.25 g, 29.0 mmol). The suspension was stirred for 1 hour at 25° C., filtered through celite, concentrated in vacuo, and the residue was purified by flash chromatography on silica eluting with 30 percent $Et_2O$/petroleum ether to give ketone Compound 11 (4.49 9,75 percent) as a white foam: $R_f$=0.51 (50 percent ether in petroleum ether); IR ($CDCl_3$) $\nu_{max}$ 3306, 2259, 1721, 1491, 1321, 1206 cm$^{-1}$; $^1$H NMR (500 MHz, $CDCl_3$): δ8.50 (d, J=7.8 Hz, 1 H, H-4), 7.53–7.10 (m, 8 H, aromatic), 5.73 (d, J=2.4 Hz, 1 H, H-6), 2176 (dt, J=15.2, 4.9 Hz, 1 H, H-9), 2.60 (ddd, J=15.2, 10.4, 6.1 Hz, 1 H, H-9), 2.37–2.28 (m, 2 H, H-7), 2.21 (bs, 1 H, C{C—H), 2.04–1.90 (m, 2 H, H-8); $^{13}$C NMR: (125 MHz, $CDCl_3$): δ201.0, 153.9, 151.0, 135.8, 129.9, 129.3, 129.0, 127.6, 126.1, 125.9, 123.0, 121.5, 77.7, 74.9, 74.2, 57.4, 47.3, 38.9, 23.8, 18.3; MS m/e (relative intensity) 359 (M+, 100), 266 (52), 222 (65), 194 (54), 180 (51), 146 (45), 69 (80); HRMS calcd. for $C_{22}H_{17}NO_4$ (M+): 359.1158, found: 359.1154; anal. calcd. for $C_{22}H_{17}NO_4$: C, 73.53; H, 4.77; N, 3.90. Found: C, 73.27; H, 4.79; N, 3.91

EXAMPLE 11

N-Phenyloxycarbonyl-6-[6-trimethylsilyl-3(Z)-hexene-1,5-diynyl]-6a:10a-epoxy-10-oxo-5,6,6a,7,8,9,10,10a-octahydrophenanthridine (Compound 13)

Palladium$^{II}$ acetate (192 mg, 0.86 mmol) and triphenylphosphine (832 mg, 3.17 mmol) in dry, degassed benzene (10 mL) were heated under argon at 60° c. for 1 hour. The resulting dark red solution was cooled to 25° C., and the (Z)-chloroenyne Compound 12 (2.88 g, 18.2 mmol) in dry, degassed benzene (20 mL) was added, followed by n-butylamine (1.92 mL, 19.4 mmol). The solution was stirred for 15 minutes at 25° C., cooled to zero degree c, and the acetylene 11 (4.49 g, 12.5 mmol) in dry, degassed benzene (50 mL) was added, followed by copper (I) iodide (512 mg, 2.69 mmol). The solution was stirred for 2 hours at 25° C., poured into saturated sodium bicarbonate solution (100 mL) and extracted. The aqueous layer was extracted with dichloromethane (2×50 mL), the combined organic layers were dried ($Na_2SO_4$), evaporated in vacuo, and the residue was purified by flash chromatography on silica eluting with 20 percent ether in petroleum ether to give the coupled product Compound 13 (4.50 g, 74 percent) as a colorless gum: $R_f$=0.51 (30 percent ether in petroleum ether); IR ($CDCl_3$) $\nu_{max}$ 2962, 1720, 1492, 1378, 1322, 1252, 1206, 846 cm$^{-1}$; $^1$H NMR (500 MHz, $CDCl_3$): δ8.36 (d, J=8.5 Hz, 1 H, H-4), 7.52–7.09 (m, 8 H, aromatic), 5.99 (d, J=1.6 Hz, 1 H, H-6), 5.82 (d, J=11.2 Hz, 1 H, olefinic), 5.66 (dd, J=11.2, 1.6 Hz, 1 H, olefinic), 2.76 (dt, J=15.3, 4.7 Hz, 1 H, H-9), 2.71 (ddd, J=15.3, 10.8, 6.1 Hz, 1 H, H-9), 2.39–2.30 (m, 2 H, H-7), 2.07–1.89 (m, 2 H, H-8), 0.25 (s, 9 H, $SiMe_3$); $^{13}$C NMR (125 MHz, $CDCl_3$): δ201.1, 150.9, 135.8, 129.9, 129.2, 128.9, 128.4, 127.7, 126.0, 125.8, 122.9, 121.4, 120.8, 118.9, 103.6, 101.5, 90.4, 83.0, 74.9, 57.5, 48.3, 38.9, 23.9, 18.2, 0.00; MS m/e (relative intensity) 481 (M+11), 360 (100), 146 (10); HRMS: calcd. for $C_{29}H_{27}O_4NSi$ (M+): 481.1709, found: 481.1705.

EXAMPLE 12

Compound 2a

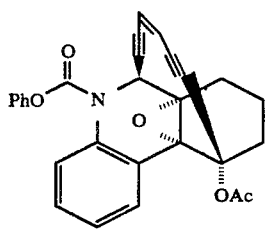

A solution of enediyne Compound 2 (100.1 mg, 0.224 mmol) in pyridine (2 mL) was treated with acetic anhydride (0.50 mL, 5.31 mmol) and DMAP (10 mg, catalytic) at 25° C. After 2 hours, the reaction mixture was poured into saturated sodium bicarbonate solution (25 mL), extracted with dichloromethane (3×25 mL), the combined organic layers were dried ($Na_2SO_4$), evaporated in vacuo, and the residue was purified by flash chromatography (silica, 30 percent ether in petroleum ether) to give acetate Compound 2a (110.7 mg, 100 percent). Compound 2a: white crystalline solid, mp 212°-214° C. dec. (from ether); $R_f$=0.55 (50 percent ether in petroleum ether); IR ($CDCl_3$) $\nu_{max}$ 3075, 2950, 2215, 1742, 1720, 1500, 1216, 769 cm$^{-1}$; $^1$H NMR (500 MHz, $CDCl_3$): δ7.92 (d, J=8.1 Hz, 1 H, aromatic), 7.50-7.09 (m, 8 H, aromatic), 5.83 (d, J=10.1 Hz, 1 H, olefinic), 5.65 (d, J=10.1 Hz, 1 H, olefinic), 5.53 (s, 1 H, N—CH(C)—C), 2.51-1.70 (m, 6 H, $CH_2$), 2.18 (s, 3 H, OAc); $^{13}$C NMR (125 MHz, $CDCl_3$): δ169.1, 150.8, 130.0, 129.3, 128.4, 128.1, 128.0, 127.2, 126.8, 125.7, 125.2, 124.3, 122.9, 121.5, 97.9, 96.5, 93.7, 88.9, 78.0, 73.5, 62.6, 50.3, 29.8, 22.7, 21.8, 18.8; MS (FAB+) m/e (relative intensity) 452 M+H, 52), 410 (37), 392 (100), 316 (32), 272 (43), 242 (30), 154 (77), 136 (70); HRMS calcd. for $C_{28}H_{28}NO_5$ (M+H) 452.1498, found 452.1469.

A solution of enedyne Compound 2a (93.0 mg, 0.206 mmol) and 1,4-cyclohexadiene (1.0 mL) in benzene (3.0 mL) was treated with p-toluene-sulfonic acid (39 mg, 0.23 mmol) and stirred at 60° C. for 2 hours. The solvent was removed in vacuo and the residue purified by flash chromatography (silica, 50 percent ether in petroleum ether) to give diol acetate Compound 15a (80.2 mg, 83 percent). Compound 15a: while crystalline solid, mp198°-200° C. (from ether).

EXAMPLE 13

Compound 15

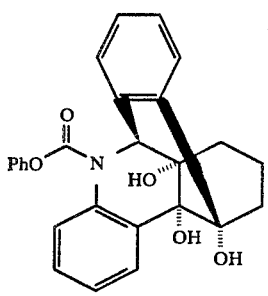

Colorless solid: $R_f$=0.22 (50 percent ether in petroleum ether); IR ($CDCl_3$) $\nu_{max}$ 3360, 3072, 2950, 1738, 1715, 1500, 1192 cm$^{-1}$; $^1$H NMR (500 MHz, $CDCl_3$):

δ7.57 (d, J=7.8 Hz, 1 H, aromatic), 7.40-7.01 (series of multiplets, 12 H, aromatic), 6.83 (bs, 1 H, O H), 5.59 (s, 1 H, N-C H(C)-C), 3.17 (m, 1 H, $CH_2$), 2.28 (m, 1 H, $CH_2$), 2.26 (s, 3 H, OAc), 1.80-1.40 (series of multiplets, 3 H, $CH_2$), 0.72 (m, 1 H, $CH_2$); $^{13}$C NMR (125 MHz, $CDCl_3$): δ174.9, 150.8, 137.7, 134.8, 133.5, 129.7, 129.3, 129.2, 129.0, 128.8, 128.5, 128.2 127.8, 127.7, 125.5, 124.8, 123.4, 121.8, 93.8, 75.1, 70.6, 61.4, 32.5, 31.4, 22.6, 19.8; MS: m/e (relative intensity) 471 (M+, 19), 245 (100), 162 (100), 94 (42); HRMS: calcd. for $C_{28}H_{25}O_6N$ (M+): 471.1682, found: 471.1683; Anal. calcd. for $C_{28}H_{25}O_6N$: C, 71.33; H, 5.34; N, 2.97. Found: C, 71.36; H, 5.54; N, 2.84.

EXAMPLE 14

Compound 15b

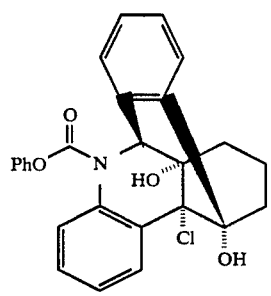

Dry HCl gas was bubbled through a solution of acetate Compound 2a (32 mg, 0.071 mmol) and 1,4-cyclohexadiene (40 mg, 0.32 mmol) in dichloromethane (4 mL) at 25° C. for 30 seconds. The solvent was removed in vacuo and the residue purified by flash chromatography (silica, 50 percent ether in petroleum ether) to give the chloride, Compound 15b (25 mg, 80 percent).

Colorless gum; $R_f$=0.21 (50 percent ether in petroleum ether); IR ($CDCl_3$) $\nu_{max}$ 3500, 2945, 1710, 1492, 1400, 1225, 789 cm$^{-1}$; $^1$H NMR (500 MHz, $CDCl_3$): δ7.72 (d, J=8.1 Hz, 1 H, aromatic), 7.45-6.96 (m, 12 H, aromatic), 5.85 (s, 1 H, benzylic), 2.56 (bs, 1 H, OH), 2.37 (bs, 1 H, OH), 2.34-1.42 (m, 6 H, $CH_2$); $^{13}$C NMR (125 MHz, $CDCl_3$): δ 151.2, 134.7, 132.6, 130.4, 129.4, 129.3, 128.6, 128.5, 128.2, 128.2, 128.1, 127.5, 125.7, 124.5, 124.2, 124.0, 121.7, 81.2, 80.4, 70.2, 62.7, 35.4, 33.7, 18.8; MS (FAB+): m/e (relative intensity) 580 (M+Cs, 100), 419 (42), 286 (100), 154 (37); HRMS: Calcd. for $C_{26}H_{22}O_4NClCs$ (M+Cs): 580.0291, found: 580.0286.

EXAMPLE 15

Compound 17

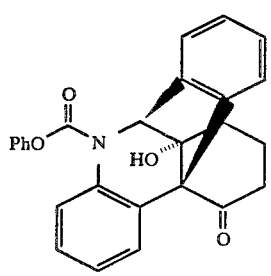

Compound 17 has been prepared by several methods as indicated below.

Method (i): A solution of the cobalt complex Compound 19 (42 mg, 0.060 mmol) in CH$_2$Cl$_2$ (1 mL) was treated with Et$_3$N+—O$^-$ (32.7 mg, 0.29 mmol) and stirred at 25° C. for 4 hours. The solution was poured into saturated sodium bicarbonate solution (25 mL) and extracted with CH$_2$Cl$_2$ (3×25 mL). The combined organic layers were dried (MgSO$_4$), evaporated in vacuo and purified by flash chromatography to give the aromatized product Compound 17 (17.7 mg, 83 percent).

Method (ii): A solution of enediyne Compound 2 (57.8 mg, 0.141 mmol) and 1,4-cyclohexadiene (0.5 mL) in benzene (1.5 mL) was treated with p-toluenesulfonic acid (29.6 mg, 0.155 mmol) was stirred at 25° C. for 24 hours. The solvent was removed in vacuo and the residue purified by flash chromatograph (silica, 50 percent ether in petroleum ether) to give keton Compound 17 (53.7 mg, 92 percent).

Method (iii): Trimethylsilyl triflate (15 μL, 0.08 mmol) was added to a solution of enediyne Compound 2 (32 mg, 0.078 mmol) and triethylsilane (40 mg, 0.32 mmol) in dichloromethane (2 mL) at −78° C. After five minutes, the mixture was quenched at −78° C. with saturated ammonium chloride solution (1 mL), diluted with either (10 mL), washed with water (2×3 mL), brine (3 mL) and dried (MgSO$_4$). The organic solvent was removed in vacuo and the residue was purified by flash chromatograph (silica, 50 percent ether in petroleum ether) to give ketone Compound 17 (22 mg, 68 percent).

Method (iv): Cry HCl gas was bubbled through a solution of enediyne Compound 2 (32 mg, 0.078 mmol) and 1,4-cyclohexadiene (40 mg, 0.32 mmol) in dichloromethane (4 mL) at 25° C. for 30 seconds. The solvent was removed in vacuo and the residue purified by flash chromatography (silica, 50 percent ether in petroleum ether) to give Compound 17 (25 mg, 78 percent).

White crystals; R$_f$=0.63 (70 percent ether in petroleum ether); mp=191°-193° C. (from methylene chloride/ether); IR (CDCl$_3$) Γ$_{max}$ 3480, 3080, 2935, 1712, 1490, 1264, 1192 cm$^{-1}$; $^1$H NMR (500 MHz, CDCl$_3$); δ8.33 (dd, J=7.9, 1.3 Hz, 1 H, aromatic), 8.09 (d, J=7.5 Hz, 1 H, aromatic), 7.54–7.02 (m, 11 H, aromatic), 5.65 (s, 1 H, benzylic), 2.75 (bs, 1 H, OH), 2.69–1.80 (m, 6 H, CH$_2$); $^{13}$C NMR (125 MHz, CDCl$_3$): δ207.5, 153.0, 150.9, 148.2, 137.1, 134.2, 129.8, 129.5, 128.5, 128.2, 127.8, 127.1, 126.1, 126.0, 124.3, 122.8, 121.8, 121.3, 82.5, 65.0, 64.1, 40.0, 30.2, 23.5; MS: m/e (relative intensity) 411 (M+, 100), 318 (58), 274 (49), 246 (12), 217 (55), 94 (29); HRMS: Calcd. for C$_{26}$H$_{21}$O$_4$N (M+): 411.1471, found: 411.1468; Anal. Calcd. for C$_{26}$H$_{21}$O$_4$N: C, 75.90; H, 5.14; N, 3.40. Found: C, 75.66; H, 5.45; N, 3.14.

EXAMPLE 16

Compound 18

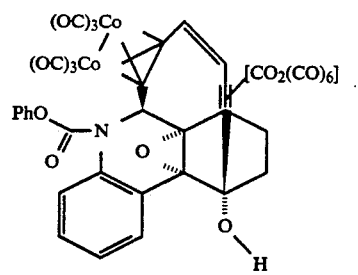

A solution of the enediyne Compound 2 (124 mg, 0.30 mmol) in CH$_2$Cl$_2$ (4 mL) was treated with Co$_2$(CO)$_8$ (260 mg, 0.76 mmol) and stirred at 25° C. for 5 minutes. The solution was concentrated in vacuo and the residue was purified by flash chromatography to give the cobalt complex Compound 18 (291 mg, 98 percent).

Green crystalline solid; mp>300° C. (from ether); R$_f$=0.80 (50 percent ether in petroleum ether); IR (CDCl$_3$) ν$_{max}$ 3500, 2950, 2872, 2095, 2070, 2025, 1725, 1492, 1207 cm$^{-1}$; $^1$H NMR (500 MHz, CDCl$_3$): δ8.87 (bs, 1 H, aromatic), 7.61–7.02 (m, 8 H, aromatic), 6.47 [bs, 1 H, N—CH(C)—C], 6.38 (bd, J=10.7 Hz, 1 H, olefinic), 6.19 (bd, J=10.7 Hz, 1 H, olefinic), 3.50 (bs, 1 H, OH), 2.70–1.71 (m, 6 H, CH$_2$); $^{13}$C NMR (125 MHz, CDCl$_3$): δ199.1, 198.6, 197.8, 151.3, 134.9, 132.9, 130.9, 129.4, 128.8, 127.2, 125.8, 125.3, 125.1, 124.8, 123.4, 121.6, 98.5, 88.9, 81.5, 80.1, 78.0, 73.9, 73.9, 63.1. 59.0, 44.2, 24.9, 17.1; MS (FAB+) m/e (relative intensity) 1114 (M+Cs, 11), 1086 (M+Cs—CO,18), 1058 (M+Cs—2CO,6), 1030 (M+Cs—3CO, 19), 1002 (M+Cs—4CO, 11), 943 (M+Cs—4CO—Co, 10), 918 (11), 890 (24), 862 (34), 813 (100); HRMS calcd. for C$_{38}$H$_{19}$O$_{16}$NCo$_4$Cs (M+Cs) 1113.7086, found 1113.7001.

EXAMPLE 17

Compound 19

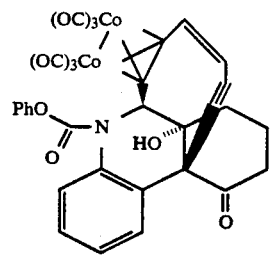

A solution of the cobalt complex Compound 18 (291 mg, 0.30 mmol) in CH$_2$Cl$_4$ (4 mL) was treated at zero degree C with trifluoroacetic acid (68.6 μL, 0.89 mmol). After 5 minutes, the mixture was poured into saturated sodium bicarbonates solution (25 mL) and extracted with CH$_2$Cl$_2$ (3×25 mL). The combined organic layers were dried (MgSO$_4$), evaporated in vacuo, and purified by flash chromatography (silica, 50 percent ether in petroleum ether) to give the keton Compound 19 (167.4 mg, 81 percent).

Brown crystalline solid; mp >300° C. (from ether); R$_f$=0.25 (50 percent ether in petroleum ether); IR (CDCl$_3$) ν$_{max}$ 3408, 2945, 2100, 2065, 2032, 1875, 1735, 1680, 1512, 1217 cm$^{-}$; $^1$H NMR (500 MHz, CDCl$_3$); δ7.81 (d, J=8.2 Hz, 1 H, aromatic), 7.42-7.11 (m, 8 H, aromatic), 7.00 (d, J=10.2 Hz, 1 H, olefinic), 6.39 [s, 1 H, N—C H(C)—C], 5.52 (d, J=10.2 Hz, 1 olefinic), 3.35-1.82 (m, 7 H, CH$_2$, OH); $^{13}$C NMR (125 MHz, CDCl$_3$): δ202.9, 198.9, 198.1, 154.3, 150.9, 144.0, 133.2, 132.8, 129.6, 128.3, 128.1, 126.7, 126.0, 125.8, 123.3, 121.8, 108.7, 93.2, 92.5, 82.1, 81.0, 68.5, 56.2, 38.0, 30.2, 21.6; MS (FAB+) m/e (relative intensity 828 (M+Cs, 17), 800 (18), 688 (74), 639 (20), 555 (32), 527 (100); HRMS calcd. for C$_{32}$H$_{19}$NO$_{10}$Co$_2$Cs (M+Cs) 827.8727, found 827.8730; Anal. calcd. for C$_{32}$H$_{19}$N O$_{10}$Co$_2$: C, 55.27; H, 2.75; N, 2.01; Co, 16.97. Found: C, 54.98; H, 2.79; N, 1.86; Co, 15.22.

EXAMPLE 18

Compound 20

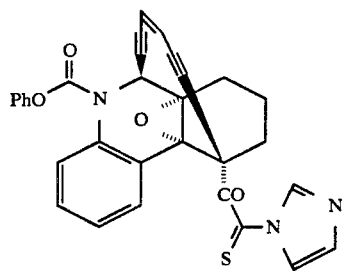

Thiocarbonyldiimidazole (180 mg, 0.99 mmol) was added to a solution of the alcohol Compound 2 (137 mg, 0.335 mmol) and 4-dimethylaminopyridine (DMAP) (25 mg, 0.18 mmol) in dichloromethane (2 mL) at 25° C. After 48 hours, the solution was concentrated in vacuo and the residue purified by flash chromatography (silica, 80 percent ether in petroleum ether) to give thionoimidazolide Compound 20 (160 mg, 95 percent). Compound 20: white crystalline solid, mp 178°-179° C. dec. (from ether/dichloromethane); R$_f$=0.62 (70 percent ether in petroleum ether); IR (CDCl$_3$) ν$_{max}$ 3042, 2912, 2195, 1710, 1500, 1495, 1212, 1105 cm$^{-1}$; $^1$H NMR (500 MHz, CDCl$_3$): δ8.49 (s, 1 H, N—CH=N), 7.71-7.05 (M, 11 H, aromatic), 5.93 (d, J=10.3 Hz, 1 H, olefinic), 5.73 (dd, J=10.3, 1.6 Hz, 1 H, olefinic), 5.60 (d, J=1.6 Hz, 1 H, N—CH—C≡C), 3.08 (d, J=11.1 Hz, 1 H, CH$_2$), 2.46-1.70 (m, 5 H, CH$_2$); $^{13}$C NMR (125 MHz, CDCl$_3$): δ179.1, 153.4, 151.0, 137.0, 135.9, 130.9, 129.4, 129.3, 128.2, 127.0, 126.4, 125.8, 125.4, 123.9, 123.2, 121.3, 117.7, 100.6, 94.3, 93.9, 88.9, 85.4, 74.5, 65.9, 63.2, 50.3, 28.0, 22.7, 18.4; MS (FAB+) m/e (relative intensity( 653 (M+Cs, 21), 419 (19), 379 (15), 286 (100), 154 (30); HRMS Calcd. for C$_{30}$H$_{21}$N$_3$O$_4$SCs (M+Cs) 653.0385, found 653.0360; Anal. calcd. for C$_{30}$H$_{21}$N$_3$O$_4$S: C, 69.35; H, 4.07; N, 8.09; S, 6.16. Found: C, 69.01; H, 4.17; N, 7.91; S, 619.

EXAMPLE 19

Compound 21

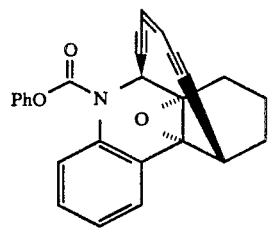

A solution of the imidazolide Compound 20 (112 mg, 0.24 mmol), azobisisobutyronitrile (AIBN; 3 mg) and tri-n-butylstannane (n—Bu$_3$SnH) (94 μL, 0.36 mmol) was heated at 75° C. for 2 hours, the solvent was removed in vacuo, and the residue was purified by flash chromatography to give the deoxygenated product Compound 21 (71 mg, 75 percent).

White crystals; R$_f$=0.62 (30 percent ether in petroleum ether); mp 248°-250° C. dec. (from ether); IR (CDCl$_3$) ν$_{max}$ 2945, 2872, 2232, 2205, 1712, 1465, 1325, 1185 cm$^{-1}$; $^1$H NMR (500 MHz, CDCl$_3$): δ7.67 (d, J=7.5 Hz, 1 H, aromatic), 7.6-7.14 (m, 8 H, aromatic), 5.84 (dd, J=10.5, 1.6 Hz, 1 H, olefinic), 5.72 (dd, J=10.5, 1.6 Hz, 1 H, olefinic), 5.57 (d, J=1.6 Hz, 1 H, N—CH—C≡), 3.85 (d, J=1.6 Hz, 1 H, C≡C—CH—C), 2.49 (m, 1 H, CH$_2$), 2.30 (m, 1 H, CH$_2$), 2.12-1.60 (m, 4 H, C H$_2$); $^{13}$C NMR (125 MHz, CDCl$_3$): δ151.0, 135.5, 129.4, 129.4, 128.2, 127.3, 125.8, 125.8, 125.4, 125.0, 122.0, 122.0, 121.5, 101.8, 94.9, 91.4, 88.8, 70.5, 61.1, 50.0, 29.8, 22.9, 22.5, 15.5; MS: m/e (relative intensity) 393 (20, M$^+$), 294 (9), 262 (15), 212 (11), 149 (42); HRMS: Calcd. for C$_{26}$H$_{19}$O$_3$N (M$^+$): 393.1365, found: 393.1332.

EXAMPLE 20

Compound 23

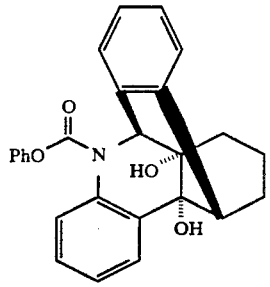

A solution of the enediyne Compound 21 (30 mg, 0.076 mmol) and 1,4-cyclohexadiene (0.5 mL) in benzene (2 mL) was treated with TsOH.H$_2$O (18 mg, 0.09 mmol) and stirred at 25° C. for 24 hours. The solvent was removed in vacuo and the residue was purified by flash chromatography to give the diol Compound 23 (26 mg, 85 percent).

Colorless gum; R$_f$=0.35 (50 percent ether in petroleum ether); IR (CDCl$_3$) ν$_{max}$ 3310, 3082, 2925, 1705, 1592, 1395, 1200 cm$^{-1}$; $^1$H NMR (500 MHz, CDCl$_3$): δ7.58 (bd, J=4.4 Hz, 1 H, aromatic), 7.47 (bd, J=7.8 Hz, 1 H, aromatic), 7.40-7.09 (m, 10 H, aromatic), 6.81 (d, J=8.1 Hz, 1 H, aromatic), 5.78 (s, 1 H, N-benzylic), 4.00 (bs, 2 H, OH(, 3.24 (s, 1 H, benzylic), 2.42-0.72 (m, 6 H, CH$_2$); $^{13}$C NMR (125 MHz, CDCl$_3$): δ151.9. 138.2, 134.7, 129.4, 129.4, 129.3, 128.8, 128.4, 128.3, 127.1, 126.9, 125.7, 125.0, 124.4, 121.8, 121.8, 121.5, 83.0, 66.2, 65.1, 51.2, 33.5, 27.1, 18.7; MS(FAB+): m/e (relative intensity) 546 (15, M+Cs), 379 (31), 312 (30), 286 (100); HRMS: Calcd. for C$_{26}$H$_{23}$O$_4$NCs (M+Cs): 546.0681, found: 546.0691.

EXAMPLE 21

Compound 23a

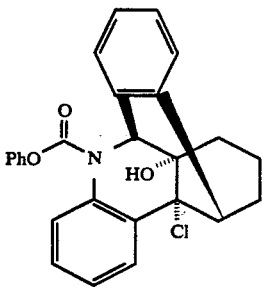

HCl gas was bubbled through a solution of the enediyne Compound 21 (30 mg, 0.076 mmol) and 1,4-cyclohexadiene (0.5 mL) in CH$_2$Cl$_2$ at 25° C. for 30 seconds. The solvent was removed in vacuo and the residue was purified by flash chromatography to give the chloride Compound 23a (27 mg, 84 percent).

Pale yellow solid; mp=114°-116° C.; R$_f$=0.62 (50 percent ether in petroleum ether); IR (CDCl$_3$) δ$_{max}$ 3500, 3065, 2932, 1712, 1495, 1382, 1200 cm$^{-1}$; $^1$H NMR (500 MHz, CDCl$_3$): δ7.71-6.73 (m, 13 H, aromatic), 5.87 (s, 1 H, N-benzylic), 3.62 (s, 1 H, benzylic), 2.52 (bs, 1 H, OH), 2.50-1.60 (m, 6 H, CH$_2$); MS: m/e (relative intensity) 564 (5, M+Cs), 419 (100), 379 (58); HRMS: Calcd. for C$_{26}$H$_{22}$O$_3$NClCs (M+Cs): 564.0343, found: 564.0351.

EXAMPLE 22

Compound 24c

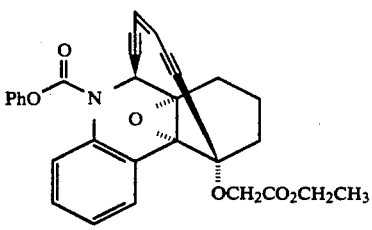

Ethyl bromoacetate (27 mg, 0.16 mmol) was added to a mixture of the alcohol Compound 2 (34 mg, 0.08 mmol) and Cs$_2$CO$_3$ (67 mg, 0.2 mmol) in anhydrous DMF (2 mL) at 60° C. The mixture was heated for 3 hours, diluted with ether (10 mL), washed with NH$_4$Cl (2×3 mL), water (2×2 mL), and brine (2 mL). The organic layer was dried (MgSO$_4$) and purified by flash chromatography to give the ester Compound 24c (37.5 mg, 91 percent.

Colorless oil; R$_f$—0.55 (50 percent ether in petroleum ether); $^1$H NMR (500 MHz, CDCl$_3$); δ8.63 (d, J=10.3 Hz, 1 H aromatic), 7.45-7.10 (m, 8 H, aromatic), 5.82 (d, J=10.5 Hz, 1 H, olefinic), 5.68 (dd, J=10.5, 1.5 Hz), 1 H, olefinic), 5.51 [d, J=1.5 Hz, 1 H, C≡C(C)CHN], 4.34[d, J=15.6 Hz, 1 H, C(O)CH$_2$O], 4.28 ]d=15.6 Hz, 1 H, C(O)CH$_2$O], 4.24 (m, 2 H, OCH$_2$CH$_3$), 2.35- 1.70 (m, 6 H, CH$_2$), 1.30 (5, J=8.2 Hz, 3 H, OCH$_2$CH$_3$); $^{13}$C NMR (125 MHz, CDCl$_3$): δ169.5, 150.9, 135.6, 131.0, 129.3, 129.3, 128.1, 127.7, 125.7, 125.6, 123.9, 122.4, 121.6, 121.6, 98.2, 96.3, 94.5, 89.0, 80.1, 73.2, 68.1, 63.2, 61.5, 50.6, 30.0, 29.8, 19.2, 14.5: HRMS calcd. C$_{30}$H$_{25}$O$_6$NCs (M+Cs), 628.0736; found: 628.0750.

Compounds 24a, b, d, e, f and g are similarly prepared

EXAMPLE 23

Alternative Preparation of Compound 5 (10-Acetoxy-7, 8, 9, 10-tetrahydrophenanthridine (a) Toluenesulfonic acid (TsOH.H$_2$O; 8 mg, 0.05 mmol) was added in one portion to a solution of the alcohol Compound 2 (18 mg, 0.045 mmol), 1,4-cyclohexadiene (0.2 mL) and benzene (0.5 mL) at 25° C. and the solution was stirred for 24 hours. The organic solvent was removed in vacuo and the residue was purified by flash chromatography to give the ketone Compound 5 (15 mg, 90 percent).

(b) Trimethylsilyl trifluoromethylsulfonate (TMSOTf; 15 μL, 0.08 mmol) was added to a solution of the alcohol Compound 2 (32 mg, 0.078 mmol) and triethylsilane (Et$_3$SiH) (40 mg, 0.32 mmol) in CH$_2$Cl$_2$ (2 mL) at −78° C. After 1 minute, the mixture was quenched at −78° C. with saturated NH$_4$Cl solution (1 mL), diluted with ether (10 mL), washed with water (2×3 mL), brine (3 mL) and then dried (MgSO$_4$). The organic solvent was removed in vacuo, and the residue was purified by flash chromatography to give the ketone Compound 5 (22 mg, 75 percent).

(c) HCl gas was bubbled through a solution of the alcohol Compound 2 (32 mg, 0.078 mmol) and 1,4-cyclohexadiene (40 mg, 0.32 mmol) in dichloromethane (4 mL) at 25° C. for 30 seconds. The solvent was removed in vacuo and the residue was purified by flash chromatography to give the keton Compound 5 (25 mg, 80 percent).

EXAMPLE 24

Compound 2b

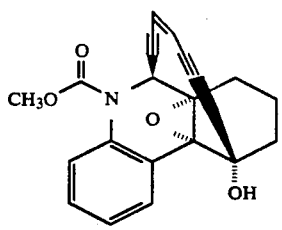

A solution of the phenyl carbamate Compound 2 (42 mg, 0.103 mmol) in dry methanol (4 mL) was treated with sodium methoxide (17 mg, 0.31 mmol) and heated at 60° C. for 2 hours. The reaction mixture was diluted with dichloromethane (25 mL), washed with sodium bicarbonate solution (25 mL), dried (Na$_2$SO$_4$), evaporated in vacuo and the residue purified by flash chromatography (silica, 40 percent ether in petroleum ether) to give methyl carbamate 2b (28.5 mg, 80 percent). 2b: white crystalline solid, mp 126°-127° C. (from ether/petroleum ether); R$_f$=0.43 (50 percent ether in petroleum ether); IR (CDCl$_3$) ν$_{max}$ 3600, 3450, 2957, 2257, 2250, 1706 cm$^{-1}$; $^1$H NMR (500 MHz, CDCl$_3$): δ8.65 (d, J=8.0 Hz, 1 H, aromatic), 7.25-7.10 (m, 3 H, aromatic), 5.81 (d, J=10.1 Hz, 1 H, olefinic), 5.69 (d, J=10.1 Hz, 1 H, olefinic), 5.45 (s, 1 H, CH—N), 3.82 (s, 3 H, OMe), 2.79 (s, 1 H, OH), 2.27-1.72 (m, 6 H, CH$_2$); $^{13}$C NMR (125 MHz, CDCl$_3$): δ135.9, 131.3, 127.8, 127.5, 126.1, 124.9, 123.9, 122.1, 100.7, 94.1, 88.3, 74.2, 73.1, 65.8, 64.2, 53.7, 50.1, 35.2, 23.2, 19.2, 15.2; MS m/e (relative intensity) 347 (M+, 100) 291 (35) 204 (50); HRMS calcd. for C$_{21}$H$_{17}$NO$_4$ (M+) 347.1158, found 347.1159. Anal. calcd. for C$_{21}$H$_{17}$NO$_4$: C, 72.61; H, 4.93; N, 4.03. Found: C, 72.63; H, 5.24; N, 3.79

EXAMPLE 25

Compound 40

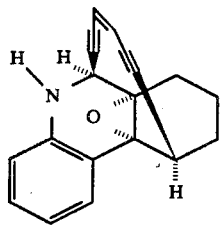

Carbamate Compound 21 (39 mg, 0.10 mmol) in THF (3 mL) was treated at zero degrees C with LiAlH$_4$ (0.25 mL of a 1.0 M solution in ether, 0.25 mmol). After stirring for 30 minutes, the reaction was quenched with saturated sodium bicarbonate solution (1 mL), diluted with ether (20 mL), washed with 1.0 M aqueous LiOH solution (2×5 mL) in order to remove phenol, dried (Na$_2$SO$_4$), filtered and stored under argon at −78° C. until required. MS (FAB+) m/e (relative intensity) 290 (97), 278 (75), 274 (M+H, 98), 235 (100); HRMS calcd. for C$_{19}$H$_{16}$NO (M+H) 274.1232, found 274.1247.

EXAMPLE 26

3-Methoxy-7,8,9,10-tetrahydrophenanthridone (Compound 220)

Prepared from 3-methoxyaniline and ethyl 2-cyclohexanonecarboxylate in 31 percent yield by following the reported procedure. [Masamune et al., J. Org. Chem., 29:681 (1969).] Compound 220: powder; mp 256°-258° C.; R$_f$=0.35 (silica, 3.2 percent methanol in dichloromethane); IR (KBr) ν$_{max}$ 3150, 3069, 2938, 2859, 2831, 1652, 1622, 1614, 1567, 1515, 1218, 1119, 1036, 915, 800 cm$^{-1}$; $^1$H NMR (300 MHz, DMSO-d$_6$) δ9.55 (s, 1 H, NH), 7.57, (d, J=9.6 Hz, 1 H, H1), 6.80-6.74 (m, 2 H, H2 and H4), 3.77 (s, 3 H, OCH$_3$), 2.76 (t, J=5.6 Hz, 1 H, H7 or H10), 2.40 (t, J=6.1 Hz, 1 H, H7 or H10), 1.80-1.65 (m, 4 H, H8 and H9); HRMS for C$_{14}$H$_{16}$NO$_2$ (M+H), calcd 230.1181, found 230.1160.

EXAMPLE 27

3-Methoxy-7,8,9,10-tetrahydrophenanthridine (Compound 221)

To a suspension of Compound 220 (2.00 g, 8.72 mmol) in dry THF (50 mL) was added dropwise DIBAL (1 M in CH$_2$Cl$_2$, 9.0 mL, 9.0 mmol) to generate a homogeneous solution. LiAlH$_4$ (1.75 g, 46.0 mmol) was added followed by reflux for two hours. The reaction mixture was quenched with saturated aqueous Na$_2$SO$_4$, diluted with ethyl ether (300 mL), dried over anhydrous Na$_2$SO$_4$, and filtered through Celite. The solvent was removed in vacuo to give mainly the corresponding secondary amine. Oxidative aromatization was carried out by stirring a solution of the crude amine in benzene (50 mL) containing silica gel (2.0 g) under oxygen atmosphere at room temperature for 24 hours. Silica gel was filtered off and washed with ethyl ether (100 mL). The combined filtrate was concentrated and purified by flash column chromatography (silica gel, 20 percent ethyl ether in benzene) to afford crystalline 221 (1.2 g, 65 percent): mp 53°-54.7° C. (from ethyl ether and petroleum ether); R$_f$=0.50 (silica, 20 percent ethyl ether in benzene); IR (CHCl$_3$) δ$_{max}$ 2941, 1623, 1507, 1421, 1344, 1230, 1161, 1034 cm$^{-1}$; $^1$H NMR (300 MHz, CDCl$_3$) δ8.54 (s, 1 H, H6), 7.79 (d, J=9.2 Hz, 1 H, H1), 7.39 (d, J=2.7 Hz, 1 H, H4), 7.17 (dd, J=9.0, 2.7 Hz, 1 H2), 3.93 (s, 3 H, OCH$_3$), 3.06 (t, J=6.0 Hz, 2 H, H7 or H10), 2.85 (t, J =6.2 Hz, 2 H, H7 or H10), 1.95-1.85 (m, 4 H, H8 and H9); HRMS for C$_{14}$H16NO (M+H), calcd 214.1232, found 214.1240.

EXAMPLE 28

1,4-Dioxaspiro[4.5]decan-6-carboxylic Acid (Compound 132)

A mixture of ethyl 2-cyclohexanonecarboxylate (100.0 mL, 97 percent, 0.606 mol), ethylene glycol (33.8 mL, 0.606 mol), and p-toluenesulfonic acid monohydrate (11.53 g, 60.6 mmol) in dry benzene (800 mL) was refluxed under argon for five hours with azeotropic removal of water. The reaction mixture was diluted with ethyl ether (500 mL), washed with saturated aqueous NaHCO$_3$ and brine, dried over anhydrous Na$_2$SO$_4$, and concentrated in vacuo to afford a crude product (135.0 g). An analytic sample was prepared by preparative TLC (silica gel plate, 9 percent ethyl ether in petroleum ether). colorless oil; R$_f$=0.16 (silica, 9 percent ethyl ether in petroleum ether); IR (CHCl$_3$) δ$_{max}$ 2943, 1728, 1448, 1377, 1253, 1234, 1214, 1185, 1157, 1087, 1045 cm$^{-1}$; $^1$H NMR (300 MHz, CDCl$_3$) δ 4.15 (q, J=7.1 Hz, 2 H, OCH$_2$CH$_3$), 4.01-3.84 (m, 4 H, OCH$_2$CH$_2$O), 2.67 (dd, J =8.2, 5.7 Hz, 1 H, COCHCH$_2$), 1.99-1.81 (m, 3 H, CH$_2$CH$_2$), 1.74-1.58 (m, 3 H, CH$_2$CH$_2$), 1.53-1.42 (m, 1 H, CH$_2$), 1.39-1.26 (m, 1 H, CH$_2$); 1.27 (t, J=7.1 Hz, 3 H, OCH$_2$CH$_3$); MS (FAB+) m/e (rel intensity) 215 (M+H, 35), 169 (100), 125 (18); HRMS for C$_{11}$H$_{19}$O$_4$ (M+H), calcd 215.1283, found 215.1283.

To a solution of the crude ester obtained above (135.0 g) in MeOH (300 mL) was added aqueous NaOH (48.48 g, 1.212 mol in 400 mL of water), and the mixture was then heated under reflux for 15 hours. After cooling to room temperature, the mixture was extracted with ethyl ether (300 mL), the aqueous layer was separated, acidified carefully (under ice-cooling) with dilute aqueous NaHSO$_4$ (167.4 g) to pH 2.0, extracted with ethyl ether (1 L×3), and dried over anhydrous Na$_2$SO$_4$. The solvent was evaporated in vacuo to give crystalline carboxylic acid Compound 132 (87.5 g, 78 percent from 2-cyclohexanonecarboxylate): colorless prisms; mp 137°-139° C. (from ethyl ether); IR (CHCl$_3$) δ$_{max}$ 3508, 3221 (br), 3026, 3017, 2946, 2900, 2868, 1757, 1710, 1381, 1141, 1085 cm$^{-1}$; $^1$H NMR (300 MHz, CDCl$_3$) δ 12.5-8.0 (br s, 1H, COOH) 4.05 (m, 4 H, OCH$_2$CH$_2$O), 2.71 (dd, J =9.2, 4.9 Hz, 1H, COCHCH$_2$), 1.56-1.42 (m, 1 3 H, CH$_2$CH$_2$), 1.76-1.56 (m, 3 H, CH$_2$CH$_2$), 1.56-1.42 (m, 1 H, CH$_2$), 1.42-1.27 (m, 1 H, CH$_2$); MS (FAB+) m/e (rel intensity) 187 (M+H, 51), 169 (100), 125 (26), 107 (13); HRMS for C$_9$H$_{15}$O$_4$ (M+H), calcd 187.0970, found 187.0970. Anal. Calcd for C$_9$H$_{14}$O$_4$: C, 58.05; H, 7.58. Found: C, 58.21; H, 7.75.

EXAMPLE 29

3-{1,4-Dioxaspiro[4.5]decan-6-carbonyl}-1,3-thiazolidine-2-thione (Compound 134)

To a solution of carboxylic acid Compound 132 (27.0 g, 0.145 mol) and 2-mercaptothiazoline (Compound 133; 17.29 g, 0.145 mol) in dry $CH_2Cl_2$ (500 mL) cooled in an ice-water bath was added DCC (35.9 g, 0.174 mol) and DMAP (1.83 g, 15.0 mmol) followed by stirring at room temperature for 14 hours. The precipitate was filtered off through Celite and the filtrate was concentrated in vacuo to give a residue. Flash column chromatography of the residue (silica gel, ethyl ether-petroleum ether-benzene=1:2:4) afforded oily yellow-colored imide Compound 134 (40.2 g, 96 percent): $R_f$=0.56 (silica, 20 percent ethyl ether in benzene); IR ($CHCl_3$) $\delta_{max}$ 2945, 1708, 1647, 1367, 1281, 1228, 1160, 1058 cm$^{-1}$; $^1$H NMR (300 MHz, $CDCl_3$) δ4.83 (t, J=7.5 Hz, 1 $COCHCH_2$), 4.64–4.39 (m, 2 H, $NCH_2CH_2S$), 4.05–3.84 (m, 4 H, $OCH_2CH_2O$), 3.42–3.16 (m, 2H, $NCH_2CH_2S$), 2.10–1.30 (m, 8 H, 4×$CH_2$); MS (FAB+) m/e (rel intensity) 288 (M+H, 74), 225 (5), 169 (100), 125 (13); HRMS for $C_{12}H_{18}NO_3S_2$ (M+H), calcd. 288.0728, found 288.0750.

EXAMPLE 30

Amide Bond Formation of Imide Compound 134 with Aminophenols:
N-(3-Hydroxyphenyl)-1,4-dioxaspiro[4.5]decan-6-carboxamide (Compound 135), Representative Procedures A solution of imide 134 (40.0 g, 0.139 mol) and 3-aminophenol (15.19 g, 0.139 mol) in THF (500 mL) was refluxed for 96 hours. The solvent was removed in vacuo to give a solid residue which was recrystallized from acetone-ethyl ether to afford 30.2 g of Compound 135. The mother liquor was concentrated and purified repeatedly by flash column chromatography (silica gel, 20 percent ethyl ether in benzene) to give 3.3 g of Compound 135. Compound 133 (15.2 g, 92 percent) was recovered. Combined weight of Compound 135: 33.5 g (87 percent). Compound 135: white crystalline solid; mp 181°–183° C. (from acetone-ethyl ether); $R_f$=0.16 (silica, 20 percent ethyl ether in benzene); IR (KBr) $\nu_{max}$ 3381, 3178 (br), 2943, 1651, 1617, 1604, 1550, 1448, 1282, 1237, 1158, 1151, 1141, 1091, 1036, 877, 755, 690 cm$^{-1}$; $^1$H NMR (300 MHz, acetone-$d_6$) δ8.73 (br s, 1 H, NH), 8.28 (s, 1 H, ArOH, exchangeable by $D_2O$), 7.35 (dd, J=2.1, 2.1 Hz, 1 H, aromatic), 7.08 (dd, J=8.0, 7.9 Hz, 1 H, aromatic), 6.99 (ddd, J=8.0, 1.9, 1.2 Hz, 1 H, aromatic), 6.52 (ddd, J=7.8, 2.4, 1.9, 1.1 Hz, 1 H, aromatic), 4.02–3.84 (m, 4 H, $OCH_2CH_2O$), 2.62 (dd, J=9.7, 5.2 Hz, 1 H, $COCH_2$), 1.99–1.24 (m, 8 H, 4×$CH_2$); MS (FAB+) m/e/ (rel intensity) 278 (M+H, 100), 216 (3), 169 (19); HRMS for $C_{15}H_{20}NO_4$ (M+H), calcd 278.1392, found 278.1401. Anal. Calcd for $C_{15}H_{19}NO_4$: C, 64.97; H, 6.91; N, 5.05. Found: C, 64.87; H, 6.97; N, 5.01.

EXAMPLE 31

N-[(3-Benzyloxy)phenyl]-1,4-dioxaspiro[4.5]decan-6-carboxamide (Compound 135)

To a solution of Compound 135 (20.0 g, 72.12 mmol) in dry THF (300 mL) cooled at zero degrees C was added NaH (60 percent, 3.03 g, 75.72 mmol) followed by stirring at zero degrees C for 10 minutes. Benzyl bromide (8.58 mL, 72.14 mmol) and tetra-n-butylammonium iodide (2.66 g, 7.20 mmol) were added and the resultant mixture was stirred at room temperature for one hour. Water was added to the reaction mixture which was extracted with ethyl acetate (500 mL), washed with brine, dried over anhydrous $Na_2SO_4$, and concentrated in vacuo to give a residue. Flash column chromatography of the residue (silica gel, ethyl ether-petroleum ether-benzene=1:2:4) afforded amide Compound 136 (19.0 g, 72 percent): white crystalline solid; mp 88°–89.5° C. (from EtOAc-petroleum ether); $R_f$=0.52 (silica, 20 percent ethyl ether in benzene); IR ($CHCl_3$) $\nu_{max}$ 3355 (br), 3014, 2945, 1684, 1600, 1539, 1492, 1441, 1287, 1157, 1082, 1029 cm$^{-1}$; $^1$H NMR (300 MHz, $CDCl_3$) δ8.34 (br, s, 1 H, NH), 7.47–7.31 (m, 6 H, aromatic), 7.19 (dd, J=8.0, 8.0 Hz, 1 H, aromatic), 6.97 (ddd, J=7.4, 1.1, 0.8 Hz, 1H, aromatic), 6.70 (ddd, J=8.2, 2.7, 0.7 Hz, 1 H, aromatic), 5.06 (s, 2 H, benzylic), 4.05–3.86 (m, 4 H, $OCH_2CH_2O$), 2.65 (dd, J=11.5, 4.3 Hz, 1 H, $COCHCH_2$), 2.08–1.22 (m, 8 H, 4×$CH_2$); MS (FAB+) m/e (rel intensity) 368 (M+H, 100), 306 (9), 199 (6), 169 (37); HRMS for $C_{22}H_{26}NO_4$ (M+H), calcd 368.1862, found 368.1850. Anal. Calcd for $C_{22}H_{25}NO_4$: C, 71.91; H, 6.86; N, 3.81. Found: C, 71.80; H, 6.76; N, 3.87.

EXAMPLE 32

N-(4-Hydroxyphenyl)-1,4-dioxaspiro[4.5]decan-6-carboxamide (Compound 205)

Compound 205 was similarly prepared from 4-aminophenol and Compound 134 as described for Compound 135 in 86 percent yield. Compound 205: white crystalline solid; mp 173°–174.4° C. (from Acetone-petroleum ether); $R_f$=0.10 (silica, 20 percent ethyl ether in benzene; IR (KBr) $\nu_{max}$ 3243 (br), 2947, 1655, 1601, 1552, 1513, 1441, 1270, 1223, 1080, 923, 840 cm$^{-1}$; $^1$H NMR (300 MHz, $CDCl_3$+DMSO-$d_6$) δ8.77 (d, J=8.9 Hz, 1 H, aromatic), 8.43 (br s, 1 H, NH), 7.33 (d, J=6.4 Hz, 1 H, aromatic), 6.80–6.40 (m, 2 H, aromatic), 3.96 (br s, 4 H, $OCH_2CH_2O$), 3.19 (br s, 1 H, ArOH) 2.59 (br s, 1 H, $COCHCH_2$), 2.00–1.20 (m, 8 H, 4×$CH_2$) MS (FAB+) m/e (rel intensity) 278 (M+H, 100), 169 (17), 109 (24); HRMS for $C_{15}H_{20}NO_4$ (M+H), calcd 278.1392, found 278.1399.

EXAMPLE 33

N-[(4-Benzyloxy)phenyl]-1,4-dioxaspiro[4.5]decan-6-carboxamide (Compound 139)

Compound 139 was similarly prepared from Compound 205 as described for Compound 136 in 78 percent yield. Compound 139: white solid; mp 145°–147° C.; $R_f$=0.49 (silica, 20 percent ethyl ether in benzene); IR ($CHCl_3$) $\nu_{max}$ 3356, 2943, 1676, 1598, 1528, 1510, 1083, 1029 cm$^{-1}$; $^1$H NMR (300 MHz, $CDCl_3$) δ8.21 (br s, 1 H, NH), 7.45–7.30 (m, 8 H, aromatic), 6.92 (m, 1 H, aromatic), 5.03 (s, 2 , benzylic), 4.04–3.90 (m, 4 H, $OCH_2CH_2O$), 2.64 (dd, J=11.3, 4.3 Hz, 1 H, $COCHCH_2$), 2.10–1.25 (m, 8 H, 4×$CH_2$); MS (FAB+) m/e (rel intensity) 368 (M+H, 100), 169 (38), 125 (8), 108 (6); HRMS for $C_{22}H_{26}NO_4$ (M+H), calcd 368.1862, found 368.1863.

EXAMPLE 34

N-[(3-Hydroxy-4-carboxy)phenyl]-1,4-dioxaspiro[4.5]decan-6-carboxamide (Compound 206)

Compound 206 was similarly prepared from 5-aminosalicylic acid and Compound 134 as described for Compound 135 in 87 percent yield, except for a modified workup procedure was used. The reaction mixture was first filtered through Celite to remove the solid materials, the filtrate was treated with saturated aqueous $NaHCO_3$, extracted with ethyl ether, and the aqueous layer was then acidified with 5 percent HCl, extracted with ethyl ether, dried over anhydrous $Na_2SO_4$, and condensed to gave the produce Compound 206 : grey solid; mp 170.5172.2° C.; IR ($CHCl_3$) $\nu_{max}$ 3403, 3348, 3073, 2945, 1678, 1619, 1543, 1528, 1491, 1446, 1291, 1083, 1036, 928 $cm^{-1}$; $^1H$ NMR (300 MHz, $CDCl_3$) δ8.42 (s, 1 H, NH), 8.07 (d, J=3.2 Hz, 1 H, aromatic), 7.90 (br s, 1 H, ArOH), 7.55 (dd, J=10.7, 3.2 Hz, 1 H, aromatic), 6.94 (d, J=10.7 Hz, 1 H, aromatic), 7.50–6.50 (br s, 1 H, COOH), 4.15–3.95 (m, 4 H, $OCH_2CH_2O$), 2.73 (dd, J=13.4, 5.2 Hz, 1 H, $COCHCH_2$), 2.10–1.20 (m, 8 H, 4×$CH_2$); MS (FAB+) m/e (rel intensity) 322 (M+H, 100) 268 (9), 169 (27), 120 (26), 107 (14); HRMS for $C_{16}H_{20}NO_6$ (M+H), calcd 322.1291, found 322.1290.

EXAMPLE 35

N-{[3-Benzyloxy-4-(benzyloxy)carbonyl]phenyl}-1,4-dioxaspiro[4.5]decan-6-carboxamide (Compound 207)

Compound 207 was similarly prepared from Compound 206 as described for Compound 136 in 77 percent yield. Compound 207: white solid; mp 99°–100.5° C.; $R_f$=0.44 (silica, 20 percent ethyl ether in benzene); IR ($CHCl_3$) $\nu_{max}$ 3350, 2944, 1721, 1679, 1534, 1500, 1454, 1298, 1083, 1030 $cm^{-1}$; $^1H$ NMR (300 MHz, $CDCl_3$) δ8.29 (br s, 1 H, NH), 7.90 (dd, J=9.1, 2.9 Hz, 1 H, aromatic), 7.71 (d, J=2.9 Hz, 1 H, aromatic), 7.43–7.28 (m, 10 H, aromatic), 6.97 (d, J=9.1 Hz, 1 H, aromatic), 4.03–3.85 (m, 4 H, $OCH_2CH_6O$), 2.63 (dd, J=11.0, 4.4 Hz, 1 H, $COCHCH_2$), 2.04–1.25 (m, 8 H, 4×$CH_2$); MS (FAB+) m/e (rel intensity) 502 (M+H, 100), 394 (10), 242 (7), 181 (7), 169 (95), 125 (16); HRMS for $C_{30}H_{32}NO_6$ (M+H), calcd 502.2230, found 502.2250.

EXAMPLE 36

3-Benzyloxy-7,8,9,10-tetrahydrophenanthridone (Compound 137a) and 1-benzyl-oxy-7,8,9,10-tetrahydrophenanthridone Compound 137b)

A solution of amide Compound 136 (29.0 g, 78.92 mmol) in THF (230 mL) and 37 percent HCl (84 mL) was heated under reflux for three hours. After cooling to room temperature, the white precipitate was collected by filtration and dried over $P_2O_5$ under vacuum to give a 82:18 mixture of Compound 137a and Compound 137b (24.1 g, 100 percent). Compounds 137a+137b: white powder; mp 288°–290° C. (dec., from THF-$H_2O$); $R_f$=0.40 (Compound 137a) and 0.36 (Compound 137b) (silica, 3.2 percent methanol in dichloromathane); IR (KBr) $\nu_{max}$ 3400, 2930, 1648, 1602, 1590, 1530, 1254, 1197, 1182 $cm^{-1}$; $^1H$ NMR (300 MHz, DMSO-$d_6$) δ9.60 (br s, 1 H, NH), 7.55 (d, J=8.9 Hz, 0.82 H, H1), 7.51–7.29 (m, 5 H, aromatic), 7.26 (t, J=8.2 Hz, 0.18 H, H3), 6.92 (d, J=8.2 Hz, 0.18 H, H2 or H4), 6.90 (d, J=2.3 Hz, 0.82 H, H4), 6.83 (dd, J=8.9, 2.3 Hz, 0.82 H, H2), 6.75 (d, J=8.2 Hz, 0.18 H, H2 or H4), 5.17 (s, 0.36 H, benzylic), 5.12 (s, 1.64 H, benzylic), 3.14 (br s, 0.36 H, H7 or H10), 2.78 (t, J=5.8 Hz, 1.64 H, H7 or H10 ), 2.53 (t, J=1.6 Hz, 0.36 H, H7 or H10), 2.46 (t, J=5.9 Hz, 1.64 H, H7 or H10), 1.86–1.50 (m, 4 H, H8 and H9); MS (FAB+) m/e (rel intensity) 306 (M+H), 100), 215 (10); HRMS for $C_{20}H_{20}NO_2$ (M+H), calcd 306.1494, found 306.1500.

EXAMPLE 37

3-Benzyloxy-7,8,9,10-tetrahydrophenanthridine (Compound 138)

To a suspension of a mixture of a 82:18 mixture of Compounds 137a and 137b (24.1 g, 78.92 mmol) in dry THF (300 mL) was added dropwise DIBAL (1 M in $CH_2Cl_2$, 78.9 mL, 78.9 mmol) to generate a homogeneous solution. $LiAlH_4$ (6.0 g, 0.158 mol) was added followed by reflux for three hours. The reaction mixture was quenched with saturated aqueous $Na_2SO_4$, diluted with ethyl ether (800 mL), dried over anhydrous $Na_2SO_4$, and filtered through Celite. The solvent was removed in vacuo to give mainly the corresponding secondary amine. Oxidative aromatization was carried out by stirring a solution of the amine in benzene (500 mL) containing silica gel (20.0 g) under oxygen atmosphere at room temperature for 24 hours. Silica gel was filtered off and washed with ethyl ether (300 mL). The combined filtrate was concentrated and purified by flash column chromatography (silica gel, 20 percent ethyl ether in benzene) to furnish crystalline Compound 138 (10.0 g, 53 percent from Compound 137b). The corresponding 1-benzyloxy isomer was not isolated. Compound 138: colorless fine needles; mp 122°–124° C. (from ethyl ether); $R_f$=0.11 (silica, 10 percent ethyl ether in benzene); IR ($CHCl_3$) $\nu_{max}$ 2943, 1621, 1506, 1423, 1345, 1299, 1241, 1161 $cm^{-1}$; $^1H$ NMR (300 MHz, $CDCl_3$) δ8.54 (s, 1 H, H6), 7.83 (d, J=11.0 Hz, 1 H, H1), 7.54–7.29 (m, 6 H, H4 and aromatic), 7.26 (dd, J=11.0, 3.2 Hz, 1 H, H2), 5.20, (s, 2 H, benzylic), 3.07 (t, J=7.5 Hz, 2 H, H7 or H10), 2.86 (t, J=7.0 Hz, 2 H, H7 or H10), 2.03–1.82 (m, 4 H, H8 H9); MS (FAB+) m/e (rel intensity) 290 (M+H, 100); HRMS for $C_{20}H_{20}NO$ (M+H), calcd 290.1545, found 290.1540. Anal. Calcd for $C_{22}H_{25}NO_4$: C, 83.01; H, 6.62; N, 4.84. Found: C, 82.86; H, 6.59; N, 4.66.

EXAMPLE 38

3-Benzyloxy-7,8,9,10-tetrahydrophenanthridine N-Oxide (Compound 222)

To a solution of Compound 138 (2.12 g, 7.33 mmol) in $CH_2Cl_2$ (40 mL) cooled in an ice-water bath was added mCPBA (50 percent, 2.53 g, 7.33 mmol) followed by stirring at 25° C. for 30 minutes. The reaction mixture was diluted with $CH_2Cl_2$, washed with saturated aqueous $NaHCO_3$ and brine, dried over anhydrous $Na_2SO_4$, and concentrated in vacuo. Ethyl ether (50 mL) was added to the residue, the precipitate was collected by filtration to provide N-oxide Compound 222 (1.97 g, 88 percent): pale-yellow powder; mp 139°–141° C. (from ethyl ether); $R_f$ =0.40 (silica, 3.2 percent methanol in dichloromethane); IR ($CHCl_3$) $\nu_{max}$ 2947, 1625, 1575, 1509, 1423, 1392, 1280, 1232, 1182, 1148 $cm^{-1}$, $^1H$ NMR (300 MHz, $CDCl_3$) δ8.37 (s, 1 H, H6), 8.22 (d, J=2.6 Hz, 1 H, H4), 7.87 (d, J=9.3 Hz, 1 H, H1), 7.53–7.37 (m., 5 H, aromatic), 7.34 (dd, J=9.3, 2.6 Hz, 1 H2), 5.26 (s, 2 H, benzylic), 3.04 (t, J=6.0, 2 H, H7 or H10), 2.81 (t, J=6.0 Hz, 2 H, H7 or H10), 2.02–1.83 (m, 4 H, H8 and H9); MS (FAB+) m/e (rel intensity) 306 (M+H, 100), 290 (16), 215 (3); HRMS for $C_{20}H_{20}HO_2$ (M°H), calcd 306.1494, found 306.1501.

EXAMPLE 39

10-Acetoxy-3-benzyloxy-7,8,9,10-tetrahydrophenanthridine (Compound 223)

A suspension of N-oxide Compound 222 (1.879 g, 6.15 mmol) in acetic anhydride (40 mL) was stirred at 25° C. for 14 hours. Acetic anhydride was removed in vacuo to give a residue which was purified by flash column chromatography (silica gel, 33 percent ethyl ether in benzene) to afford Compound 223 (1.714 g, 80 percent): white crystalline solid; mp 70°-72° C. (from benzene-petroleum ether); $R_f=0.40$ (silica, 33 percent ethyl ether in benzene); IR (CHCl$_3$) $v_{max}$ 2952, 1730, 1620, 1508, 1240, 1016 cm$^{-1}$; $^1$H NMR (300 MHz, CDCl$_3$) $\delta$8.65 (s, 1 H, H6), 7.69 (d, J=9.2 Hz, 1 H, H1), 7.51 (d, J=2.7 Hz, 1 H, H4), 7.48 (d, J=6.9 Hz, 2 H, aromatic), 7.43-7.31 (m, 3 H, aromatic), 7.28 (dd, J=9.2, 2.6 Hz, 1 H, H2), 6.55 (t, J=3.0 Hz, 1 H, H10), 5.20 (s, 2 H, benzylic), 3.08-2.96 (m, 1 H, H7), 2.88-2.76 (m, 1 H, H7), 2.28-2.20 (m, 1 H, H8 or H9), 2.07 (s, 3 H, COCH$_3$), 2.03-1.85 (m, 3 H, H8 and H9); MS (FAB+) m/e (rel intensity) 348 (M+H, 100), 288 (12), 258 (3); HRMS for C$_{22}$H$_{22}$NO$_3$ (M+H), calcd 348.1600, found 348.1600. Anal. Calcd for C$_{22}$H$_{21}$NO$_3$: C, 76.06; H, 6.09; N, 4.03. Found: C, 76.04; H, 6.05; N, 3.92.

EXAMPLE 40

3-Benzyloxy-10-hydroxy-7,8,9,10-tetrahydrophenanthridine (Compound 224)

To a solution of Compound 223 (1.425 g, 410 mmol) in MeOH (25 mL) was added solid K$_2$CO$_3$ (120 mg, 0.87 mmol) followed by stirring at 25° C. for three hours. The solvent was removed in vacuo, the residue was purified by passing through a short column (silica gel, elution with ethyl ether) to furnish Compound 224 (1.23 g, 98 percent): white crystalline solid; mp 155°-157° C. (from CH$_2$Cl$_2$-Et$_2$O); $R_f=0.12$ (silica, 33 percent ethyl ether in benzene); IR (CHCl$_3$) $v_{max}$ 3602, 2948, 1620, 1507, 1455, 1348, 1298, 1242, 1150 cm$^{-1}$; $^1$H NMR (300 MHz, CDCl$_3$) $\delta$8.41 (s, 1 H, H6), 8.09 (d, J=9.2 Hz, 1 H, H1), 7.47 (d, J=6.9 Hz, 2 H, aromatic), 7.42-7.30 (m, 4 H, H4 and aromatic), 7.25 (dd, J=9.2, 2.9 Hz, 1 H, H2), 5.32 (t, J=3.5 Hz, 1 H, H10), 5.13 (s, 2 H, benzylic), 2.89-2.65 (m, 2 H, H7), 2.28-2.16 (m, 1 H, H8 or H9), 2.12-1.82 (m, 3 H, H8 or H9); MS (FAB+) m/e (rel intensity) 306 (M+H, 100), 290 (6); HRMS for C$_{20}$H$_{20}$NO$_2$ (M+H), calcd 306.1494, found 306.1495. Anal. Calcd for C$_{20}$H$_{19}$NO$_2$: C, 78.66; H, 6.27; N, 4.59. Found: C, 78.80; H, 6.27; N, 4.50.

EXAMPLE 41

3-Benzyloxy-10-[(tert-butyldimethylsilyl)oxy]-7,8,9,10-tetrahydro-phenanthridine (Compound 225)

To a suspension of Compound 224 (1.10 g, 3.60 mmol) in dry CH$_2$Cl$_2$ (10 mL) under ice-cooling was added successively 2,6-lutidine (0.59 mL, 5.07 mmol) and tert-butyldimethylsilyl trifluoromethanesulfonate (0.99 mL, 4.31 mmol), the resultant homogeneous solution was then stirred at 25° C. for 30 minutes. The reaction mixture was diluted with CH$_2$Cl$_2$ (20 mL), washed with brine, dried over anhydrous Na$_2$SO$_4$, and evaporated in vacuo. The residue was purified by flash column chromatography (silica gel, ethyl ether-petroleum ether-benzene=1:2:2) to give Compound 225 (1.475 g, 98 percent): white solid; mp 123°-125° C.; $R_f=0.50$ (silica, 33 percent ethyl ether in benzene); IR (CHCl$_3$) $v_{max}$ 2952, 2933, 1621, 1506, 1336, 1295, 1256, 1240, 1174, 1151, 1090, 1025, 838 cm$^{-1}$; $^1$H NMR (300 MHz, CDCl$_3$) $\delta$8.61 (s, 1 H, H6), 7.98 (d, J=9.2 Hz, 1 H, 1), 7.55-7.48 (m, 3 H, H4 and aromatic), 7.46-7.34 (m, 3 H, aromatic), 7.27 (dd, J=9.2, 2.7 Hz, 1 H, H2), 5.42 (t, J=2.6 Hz, 1 H, H10), 5.20 (s, 2 H, benzylic), 3.04-2.93 (m, 1 H, H7), 2.87-2.72 (m, 1 H, H7), 2.26-2.05 (m, 2 H, H8 or H9), 1.92-1.76 (m, 2 H, H8 or H9), 0.84 (s, 9 H, SiC(CH$_3$)$_3$), 0.22 (s, 6 H, Si(CH$_3$)$_2$); MS (FAB+) m/e (rel intensity) 420 (M+H, 100), 362 (23), 330 (3), 288 (9); HRMS for C$_{26}$H$_{34}$NO$_2$Si (M+H), calcd 420.2359, found 420.2360.

EXAMPLE 42

10-[(tert-Butyldimethylsilyl)oxy]-3-hydroxy-7,8,9,10-tetrahydrophenanthridine (Compound 141a)

A solution of Compound 225 (2.00 g, 4.77 mmol) in EtOH (80 mL) was hydrogenated over 10 percent Pd/C (1.00 g) under hydrogen atmosphere (ambient pressure) for four hours. The catalyst was removed by filtration through Celite with elution by 50 percent Et$_3$N in THF (1.5 L). The combined filtrate was evaporated in vacuo to provide Compound 141a (1.40 g, 89 percent): white crystalline solid; mp 248°-250° C. (dec., from MeOH—Et$_3$N); $R_f=0.48$ (silica, 3.2 percent methanol in dichloromethane); IR (KBr) $v_{max}$ 3400, 2929, 2857, 1622, 1619, 1611, 1477, 1404, 1249, 1238, 1212, 1088, 1034, 838, 773 cm$^{-1}$; $^1$H NMR (300 MHz, CDCl$_3$) $\delta$9.99 (br s, 1 H, ArOH), 8.52 (s, 1 H, H6), 7.91 (d, J=9.0 Hz, 1 H, H1), 7.20 (d, J=2.4 Hz, 1 H, H4), 7.14 (dd, J=9.0, 2.4 Hz, 1 H, H2), 5.43 s, 1 H, H10), 2.95-2.84 (m, 1 H, H7), 2.79-2.65 (m, 1 H, H7), 2.14-2.04 (m, 1 H, H8 or H9), 2.00-1.87 (m, 1 H, H8 or H9), 1.86-1.65 (m, 2 H, H8 or H9), 0.79 (s, 9 H, SiC(CH$_3$), 0.00 (s, 3 H, SiCH$_3$), $-0.02$ (s, 3 H, SiCH$_3$); MS (FAB+) m/e (rel intensity) 330 (M+H, 100), 272 (14), 198 (9); HRMS for C$_{19}$H$_{28}$NO$_2$Si (M+H), calcd 330.1889, found 330.1890. Anal Calcd for C$_{19}$H$_{27}$NO$_2$Si: C, 69.26; H, 8.26; N, 4.25. Found: C, 69.10; H, 8.17; N, 4.16.

EXAMPLE 43

3-(Trimethylacetyl)-1,3-thiazolidine-2thione (Compound 226)

To a suspension of NaH (60 percent, 1.06 g, 26.5 mmol) in dry THF (10 mL) cooled at zero degrees C was added a solution of 2-mercaptothiazoline (3.0 g, 25.17 mmol) in dry THF (20 mL) followed by stirring at zero degrees C for 10 minutes. To the mixture was added trimethylacetyl chloride (3.1 mL, 25.17 mmol), the resultant mixture was then stirred at 25° C. for two hours. Water was added to the reaction mixture followed by extraction with ethyl acetate (100 mL), dry over anhydrous Na$_2$SO$_4$, and removal of the solvent in vacuo to give a crude product. Flash column chromatography of the crude product (silica gel, 17 percent ethyl ether in petroleum ether) afforded Compound 226 (4.68 g, 91 percent): pale-yellow solid; mp 48°-50° C.; $R_f=0.19$ (silica, 17 percent ethyl ether in petroleum ether); IR (CHCl$_3$) $v_{max}$ 2980. 1808, 1738, 1480, 1463, 1396, 1388, 1286, 1251, 1139, 1044, 1003, 874 cm$^{-1}$; $^1$H NMR (300 MHz, CDCl$_3$) $\delta$4.21 (t, J=7.3 Hz, 2 H, NCH$_2$CH$_2$S), 3.51 (t, J =7.3 Hz, 2 H, NCHH$_2$CH$_2$S), 1.41 (s, 9 H, C(CH$_3$); MS (FAB+) m/e (rel intensity) 204 (M+H, 100), 120 (27); HRMS for C$_8$H$_{14}$NOS$_2$ (M+H), calcd 204.0517, found 204.0500.

EXAMPLE 44

10-[(tert-Butyldimethylsilyl)oxy]-3-(trimethylacetoxy)-7,8,9,10-tetrahydrophenanthridine (Compound 142a)

To a suspension of Compound 141a (1.28 g, 3.88 mmol) in dry THF (50 mL) cooled in an ice-water bath was added NaH (60 percent, 163 mg, 4.08 mmol) followed by stirring for 10 minutes. A yellow-colored solution of Compound 226 (0.789 g, 3.88 mmol) in dry THF (10 mL) was added, and the mixture was then stirred at 25° C. for five minutes. The reaction mixture was quenched with water, extracted with ethyl acetate (50 mL), washed with brine, dried over anhydrous $Na_2SO_4$, and evaporated in vacuo to give a residue. Flash column chromatography of the residue (silica gel, 20 percent ethyl ether in benzene) provided Compound 142a (1.59 g, 99 percent): white powder; mp 125°–126.5° C.; $R_f$=0.49 (silica, 20 percent ethyl ether in benzene); IR $(CHCl_3)$ $\nu_{max}$ 2957, 2934, 1750, 1261, 1131, 1116, 1027 cm$^{-1}$; $^1$H NMR (300 MHz, $CDCl_3$) $\delta$8.58 (s, 1 H, H6), 7.98 (d, J=9.1 Hz, 1 H, H1), 7.67 (d, J=2.1 Hz, 1 H, H4), 7.21 (dd, J=9.1 2.1 Hz, 1 H, H2), 5.33 (t, J=2.9 Hz, 1 H, H10), 2.90 (br dd, J=17.2, 3.3 Hz, 1 H, H7), 2.72 (ddd, J=17.2, 11.2, 5.7 Hz, 1 H, H7), 2.17–1.96 (m, 2 H, H8 or H9), 1.83–1.67 (m, 2 H, H8 or H9), 1.31 (s, 9 H, $COC(CH_3)_3$), 0.74 (s, 9 H, $SiC(CH_3)_3$), 0.12 (s, 6 H, $Si(CH_3)_2$); MS (FAB+) m/e (rel intensity) 414 (M+H, 100), 357 (9), 330 (12), 283 (5), 198 (10); HRMS for $C_{24}H_{36}NO_3Si$ (M+H), calcd 414.2464, found 414.2484. Anal. Calcd for $C_{24}H_{35}NO_3Si$: C, 69.69; H, 8.53; N, 3.39. Found: C, 69.68; H, 8.44; N, 3.23.

EXAMPLE 45

10-[(tert-Butyldimethylsilyl)oxy]-3-[(2-nitrobenzyl)oxy]-7,8,9,10-tetrahydrophenanthridine (Compound 143a)

To a suspension of Compound 141a (1.00 g, 3.03 mmol) in dry THF (20 mL) cooled in an ice-water bath was added NaH (60 percent, 128 mg, 3.19 mmol) followed by stirring for 10 minutes. To the resultant solution was added 2-nitrobenzyl bromide (0.689 g, 3.19 mmol), and tetra-n-butylammonium iodide (0.11 g, 0.3 mmol), and the mixture was then stirred at 25° C. for one hour. Water was added to the reaction mixture followed by extraction with ethyl acetate (50 mL), washing with brine, dry over anhydrous $Na_2SO_4$, and concentration in vacuo to give a crude product. Flash column chromatography of the crude product (silica gel, 20 percent ethyl ether in benzene) afforded Compound 143a (1.27 g, 90 percent(: pale-yellow solid; mp 150°–152° C.; $R_f$=0.33 (silica, 20 percent ethyl ether in benzene); IR $(CHCl_3)$ $\nu_{max}$ 2953, 2933, 1623, 1528, 1343, 1090, 1027, 838 cm$^{-1}$; $^1$H NMR (300 MHz, $CDCl_3$) $\delta$ 8.60 (s, 1 H, H6), 8.21 (dd, J=8.0, 0.9 Hz, 1 H, aromatic), 8.01 (d, J=9.2 Hz, 1 H, H1), 7.92 (d, J=7.8 Hz, 1 H, aromatic), 7.68 (dt, J=7.8, 0.9 Hz, 1 H, aromatic), 7.50 (t, J=8.0 Hz, 1 H, aromatic), 7.44 (d, J=2.6 Hz, 1 H, H4), 7.32 (dd, J=9.2, 2.6 Hz, 1 H, H2), 5.66 (s, 2 H, benzylic), 5.42 (t, J=3.1 Hz, 1 H, H10), 2.97 (br dd, J=14.0, 4.0 Hz, 1 H, H7), 2.86–2.72 (m, 1 H, H7), 2.25–2.15 (m, 2H, H8 or H9), 1.90–1.80 (m, 2 H, H8 or H9), 0.85 (s, 9 H, $SiC(CH_3)_3$), 0.22 (s, 6 H, $Si(CH_3)_2$); MS (FAB+) m/e (rel intensity 465 (N+Cs, 100), 407 (19), 330 (26), 198 (17), 136 (18); HRMS for $C_{26}H_{32}N_2O_4SiCs$ (M+Cs), calcd 465.2210, found 465.2210. Anal. Calcd for $C_{26}H_{32}N_2O_4Si$: C, 67.21; H, 6.94; N, 6.03. Found: C, 67.31; H, 6.91; N, 5.96.

EXAMPLE 46

10-[(tert-Butyldimethylsilyl)oxy]-3-methoxy-7,8,9,10-tetrahydrophenanthridine (Compound 208)

Prepared from the m-anisidine reaction product with Compound 134 by following the sequence described for Compound 225. Compound 208: white solid; mp 102°–104° C.; $R_f$=0.53 (silica, 50 percent ethyl ether in benzene); IR $(CHCl_3)$ $\nu_{max}$ 2951, 2933, 2857, 1624, 1508, 1472, 1336, 1257, 1090, 1033, 975, 870, 838 cm$^{-1}$; $^1$H NMR (300 MHz, $CDCl_3$) $\delta$8.60 (s, 1 H, H6), 7.95 (d, J=9.2 Hz, 1 H, H1), 7.41 (d, J=2.6 Hz, 1 H, H4), 7.19 (dd, J =9.2, 2.6 Hz, 1 H, H2), 5.41 (t, J=3.1 Hz, 1 H, H10), 3.94 (s, 3 H, $OCH_3$), 3.20–2.92 (m, 1 H, H7), 2.86–2.72 (m, 1 H, H7), 2.27–2.03 (m, 2 H, H8 or H9), 1.90–1.75 (m, 2 H, H8 or H9), 0.81 (, 9 H, $SiC(CH_3)_3$), 0.20 (s, 6 H, $Si(CH_3)_2$); MS (FAB+) m/e (rel intensity) 344 (M+H), 100), 286 (15), 212 (21); HRMS for $C_{20}H_{30}NO_2Si$ (M+H), calcd 344.2046, found 344.2075.

EXAMPLE 47

Addition of Ethynylmagnesium Bromide to Quinoline Derivatives. N-[(Phenyloxy)carbonyl]-10-[(tert-butyldimethylsilyl)oxy]-6-ethynyl-3-(trimethylacetoxy)-5,6,7,8,9,10-hexahydrophenanthridine (Compound 142b)

Representative Procedures. To a solution of Compound 142a (5.066 g, 12.25 mmol) in dry THF (50 mL) cooled in a dry ice-acetone bath (−78° C.) was added ethynylmagnesium bromide (0.5 M in THF, 36.8 mL, 18.40 mmol) and phenyl chloroformate (2.3 mL, 18.33 mmol). The reaction mixture was then warmed to zero degrees C during 15 minutes, quenched with saturated aqueous $NH_4Cl$, extracted with ethyl acetate (200 mL), washed with brine, dried over anhydrous $Na_2SO_4$, and concentrated in vacuo. Flash column chromatography of the residue (silica gel, 33 percent ethyl ether in benzene) gave Compound 142b (6.68 g, 97 percent) as a 69:31 mixture of trans and cis isomers. Compound 142b: amorphous solid; mp 66°–68° C.; $R_f$=0.61 (silica, 20 percent ethyl ether in petroleum ether); IR $(CHCl_3)$ $\nu_{max}$ 3306, 2957, 2933, 1746 (shoulder), 1731 (shoulder), 1720, 1500, 1384, 1311, 1201, 1183, 1119, 1025, 838 cm$^{-1}$; $^1$H NMR (300 MHz, $CDCl_3$) $\delta$ 7.65 (d, J=8.6 Hz, 0.31 H, H1), 7.44–7.34 (m, 3.69 H, aromatic), 7.28–7.17 (m, 3.31 H, aromatic), 6.92 (dd, J=8.6, 2.3 Hz, 0.69 H, H2), 5.66 (d, J=2.3 Hz, 0.69 H, H6), 5.61 (d, J=2.0 Hz, 0.31 H, H6), 4.96 (t, J=3.0 Hz, 0.69 H, H10), 4.64 (br s, 0.31 H, H10), 2.53–1.64 (m, 7 H, acetylenic, H7, H8 and H9), 1.33 and 1.32 (s, 9 H, $COC(CH_3)_3$), 0.93 (s, 2.79 H, $SiC(CH_3)_3$), 0.82 (s, 6.21 H, $SiC(CH_3)_3$), 0.25 (s, 0.93 H, $SiCH_3$), 0.19 (s, 2.07 H, $SiCH_3$), 0.10 (s, 2.07 H, $SiCH_3$), 0.09 (s, 2.07 H, $SiCH_3$); MS (FAB+) m/e (rel intensity) 692 (M+Cs, 68), 534 (11), 502 (52), 428 (29), 222 (12); HRMS for $C_{33}H_{41}NO_5SiCs$ (M+Cs), calcd 692.1808, found 692.1849. Anal. Calcd for $C_{33}H_{41}NO_5Si$: C, 70.81; H, 7.38; N, 2.50. Found: C, 69.04; H, 7.31; N, 2.35.

EXAMPLE 48

N-[(Phenyloxy)carbonyl]-10-[(tertbutyldimethylsilyl)oxy]-6-ethy-nyl-3-methoxy-5,6,7,8,9,10-hexahydrophenanthridine (Compound 227)

Prepared from Compound 208 in 99 percent yield as a 84:16 mixture. Compound 226: amorphous solid; $R_f$=0.25 (silica, 9 percent ethyl ether in petroleum ether); IR (CHCl₃) ν$_{max}$ 3303, 2954, 2931, 1703, 1576, 1432, 1302, 1288, 1259, 1073, 928 cm⁻¹; ¹H NMR (300 MHz, CDCl₃) δ 7.57–6.70 (m, 8 H, aromatic), 5.64 (d, J=2.1 Hz, 0.84 H, H6), 5.59 (br, 0.16 H, H6), 4.94 (br, 0.84 H, H10), 4.64 (br, 0.16 H, H10), 3.81 (s, 3 H, OC$\underline{H}$₃), 2.50–1.60 (m, 7 H, acetylenic, H7, H8 and H9), 0.93 (s, 1.44 H, SiC(C$\underline{H}$₃)₃), 0.82 (s, 7.56 H, SiC(C$\underline{H}$₃)₃), 0.26 (s, 0.48 H, SiC$\underline{H}$₃), 0.18 (s, 0.48 H, SiC$\underline{H}$₃), 0.09 (s, 2.52 H, SiC$\underline{H}$₃), 0.8 (s, 2.52 H, SiC$\underline{H}$₃); MS (FAB+) m/e (rel intensity 622 (M+Cs, 23), 464 (34), 432 (82), 358 (52), 236 (27); HRMS for C₂₉H₃₅NO₄SiCs (M+Cs), calcd 622.1390, found 622.1390.

EXAMPLE 49

N-[(Phenyloxy)carbonyl]-3-benzyloxy-10-[(tert-butyl-dimethylsilyl)-oxy]-6-ethynyl-5,6,7,8,9,10-hexahydrophenanthridine (Compound 140c)

Prepared from Compound 140a in 90 percent yield as a 79:21 mixture. Compound 140c: amorphous solid; mp 76.5°–78.2° C.; R$_f$=0.30 (silica, 9 percent ethyl ether in petroleum ether); IR (CHCl₃) ν$_{max}$ 3305, 2951, 2931, 1716, 1611, 1506, 1385, 1310, 1094, 1024, cm⁻¹; ¹H NMR (300 MHz, CDCl₃) δ 7.58–6.78 (m, 13 H, aromatic), 5.63 (d, J=2.0 Hz, 0.79 H, H6), 5.60 (br s, 0.21 H, H6), 5.06 (s, 2 H, benzylic), 4.95 (br, 0.79 H, H10), 4.64 (br, 0.21 H, H10), 2.50–1.60 (m, 7 H, acetylenic, H7, H8 and H9), 0.94 (s, 1.89 H, SiC(C$\underline{H}$₃)₃), 0.82 (s, 7.11 H, SiC(C$\underline{H}$₃)₃), 0.26 (s, 0.63 H, SiC$\underline{H}$₃), 0.19 (s, 0.63 H, SiC$\underline{H}$₃), 0.10 (s, 2.37 H, SiC$\underline{H}$₃), 0.8 (s, 2.37 H, SiC$\underline{H}$₃); MS (FAB+) m/e (rel intensity) 698 (M+Cs, 26), 540 (12), 508 (35), 434 (19); HRMS for C₃₅H₃₉NO₄SiCs (M+Cs), calcd 698.1703, found 698.1754.

EXAMPLE 50

N-[(Phenyloxy)carbonyl]-10-[(tertbutyldimethylsilyl)oxy]-6-ethynyl-3-[(2-nitrobenzyl)oxy]-5,6,7,8,9,10-hexahydrophenanthridine (Compound 143b)

Prepared from Compound 143a in 98 percent yield as a 79:21 mixture. Compound 143b: amorphous solid; mp 188°–190° C.; R$_f$=0.33 (silica, 20 percent ethyl ether in petroleum ether); IR (CHCl₃) ν$_{max}$ 3306, 3018, 2952, 2933, 1717, 1612, 1527, 1505, 1385, 1344, 1306, 1199, 838 cm⁻¹; ¹H NMR (300 MHz, CDCl₃) δ 8.12 (d, J=7.8 Hz, 1 aromatic), 7.89 (d, J=7.8 Hz, 1 H, aromatic), 7.62 (t, J=7.2 Hz, 1 H, aromatic), 7.59 (d, J=8.7 Hz, 0.21H, H1), 7.46–7.12 (m, 7.79 H, H1, H4 and aromatic), 6.86–6.79 (m, 1 H, H2), 5.64 (d, J=1.8 Hz, 0.79 H, H6), 5.59 (br s, 0.21 H, H6), 5.51 (s, 2 H, benzylic), 4.95 (br s, 0.79 H, H10), 4.64 (br s, 0.21 H, H10), 2.51–1.55 (m, 7 H, acetylenic, H7, H8, and H9), 0.94 (s, 1.89 H, SiC(C$\underline{H}$₃)₃), 0.82 (s, 7.11 H, SiC(C$\underline{H}$₃)₃), 0.26 (s, 0.63 H, SiC$\underline{H}$₃), 0.19 (s, 0.63 H, SiC$\underline{H}$₃), 0.09 (s, 2.37 H, SiC$\underline{H}$₃) 0.08 (s, 2.37 H, SiC$\underline{H}$₃); MS (FAB+) m/e (rel intensity) 743 (M+Cs, 78), 610 (11), 553 (32), 479 (24), 222 (9), 133 (100); HRMS for C₃₅H₃₈N₂O₆SiCs (M+Cs), calcd 743.1553, found 743.1554. Anal. Calcd for C₃₅H₃₈N₂O₆Si: C, 568.83; H, 6.27; N, 4.59. Found: C, 68.98; H, 6.38; N, 4.42.

EXAMPLE 51

N-[(Phenyloxy)carbonyl]-10-[tertbutyldimethylsilyl)oxy]6a,
10a-epoxy-6-ethynyl-3-(trimethylacetoxy)-5,6,6a,7,8,9,10,10a-octahydrophenanthridine (Compound 228)

To a solution of Compound 142a (6.4 g, 12.25 mmol) in CH₂Cl₂ (100 mL) cooled at zero degrees C was added mCPBA (50 percent, 8.46 g, 24.51 mmol) followed by stirring at 25° C. for three hours. The reaction mixture was diluted with CH₂Cl₂ (100 mL), washed with saturated aqueous NaHCO₃, and brine, dried over anhydrous NaSO₄, and evaporated in vacuo. The residue was purified by flash column chromatography (silica gel, benzene) to furnish Compound 228 (7.0 g, 99 percent) as a 71:29 diastereomeric mixture. Diastereomeric pure samples of Compound 228 were obtained by perparative TLC (silica gel plate, benzene); Major isomer: white amorphous solid; mp 78°–80° C.; R$_f$=0.38 (silica, benzene); IR (CHCl₃) ν$_{max}$ 3307, 2956, 1748 (shoulder), 1724, 1382, 1306, 1202, 1183, 1119, 838 cm⁻¹; ¹H NMR (300 MHz, CDCl₃) δ7.86 (d, J=8.6 Hz, 1 H, H1), 7.42–7.11 (m, 6 H, H4 and aromatic), 6.99 (d, J=8.6 Hz, 1 H, H2), 5.57 (br s, 1 H, H6), 4.77 (dd, J=9.8, 5.7 Hz, 1 H, H10), 2.33 (dd, J=13.9, 5.9 Hz, 1 H, H7), 1.96–1.81 (m, 2 H, H7 and H8 or H9), 1.80–1.53 (m, 3 H, H8 and H9), 1.34 (s, 9 H, COC(C$\underline{H}$₃)₃), 0.89 (s, 9 H, SiC(C$\underline{H}$₃)₃), 0.21 (s, 3 H, SiC$\underline{H}$₃), 0.07 (br s, 3, SiC$\underline{H}$₃); MS (FAB+) m/e (rel intensity) 576 (M+H, 25), 518 (100), 444 (8), 330 (7); HRMS for C₃₃H₄₂NO₆Si (M+H), calcd 576.2781, found 576.2760. Minor isomer: colorless gum; R$_f$=0.27 (silica, benzene); IR (CHCl₃)ν$_{max}$ 3306, 2958, 2934, 1748 (shoulder), 1721, 1683, 1495, 1382, 1307, 1201, 1178, 1122, 837 cm⁻¹; ¹NMR (300 MHz, CDCl₃) δ7.61 (d, J=8.6 Hz, 1 H, H1), 7.39–7.11 (m, 6 H, H4 and aromatic), 6.96 (dd, J=8.6, 2.4 Hz, 1 H, H2), 5.53 (d, J=2.1 Hz, 1 H, H6), 4.90 (d, J=2.6 Hz, 1 H, H10), 2.49–2.37 (m, 1 H, H7), 2.09–1.82 (m, 4 H, 7, H8 and H9 ), 1.77–1.66 (m, 1 H, H8 or H9), 1.33 (s, 9 H, COC(C$\underline{H}$₃)₃), 0.83 (s, 9 H, SiC(C$\underline{H}$₃)₃), 0.26 (s, 3 H, SiC$\underline{H}$₃), 0.16 (s, 3 H, SiC$\underline{H}$₃); MS (FAB+) m/e (rel intensity) 576 (M+H, 92), 559 (34), 529 (22), 518 (100), 444 (86), 360 (8), 266 (13), 238 (29); HRMS for C₃₃H₄₂NO₆Si (M+H), calcd 576.2781, found 576.2799.

EXAMPLE 52

N-[(Phenyloxy)carbonyl]-6-ethynyl-10-oxo-3-(trimethylacetoxy)-5,6,7,8,9,10-hexahydrophenanthridine (Compound 229)

To a solution of Compound 228 (7.0 g, 12.16 mmol) in wet CHCl₃ (100 mL) was added BF₃.OEt₂ (7.48 mL, 60.82 mmol). The mixture was stirred at 25° C. (1.5 hours) until TLC indicated complete conversion of Compound 228. Silica gel (10.0 g) was added to the reaction mixture followed by stirring at 25° C. for another 12 hours. Silica gel was filtered off through Celite and washed with ethyl ether (100 mL). The solvent was removed in vacuo, and the residue was purified by flash column chromatography (silica gel, 10 percent ethyl ether in benzene) to provide Compound 229 (3.91 g, 73 percent). A more polar component (about 1.0 g) was also isolated which could not be converted to Compound 229 in the presence of silica gel for prolonging reaction time. Compound 229: white solid; mp 140°–142° C.; R$_f$=0.44 (silica, 10 percent ethyl ether in benzene): IR (CHCl₃) δ$_{max}$ 3305, 2977, 1737 (shoulder), 1720, 1705, 1684, 1607, 1577, 1495, 1382, 1306, 1201, 1178, 1122 cm⁻¹; ¹H NMR (300 MHz, CDCl₃) 67 8.25 (d, J=8.7 Hz, 1 H, H1), 7.43–7.35 (m, 3 H, H4 and aromatic), 7.28–7.16 (m, 3 H, aromatic), 6.98 (dd, J=8.7, 2.4 Hz, 1 H, H2), 5.86 (d, J=2.4 Hz, 1 H, H6), 2.87–2.51 (m, 4 H, H7 and H9), 2.26 (d, J=2.4 Hz, 1 H, acetylenic), 2.24–2.08 (m, 2 H, H8), 1.33 (s, 9 H, COC(C$\underline{H}$₃)₃); MS (FAB+), m/e (rel intensity) 444 (M+H), 82), 350 (15), 266 (20), 238 (15); HRMS for C₂₇H₂₆NO₅ (M+H), calcd 444.1811, found 444.1842.

EXAMPLE 53

N-[(Phenyloxy)carbonyl]-6a, 10a-epoxy-6-ethynyl-10-oxo-3-(trime-thylacetoxy)-5,6,6a, 7,8,9,10,10a-octahydrophenanthridine (Compound 230)

To a mixture of Compound 231 (2.15 g, 4.85 mmol) in CH$_2$Cl$_2$ (50 mL) and saturated aqueous NaHCO$_3$ (50 mL) cooled at zero degrees C was added mCPBA (50 percent, 2.01 g, 5.82 mmol) followed by stirring at 25° C. for 10 minutes. The reaction mixture was diluted with CH$_2$Cl$_2$(50 mL), washed with saturated aqueous NaHCO$_3$ and brine, dried over anhydrous Na$_2$SO$_4$, and evaporated in vacuo. Flash column chromatography of the residue (silica gel, 10 percent ethyl ether in benzene) afforded Compound 230 (1.5 g, 67 percent): amorphous solid; mp 164°-166° C.; R$_f$=0.56 (silica, 10 percent ethyl ether in benzene); IR (CHCl$_3$) ν$_{max}$ 3306, 2976, 1749 (shoulder), 1721, 1494, 1379, 1305, 1203, 1181, 1122 cm$^{-1}$; $^1$H NMR (300 MHz, CDCl$_3$) δ8.40 (d, J=8.8 Hz, 1 H, H1), 7.41-7.33 (m, 3 H, H4 and aromatic), 7.25-7.10 (m, 3 H, aromatic), 7.00 (dd, J=8.8, 2.3 Hz, 1 H, H2), 5.73 (d, J=2.3 Hz, 1 H, H6), 2.75 (ddd, J=15.6, 5.2, 5.2 Hz, 1 H, H9), 2.60 (ddd, J=15.6, 10.0, 6.5 Hz, 1 H, H9), 2.38-2.22 (m, 3 H, acetylenic and H7), 2.08-1.85 (m, 2 H, H8), 1.34 (s, 9 H, COC(CH$_3$)$_3$); MS m/e (rel intensity) 460 (M+H, 91), 376 (16), 255 (4),215 (23), 154 (100); HRMS for C$_{27}$H$_{26}$NO$_6$ (M+H), calcd 460.1760, found 460.1760.

EXAMPLE 54

N-[(Phenyloxy)carbonyl]-6a, 10a-epoxy-10-oxo-3-(trimethylacetoxy)-6-[6-trimethylsilyl-3(Z)-hexene-1,5-diynyl]-5,6,6a, 7,8,9,10,10a-octahydrophenanthridine (Compound 231)

A mixture of Pd(PPh$_3$)$_4$ (185 mg, 0.16 mmol), 1-chloro-4-(trimethylsilyl)-but-1-en-3-yne (0.776 g, 4.89 mmol), and diethylamine(0.51 L, 4.93 mmol) in degassed benzene (5 mL) was stirred at 25° C. for 15 minutes. The resultant solution was added to a mixture of Compound 230 (1.50 g, 3.26 mmol) and CuI (124 mg, 0.65 mmol) in degassed benzene (15 mL) via a syringe followed by stirring at 25° C. for one hour. The reaction mixture was quenched by saturated aqueous NH$_4$Cl, extracted with ethyl ether (80 mL), washed with brine, dried over anhydrous Na$_2$SO$_4$, and concentrated in vacuo. Purification of the residue by flash column chromatography (silica gel, 25 percent ethyl ether in petroleum ether) provided a solid product Compound 231 (0.606 g, 32 percent): R$_f$=0.43 (silica, 50 percent ethyl ether in petroleum ether); IR (CHCl$_3$) ν$_{max}$ 2964, 1721, 1494, 1378, 1305, 1270, 1253, 1202, 1181, 1122, 846 cm$^{-1}$; $^1$H NMR (300 MHz, CDCl$_3$) δ8.40 (d, J=8.7 Hz, 1 H, H1), 7.44-7.10 (m, 6 H, H4 and aromatic), 6.99 (dd, J=8.7, 2.4 Hz, 1 H, H2), 5.98 (d, J=1.5 Hz, 1 H, H6), 5.84 (d, J=11.1 Hz, 1 H, olefinic), 5.69 (br d, J =11.1 Hz, 1 H, olefinic), 2.81-2.66 (m, 2 H, H9), 2.41-2.26 (m, 2 H, H7), 2.10-1.86 (m, 2 H, H8), 1.33 (s, 9 H, COC(CH$_3$)$_3$), 0.22 (s, 9 H, SiC(CH$_3$)$_3$); MS (FAB+) m/e (rel intensity) 582 (M+H, 100), 525 (13), 460 (48), 406 (8), 360 (60),320 (8), 279 (25), 246 (5); HRMS for C$_{34}$H$_{36}$NO$_6$Si (M+H), calcd 582.2312, found 582.2322.

EXAMPLE 55

N-[(Phenyloxy)carbonyl]-6a, 10a-epoxy-6-[3(Z)-hexene-1,5-diynyl]-10-oxo-3-(trimethylacetoxy)-5,6,6a, 7,8,9,10,10a-octahydrophenanthridine (Compound 213)

Method A. To a solution of Compound 231 (0.38 g, 0.65 mmol) in THF-EtOH-H$_2$O (1:1:1, 12 mL) cooled at zero degrees C was added silver nitrate (0.442 g, 2.60 mmol) followed by stirring at 25° C. for one hour. Potassium cynide (0.296 g, 4.55 mmol) was added to the reaction mixture followed by stirring at 25° C. for another 10 minutes. The reaction mixture was diluted with CH$_2$Cl$_2$ (30 mL), washed with saturated aqueous NaHCO$_3$, dried over anhydrous Na$_2$SO$_4$, and concentrated in vacuo. The residue was purified by flash column chromatography (silica gel, 33 percent ethyl ether in petroleum ether) to give a solid product Compound 213 (0.22 g, 66 percent).

Method B. To a mixture of Compound 212 (3.50 g, 7.09 mmol) in CH$_2$Cl$_2$ (50 mL) and saturated aqueous NaHCO$_3$ (10 mL) cooled at zero degrees C was added mCPBA (50 percent, 2.94 g, 8.51 mmol) followed by stirring at 25° C. for 10 minutes. The reaction mixture was diluted with CH$_2$Cl$_2$(200 mL), washed with saturated aqueous NaHCO$_3$ and brine, dried over anhydrous Na$_2$SO$_4$, and concentrated in vacuo. Flash column chromatography of the residue (silica gel, 33 percent ethyl ether in petroleum ether) afforded Compound 213 (1.12 g, 45 percent based on 71 percent conversion of Compound 212; 1.0 g of Compound 212 was recovered): R$_f$=0.60 (silica, 50 percent ethyl ether in petroleum ether); IR (CHCl$_3$) ν$_{max}$ 3304, 2976, 1748 (shoulder), 1720, 1495, 1377, 1305, 1202, 1181, 1122 cm$^{-1}$; $^1$H NMR (300 MHz, CDCl$_3$) δ8.42 (d, J=8.7 Hz, 1 H, H1), 7.42-7.33 (m, 3 H, H4 and aromatic), 7.2714 7.10 (m, 3 H, aromatic), 6.99 (dd, J=8.8, 2.2 Hz, 1 H, H2), 5.94 (s, 1 H, H6), 5.80 (s, 2 H, olefinic), 3.30 (s, 1 H, acetylenic), 2.82-2.63 (m, 2 H, H9), 2.41-2.27 (m, 2 H, H7), 2.09-1.88 (m., 2 H, H8) 1.33 (s, 9 H, COC(CH$_3$)$_3$); MS (FAB+) m/e (rel intensity) 510 (M+H, 38), 434 (23), 350 (4), 307 (14), 215 (11); HRMS for C$_{31}$H$_{28}$NO$_6$ (M+H), calcd 510.1917, found 510.1966.

EXAMPLE 56

N-[(Phenyloxy)carbonyl]-10-[(tert-butyldimethylsilyl)oxy]-3-(trimethylacetoxy)-6-[6-trimethylsilyl-3(Z)-hexene-1,5-diynyl]-5,6,7,8,9,10-hexahydrophenanthridine (Compound 209)

A mixture of Pd(PPh$_3$)$_4$ (1.65 g, 1.43 mmol), 1-chloro-4-(trimethylsilyl-but-1-en-3-yne (5.80 g, 36.6 mmol), and n-propylamine (3.5 mL, 42.9 mmol) in degassed benzene (100 mL) was stirred at 25° C. for 15 minutes. The resultant solution was added to a mixture of Compound 142a (69:31 mixture of steromers, 16.0 g, 28.6 mmol) and CuI (1.09 g, 5.7 mmol) in degassed benzene (300 mL) via a syringe followed by stirring at 25° C. for 8 hours. The reaction was quenched with saturated aqueous NH$_4$Cl, extracted with ethy ether (300 mL), washed with brine, dried over anhydrous Na$_2$SO$_4$, and concentrated in vacuo. Purification of the crude product by flash column chromatography (silica gel, 10 percent ethyl ether in petroleum ether) gave Compound 209 (13.0 g, 67 percent) as a mixture of diastereomers. Major isomer: R$_f$=0.44 (silica, 10 percent ethyl ether in petroleum ether); IR (CHCl$_3$) ν$_{max}$ 2958, 2932, 1748 (shoulder), 1730, (shoulder), 1718, 1494, 1383, 1310, 1181, 1118, 1028, 845 cm$^{-1}$; $^1$H NMR (300 MHz, CDCl$_3$) δ

7.40–7.16 (m, 7 H, H1, H4, and aromatic), 6.88 (dd, J=8.6, 2.3 Hz, 1 H, H2), 5.87 (s, 1 H, H6), 5.74 and 5.71 (ABq, J=11.1 Hz, olefinic), 4.93 (br s, 1 H, H10), 2.59–2.46 (m, 1 H, H7), 2.23 (br d, J=18.2 Hz, 1 H, H7), 2.00–1.82 (m, 3 H, H8 and H9), 1.74–1.61 (m, 1 H, H8 or H9), 1.30 (s, 9 H, COC(CH$_3$)$_3$), 0.80 (s, 9 H, SiC(CH$_3$)$_3$), 0.16 (s, 9 H, Si(CH$_3$)$_3$), 0.08 (s, 3 H, SiCH$_3$), 0.06 (s, 3 H, SiCH$_3$); MS (FAB+) m/e (rel intensity) 814 (M+Cs, 100), 681 (9), 624 (42), 588 (7), 534 (22); HRMS for C$_{40}$H$_{51}$NO$_5$Si$_2$Cs (M+Cs), calcd 814.2360, found 814.2360. Minor isomer: R$_f$=0.40 (silica, 10 percent ethyl ether in petroleum ether); IR (CHCl$_3$) $\nu_{max}$ 2958, 2934, 1745, (shoulder), 1727 (shoulder), 1717, 1494, 1382, 1310, 1182, 1118, 1018, 844 cm$^{-1}$; $^1$H NMR (300 MHz, CDCl$_3$) δ 7.63 (d, J=8.6 Hz, 1 H, H1), 7.50 (br s, 1 H, H4), 7.40–7.32 (m, 2 H, aromatic), 7.24–7.15 (m, 3 H, aromatic), 6.89 (dd, J=8.6, 2.3 Hz, 1 H, H2), 5.83 (s, 1 H, H6), 5.75 (s, 2 H, olefinic), 4.63 (br s, 1 H, H10), 2.55 (dd, J=17.7, 4.8 Hz, 1 H, H7), 2.27–1.95 (m, 3 H, H7 and H8 or H9), 1.76–1.53 (m, 2H, H8 or H9), 1.29 (s, 9 H, COC(CH$_3$)$_3$), 0.91 (s, 9 H, SiC(CH$_3$)$_3$), 0.22 (s, 3 H, SiCH$_3$), 0.17 (s, 9 H, Si(CH$_3$)$_3$), 0.16 (s, 3 H, SiCH$_3$); MS (FAB+) m/e (rel intensity) 814 (M+Cs, 100), 681 (45), 624 (27), 588 (26), 534 (60); HRMS for C$_{40}$H$_{51}$NO$_5$Si$_2$Cs (M+Cs), calcd 814.2360, found 814.2361.

EXAMPLE 57

N-[(Phenyloxy)carbonyl]-10-[(tert-butyldimethylsilyl)oxy]-6a,10a-epoxy-3-(trimethylacetoxy)-6-[6-trimethylsilyl-3(Z)-hexene-1,5-diynyl]-5,6,6a,7,8,9,10,10a-octahydrophenanthridine (Compound 210)

To a solution of Compound 209 (mixture of diastereomers, 13.0 g, 19.06 mmol) in CH$_2$Cl$_2$(100 mL) cooled at zero degrees C was added mCPBA (50 percent, 7.9 g, 22.98 mmol) followed by stirring at 25° C. for one hour. The reaction mixture was diluted with CH$_2$Cl$_2$ ()500 mL), washed with saturated aqueous NaHCO$_3$, dried over anahydrous Na$_2$SO$_4$, and concentrated in vacuo. The residue was purified by flash column chromatography (silica gel, 10 percent ethyl ether in petroleum ether) to afford Compound 210 (9.5 g, 71 percent) as a mixture of diastereomers. Major isomer: R$_f$=0.38 (silica, 10 percent ethyl ether in petroleum ether); IR (CHCl$_3$) $\nu_{max}$ 2958, 2933, 1730 (shoulder), 1721, 1382, 1307, 1118, 846 cm$^{-1}$; $^1$H NMR (300 MHz, CDCl$_3$) δ 7.28 (d, J=8.6 Hz, 1 H, H1), 7.40–7.10 (m, 6 H, H4 and aromatic), 6.95 (dd, J=8.6, 1.9 Hz, 1 H, H2), 5.84–5.62 (m, 3 H, H6 and olefinic), 4.76 (dd, J=9.6, 5.7 Hz, 1 H, H10), 2.45 (dd, J=14.5, 4.6 Hz, 1 H, H7), 1.97–1.57 (m, 5 H, H7, H8 and H9), 1.31 (br s, 9 H, COC(CH$_3$)$_3$), 0.87 (s, 9 H, SiC(CH$_3$)$_3$), 0.19 (s, 12 H, Si(CH$_3$)$_3$), 0.06 (s, 3 H, SiCH$_3$); MS (FAB+) m/e (rel intensity) 830 (M+Cs, 100), 681 (6), 624 (9), 534 (11); HRMS for C$_{40}$H$_{51}$NO$_6$Si$_2$Cs (M+Cs), calcd 830.2309, found 830.2361. Minor isomer: R$_f$=0.22 (silica, 10 percent ethyl ether in petroleum ether); IR (CHCl$_3$) $\nu_{max}$ 2958, 2933, 1747 (shoulder), 1721, 1494, 1381, 1306, 1256, 1181, 1118, 909, 844 cm$^{-1}$; $^1$H NMR (300MHz, CDCl$_3$) δ 7.58 (d, J=8.7 Hz, 1 H, H1), 7.40–7.10 (m, 6 H, H4 and aromatic), 6.95 (dd, J=8.7, 2.5 Hz, 1 H, H2), 5.80–5.60 (m, 3 H, H6 and olefinic), 4.89 (d, J=2.4 Hz, 1 H, H10), 2.66–2.50 (m, 1 H, H7), 2.18–1.63 (m, 5 H, H7, H8 and H9), 1.31 (br s, 9 H, COC(CH$_3$)$_3$), 0.94 and 0.79 (s, 9 H, SiC(CH$_3$)$_3$), 0.23, 0.21 and 0.19 (s, 9 H, Si(CH$_3$)$_3$), 0.14 (s, 3 H, SiCH$_3$), 0.06 (s, 3 H, SiCH$_3$); MS (FAB+) m/e (rel intensity) 830 (M+Cs, 100), 708 (8), 640 (13), 534 (7); HRMS for C$_{40}$H$_{51}$NO$_6$Si$_2$Cs (N+Cs), calcd 830.2309, found 830.2296.

EXAMPLE 58

N-[(Phenyloxy)carbonyl]-10-oxo-3-(trimethylacetoxy)-6-[6-trime-thylsilyl-3-(Z)-hexene-1,5-diynyl]-5,6,7,8,9,10-hexahydrophenanthridine (Compound 211)

To a solution of Compound 219 (9.5 g, 13.6 mmol) in wet (CHCl$_3$ (150 mL) cooled at zero degrees C was added BF$_3$. OEt$_2$ (8.4 mL, 68.0 mmol) followed by stirring at 25° C. for 10 minutes. The reaction mixture was diluted with CH$_2$Cl$_2$ (400 mL), washed with saturated aqueous NaHCO$_3$, dried over anhydrous Na$_2$SO$_4$, and concentrated in vacuo. The residue was then dissolved in THF (50 mL) and treated with 48 percent aqueous HBr (5 mL) at 25° C. for 40 minutes with stirring. The reaction mixture was diluted with ethyl ether (400 mL), washed with saturated aqueous NaHCO$_3$ and brine, dried over anhydrous Na$_2$SO$_4$, and concentrated in vacuo. Flash column chromatography of the residue (silica gel, 33 percent ethyl ether in petroleum ether) gave Compound 211 (2.80 g, 34 percent) and Compound 212 (1.30 g, 18 percent). Compound 211: R$_f$=0.52 (silica, 50 percent ethyl ether in petroleum ether); IR (CHCl$_3$) δ$_{max}$ 2970, 1719, 1681, 1606, 1494, 1381, 1307, 1179, 1123, 846 cm$^{-1}$; $^1$H NMR (300 MHz, CDCl$_3$) δ 8.26 (d, J=8.7 Hz, 1 H, H1), 7.45–7.18 (m, 6 H, H4 and aromatic), 6.98 (dd, J=8.7, 2.4 Hz, 1 H, H2), 6.11 (d, J=0.9 Hz, 1 H, H6), 5.84 (d, J=11.1 Hz, 1 H, olefinic), 5.72 (dd, J=11.1, 1.7 Hz, 1 H, olefinic), 2.90 (dt, J=18.9, 4.5 Hz, 1 H, H9), 2.77–2.53 (m, 3 H, H7 and H9), 2.24–2.12 (m, 2 H, H8), 1.34 (s, 9 H, COC(CH$_3$)$_3$), 0.21 (s, 9 H, Si(CH$_3$)$_3$); MS (FAB+) m/e (rel intensity) 698 (M+Cs, 100), 565 (6); HRMS for C$_{34}$H$_{35}$NO$_5$SiCs (M+Cs), calcd 698.1339, found 698.1339.

EXAMPLE 59

N-[(Phenyloxy)carbonyl]-6-[3-(Z)-hexene-1,5-diynyl]-10-oxo-3-(trime-thylacetoxy)-5,6,7,8,9,10-hexahydrophenanthridine (Compound 212)

To a solution of Compound 211 (2.80 g, 4.95 mmol) in THF-EtOH-H$_2$O (1:1:1, 300 mL) was added silver nitrate (3.36 g, 19.8 mmol) followed by stirring at 25° C. for one hour. Potassium cynide (2.26 g, 34.65 mmol) was added to the reaction mixture following by stirring at 25° C. for another 10 minutes. The reaction mixture was diluted with CH$_2$Cl$_2$ (300 mL), washed with brine, dried over anhydrous Na$_2$SO$_4$, and concentrated in vacuo. The residue was purified by flash column chromatography (silica gel, 50 percent ethyl ether in petroleum ether) to furnish Compound 212 (2.20 g, 90 percent): R$_f$=0.43 (silica, 50 percent ethyl ether in petroleum ether); IR (CHCl$_3$) δ$_{max}$ 3302, 2959, 1740 (shoulder), 1725 (shoulder), 1719, 1680, 1606, 1494, 1381, 1307, 1177, 1123 cm$^{-1}$; $^1$H NMR (300 MHz, CDCl$_3$) δ8.25 (d, J=8.8 Hz, 1 H, H1), 7.50–7.17 (m, 6 H, H4 and aromatic), 6.95 (dd, J=8.8, 1.1 Hz, 1 H, H2), 6.06 (s, 1 H, H6), 5.79 (s, 2 H, (olefinic), 3.32 (d, J=1.0 Hz, 1 H, acetylenic), 2.86 (dt, J=18.9, 4.5 Hz, 1 H, H9), 2.76–2.51 (m, 3 H, H7 and H9), 2.23–2.16 (m, 2 H, H8), 1.33 (s, 9 H, COC(CH$_3$)$_3$), MS (FAB+) m/e (rel intensity) 626 (M+Cs, 16), 418 (13); HRMS for C$_{31}$H$_{27}$NO$_5$Cs (M+Cs), calcd 626.0944, found 626.0975.

EXAMPLE 60

Compound 59a

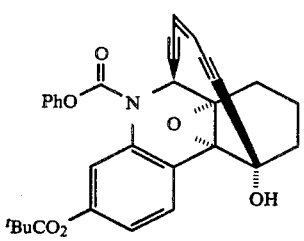

To a solution of Compound 213 (1.12 g, 2.20 mmol) in dry toluene (220 mL, 0.01 M) cooled in a dry ice-acetone (−78° C.) bath was added LDA (1.5 M in cyclohexane, 1.47 mL, 2.20mmol) followed by stirring at −78° C. for 20 minutes. The reaction was quenched with saturated aqueous NH$_4$Cl at −78° C., and allowed to warm to room temperature. Saturated aqueous NaHCO$_3$ was added to the mixture followed by extraction with ethyl ether (200 mL), dry over anhydrous Na$_2$SO$_4$, and concentration in vacuo. The residue was flash column chromatographied (silica gel, 40 percent ethyl ether in petroleum ether) to afford a crystalline Compound 59a (900 mg, 80 percent): colorless plate-like crystals; mp 181°-183° C. (dec., from ethyl ether, 1 mol of ethyl ether were complexed in the crystalls as determined by $^1$H NMR, X-ray and elemental analyses); R$_f$=0.44 (silica, 50 percent ethyl ether in petroleum ether); IR (CHCl$_3$) ν$_{max}$ 3593, 2979, 1748 (shoulder), 1723, 1494, 1382, 1306, 1196, 1115 cm$^{-1}$; $^1$H NMR (300 MHz, CDCl$_3$) δ8.62 (d, J=8.7 Hz, 1 H, aromatic), 7.41-7.32 (m 2 H, aromatic), 7.25-7.13 (m, 4 H, aromatic), 6.96 (dd, J=8.7, 2.4 Hz, 1 H, aromatic), 5.84 (d, J=9.9 Hz, 1 H, olefinic), 5.69 (dd, J=9.9, 1.6 Hz, 1 H, olefinic), 5.53 (d, J=1.6 Hz, 1 H, NCHm), 2.43 (br s, 1 H, OH), 2.32 (dd, J=14.7. 7/8 Hz, 1 H, CH$_2$), 2.25-2.09 (m, 2 H, CH$_2$), 2.08-1.86 (m, 2 H, CH$_2$), 1.78-1.67 (m, 1 H, CH$_2$), 1.32 (s, 9 H, COC(CHH$_3$)$_3$); MS m/e (rel intensity) 510 (M+H, 100), 416 (28), 332 (11), 288 (17), 258 (11); HRMS for C$_{31}$H$_{28}$NO$_6$ (M+H), calcd 510.1917, found 510.1920. Anal. Calcd for C$_{31}$H$_{27}$NO$_6$+(CH$_3$CH$_2$)$_2$O: C, 72.02; H, 6.39; N, 2.40. Found: C, 72.02; H, 6.43; N, 2.38.

EXAMPLE 61

X-ray Crystal Structure Analysis of Compound 59a

A colorless plate-like crystal of Compound 59a formed from ethyl ether having approximate dimensions of 0.14×0.38×0.75 mm was mounted on a glass fibre along the longest dimension. Data collections were performed on Siemens R3m/V diffractometer with graphite-monochromated MoKa radiation (1=0.71073 Å). Crystal data were obtained as follows: a=9.140 (5) Å, b=13.017 (5) Å, c=14.645 (7) Å, a=65.31 (3)°, b=82.80 (4)°, g=76.50 (4)° in a triclinic unit cell with space group of P1 No. 2 C$_i^1$), Z=2 and a calculated density of 1.260 mg/m$^3$.

EXAMPLE 62

Deoxygenation of Compound 59a, Compound 213a

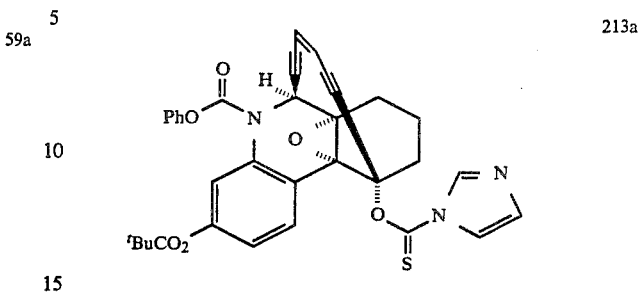

A mixture of Compound 59a (120 mg, 0.235 mmol), thiocarbonyldiimidazole (126 mg, 0.705 mmol), and DMAP (14.4 mg, 0.118 mmol) in CH$_2$Cl$_2$ (1 mL) was stirred at 25° C. for 22 hours. The solvent was removed in vacuo and the residue was purified by flash column chromatography (silica gel, 66 percent ethyl ether in petroleum ether) to afford Compound 213 (85 mg, 58 percent) together with recovery of Compound 59a (40 mg, 33 percent). Compound 212: pale-yellow solid; mp >320° C. (dec.); R$_f$=0.24 (silica, 50 percent ethyl ether in petroleum ether); IR (CHCl$_3$) ν$_{max}$ 2979, 1749 (shoulder), 1725, 1494, 1386, 1334, 1307, 1286, 1247, 1231, 1195, 1117, 1104, 967 cm$^{-1}$; H NMR (300 MHz, CDCl$_3$) δ8.40 (br s, 1 H, imidazole), 7.65 (d, J=8.9 Hz, 2 H, imidazole and aromatic), 7.44-7.18 (m, 6 H, imidazole and aromatic), 7.05 (br s, 1 H, aromatic), 6.90 (dd, J=8.7., 2.4 Hz, 1 H, aromatic), 5.95 (d, J=10.1 Hz, 1 H, olefinic), 5.76 (dd, J=10.1, 1.6 Hz, 1 H, olefinic), 5.60 (d, J=1.6 Hz, 1 H, NCH), 3.09 (br d, J=12.1 Hz, 1 H, CH$_2$ ), 2.50-2.05 (m, 4 H, CH$_2$CH$_2$), 1.92-1.78 (m, 1 H, CH$_2$), 1.31 (s, 9 H, COC(CH$_3$)$_3$); MS (FAB+) m/e (rel intensity) 752 (M+Cs, 56), 642 (10), 560 (15), 492 (39), 372 (13), 336 (9), 288 (36), 258 (38), 232 (36), 207 (37), 169 (41); HRMS for C$_{35}$H$_{29}$N$_3$O$_6$SCs (M+Cs), calcd 752.0831, found 752.0803.

EXAMPLE 63

Compound 59b

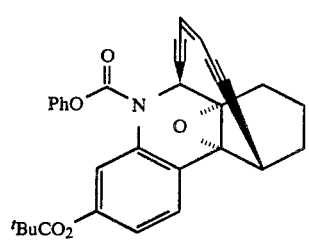

To a solution of Compound 213 (75 mg, 0.121 mmol) in dry PhMe (3 mL) was added AIBN (5 mg, 0.03 mmol) and Bu$_3$SnH (65 mL, 0.242 mmol) followed by heating at 80° C. for one hour. The solvent was removed in vacuo and the residue was purified by preparative TLC (silica gel plate, 33 percent ethyl ether in petroleum ether) to give Compound 59b (41 mg, 69 percent) and the hydrolized product Compound 59a (5.6 mg, 9 percent(. Compound 59b: colorless crystalline solid; mp 99°-101.0° C. (from ethyl ether); R$_f$=0.25 (silica, 20 percent ethyl ether in petroleum ether); IR (CHCl$_3$) ν$_{max}$ 2960, 2937, 1748 (shoulder), 1723, 1494, 1379, 1204, 1273, 1199, 1182, 1116, 909 cm$^{-1}$; $^1$H NMR (300 MHz, CDCl₃) δ7.59 (d, J=8.6 Hz, 1 H, aromatic), 7.41–7.33 (m, 2 H, aromatic), 7.25–7.13 (m 4 H, aromatic), 6.99 (dd, J=8.6, 2.3 Hz, 1 H, aromatic), 5.79 (dd, J=9.8, 1.3 Hz, 1 H, olefinic), 5.68 (dd, J=9.8, 1.4 Hz, 1 H, olefinic), 5.53 (br s, 1 H, NCH), 3.77 (br s, 1 H, C≡C—CH), 2.41 (dd, J=14.2, 8.0 Hz, 1 H, CH₂) 2.22 (dd, J=15.2, 9.0 Hz, 1 H, CHhd 2), 2.09–1.88 (m, 2 H, CH₂), 1.87–1.77 (m, 1 H, CH₂), 1.66–1.58 (m, 1 H, CH₂), 1.32 (s, 9 H, COC(CH₃)₃); MS (FAB+) m/e (rel intensity) 626 (M+Cs, 28), 179 (23); HRMS for $C_{31}H_{27}NO_5Cs$ (M+Cs), calcd 626.0944, found 626.0944.

EXAMPLE 64

N-[(Phenyloxy)carbonyl]-10](tert-butyldimethylsilyl-)oxy]-3-[(2-nitrobenzyl)oxy]-6-[6-trimethylsilyl-3(Z)-hexene-1,5-diynyl]-5,6,7,8,9,10-hexa-hydrophenanthridine (Compound 232)

A mixture of Pd(PPh₃)₄ (1.12 g, 0.97 mmol), 1-chloro-4-(trimethylsilyl)-but-1-3n-3-yne (4.60 g, 28.98 mmol), and n-propylamine (2.38 mL, 28.98 mmol) in degassed benzene (100 mL) was stirred at 25° C. for 15 minutes. The resultant solution was added to a mixture of Compound 143b (79:21, mixture of diastereomers, 11.80 g, 19.32 mmol) and CuI (0.74 g, 3.86 mmol) in degassed benzene (300 mL) via a syringe followed by stirring at 25° C. for five hours. The reaction was quenched with saturated aqueous NH₄Cl, extracted with ethyl ether (500 mL), washed with brine, dried over anhydrous Na₂SO₄, and concentrated in vacuo. Purification of the crude product by flash column chromatography (silica gel, 20 percent ethyl ether in petroleum ether) gave Compound 232 (12.3 g, 87 percent): amorphous solid; $R_f$=0.51 (silica, 25 percent ethyl ether in petroleum ether); IR (CHCl₃) $v_{max}$ 2957, 2932, 1716, 1613, 1506, 1495, 1384, 1344, 1306, 1253, 1200, 1093, 1025, 858, 844 cm⁻¹; ¹H NMR (300 MHz, CDCl₃) δ8.19 (d, J=8.1 Hz, 1 H, aromatic), 7.97 (d, J=7.7 Hz, 1 H, aromatic), 7.80–7.17 (m, 9 H, H1, H4 and aromatic), 6.93–6.84 (m, 1 H, H2), 5.96 (br s, 0.79 H, H6), 5.93 (br s, 0.21 H, H6), 5.88–5.77 (m, 2 H, olefinic), 5.58 (s, 2 H, benzylic), 5.03 (br s, 0.79 H, H10), 4.73 (br s, 0.21 H, H10), 2.67–2.50 (m, 1 H, H7), 2.39–2.26 (m, 1 H, H7), 2.16–1.91 (m, 3 H, H8 and H9), 1.84–1.70 (m, 1 H, H8 or H9), 1.02 (s, 1.89 H, SiC(CH₃)₃), 0.90 (s, 7.11 H, SiC(CH₃)₃), 0.27 (s, 9 H, Si(CH₃)₃), 0.18 (s, 3 H, SiCH₃), 0.16 (s, 3 H, SiCH₃); MS (FAB+) m/e (rel intensity) 865 (M+Cs, 72), 732 (42), 675 (82), 639 (28), 585 (100), 450 (34), 330 (39), 279 (52), 198 (42); HRMS for $C_{42}H_{48}N_2O_6Si_2Cs$ (M+Cs), calcd 865.2105, found 865/2111.

EXAMPLE 65

N-[(Phenyloxy)carbonyl]-6a, 10a-epoxy-10-hydroxy-3-[(2-nitroben-zyl)oxy]-6-[6-trimethylsilyl-3(Z)-hexene-1,5-diynyl]-5,6,6a,7,8,9,10,10a-octahydrophenanthridine (Compound 234)

To a solution of Compound 232 (0.40 g, 0.546 mmol) in CH₂Cl₂ (10 mL) cooled at zero degrees C was added mCPBA (50 percent, 188 mg, 0.546 mmol) followed by stirring at 25° C. for one hour. The reaction mixture was diluted with CH₂Cl₂ (50 mL), washed with saturated aqueous NaHCO₃, dried over anhydrous Na₂SO₄, and concentrated in vacuo to yield a crude product Compound 233. To a solution of the crude Compound 233 obtained above in wet CHCl₃ (10 mL) was added BF₃.OEt₂ (0.20 mL, 1.67 mmol) followed by stirring at 25° C. for 10 minutes. The reaction mixture was diluted with CH₂Cl₂ (50 mL), washed with saturated aqueous NaHCO₃, dried over anhydrous Na₂SO₄, and concentrated in vacuo. The residue was purified by flash column chromatography (silica gel, 20 percent ethyl ether in benzene) to afford Compound 234 (0.28 g, 81 percent from 51): amorphous solid; $R_f$=0.45 (silica, 50 percent ethyl ether in petroleum ether); IR (CHCl₃) $v_{max}$ 3568, 2961, 1723, 1615, 1527, 1379, 1343, 1305, 1253, 1202, 1026, 846 cm⁻¹; ¹H NMR (300 MHz, CDCl₃) δ 8.06 (d, J=8.1 Hz, 1 H, aromatic), 7.82 (d, J=7.7 Hz, 1 H, aromatic), 7.58 (t, J=7.5 Hz, 1 H, aromatic), 7.47 (br s, 1 H, H4), 7.41–7.17 (m, 5 H, aromatic), 7.06 (d, J=7.9 Hz, 2 H, H1 and aromatic), 6.86 (dd, J=8.6, 2.4 Hz, 1 H, H2), 5.86 (d, J=11.1 Hz, 1 H, olefinic), 5.74 (dd, J=11.1, 1.6 Hz, 1 H, olefinic), 5.61 (d, J=1.6 Hz, 1 H, H6), 5.47 (s, 2 H, benzylic), 4.34 (s, 1 H, H10), 2.64–2.50 (m, 2 H, H7), 2.44 (dt, J=12.8, 4.8 Hz, H9), 2.37–2.18 (m, 1 H, H8) 2.16–2.03 (m, 1 H, H8), 1.93 (br d, J=13.2 Hz, 1 H, H9), 0.21 (s, 9 H, Si(CH₃)); MS (FAB+) m/e (rel intensity) 767 (M+Cs, 100), 359 (8), 312 ()20), 286 (8); HRMS for $C_{36}H_{34}N_2O_7SiCs$ (M+Cs), calcd 767.1190, found 767.1114.

EXAMPLE 66

N-[(Phenyloxy)carbonyl]-3-[(2-nitrobenzyl)oxy]-10-oxo-6-[6-trime-thylsilyl-3(Z)-hexene-1,5-diynyl]-5,6,7,8,9,10-hexahydrophenanthridine (Compound 235)

Method A

A solution of Compound 234 (0.26 g, 0.41 mmol) in THF (10 mL) and 48 percent aqueous HBr (1 mL) was stirred at 25° C. for two hours. The reaction mixture was diluted with ethyl ether (30 mL), washed with saturated aqueous NaHCO₃ and brine, dried over anhydrous Na₂SO₄, and concentrated in vacuo. Flash column chromatography of the residue (silica gel, 50 percent ethyl ether in petroleum ether) gave Compound 235 (0.208 g, 82 percent).

Method B

To a solution of Compound 232 (12.3 g, 16.78 mmol) in CH₂Cl₂ (300 mL) cooled at zero degrees C was added mCPBA (50 percent, 5.79 g, 16.78 mmol) followed by stirring at 25° C. for one hour. The reaction mixture was diluted with CH₂Cl₂ (500 mL), washed with saturated aqueous NaHCO₃, dried over anhydrous Na₂SO₄, and concentrated in vacuo to yield a crude product Compound 233. To a solution of the crude Compound 233 obtained above in wet CHCl₃ (300 mL) was added BF₃.OEt₂ (6.2 mL, 50.34 mmol) followed by stirring at 25° C. for 10 minutes. The reaction mixture was diluted with CH₂Cl₂ (500 mL), washed with saturated aqueous NaHCO₃, dried over anhydrous NaSO₄, and concentrated in vacuo to afford a crude product Compound 234.

A solution of the crude Compound 234 obtained above in THF (300 mL) and 48 percent aqueous HBr (30 mL) was stirred at 25° C. for 1.5 hours. The reaction mixture was diluted with ethyl ether (500 mL), washed with saturated aqueous NaHCO₃ and brine, dried over anhydrous Na₂SO₄, and concentrated in vacuo. The residue was purified by flash column chromatagraphy (silica gel, 50 percent ethyl ether in petroleum ether) to afford Compound 234 (5.50 g, 53 percent from Compound 232): amorphous solid; $R_f$=0.45 (silica, 50 percent ethyl ether in petroleum ether); IR (CHCl₃) $v$2957, 1717, 1681, 1612, 1527, 1504, 1382, 1343, 1306, 1253, 1201, 846 cm⁻¹; ¹H NMR (300 MHz, CDCl₃) δ8.17 (d, J=9.0 Hz, 1 H, H1), 8.08 (d, J=8.0 Hz, 1 H, aromatic), 7.84 (d, J=7.7 Hz, 1 H, aromatic), 7.59 (t, J=7.5 Hz, 1 H, aromatic), 7.43-7.05 (m, 7 H, H4 and aromatic), 6.89 (dd, J=8.9, 2.4 Hz, 1 H, H2), 6.08 (d, J=1.8 Hz, 1 H, H6), 5.83 (d, J=11.1 Hz, 1 H, olefinic), 5.72 (dd, J=11.1, 1.8 Hz, 1 H, olefinic), 5.53 (s, 2 H, benzylic), 2.86 (dt, J=18.9, 4.6 Hz, 1 H, H9),2.78- 2.50 (m, 3 H, H7 and H9), 2.23-2.09 (m, 2 H, H8), 0.20 (s, 9 H, Si(CH$_3$)$_3$); MS (FAB+) m/e (rel intensity) 749 (M+Cs, 12), 312 (7), 286 (8), 133 (100); HRMS for C$_{36}$H$_{32}$N$_2$O$_6$SiCs (M+Cs+), calcd 749.1084, found 749.1095.

EXAMPLE 67

N-[(Phenyloxy)carbonyl]-6-[3(Z)-hexene-1,5,-diynyl]-3-[(2-nitroben-zyl)oxy]-10-oxo-5,6,7,8,9,10-hexahydrophenanthridine (Compound 235)

To a solution of Compound 235 (5.50 g, 8.92 mmol) in THF-EtOH-H$_2$O (1:1:1, 450 mL) was added silver nitrate (6.06 g, 35.67 mmol) followed by stirring at 25° C. for one hour. Potassium cynide (4.07 g, 62.44 mmol) was added to the reaction mixture followed by stirring at 25° C. for another 10 minutes. The reaction mixture was diluted with CH$_2$Cl$_2$ (500 mL), washed with brine, dried over anhydrous Na$_2$SO$_4$, and concentrated in vacuo. The residue was purified by flash column chromatography (silica gel, 50 percent ethyl ether in petroleum ether) to furnish Compound 236 (4.03 g, 83 percent): amorphous solid; R$_f$=0.38 (silica, 50 percent ethyl ether in petroleum ether); IR (CHCl$_3$) $\nu_{max}$ 3304, 2929, 1717, 1680, 1611, 1527, 1504, 1494, 1382, 1343, 1306, 1270, 1201 cm$^{-1}$; $^1$H NMR (300 MHz, CDCl$_3$) 8.16 (d, J =8.8 Hz, 1 H, H1) 8.08 (d, J=8.1 Hz, 1 H, aromatic), 7.82 (d, J=7.8 Hz, 1 H, aromatic), 7.59 (t, J=7.4 Hz, 1 H, aromatic), 7.43-7.05 (m, 7 H, H4 and aromatic), 6.89 (dd, J=8.9, 2.4 Hz, 1 H, H2), 6.03 (s, 1 H, H6), 5.79 (s, 2 H, olefinic), 5.53 (s, 2 H, benzylic), 3.16 (s, 1 H, acetylenic), 2.84 (dt, J=18.8, 4.7 Hz, 1 H, H9), 2.75-2.49 (m, 3 H, H7 and H9), 2.22-2.07 (m, 2 H, H8); MS (FAB+) m/e (rel intensity) 677 (M+Cs, 5), 653 (19), 419 (16), 312 (29), 286 (24); HRMS for C$_{33}$H$_{24}$N$_2$O$_6$ Cs (M+Cs), calcd 677.0689, found 677.0639.

EXAMPLE 68

N-[(Phenyloxy)carbonyl]-6a,10a-epoxy-6-[3(Z)-hexene-1,5-diynyl]-3-[(2-nitrobenzyl)oxy]-10-oxo-5,6,6a,7,8,9,10,10a-octahydrophenanthridine (Compound 237)

To a solution of Compound 236 (4.00 g, 7.35 mmol) in CH$_2$Cl$_2$ (70 mL) and saturated aqueous NaHCO$_3$(70 mL) was added mCPBA (50 percent, 5.07 g, 14.70 mmol) followed by stirring at 25° C. for one hour. The reaction mixture was diluted with CH$_2$Cl$_2$ (200 mL), washed with saturated aqueous NaHCO$_3$, dried over anhydrous Na$_2$SO$_4$, and concentrated in vacuo to yield a crude product. Flash column chromatography of the crude product (silica gel, 50 percent ethyl ether in petroleum ether) gave Compound 237 (2.43 g, 59 percent): amorphous solid; R$_f$=0.45 (silica, 50 percent ethyl ether in petroleum ether); IR (CHCl$_3$) $\nu_{max}$ 3303, 2952, 1720, 1615, 1528, 1506, 1494, 1380, 1344, 1307, 1253, 1200 cm$^{-1}$; $^1$H NMR (300 MHz, CDCl$_3$) δ8.33 (d, J=9.0 Hz, 1H, H1), 8.11 (d, J=8.0 Hz, 1 H, aromatic), 7.81 (d, J=7.7 Hz, 1 H, aromatic), 7.59 (t, J=7.2 Hz, 1 H, aromatic), 7.44-6.98 (m, 7 H, H4 and aromatic), 6.90 (dd, J=9.0, 2.0 Hz, 1 H, H2), 5.91 (s, 1 H, H6), 5.79 (s, 2 H, olefinic), 5.52 (s, 2 H, benzylic), 3.20 (d, J=1.1 Hz, 1 H, acetylenic), 2.80-2.62 (m, 2 H, H9), 2.38-2.25 (m, 2 H, H7), 2.09-1.85 (m, 2 H, H8); MS (FAB+) m/e (rel intensity) 693 (M+Cs, 14), 653 (12), 468 ) 7), 417 (8), 377 (9), 312 (33), 215 (23); HRMS for C$_{33}$H$_{24}$N$_2$O$_7$Cs (M+Cs), calcd 693.0638, found 693.0651.

EXAMPLE 69

Compound 43

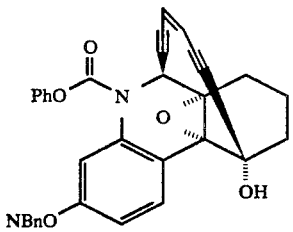

To a solution of Compound 237 (2.43 g, 4.33 mmol) in dry PhMe (400 mL) cooled at −78° C. was added LDA (1.5 M in cyclohexane, 2.90 mL, 4.35 mmol) followed by stirring at −78° C. for 20 minutes. The reaction was quenched with saturated aqueous NH$_4$Cl, extracted with ethyl ether (200 mL), dried over anhydrous Na$_2$SO$_4$, and concentrated in vacuo. The residue was purified by flash column chromatography (silica gel, 50 percent ethyl ether in petroleum ether) to afford Compound 43 (1.01 g, 42 percent) along with the recovery of Compound 237 (260 mg, 11 percent). Compound 43: amorphous solid; mp>200° C. (dec.); R$_f$=0.24 (silica 50 percent ethyl ether in petroleum ether); IR (C$_6$H$_6$) $\nu_{max}$ 3554, 2954, 2927, 1728, 1615, 1529, 1506, 1494, 1378, 1343, 1302, 1280, 1202 cm$^{-1}$; $^1$H NMR (300 MHz, C$_6$D$_6$) δ8.97 (d, J=9.0 Hz, 1 H, aromatic), 7.72 (d, J=8.3 Hz, 1 H, aromatic), 7.52 (d, J=7.7 Hz, 1 H, aromatic), 7.13-7.01 (m, 5 H, aromatic), 6.97-6.87 (m, 2 H, aromatic), 6.81 (br d, J=8.9 Hz, 1 H, aromatic), 6.66 (t, J=7.9 Hz, 1 H, aromatic), 5.90 (br s, 1 H, NCH), 5.31 (d, J=10.1 Hz, 1 H, olefinic), 5.17 (dd, J=10.1, 1.7 Hz, 1 H, olefinic), 5.13 and 5.04 (ABq, J=16.0 Hz, 2 H, benzylic), 2.29 (br s, OH), 2.15-1.85 (m, 4 H, CH$_2$CH$_2$), 1.70-1.60 (m, 1 H, CH$_2$), 1.37-1.29 (m, 4 H, CH$_2$); $^{13}$C NMR (125 MHz, C$_6$D$_6$) δ 157.8, 151.7, 146.9, 138.0, 134.0, 133.5, 133.3, 129.6, 128.5, 125.5, 124.6, 124.2, 122.3, 122.2, 113.5, 102.0, 94.8, 93.9, 89.0, 74.1, 73.5, 67.0, 64.9, 51.1, 35.2, 23.1, 19.6 (other peaks corresponding to the aromatic carbons overlap with the solvent peaks); MS (FAB+) m/e (rel intensity( 561 (M+H, 13),340 (9), 306 (9), 281 (10), 253 (14), 239 (16), 221 (21), 202 (27), 191 (31), 178 (37), 165 (59); HRMS for C$_{33}$H$_{25}$N$_2$O$_7$ (M+H), calcd 561.1162, found 561.1162.

EXAMPLE 70

Base-induced Bergman Cycloaromatization of Compound 59a, Compound 238

A solution of Compound 59a (16.0 mg, 0.0314 mmol) in EtOH-H$_2$O (3:1, 6.23 mL) containing 0.02 M_LiOH (0.125 mmol, pH about 11.5) was stirred at 25° C. for six hours. The solvent was removed in vacuo to give a residue to which brine was added followed by acidification with 5 percent HCl, extraction with CH$_2$Cl$_2$ (20 mL), dry over anhydrous Na$_2$SO$_4$, and removal of the solvent in vacuo. The crude product was purified by preparative TLC (silica gel plate, 50 percent ethyl ether in benzene) to afford Compound 238 (7.5 mg, 56 percent): R$_f$=0.33 (silica, 50 percent ethyl ether in benzene); IR (CHCl$_3$) $\nu_{max}$ 3583, 3375, 2929, 1725 (shoulder), 1701, 1614, 1502, 1447, 1398, 1381, 1299, 1276, 1255, 1087, 1052 cm$^{-1}$; $^1$H NMR (300 MHz, CDCl$_3$) δ 7.39-7.32 (m, 2 H, aromatic), 7.29 (d, J=8.6 Hz, 1 H, aromatic), 7.25-7.15 (m, 3 H, aromatic), 6.49 (dd, J=8.6, 2.5 Hz, 1 H, aromatic), 5.54 (s, 1 H, NC$\underline{H}$), 5.35 (br s, 1 H, ArO$\underline{H}$), 4.40-4.24 (m, 2 H, NC(O)OC$\underline{H}_2$CH$_3$), 3.99 (dq, J=9.7, 7.0 Hz, 1 H, OC$\underline{H}_2$CH$_3$), 3.50 (dq, J=9.7, 7.0 Hz, 1 H, OC$\underline{H}_2$CH$_3$), 2.60 (br s, 1 H, O$\underline{H}$), 2.35 (td, J=12.8, 4.6 Hz, 1 H, C$\underline{H}_2$), 2.23 (td, J=13.9, 6.2 Hz, 1 H, C$\underline{H}_2$), 1.77 (dd, J=13.4, 4.8 Hz, 1 H, C$\underline{H}_2$), 1.64 (br s,1 H, O$\underline{H}$), 1.56-1.45 (m, 1 H, C$\underline{H}_2$), 1.41 (t, J=7.0 Hz, 3 H, NC(O)OCH$_2$C$\underline{H}_3$), 1.39-1.26 (m, 1 H, C$\underline{H}_2$), 1.24 (t, J=6.9 Hz, 3 H, OCH$_2$C$\underline{H}_3$), 0.82-0.63 (m, 1 H, C$\underline{H}_2$); $^{13}$C NMR (125 MHz, CDCl$_3$) δ 155.3, 154.7, 140.3, 137.4, 133.5, 130.3, 128.9, 127.5, 124.3, 111.0, 109.6, 81.0, 80.4, 72.2, 64.8, 62.6, 62.0, 35.9, 32.2, 19.1, 16.3, 14.6, MS (FAB+) m/e (rel intensity) 425 (M, 10), 362 (8), 290 (4), 217 (5), 165 (13); HRMS for C$_{24}$H$_{27}$NO$_6$Cs (M+Cs), calcd 558.0893, found 558.0893.

EXAMPLE 71

Based-induced Bergman Cyclization of Compound 59b, Compound 239

A solution of Compound 59a (10.0 mg, 0.0201 mmol) in EtOH-H$_2$O (3:1, 4.0 mL) containing 0.02 M LiOH (0.080 mmol) was stirred at 25° C. for four hours. The reaction mixture was extracted with CH$_2$Cl$_2$ (20 mL), dried over anhydrous Na$_2$SO$_4$, and concentrated in vacuo. The crude product was purified by preparative TLC (silica gel plate, 33 percent ethyl ether in benzene) to afford Compound 239 (3.4 mg, 42 percent): R$_f$=0.40 (silica, 33 percent ethyl ether in benzene); IR (CHCl$_3$) ν$_{max}$ 3594, 2927, 1732, 1707, 1612, 1377, 1250, 1109, 1050 cm$^{-1}$; $^1$H NMR (300 MHz, acetone-d$_6$) δ 8.20 (s, 1 H, ArO$\underline{H}$), 7.34 (dd, J=6.8, 2.1 Hz, 1 H, aromatic), 7.22 (d, J=8.5 Hz, 1 H, aromatic), 7.15-7.04 (m, 3 H, 1 H, aromatic), 6.85 (dd, J=6.7, 2.1 Hz, 1 H, aromatic), 6.51 (dd, J=8.5, 2.4 Hz, 1 , aromatic), 5.55 (s, 1 H, NC$\underline{H}$), 4.25 (q, J=7.0 Hz, 2 H, NC(O)OC$\underline{H}_2$CH$_3$), 3.95 (dq, J=9.9, 7.0 Hz, 1 H, OC$\underline{H}_2$CH$_3$), 3.85 (s, 1 H, O$\underline{H}$), 3.48 (dq, J=9.0, 7.0 Hz, 1 H, OC$\underline{H}_2$CH$_3$), 3.12 (t, J=3.0 Hz, 1 H, C≡C—C$\underline{H}$), 2.38 (tdd, J=12.6, 3.6, 3.6 Hz, 1 H, C$\underline{H}_2$), 2.30 (td, J=13.8, 6.0 Hz, 1 H, C$\underline{H}_2$), 1.80 (dd, J =13.2, 4.8 Hz, 1 H, C$\underline{H}_2$), 1.38-1.32 (m, 1 H, C$\underline{H}_2$), 1.35 (t, J=7.0 Hz, 3 H, NC(O)OCH$_2$C$\underline{H}_3$), 1.26-1.15 (m, 1 H, C$\underline{H}_2$), 1.14 (t, J=7.0 Hz, 3 Hz, 3 H, OCH$_2$C$\underline{H}_3$), 0.88-0.75 (m, 1 H, C$\underline{H}_2$); MS (FAB+) m/e (rel intensity) 542 (M+Cs, 18), 409 (35), 364 (15), 318 (29), 286 (25), 233 (15), 221 (29), 178 (20), 165 (31); HRMS for C$_{24}$H$_{27}$NO$_5$Cs (M+Cs), calcd 542.0944, found 542.0961.

EXAMPLE 72

Compound 200

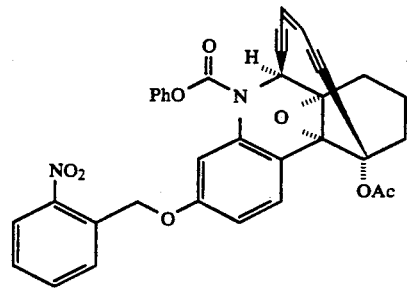

A solution of Compound 43 (100.0 mg, 0.178 mmol) and DMAP (2.2 mg, 0.0178 mmol) in pyridine (2.0 mL) and Ac$_2$O (1.0 mL) was stirred for two hours at 25° C. The reaction was extracted with CH$_2$Cl$_2$ (30 mL), washing with saturated aqueous NaHCO$_3$, dried over anhydrous Na$_2$SO$_4$, and concentrated in vacuo. The residue was purified by flash column chromatography (silica gel, 40 percent ethyl ether in petroleum ether) to afford Compound 200 (82.5 mg, 77 percent): amorphous solid; R$_f$=0.43 (silica, 50 percent ethyl ether in petroleum ether); IR (CHCl$_3$) ν$_{max}$ 2956, 1723, 1615, 1526, 1506, 1494, 1379, 1343, 1303, 1288, 1162, 1150, 1071, 1035, 1025 cm$^{-1}$; $^1$H NMR (300 MHz, CDCl$_3$) δ8.10 (d, J=8.1 Hz, 1 H, aromatic), 7.86 (d, J=9.1 Hz, 1 H, aromatic), 7.83 (d, J=10.0 Hz, 1 H, aromatic), 7.60 (t, J=7.3 Hz, 1 H, aromatic), 7.45-7.02 (m, 7 H, H4 and aromatic), 6.87 (dd, J=8.9, 2.5 Hz, 1 H, H2), 5.90 (d, J=10.2 Hz, 1 H, olefinic), 5.73 (dd, J=9.8 1.7 Hz, 1 H, olefinic), 5.52 (s, 1 H, H6), 5.51 (s, 2 H, benzylic), 2.22 (s, 3 H, COCH$_3$), 2.56-2.08 (m, 5 H, CH$_2$CH$_2$CH$_2$), 1.79-1.70 (m, 1 H, C$\underline{H}_2$); $^{13}$C NMR (125 MHz, C$_6$D$_6$) δ 169.3, 157.4, 150.8, 146.7, 137.1, 134.0, 133.4, 131.1, 129.4, 129.4, 128.4, 128.3, 125.9, 125.0, 125.0, 124.4, 123.0, 121.5, 121.5, 120.5, 113.2, 112.2, 97.5, 95.5, 93.7, 88.8, 77.8, 73.8, 66.9, 63.0, 50.4, 29.5, 22.9, 21.9, 18.4; HRMS for C$_{35}$H$_{26}$N$_2$O$_8$Cs (M+Cs), calcd 735.0743, found 735.0749.

EXAMPLE 73

Photo-deprotection of Compound 43; Compound 42

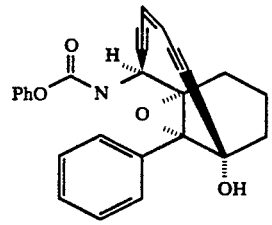

A solution of Compound 43 (5.0 mg, 0.00892 mmol) in THF-d$_8$ (0.5 mL) and D$_2$O (50 mL) charged in a NMR tube was irradiated with a Hanover high-pressure mercury arc (pyrex filter) cooled in an ice-water bath (0°-5° C.). The reaction was monitored by $^1$H NMR and after irradiation for 40 minutes, Compound 43 was completely converted into Compound 42. Attempts to purification of Compound 42 lead entirely to decomposition. Compound 42: R$_f$=0.63 (silica, 50 percent ethyl ether in benzene); $^1$H NMR (300 MHz, THF-d$_8$-D$_2$), 10:1) δ 8.53 (d, J = 8.8 Hz, 1 H, H1), 7.45-7.10 (m, 5 H, aromatic), 6.88 (d, J = 2.5 Hz, 1 H, H4), 6.63 (dd, J = 2.5, 8.8 Hz, 1 H, H2), 5.97 (d, J = 10.0 Hz, 1 H, olefinic), 5.78 (dd, J = 10.0, 1.6 Hz, 1 H, olefinic)(,5.46 (br s, 1 H H6), 2.35-1.55 (m, 6 H, H7, H8, and H9).

EXAMPLE 74

Photo-deprotection of Compound 200; Compound 201

A solution of Compound 200 (34.0 mg, 0.0564 mol) in THF (5mL) and H$_2$O (0.5 mL) charged in a testing tube was irradiated with a Hanover high-pressure mercury arc (pyrex filter) cooled in an ice-water bath (0°-5° C.) for 40 minutes. The reaction mixture was extracted with ethyl ether (30 mL), washed with brine, dried over anhydrous Na$_2$SO$_4$, and concentrated in vacuo. The crude product was purified by flash column chromatography (silica gel, 50 percent ethyl ether in petroleum ether) to afford Compound 201 (22.0 mg, 83 percent): yellow amorphous solid; R$_f$=0.20 (silica, 50 percent ethyl ether in petroleum ether); IR (CHCl$_3$) $\nu_{max}$ 3303, 2955, 2928, 1723, 1619, 1494, 1381, 1293, 1163, 1150, 1071 cm$^{-1}$; $^1$H NMR (300 MHz, CDCl$_3$) δ7.77 (d, J = 8.8 Hz, 1 H, H1), 7.36 (t, J = 7.6 Hz, 2 H, aromatic), 7.22 (t, J = 7.3 Hz, 1 H, aromatic), 7.13 (D, J = 7.9 Hz, 2 H, aromatic), 6.97 (br s, 1 H, H4), 6.67 (dd, J = 9.0, 2.6 Hz, 1 H, H2), 5.89 (d, J = 10.1 Hz, 1 H, olefinic), 5.71 (dd, J = 10.1, 1.7 Hz, 1 H, olefinic), 5.51 (d, J = 1.7 Hz, 1 H, H6), 5.18 (br s, 1 H, ArOH), 2.20 (s, 3 H, COCH$_3$), 2.53-1.97 (m, 5 H, CH$_2$CH$_2$CH$_2$), 1.78-1.68 (m, 1 H, CH$_2$); HRMS for C$_{28}$H$_{21}$NO$_6$Cs (M+Cs), calcd 600.0423, found 600.0441.

EXAMPLE 75

Compound 202

A solution of Compound 201 (16.0 mg, 0.0342 mmol) in pyridine (0.5 mL) and Ac$_2$O (1.0 mL) was stirred for 30 minutes at 25° C. The reaction was extracted with ethyl ether (10 mL), washed with saturated aqueous NaHCO$_3$, dried over anhydrous Na$_2$SO$_4$, and concentrated in vacuo. The residue was purified by preparative TLC (silica gel plate, 67 percent ethyl ether in petroleum ether) to afford Compound 202 (16.0 mg, 92 percent(: pale-yellow solid; R$_f$=0.24 (silica, 50 percent ethyl ether in petroleum ether); IR (CHCl$_3$) $\nu_{max}$ 2958, 1725, 1614, 1502, 1494, 1372, 1307, 1252, 1247, 1182, 1150, 1072, 1026 cm$^{-1}$; $^1$H NMR (300 MHz, CDCl$_3$) δ 7.92 (d, J = 8.6 Hz, 1 H, H1), 7.37 (t, J = 7.7 Hz, 2 H, aromatic), 7.29 (br s, 1 H, H4), 7.22 (t, J = 7.1 Hz, 1 H, aromatic), 7.16 (d, J = 8.1 Hz, 2 H, aromatic), 700 (dd, J = 9.2, 2.4 Hz, 1 H, H2),5.90 (d, J = 10.3 Hz, 1 H, olefinic), 5.72 (br d, J = 10.3 Hz, 1 H, olefinic), 5.54 (br s, 1 H, H6), 2.55-2.48 (m, 1 H, CH$_2$), 2.41-2.07 (m, 4 H, CH$_2$CH$_2$), 2.27 (s, 3 H, COCH$_3$), 2.21 (s, 3 H, COCH$_3$), 1.79-1.70 (m, 1 H, CH$_2$); HRMS for C$_{30}$H$_{23}$NO$_7$Cs (M+Cs), calcd 642.0529, found 642.0529.

EXAMPLE 76

Reaction of Compound 42 with Nucleophiles; General Procedure

A crude solution of Compound 42 prepared from Compound 43 (20.0 mg, 0.0357 mmol) in THF (2.0 mL) and H$_2$O (0.2 mL) as described above was diluted to 3.0 mL in THF, to which potassium phosphate monobasic-sodium hydroxide buffer solution (0.5 M, pH 8.0) (3.0 mL), and EtOH (3.0 mL), or EtSH (0.6 mL), or PrNH$_2$ (3.0 mL) was added. The resultant mixture was then stirred under argon at 25° C. until TLC showed that Compound 42 was completely disappeared (1.5 hours). The reaction mixture was diluted with brine, extracted with CH$_2$Cl$_2$ (10 mL×2), dried over anhydrous Na$_2$SO$_4$, and concentrated in vacuo. The crude product was purified by preparative TLC (silica gel plate, 50 percent ethyl ether in benzene for Compound 44a and 44b and 3.2 percent MeOH in CH$_2$Cl$_2$ for Compound 44c) to give the Bergman cycloaromatization products Compounds 44a, 44b, and 44c, respectively.

Compound 44a:

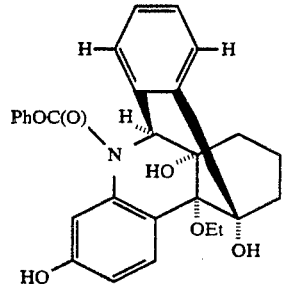

44a 31 percent from Compound 43; R$_f$=0.48 (silica, 50 percent ethyl ether in benzene); IR (CHCl$_3$) $\nu_{max}$ 3587, 3390 (br), 2929, 1718, 1615, 1494, 1383, 1345, 1298, 1277, 1163, 1085 cm$^{-1}$; $^1$H NMR (300 MHz, CDCl$_3$) δ 7.49-7.44 (m, 1 H, aromatic), 7.41-7.35 (m, 4 H, aromatic), 7.26-7.16 (m, 5 H, aromatic), 7.11 (br s, 1 H, aromatic), 6.36 (dd, J = 8.6, 2.5 Hz, 1 H, aromatic), 5.89 (br s, 1 H, ArOH), 5.67 (s, 1H, NCH), 3.97 (dq, J = 9.6, 6.9 Hz, 1 H, OCH$_2$CH$_3$),3.51 (dq, J=9.6, 6.9 Hz, 1 H, OCH$_2$CH$_3$), 2.72 (br s, 1 H, OH), 2.44 (br s, 1 H, OH), 2.35 (td, J = 12.7, 4.5 Hz, 1 H, CH$_2$), 2.22 (td, J = 13.9, 6.0 Hz, 1 H, CH$_2$), 1.81 (dd, J = 13.0, 3.8 Hz, 1 H, CH$_2$), 1.50 (br d, J = 14.0 Hz, 1 H, CH$_2$), 1.35 (br d, J = 11.3 Hz, 1 H, CH$_2$), 1.23 (t, J = 6.9 Hs, 3 H, OCH$_2$CH$_3$), 0.71 (ddddd, J = 13.8, 13.8, 4.5, 4.5 Hz, 1 H, CH$_2$); MS (FAB+) m/e (rel intensity) 606 (M+Cs, 55), 473 (M, 13); HRMS for C$_{28}$H$_{27}$NO$_6$Cs (M+CS), calcd 606.0893, found 606.0903.

Compound 44b:

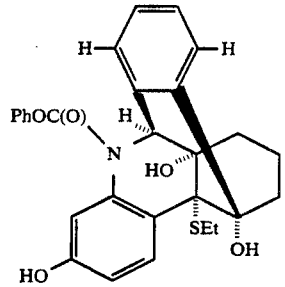

44b 34 percent from Compound 43; R$_f$=0.56 (silica, 50 percent ethyl ether in benzene); IR (CHCl$_3$) $\nu_{max}$ 3590, 3365 (br), 3013, 2956, 2931, 1717, 1616, 1494, 1456, 1385, 1299, 1070, 921 cm$^{-1}$; $^1$H NMR (300 MHz, CDCl$_3$) δ 7.68 (d, J = 8.7 Hz, 1 H, aromatic), 7.51-7.33 (m, 5 H, aromatic), 7.31-7.19 (m, 4 H, aromatic), 7.08 (br s, 1 H, aromatic), 6.56 (dd, J = 8.7, 2.7 Hz, 1 H, aromatic), 5.78 (s, 1 H, NCH), 5.02 (br s, 1 H, ArOH), 2.74 (s, 1 H, OH), 2.68-2.54 (m, 2 H, SCH$_2$CH$_3$), 2.32-2.22 (m, 1 H, CH$_2$), 2.18 (dd, J = 12.9, 8.4 Hz, 1 H, CH$_2$), 2.13 (s, 1 H, OH), 1.85 (dd, J=13.5, 4.9 Hz, 1 H, CH$_2$), 1.46 (dd, J=13.5, 4.8 Hz, 1 H, CH$_2$), 1.33-1.22 (m, 1 H, CH$_2$), 1.20 (t, J=7.5 Hz, 3 H, SCH$_2$CH$_3$), 0.81-0.63 (m, 1 H, CH$_2$); HRMS (FAB+) for C$_{28}$H$_{27}$NO$_5$SCs (M+Cs), calcd 622.0664, found 622.0670.

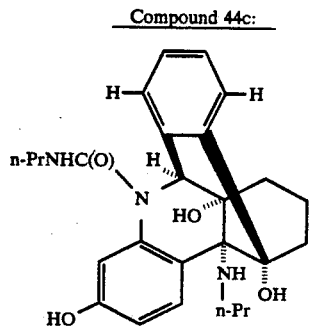

Compound 44c:

46 percent from Compound 43; R$_f$=0.33 (silica, 4.8 percent MeOH in CH$_2$Cl$_2$); IR (CHCl$_3$) $\nu_{max}$ 3591, 3439, 3270, 2964, 2935, 1727, 1645, 1613, 1500, 1459, 1416, 1252, 1188, 1070 cm$^{-1}$; $^1$H NMR (300 MHz, CDCl$_3$) 7.43 (dd, J=5.3, 3.5 Hz, 1 H, aromatic), 7.25-7.10 (m, 4 H, aromatic), 6.56 (dd, J=8.4, 2.2 Hz, 1 H, aromatic), 6.53 (d, J=2.2 Hz, 1 H, aromatic), 5.58 (s, 1 H, NCH), 5.46 (t, J=5.6 Hz, 1 H, CONHCH$_2$), 3.19-2.95 (m, 2 H, CONHCH$_2$CH$_2$), 2.80 (dt, J=11.3, 6.3 Hz, 2 H, NHCH$_2$CH$_2$), 2.53-2.26 (m, 5 H, NHCH$_2$CH$_2$, CH$_2$, OH), 1.84 (s, 1 H, OH), 1.68 (dd, J=12.4, 4.7 Hz, 1 H, CH$_2$), 1.61-1.36 (m, 5 H, CONHCH$_2$CH$_2$, NHCH$_2$CH$_2$, CH$_2$), 0.94 (t, J=7.3 Hz, 3 H, CONHCH$_2$CH$_2$CH$_3$), 0.89 (dd, J=4.8, 2.4 Hz, 1 H, CH$_2$), 0.83 (t, J=7.3 Hz, 32 H, NHCH$_2$CH$_2$CH$_3$), 0.78-0.59 (m, 1 H, CH$_2$); MS (FAB+) m/e (rel intensity) 584 (M+Cs, 19), 452 (M+H, 20); HRMS for C$_{26}$H$_{34}$N$_3$O$_4$ (M+H), calcd 452.2549, found 452.2549.

EXAMPLE 77

Reaction of Compound 201 with Ethanol; Compounds 203 and 204

The reaction was similarly carried out as described above for Compound 43. The Bergman cycloaromatization products Compounds 203 and 204 were isolated by preparative TLC (silica gel plate, 50 percent ethyl ether in benzene) as a mixture as a 65:35 mixture, (20 percent combined yield). R$_f$=0.56 (silica, 50 percent ethyl ether in benzene); IR (CHCl$_3$) $\nu_{max}$ 3302, 2952, 1724, 1613, 1494, 1383, 1368, 1297, 1255, 925 cm$^{-1}$; $^1$H NMR (300 MHz, CDCl$_3$) $\delta$7.67 (d, J=9.0 Hz, 1 H, aromatic), 7.60-7.15 (m, 6.25 H, aromatic), 7.02 (br s, 1 H, aromatic), 6.60-6.53 (m, 2 H, aromatic), 5.91 (s, 0.65 H, NCH), 5.69 (s, 0.35 H, NCH), 5.12 (s, 0.65 H, ArOH), 5.04 (s, 0.35 H, ArOH), 4.00-3.92 (m, 0.7 H, NC(O-)OCH$_2$CH$_3$), 3.60-2.49 (m, 0.65 H, OCH$_2$CH$_3$), 3.21 (td, J=13.0, 4.5 Hz, 0.65 H, OCH$_2$CH$_3$), 2.90 (td, J=13.3, 4.6 Hz, 0.7 H, OCH$_2$CH$_3$),2.66 (s, 1 H, OH), 2.62 (br d, J=13.3 Hz, 1 H, CH), 2.40-2.14 (m, 3 H, CH$_2$CH$_2$), 2.25 (s, 1.95 H, COCH$_3$), 2.16 (s, 1.05 H, COCH$_3$),1.95 (dd, J=13.6, 4.4 Hz,0.65 H, CH$_2$), 1.80 (dd, J=13.1, 4.3 Hz, 0.35 H, CH$_2$), 1.23 (t, J=7.0 Hz, 4.05 H, NC(O-)OCH$_2$CH$_3$, OCH$_2$CH$_3$),0.90-0.70 (m, 1 H, CH$_2$).

EXAMPLE 78

Reaction of Compound 42 with Molecular Oxygen; Compound 54

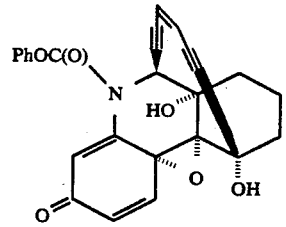

A crude solution of Compound 42 prepared from Compound 43 (80.0 mg, 0.143 mmol) in THF (8.0 mL) and H$_2$O (0.8 mL) as described above was mixed with potassium phosphate monobasic-sodium hydroxide buffer solution (0.05 M, pH 8.0) (8.0 mL) and ethanol (8.0 mL) followed by stirring in open air at 25° C. for 1.5 hours. The reaction mixture was diluted with brine, extracted with CH$_2$Cl$_2$ (30 mL×2), dried over anhydrous Na$_2$SO$_4$, and concentrated in vacuo. The crude product was purified by preparative TLC (silica gel plate, 50 percent ethyl ether in benzene) to provide Compound 44a (22.6 mg, 33 percent from Compound 43) and Compound 54 (5.6 mg, 9 percent from Compound 43). Compound 54: R$_f$=0.41 (silica, 50 percent ethyl ether in benzene); UV (CHCl$_3$) $\lambda_{max}$ (log $\epsilon$) 310 (shoulder, 3.645), 290 (shoulder, 3.955), 258 (4.160) nm; IR (CHCl$_3$) $\nu_{max}$ 3545, 2927, 1733, 1666, 1608, 1403, 1381, 1349, 1296, 1285, 1198 cm$^{-1}$; $^1$H NMR (300 MHz, CDCl$_3$) $\delta$ 7.87 (d, J=10.4 Hz, 1 H, olefinic), 7.44-7.35 (m, 3 H, aromatic), 7.20-7.14 (m, 2 H, aromatic), 6.76 (d, J=2.2 Hz, 1 H, olefinic), 6.51 (dd, J=10.4, 2.2 Hz, 1 H, olefinic), 5.92 (d, J=9.9 Hz, 1 H, olefinic), 5.86 (dd, J=9.9, 1.7 Hz, 1 H, olefinic), 5.21 (d, J=1.7 Hz, 1 H, NCH), 3.74 (d, J=2.3 Hz, 1 H, OH, exchangeable with D$_2$O), 3.23 (dddd, J=14.7, 9.7, 9.7, 2.3 Hz, 1 H, CH$_2$), 2.34-2.15 (m, 2H, CH$_2$), 2.29 (s, 1 H, OH, exchangeable with D$_2$O), 2.15-1.95 (m, 2 H, CH$_2$), 1.88 (ddd, J=14.7, 8.3, 1.8 Hz, 1 H, CH$_2$); $^{13}$C NMR (125 MHz, CDCl$_3$), d185.5, 151.8, 150.4, 147.6, 138.9, 134.2, 129.7, 129.7, 127.9, 126.3, 123.8, 123.3, 121.3, 121.3, 98.3, 93.9, 90.5, 89.1, 79.3, 74.9, 68.3, 59.8, 59.5, 33.6, 26.4, 14.2; HRMS (FAB+) for C$_{26}$H$_{19}$NO$_6$Cs (M+Cs), calcd 574.0267, found 574.0284.

EXAMPLE 79

Compound 55

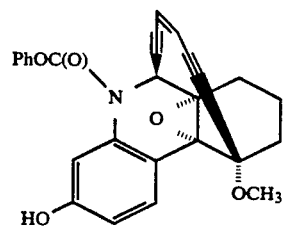

The isolable Compound 55 was obtained from Compound 43 by methylation and photo-deprotection. Compound 55: R$_f$=0.76 (silica, 50 percent ethyl ether in benzene); IR (CHCl$_3$) $\nu_{max}$ 3450, 3004, 2979, 2875, 1720, 1384, 1299, 1198, 1151, 1111 cm$^{-1}$; $^1$H NMR (500 MHz, CDCl₃) δ8.22 (d, J=8.8 H, 1 H, aromatic), 7.35-7.28 (m, 2H, aromatic), 7.18 (t, J=7.3 Hz, 1 H, aromatic), 7.12 (br d, J=6.9 Hz, 2 H, aromatic), 6.89 (br s, 1H, aromatic), 6.65 (dd, J=8.8, 2.7 Hz, 1 H, aromatic), 5.82 (d, J=10.0 Hz, 1H, olefinic), 5.67 (dd, J=10.0, 1.7 Hz, 1 H, olefinic), 5.48 (s, 1 H, NCH), 5.28 (br s, 1 H, ArOH), 3.47 (s, 3 H, OCH₃), 2.28 (dd, J=15.1, 8.2 Hz, 1 H, CH₂), 2.23-2.10 (m, 2, CH₂), 2.00-1.87 (m, 2 H, CH₂),1.78-1.70 (m, 1 Hd, CH₂); ¹³C NMR (125 MHz, CDCl₃) δ 155.1, 150.9, 136.8, 133.2, 131.9, 130.1, 129.3, 129.3, 125.8, 124.2, 124.1, 122.2, 121.6, 120.5, 113.0, 99.5, 94.9, 93.9, 88.4, 79.3, 72.1, 63.2, 52.1, 50.5, 28.5, 23.2, 18.9; HRMS (FAB+) for C₂₇H₂₁NO₅Cs (M+Cs), calcd 572.0474, found 572.0429.

EXAMPLE 80

Reaction of Compound 55 with Molecular Oxygen; Compounds 58 and 62

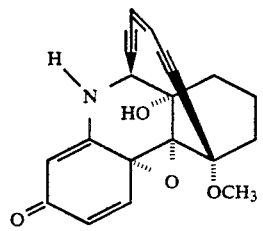

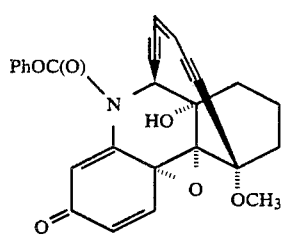

The reaction of Compound 55 with molecular oxygen was similarly carried out as described above for Compound 42 in THF-pH 9.0 buffer solution (boric acid-potassium chloride-sodium hydroxide) (1:1) at 25° C. in open air for 48 hours to provide Compound 58 (35 percent) and Compound 62 (25 percent). Compound 58: R$_f$=0.31 (silica, ethyl ether); UV (CHCl₃) λ$_{max}$ (log ε) 330 (3.09), 285 (shoulder, 3.38), 256 (3.17) 244 (shoulder, 3.58) nm; IR (CHCl₃) ν$_{max}$ 3527, 3385, 2956, 2929, 2856, 1656, 1597 cm⁻¹; ¹H NMR (500 MHz, CDCl₃) δ 7.37 (d, J=10.3 Hz, 1 H, olefinic), 6.36 (dd, J=10.4, 20. Hz, 1 H, olefinic), 5.85 (d, J=9.8 Hz, 1H, olefinic), 5.86 (dd, J=9.8, 1.7 Hz, 1H, olefinic),4.13 (d, J=4.0 Hz, 1 H, OH, exchangeable with D₂O), 4.07 (d, J=3.0 Hz, 1 H, olefinic), 3.72 (dd, J=4.2, 1.7 Hz, 1 H, NCH), 3.41 (s, 3 H, OCH₃) 3.20 (m, 1 H, CH₂), 2.36 (m, 1 H, CH₂), 2.10 (m, 2 H, CH₂), 1.88 (m, 1 H, CH₂), 1.74 (m 1 H, CH₂); ¹³C NMR (125 MHz, C₆D₆) δ 184.4, 157.2, 137.7, 134.8, 123.3, 122.6, 113.3, 98.8, 98.4, 90.7, 87.2, 78.1, 74.8, 74.0, 58.4, 57.8, 51.5, 27.5, 27.4, 14.3; HRMS (FAB+) for C₂₀H₁₇NO₄Cs (M+Cs), calcd 468.0212, found 468.0254.

EXAMPLE 81

Acid-induced Bergman Cyclization of Compound 41; Compound 240

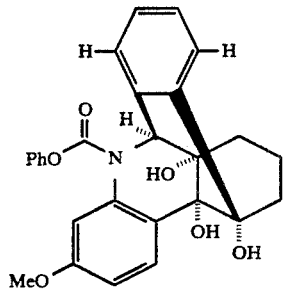

To a solution of Compound 41 (10.0 mg, 0.023 mmol) in benzene (1.0 mL) and 1,4-cyclohexadiene (1.0 mL) was added TsOH.H₂O (4.4 mg, 0.023 mmol) followed by stirring at 25° . for 1.5 hours. The reaction was quenched with saturated aqueous NaHCO₃, extracted with CH₂Cl₂(10 mL), dried over anhydrous Na₂SO₄, and concentrated in vacuo. The crude product was purified by preparative TLC (silica gel plate, 50 percent ethyl ether in benzene) to afford Compound 4 (3.3 mg, 32 percent): R$_f$=0.14 (silica, 50 percent ethyl ether in benzene); IR (CHCl₃) δ$_{max}$3294, 2917, 1718, 1616, 1511, 1498, 1380, 1294, cm⁻¹; ¹H NMR (300 MHz, CDCl₃) δ 7.61 (d, J=8.8 Hz, 1 H, aromatic), 7.56-7.20 (m, 10 H, aromatic), 6.69 (dd, J=8.9, 2.8 Hz, 1 H, aromatic), 5.88 (s, 1 H, NCH), 3.69 (s, 1 H, OH), 3.67 (s, 3 H, OCH₃), 2.89 (s, 1 H, OH), 2.29 (s, 1 H, OH), 2.48-2.18 (m, 3 H, CH₂), 1.87 (dd, J=13.6, 5.0 Hz, 1 H, CH₂), 1.47 (br d, J=12.8 Hz, 1 H, CH₂), 0.95-0.75 (m, 1 H, CH₂); HRMS for C₂₇H₂₅NO₆Cs (M+Cs), calcd 592.0736, found 592.0700.

EXAMPLE 82

Compound 24b

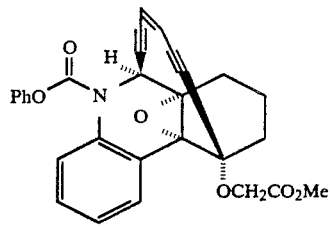

To a mixture of Compound 21 (300 mg, 0.73 mmol), cesium carbonate (480 mg, 1.46 mmol) and methyl bromoacetate (0.21 mL, 2.19 mmol) in acetonitrile (9 mL) was added 18-crown-6 (117 mg, 0.44 mmol) at zero degrees C. The cooling bath was then removed and the mixture was stirred at ambient temperature for 10 hours. The reaction mixture was diluted with ethyl acetate (40 mL) and washed sequentially with saturated ammonium chloride (10 mL), saturated sodium bicarbonate (10 mL), and brine (10 mL) and dried (MgSO₄). The solvent was removed in vacuo and the residue was purified by flash column chromatography (silica, 5 percent ethyl acetate in benzene) to give 323 mg (92 percent) of Compound 24b: colorless crystals; mp 198°-200° C. (dec., from dichloromethane); R$_f$=0.55 (silica, 40 percent ethyl acetate in petroleum ether); IR (film) $v_{max}$ 3081, 3048, 3016, 2949, 2194, 1757, 1712, 1599, 1488, 1206, 1125 cm$^{-1}$; $^1$H NMR (500 MHz, CDCl$_3$) δ 8.53 (d, J=8.1 Hz, 1 H, aromatic), 7.36 (br s, 1 H, aromatic), 7.31 -7.20 (m, 3 H, aromatic), 7.19-7.10 (m, 2 H, aromatic), 7.08-7.02 (m, 2 H, aromatic), 5.74 (d, J=10.0 Hz, 1 H, olefinic), 5.59 (dd, J=10.0, 1.4 Hz, 1H, olefinic), 5.45 (br s, 1 H, NC H$\underline{C}$≡C), 4.30 (d, J=15.5 Hz, 1 H, CH$_2$COOCH$_3$), 4.21 (d, J=15.5 Hz, 1 H, CH$_2$COOCH$_3$), 3.72 (s, 3 H, OCH$_3$), 2.25 (dd, J=15.0, 8.2 Hz, 1 H, CH$_2$), 2.22-2.06 (m, 2 H, CH$_2$), 1.96-1.85 (m, 1H, CH$_2$), 1.82 (br d, J=12.5 Hz, 1H, CH$_2$), 1.73-1.66 (m, 1 H, C$\underline{H_2}$); $^{13}$C NMR (125MHz, CDCl$_3$) δ 169.7, 135.5, 130.8, 129.3, 129.2, 128.0, 127.6, 125.6, 125.6, 123.8, 122.4, 121.5, 98.3, 95.7, 93.9, 88.4, 79.8, 72.9, 63.0, 62.6, 52.0, 50.3, 29.2, 23.1, 18.9; MS (FAB+) m/e (rel intensity) 614 (M+Cs, 100),526 (13); HRMS for C$_{29}$H$_{23}$NO$_6$Cs (M+Cs), calcd 614.0580, found 614.0574.

EXAMPLE 83

Compound 260

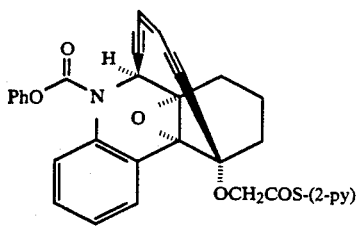

A solution of Compound 24c (323 mg, 0.67 mmol) in THF (4 mL) was treated with 0.5 N lithium hydroxide (4 mL) at zero degrees C for 0.5 hours. Acidification with 5 percent aqueous hydrochloric acid, extraction with ethyl acetate (5 mL) and drying over MgSO$_4$ provided the corresponding crude acid Compound 24a as a white foam. This material was immediately treated in CH$_2$Cl$_2$ (15 mL) with 2,2'-dipyridyldisulfide (266 mg, 1.26 mmol) and triphenylphosphine (330 mg, 1.26 mmol) at zero degrees C for 0.5 hours. The organic solvent was removed in vacuo and the residue was purified by flash column chromatography (silica, 20 percent ethyl acetate in benzene) to give 368 mg (96 percent) of Compound 260: pale yellow foam; R$_f$=0.45 (silica, 10 percent ethyl acetate in benzene); IR (film) $v_{max}$ 3051, 2950, 2200, 1721, 1571, 1451, 1420, 1378, 1320, 1278, 1202, 1115 cm$^{-1}$; $^1$H NMR (500 MHz, CDCl$_3$) δ 8.56 (br d, J=4.0 Hz, 1 H, aromatic), 8.42 (br d, J=7.9 Hz, 1 H, aromatic), 7.63 (td, J=7.7, 1.3 Hz, 1 H, aromatic), 7.52-7.48 (d, J=7.9 Hz, 1 H, aromatic), 7.38 (br, s, 1 H, aromatic), 7.28-7.03 (m 8 H, aromatic), 5.75 (d, J=10.0 Hz, 1 H, olefinic), 5.9 (dd, J=10.0, 0.8 Hz, 1 H, olefinic), 5.45 (br s, 1 H, NC H$\underline{C}$≡C), 4.50 (d, J=15.8 Hz, 1 H, CH$_2$COS), 4.37 (d, J=15.8 Hz, 1 H, CH$_2$COS), 2.30-2.07 (m, 2 H, CH$_2$), 2.12 (dt, J=17.0, 10.0 Hz, 1 H, CH$_2$), 1.98-1.88 (m, 2 H, CH$_2$), 1.75-1.68 (m, 1 H, C$\underline{H_2}$); $^{13}$C NMR (125 MHz, CDCl$_3$) δ 195.8, 150.4, 149.3, 137.3, 137.2, 135.5, 130.6, 130.6, 129.2, 128.2, 128.0, 127.3, 126.3, 125.6, 125.6, 123.6, 122.6, 121.4, 121.0, 97.9, 96.1, 93.8, 88.4, 80.0, 73.1, 69.8, 62.9, 50.2, 29.2, 23.0, 18.9; MS (FAB+) m/e (rel intensity) 693 (M+Cs, 100), 600 (30), 561 (12), 221 (29); HRMS for C$_{33}$H$_{24}$N$_2$O$_5$SCs (M+Cs), calcd 693.0460, found 693.0467.

EXAMPLE 84

Compound 261

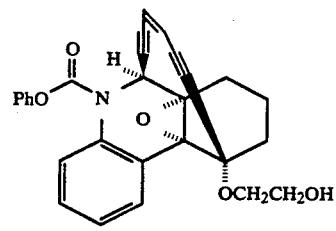

To a mixture of Compound 260 (368 mg, 0.65 mmol) and sodium borohydride (260 mg, 6.7 mmol) in dichloromethane (10 mL) was added 2-propanol (10 mL) dropwise at zero degrees C. After being stirred for 0.5 hours, the reaction mixture was diluted with ethyl acetate (20 mL) and washed with saturated sodium bicarbonate (10 mL) and brine (10 mL). The organic layer was dried (MgSO$_4$), evaporated in vacuo and the residue was purified by flash column chromatography (silica, 10 percent ethyl acetate in benzene) to give 200 mg (68 percent) of Compound 261: R$_f$=0.29 (silica, 40 percent ethyl acetate i petroleum ether); IR (film) $v_{max}$ 3504, 2939, 2187, 1721, 1595, 1490, 1458, 1379, 1321, 1203, 1148, 1107 cm$^{-1}$; $^1$H NMR (500 MHz, CDCl$_3$) δ 8.33 (dd, J=8.1, 1.4 Hz, 1 H, aromatic), 7.36 (br s, 1 H, aromatic), 7.32-7.02 (m, 7 H, aromatic), 5.74 (d, J=10.0 Hz, 1 H, olefinic), 5.58 (dd, J=10.0, 1.7 Hz, 1 H, olefinic), 5.45 (br s, 1 H, NC H$\underline{C}$≡C), 3.82-3.65 (m, 4 H, CH$_2$CH$_2$OH), 2.22 (dd, J=15.0, 9.0 Hz, 1 H, C$\underline{H}$ $_2$), 2.22-2.07 (m, 3 H, CH$_2$OH), 1.95-1.82 (m, 2 H, C$\underline{H_2}$), 1.72-1.63 (m, 1 H, CH$_2$); $^{13}$C NMR (125 MHz, CDCl$_3$) δ 150.0, 135.9, 130.7, 129.3, 127.9, 127.9, 126.4, 125.7, 125.3, 123.9, 122.3, 121.5, 99.1, 95.6, 93.8, 88.5, 78.8, 73.1, 65.9, 63.3, 61.8, 50.3, 29.3, 23.2, 18.8; MS (FAB+) m/e (rel intensity) 586 (M+Cs, 100), 552 (6), 434 )10); HRMS for C$_{28}$H$_{23}$NO$_5$Cs (M+Cs), calcd 586.0631, found 586.0637.

EXAMPLE 85

Compound 262

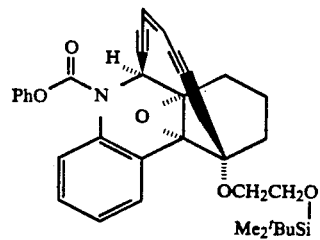

A solution of Compound 261 (200 mg, 0.44 mmol) in dichloromethane (8 mL) cooled at 31 78° C. was treated with 2,6-lutidine (0.16 mL, 1.34 mmol) and tert-butyldimethylsilyl triflate (0.23 mL, 1.01 mmol). The mixture was then allowed to warm to zero degrees C during 1 hour, diluted with ethyl ether (15 mL), washed with brine (10 mL), and dried (MgSO$_4$). The solvent was removed in vacuo and the residue was purified by flash column chromatography (silica, 20 percent ethyl ether in petroleum ether) to give 252 mg (99 percent) of Compound 262; colorless foam; R$_f$=0.37 (silica, 10 percent ethyl acetate in petroleum ether); IR (film) $\nu_{max}$ 3051, 2932, 2204, 1724, 1595, 1491, 1462, 1378, 1320, 1277, 1245, 1203, 1097 cm$^{-1}$; $^1$NMR (500 MHz, CDCl$_3$) δ 8.55 (dd, J=8.1, 1.2 Hz, 1 H, aromatic), 7.45 (br s, 1 H, aromatic), 7.40–7.12 (m, 7 H, aromatic), 5.83 (d, J=10.0 Hz, 1 H, olefinic), 5.67 (dd, J=10.0, 1.7 Hz, 1 H, olefinic), 5.54 (br s, 1 H, NC H̲C≡C), 3.94–3.72 (m, 4 H, CH$_2$CH$_2$OTBS), 2.33 (dd, J=15.1, 8.6 Hz, 1 H, CH$_2$), 2.28–2.17 (m, 2 H, CH$_2$), 2.05–1.93 (m, 2 H, CH$_2$), 1.82–1.73 (m, 1 H, CH$_2$), 0.94 (s, 9 H, SiC(CH$_3$)$_3$), 0.12 (s, 6 H, Si(CH$_3$)$_2$); $^{13}$C NMR (125 MHz, CDCl$_3$) δ 151.0, 135.6, 131.2, 129.3, 128.1, 127.8, 126.3, 125.6, 125.4, 124.1, 122.1, 121.5, 99.7, 95.1, 93.9, 88.5, 78.8, 72.9, 66.4, 63.3, 62.4, 50.4, 29.3, 25.9, 23.3, 18.4, −5.2, −5.3; MS (FAB+) m/e (rel intensity) 700 (M+Cs, 100); HRMS for C$_{34}$H$_{37}$NO$_5$SiCs (M+Cs), calcd 700.1495, found 7006.1488.

EXAMPLE 86

Compound 263

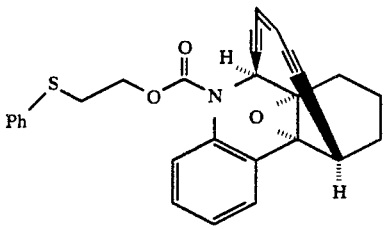

263

Representative Procedure

To a suspension of NaH (60 percent, 16.0 mg, 0.40 mmol) in THF (1 mL) cooled at zero degrees C was added 2-(phenylthio)ethanol (61.7 mg, 0.40 mmol) followed by stirring at zero degrees C for 10 minutes. To the resultant solution cooled at zero degrees C was added a solution of Compound 21 (80.0 mg, 0.20 mmol) in THF (1 mL). After stirring at zero degrees C for 5 minutes, the reaction mixture was quenched with saturated aqueous NH$_4$Cl, extracted with ethyl acetate, washed with saturated brine, dried over anhydrous Na$_2$SO$_4$, and concentrated in vacuo. The residue was purified by flash column chromatography (silica, 15 percent ethyl acetate in benzene) to give 87.1 mg (96 percent) of Compound 263: pale-yellow gum; R$_f$=0.47 (silica, 40 percent ethyl ether in petroleum ether); IR (CDCl$_3$) δ$_{max}$ 2920, 1710, 1350 cm$^{-1}$; $^1$H NMR (500 MHz, CDCl$_3$) δ 7.57 (dd, J=8.0, 1.0 Hz, 1 H, aromatic), 7.42–7.16 (m, 8 H, aromatic), 5.57 (dd, J=10.0, 1.5 Hz, 1 H, olefinic), 5.63 (dd, J=10.0, 1.5 Hz, 1 H, olefinic), 5.41 (br s, 1 H, NCH̲), 4.40–4.15 (m, 2 H, SCH$_2$CH$_2$), 3.78 (two sets of br s, 1 H, C≡CCHCH2), 3.15 (m, 2 H, SCH$_2$), 2.37 (dd, J=15.0, 8.5 Hz, 1 H, CH$_2$) 2.20 (ddd, J=15.5, 9.5, 9.5 Hz, 1 H, CH$_2$), 1.93 (m, 2 H, CH$_2$), 1.78 (dd, J=13.0, 3.5 Hz, 1 H, CH$_2$), 1.58 (m, 1 H, CH$_2$); HRMS for C$_{28}$H$_{23}$NO$_3$SCs (M+Cs), calcd 586.0453, found 586.0453.

EXAMPLE 87

Compound 264

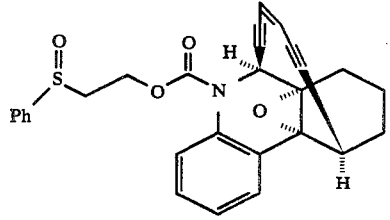

264

Representative Procedure

A solution of Compound 263 (16.6 mg, 0.0366 mmol) in CH$_2$Cl$_2$ cooled at zero degrees C was treated with mCPBA (6.9 mg, 0.0403 mmol) followed by stirring at zero degrees C for 30 minutes. The reaction mixture was quenched with dimethyl sulfide, diluted with CH$_2$Cl$_2$ (30 mL), and washed with saturated aqueous NaHCO$_3$ (2×30 mL). The organic layer was dried over anhydrous Na$_2$SO$_4$, concentrated in vacuo, and purified by flash column chromatography (silica, 100 percent ethyl ether) to give 15.1 mg (86 percent) of Compound 264: pale-yellow gum; R$_f$=0.25 (silica, 100 percent ethyl ether); IR (film) ξ$_{max}$ 2930, 1713, 1494, 1392, 1321, 1272, 1230, 1048 cm$^{-1}$; $^1$H NMR (500 MHz, CDCl$_3$) δ 7.70 (m, 9 H, aromatic), 5.76 (d, J=10.0 Hz, 1 H, olefinic), 5.64 (d, J=10.0 Hz, 1 H, olefinic), 5.39 (br s, 1 H, NCH̲), 4.63–4.31 (m, 2 H, SOCH$_2$CH$_2$), 3.76 (s, 1 H, C≡CCHCH$_2$), 3.18–2.98 (m, 2 H, SOCH$_2$), 2.38 (dd, J=15.0, 8.5 Hz, 1 H, CH$_2$), 2.22 (m, 1 H, CH$_2$), 1.96 (m, 2 H, CH$_2$), 1.79 (m, 1 H, CH$_2$), 1.59 (m, 1 H, CH$_2$), ; HRMS for C$_{28}$H$_{23}$NO$_4$SCs (M+Cs), calcd 602.0402, found 602.0426.

EXAMPLE 88

Compound 45

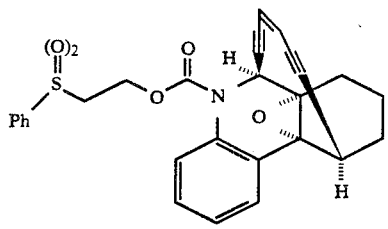

45

Representative Procedure

A solution of Compound 263 (126.0 mg, 0.278 mmol) in CH$_2$Cl$_2$ (3 mL) was treated with mCPBA (119.0 mg, 0.695 mmol) at zero degrees C followed by stirring at 25° C. for 30 minutes. The reaction mixture was quenched with dimethyl sulfide, diluted with CH$_2$Cl$_2$ (70 mL), and washed with saturated aqueous NaHCO$_3$ (2×70 mL). The organic layer was dried over anhydrous Na$_2$SO$_4$, concentrated in vacuo, and purified by flash column chromatography (silica, 70 percent ethyl ether in petroleum ether) to give 108.0 mg (80 percent) of Compound 45: colorless gum; R$_f$=0.23 (silica, 70 percent ethyl ether in petroleum ether); IR (CDCl$_3$) $\nu$max 2975, 2950, 1715, 1360, 1300, 1150 cm$^{-1}$; $^1$H NMR (500 MHz, CDCl$_3$) δ 7.92–7.10 (m, 9 H, aromatic), 5.73 (dd, J=10.0, 1.5 Hz, 1 H, olefinic), 5.63 (dd, J=10.0, 1.0 Hz, 1 H, olefinic), 5.45–4.85 (br s, 1 H, NCH), 4.65–4.22 (m, 2 H, SO$_2$CH$_2$CH$_2$), 3.73 (br s, 1 H, C≡CCHCH$_2$), 3.60–3.36 (m, 2 H, SO$_2$CH$_2$), 2.34 (m, 1 H, CH$_2$), 2.18 (ddd, J=15.5, 9.5, 9.5 Hz, 1 H, CH$_2$), 2.02–1.84 (m, 2 H, CH$_2$), 1.78 (m, 1 H, CH$_2$), 1.58 (m, 1 H, CH$_2$); $^{13}$C NMR (125 MHz, CDCl$_3$) δ 134.0, 129.3, 128.5, 128.1, 127.9, 127.1, 125.2, 124.8, 121.9, 101.7, 93.7, 91.2, 88.6, 70.1, 60.9, 59.3, 55.0, 49.4, 29.3, 32.1, 22.3, 15.6; HRMS for C$_{28}$H$_{23}$NSO$_5$Cs (M+Cs), calcd 618.0351, found 618.0352.

EXAMPLE 89

Compound 265

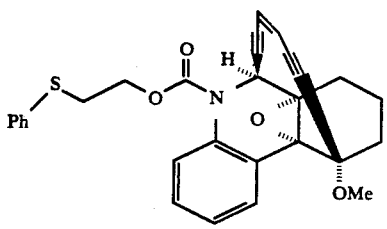

Similarly prepared in 90 percent yield as described for Compound 263. Compound 265: pale-yellow gum; R$_f$=0.32 (silica, 40 percent ethyl ether in petroleum ether); IR (film) νmax 2952, 1714 cm$^{-1}$; $^1$H NMR (500 MHz, CDC13) δ 8.38 (d, J=8.3, 1 H, aromatic), 7.43–7.13 (m, 8 H, aromatic), 5.82 (d, J=10.0 Hz, 1 H, olefinic), 5.66 (dd, J=10.0, 2.0 Hz, 1 H, olefinic), 5.41 (br s, 1 H, NCH), 4.42–4.12 (m, 2 H, SCH$_2$CH$_2$), 3.47 (s, 3 H, OCH$_3$), 3.13 (m, 2 H, SCH$_2$), 2.38–1.68 (m, 6 H, CH$_2$); HRMS for C$_{29}$H$_{26}$NO$_4$S (M+H), calcd 484.1582, found 484.1582.

EXAMPLE 90

Compound 266

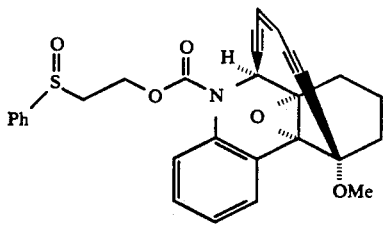

Similarly prepared in 90 percent yield as described for Compound 264. Compound 266: pale-yellow gum; R$_f$=0.25 (silica, 100 percent ethyl ether); IR (film) νmax 2929, 1711, 1492, 1393, 1321, 1276, 1242, 1090, 1090, 1048, 737 cm$^{-1}$; $^1$H NMR (500 MHz, CDCl$_3$) δ 8.36 (dd, J=7.5, 2.5 Hz, 1 H, aromatic), 7.70–7.13 (m, 1 H, aromatic), 5.83 (d, J=10.0 Hz, 1 H, olefinic), 5.65 (dd, J=10.0, 2.0 Hz, 1 H, olefinic), 5.42 (br s, 1 H, NCH), 4.62–4.30 (m, 2 H, SOCH$_2$CH$_2$), 3.48 (s, 3 H, OCH$_3$), 3.18–2.85 (m, 2 H, SOCH$_2$), 2.30 (dd, J=15.0, 8.5 Hz, 1 H, CH$_2$), 2.17 (m, 2 CH$_2$), 1.93 (m, 2 H, CH$_2$), 1.76 (m, 1 H, CH$_2$); HRMS for C$_{29}$H$_{25}$NO$_5$SCs (M+Cs), calcd 632.0508, found 632.0494.

EXAMPLE 91

Compound 47

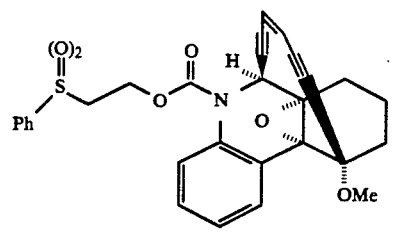

Similarly prepared in 79 percent yield as described for Compound 45. Compound 47: white crystalline solid; mp 183°–184° C. (from CH$_2$Cl$_2$-petroleum ether); R$_f$=0.26 (silica, 70 percent ethyl ether in petroleum ether); IR (CDCl$_3$) δmax 2930, 1710, 1410, 1325, 1145 cm$^{-1}$; $^1$H NMR (500 MHz, CDCl$_3$) δ 8.36–7.00 (m, 9 H, aromatic), 5.81 (d, J=10.0 Hz, 1H, olefinic), 5.64 (d, J=10.0 Hz, 1 H, olefinic), 5.47 (br s, 1 H, NCH), 4.55–4.42 (two sets of br singlets due to rotamers, 2 H, SO$_2$CH$_2$CH$_2$), 3.47 (br s, 5 H, OCH$_3$ and SO$_2$CH$_2$), 2.66 (m, 1 H, CH$_2$); $^{13}$C NMR (125 MHz, CDCl$_3$) δ 134.1, 130.8, 129.4, 127.9, 127.8, 126.2, 125.2, 123.9, 122.2, 99.3, 95.2, 93.8, 88.3, 79.2, 72.8, 59.3, 55.1, 52.0, 50.0, 28.2, 23.1, 18.8; HRMS for C$_{29}$H$_{26}$NO$_6$S (M+H), calcd 516.1481, found 516.1470.

EXAMPLE 92

Compound 267

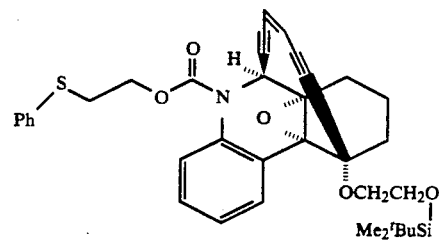

Similarly prepared in 98 percent yield as described for Compound 263. Compound 267: R$_f$=0.17 (silica, 10 percent ethyl acetate in petroleum ether); IR (film) νmax 3055, 2931, 2192, 1708, 1581, 1489, 1460, 1393, 1320, 1277, 1246, 1102, 1026 cm$^{-1}$; $^1$H NMR (500 MHz, CDCl$_3$) δ 8.51 (br d, J=7.2 Hz, 1 H, aromatic), 7.42 (br d, J=7.5 Hz, 1 H, aromatic), 7.40–7.26 (m, 5 H, aromatic), 7.25–7.16 (m, 2 H, aromatic), 5.82 (d, J=10.0 Hz, 1 H, olefinic), 5.66 (dd, J=10.0, 1.2 Hz, 1 H, olefinic), 5.46 (br s, 1 H, NCHC≡C), 4.39 (dt, J=11.0, 7.1 Hz, 1 H, OCH2CH2SPh), 4.25 (br s, 1 H, OCH$_2$CH$_2$SPh), 3.92–3.69 (m, 4 H, CH$_2$CH$_2$OTBS), 3.24–3.10 (m, 2 H, CH$_2$CH$_2$SPh), 2.30 (dd, J=15.0, 8.2 Hz, 1 H, CH$_2$), 2.26–2.13 (m, 2 H, CH$_2$) 2.23–1.92 (m, 2 H, CH$_2$), 1.79–1.73 (m, 1 H, CH$_2$), 0.95 (s, 9 H, SiC(CH$_3$)$_3$), 0.12 (s, 6 H, Si(CH$_3$)$_2$); $^{13}$C NMR (125 MHz, CDCl$_3$) δ 154.5, 135.7, 134.9, 131.1, 129.9, 129.0, 127.9, 127.6, 126.5, 126.1, 125.0, 123.9, 122.1, 99.7, 94.9, 94.1, 88.3, 78.8, 73.0, 66.3, 64.6, 62.4, 50.0, 32.3, 29.2, 25.9, 23.3, 18.8, −5.2, −5.3; MS (FAB+) m/e (rel intensity 760 (M+Cs, 100); HRMS for C$_{36}$H$_{41}$NO$_5$SiSCs (M+Cs), calcd 760.1529, found 760.1529.

EXAMPLE 93

Compound 268

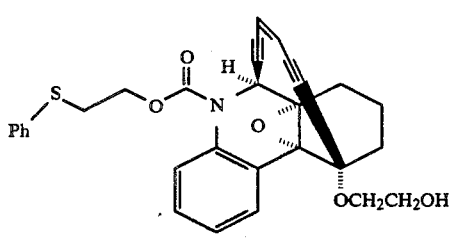

A solution of Compound 267 (320 mg, 0.51 mmol) on THF (10 mL) was treated with tetra-n-butylammonium fluoride (0.87 mL, 1.0 M solution in THF, 0.87 mmol) at zero degrees C for 0.5 hour. The solvent was evaporated in vacuo and the residue was purified by flash column chromatography (silica, 20 percent ethyl acetate in benzene) to give 252 mg (96 percent) of Compound 268: white foam; $R_f=0.63$ (silica, 30 percent ethyl acetate in benzene): IR (film) $\nu$max 3482, 3055, 2936, 2198, 1705, 1581, 1490, 1455, 1395, 1321, 1278, 1108, 1060 cm$^{-1}$; $^1$H NMR (500 MHz, CDCl$_3$) $\delta$ 8.29 (dd, J=8.1, 1.2 Hz, 1 H, aromatic), 7.35-7.07 (m, 8 H, aromatic), 5.72 (d, J=10.0 Hz, 1 H, olefinic), 5.57 (dd, J=10.0, 1.7 Hz, 1 H, olefinic), 5.38 (br s, 1 H, NCHC≡C), 4.29 (dt, J=11.0, 7.2 Hz, 1 H, PhSCH$_2$CH$_2$O), 4.14 (br s, 1 H, PhSCH$_2$CH$_2$O), 3.82-3.71 (m, 3, CH$_2$CH$_2$OH), 3.68-3.62 (m, 1 H, CH$_2$CH$_2$OH), 3.14-3.00 (m, 2 H, PhSCH$_2$), 2.21 (dd, J=14.8, 7.8 Hz, 1 H, CH$_2$), 2.18-2.04 (m, 2 H, CH$_2$), 2.00 (br s, 1 H, OH), 1.92-1.82 (m, 2 H, CH$_2$), 1.72-1.63 (m, 1 H, CH$_2$); $^{13}$C NMR (125 MHz, CDCl$_3$) $\delta$ 154.5, 135.8, 134.9, 130.6, 129.9, 129.9, 129.1, 127.8, 126.6, 126.4, 125.0, 123.7, 122.3, 99.1, 95.6, 94.1, 88.3, 78.8, 73.3, 65.9, 64.6, 63.2, 61.9, 50.0, 32.3, 29.3, 23.3, 18.9; MS (FAB+) m/e (rel intensity) 646 (M+Cs, 100), 539 (12); HRMS for C$_{30}$H$_{27}$NO$_5$SCs (M+Cs), calcd 646.0664, found 646.0651.

EXAMPLE 94

Compound 120

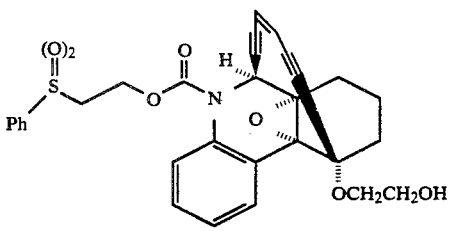

Similarly prepared in 82 percent yield as described for Compound 45. Compound 120: $R_f=0.30$ (silica, 30 percent ethyl acetate in benzene); IR (film) $\nu$max 3519, 2932, 2188, 1710, 1492, 1450, 1400, 1320, 1290, 1145, 1108, 1068 cm$^{-1}$; $^1$H NMR (500 MHz, CDCl$_3$) $\delta$ 8.28-8.22 (m, 1 H, aromatic), 7.82-7.74 (m, 2 H, aromatic), 7.53-7.37 (m, 3H, aromatic), 7.15-7.00(m, 3 H, aromatic), 5.68 (dd, J=10.0, 5.0 Hz, 1 H, olefinic), 5.54-5.49 (m, 1 H, olefinic), 5.20 (br s, 1 H, NCHC≡C), 4.46-4.38 (m, 1 H, OCH$_2$CH$_2$SO$_2$Ph), 4.37-4.27 (m, 1 H, OCH$_2$C$_2$SO$_2$Ph), 3.78-3.60 (m, 4 H, CH$_2$CH$_2$OH), 3.40-3.12 (m, 2, CH$_2$CH$_2$SO$_2$Ph), 2.22-2.18 (m, 1 H, CH$_2$, OH), 1.90-1.78 (m, 2 H, CH2),1.67-1.60 (m, 1 H, CH$_2$); $^{13}$C NMR (125 MHz, CDCl$_3$), $\delta$ 154.1, 138.8, 135.4, 134.0, 133.3, 130.6, 129.4, 128.3, 127.9, 127.8, 125.2, 123.8, 122.2, 98.9, 95.6, 93.8, 88.4, 78.7, 73.1, 65.9, 63.2, 61.9, 59.4, 55.1, 50.0, 29.3, 23.1, 18.8; MS (FAB+) m/e (rel intensity) 678 (M+Cs, 100); HRMS for C$_{30}$H$_{27}$NO$_7$SCs (M+Cs), calcd 678.0563, found 678.0563.

EXAMPLE 95

Compound 48

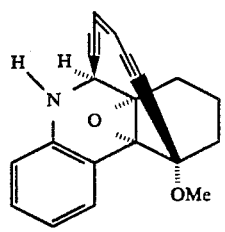

A solution of Compound 47 (30.0 mg, 0.058 mmol) in benzene (0.5 mL) was treated with DBU (10.6 mg, 0.069 mmol) at 5° C. for 30 minutes. The reaction mixture was diluted with CH$_2$Cl$_2$ (40 mL), washed with saturated aqueous NaHCO$_3$ (40 mL), dried over anhydrous Na$_2$SO$_4$, and concentrated in vacuo. The residue was purified by flash column chromatography (silica, 50→60 percent ethyl ether in petroleum ether) to give 17.0 mg (97 percent) of Compound 48: crystalline solid; mp>300° C.; $R_f=0.61$ (silica, 70 percent ethyl ether in petroleum ether); IR (CDCl$_3$) $\nu$max 3400, 2950, 2850, 1100, 1080 cm$^{-1}$; $^1$H NMR (500 MHz, CDCl$_3$), $\delta$8.32 (d, J=7.3 Hz, 1 H, aromatic), 7.11 (dd, J=7.3, 7.3 Hz, 1 H, aromatic), 6.82 (dd, J=7.3, 7.3 Hz, 1 H, aromatic), 6.55 (d, J=7.3, 1 H, aromatic), 5.83 (d, J=8.8 Hz, 1 H, olefinic), 5.73 (dd, J=8.8, 1.7 Hz, 1 H, olefinic), 4.32 (d, J=1.7 Hz, 1 H, NCH), 4.00 (br s, 1 H, NH), 3.50 (s, 3 H, OCH$_3$), 2.36-1.68 (m, 6 H, CH$_2$); $^{13}$C NMR (125 MHz, CDCl$_3$) $\delta$ 142.2, 131.0, 128.3, 123.1, 122.5, 122.0, 119.3, 115.9, 100.2, 96.9, 94.6, 87.3, 79.6, 72.9, 62.9, 29.0, 24.6, 19.0; HRMS for C$_{20}$H$_{17}$NO$_2$ (M+), calcd 303.1337, found 303.1348.

EXAMPLE 96

Trapping of Free Amino Epoxide Compound 40 with Nucleophiles; Compound 49

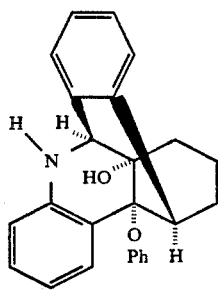

Representative Procedure

A solution of Compound 45 (9.5 mg, 0.0196 mmol) in a 4:1 mixture of dioxane-water (1 mL) was treated with Cs$_2$CO$_3$ (19.0 mg, 0.059 mmol) and 18-drown-6 (3.1 mg, 0.012 mmol) at zero degrees C followed by stirring at 25° C. for 1 hour to generate a crude solution of Compound 40 (high yield as checked by TLC). Phenol (3.7 mg, 0.039 mmol) was added to the above solution and stirring was continued for another two hours at 25° C. The reaction mixture was diluted with ethyl acetate (50 mL), washed with saturated aqueous NaHCO$_3$ (1×50 mL), dried over anhydrous Na$_2$SO$_4$, and concentrated in vacuo. The residue was purified by flash column chromatography (silica, 40→60 percent ethyl ether in petroleum ether) to give 2.5 mg (25 percent) of Compound 49: R$_f$=0.35 (silica, 70 percent ethyl ether in petroleum ether); IR (CDCl$_3$), $\nu$max 3250, 3400, 2940 cm$^{-1}$; $^1$HNMR (500 MHz, CDCl$_3$) δ 7.31 (dd, J=7.5, 1.5 Hz, 1 H, aromatic), 7.16 (m, 3 H, aromatic), 7.05 (m, 2 H, aromatic), 6.98 (ddd, J=7.5, 7.5, 1.5 Hz, 1.0 Hz, 1 H, aromatic), 6.93 (d, J=7.5 Hz, 1 H, aromatic), 6.80 (m, 3 H, aromatic), 6.72 (ddd, J=7.5, 7.5, 1.0 Hz, 1 H, aromatic), 6.46 (dd, J=8.0, 1.0 Hz, 1 H, aromatic), 4.17 (br s, 1 H O$\underline{\text{H}}$ or N$\underline{\text{H}}$, exchangeable with D$_2$O), 4.12 (s, 1 H, NC$\underline{\text{H}}$), 3.60 (s, 1 H, O$\underline{\text{H}}$ or N$\underline{\text{H}}$, exchangeable with (D$_2$O), 3.55 (dd, J=3.0, 3.0 Hz, 1 H, C≡CC$\underline{\text{H}}$CH$_2$), 2.65 (dddd, J=13.0, 13.0, 4.5, 4.5 Hz, 1 H, C$\underline{\text{H}}_2$), 2.30 (ddd, J=14.0, 14.0, 6.5 Hz, 1 H, C$\underline{\text{H}}_2$), 1.70 (dd, J=14.0, 5.0 Hz, 1 H, C$\underline{\text{H}}_2$), 1.50 (m, 1 H, C$\underline{\text{H}}_2$), 1.38 (m, 1 H, C$\underline{\text{H}}_2$), 0.90 (m, 1 H, C$\underline{\text{H}}_2$); HRMS for C$_{25}$H$_{23}$NO$_2$Cs (M+Cs), calcd 502.0783, found 502.0772.

EXAMPLE 97

Compound 50

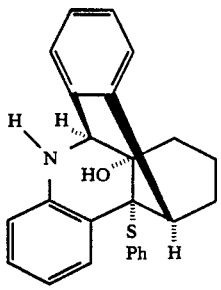

Prepared in 33 percent yield from Compound 45 and thiophenol as described for Compound 49. Compound 50: R$_f$=0.40 (silica, 70 percent ethyl ether in petroleum ether); IR (CDCl$_3$) $\nu$max 3450, 3390, 3070 2930, 2870, 1490, 1470 cm$^{-1}$; $^1$H NMR (500 MHz, CDCl$_3$) δ 7.63 (d, J=7.5 Hz, 1 H, aromatic), 7.35 (m, 2 H, aromatic), 7.18 (d, J=7.0 Hz, 1 H, aromatic), 7.14 (t, J=7.0 Hz, 1 H, aromatic), 7.09 (t, J=7.0 Hz, 1 H, aromatic), 7.03 (m, 3 H, aromatic), 6.87 (d, J=7.0 Hz, 1 H, aromatic), 6.80 (t, J=7.0 Hz, 1 H, aromatic), 6.61 (t, J=7.0 Hz, 1H, aromatic), 6.31 (d, J=7.5 Hz, 1 H, aromatic), 4.12 (two sets of singlets, 2 H, N$\underline{\text{H}}$ and NC$\underline{\text{H}}$), 3.73 (s, 1 H, O$\underline{\text{H}}$), 3.62 (t, J=2.8 Hz, 1 H, ArC$\underline{\text{H}}$CH$_2$), 2.80 (ddd, J=12.8, 12.8, 5.6 Hz, 1 H, C$\underline{\text{H}}_2$), 2.41 (dddd, J=12.8, 12.8, 4.5, 4.5 Hz, 1 H, C$\underline{\text{H}}_2$), 1.75 (dd, J=13.2, 4.9 Hz, 1 H, C$\underline{\text{H}}_2$), 1.54 (m, 1 H, C$\underline{\text{H}}_2$), 1.39 (br d, J=13.2, 1 H, C$\underline{\text{H}}_2$), 0.90 (m, 1 H, C$\underline{\text{H}}_2$); $^{13}$C NMR (125 MHz, CDCl$_3$) δ 141.6, 139.2, 137.1, 135.1, 133.7, 130.6, 128.1, 127.8, 127.4, 127.0, 126.8, 126.4, 119.9, 115.8, 70.4, 62.1, 55.6, 33.3, 29.8, 28.0, 18.8; HRMS for C$_{25}$H$_{23}$NOs (M+), calcd 385.1500, found 385.1500.

EXAMPLE 98

Acid-Induced Bergman Cycloaromatization of Free Amino Epoxide Compound 48; Compound 51

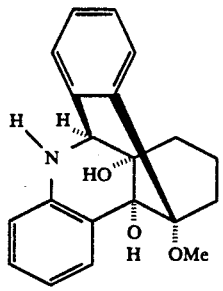

A solution of Compound 48 (10.0 mg, 0.033 mmol) in a 4:1:1 mixture of dioxane, water, and 1,4-cyclohexadiene (0.5 mL) was treated with TsOH.H$_2$O (3.1 mg, 0.016 mmol) at 60° C. for 5 minutes. The reaction mixture was diluted with ethyl acetate, washed with saturated aqueous NaHCO$_3$, dried over anhydrous Na$_2$SO$_4$, and concentrated in vacuo. The residue was purified by flash column chromatography (silica, 5→10 percent ethyl ether in petroleum ether) to give 2.1 mg (20 percent) of Compound 51: yellowish gum; R$_f$=0.37 (silica, 70 percent ethyl ether in petroleum ether); IR (film) $\nu_{max}$ 3380, 29234, 2854, 1082 cm$^{-1}$; $^1$H NMR (500 MHz, CDCl$_3$) δ 7.63 (dd, J=8.0, 1.5 Hz, 1 H, aromatic), 7.39 (m, 1 H, aromatic), 7.19 (m, 3 H, aromatic), 6.89 (ddd, J=7.5, 7.5, 1.5 Hz, 1 H, aromatic), 6.38 (dd, J=8.0, 1.0 Hz, 1 H, aromatic), 4.16 (s, 1 H, NC$\underline{\text{H}}$), 3.90 (s, 3 H, OC$\underline{\text{H}}_3$), 3.66 (s, 1 H, O$\underline{\text{H}}$ or N$\underline{\text{H}}$, exchangeable with D$_2$O), 2.78 (s, 1 H, O$\underline{\text{H}}$ or N$\underline{\text{H}}$, exchangeable with D$_2$O), 2.75 (ddd, J=13.0, 13.0, 4.5 Hz, 1 H, C$\underline{\text{H}}_2$), 2.30 (m, 1 H, C$\underline{\text{H}}_2$), 2.23 (ddd, J=14.0, 14.0, 6.5 Hz, 1 H, C$\underline{\text{H}}_2$), 2.0 (m, 1 H, C$\underline{\text{H}}_2$), 1.57 (m, 1 H, C$\underline{\text{H}}_2$), 1.65 (dd, J=13.5, 5.0 Hz, 1 H, C$\underline{\text{H}}_2$); HRMS for C$_{20}$H$_{21}$NO$_3$Cs (M+Cs), calcd 456.0576, found 456.0603.

EXAMPLE 99

2-Acetoxy-7,8,9,10-tetrahydrophenanthridine (Compound 274)

A mixture of 2-methoxy-7,8,9,10-tetrahydrophenanthridine (Compound 273, 48.17 g, 226 mmol) and sodium ethanethiolate (43.69 g, 520 mmol) in dry DMF was heated at 160° C. for 4 hours. After the reaction mixture was cooled to zero degrees C, acetic anhydride (63.9 ML, 678 mmol) was added and the reaction mixture was stirred for 30 minutes. The resulting thick white slurry was poured into 0.1 M pH 7.5 phosphate buffer (1.6 L) and extracted with ether (3×400 mL). The combined organic layers were washed with water (3×300 mL) and brine (300 mL), dried (MgSO$_4$), filtered through a 3 cm×3 cm plug of silica, and evaporated in vacuo. The residue was purified by recrystallization from ethyl acetate-hexanes to give 45.70 g (86 percent) of Compound 274: white crystalline solid; mp 118°-119° C.; R$_f$=0.39 (silica, 50 percent ethyl acetate in dichloromethane); IR (CHCl$_3$) $\nu_{max}$ 3018, 2938, 2861, 1758, 1507, 1369, 1193, 1174 cm$^{-1}$; $^1$H NMR (300 MHz, CDCl$_3$) δ 8.60 (s, 1 H, H6), 8.06 (d, J=9.0 Hz, 1 H, H4), 7.61 (d, J=2.5 Hz, 1 H, H1), 7.36 (dd, J=9.0, 2.5 Hz, 1 H, H3), 3.03 (t, J=6.0 Hz, 2 H, H7 or H10), 2.89 (t, J=6.0 Hz, 2 H, H7 or H10), 2.37 (s, 3 H, OCOCH$_3$), 1.98-1.86 (m, 4 H, H8 and H9); $^{13}$C NMR (125 Mz, CDCl$_3$) δ 169.5, 152.3, 148.4, 144.3, 140.9, 131.3, 130.1, 128.0, 122.9, 113.8, 27.0, 24.8, 22.2, 22.1, 21.1; MS (FAB+) m/e (rel intensity 242 (M+H, 100), 200 (25); HRMS for C$_{15}$H$_{16}$NO$_2$ (M+H), calcd 242.1181, found 242.1181. Anal. Calcd for C$_{15}$H$_{15}$NO$_2$: C, 74.67; H, 6.27; N, 5.80. Found: C, 74.66; H, 6.37; N, 5.64.

EXAMPLE 100

2-Hydroxy-7,8,9,10-tetrahydrophenanthridine (Compound 275)

To a solution of Compound 274 (26.50 g, 110 mmol) in dry methanol (150 mL) was added Dowex 1×8−200 hydroxide form (0.40 g, catalytic), and tetra-n-butylammonium bromide (50 mg, catalytic), and the resulting mixture was stirred at 60° C. for 24 hours. The reaction mixture was cooled, diluted with ethyl ether (100 mL) and filtered to give 21.47 g (98 percent) of Compound 275: white crystalline solid; mp 284°-286° C. (dec.); R$_f$=0.25 (silica, 50 percent ethyl acetate in dichloromethane); IR (CHCl$_3$) ν$_{max}$ 2933, 2906, 2850, 2582, 1627, 1503, 1421 cm$^{-1}$; $^1$H NMR (500 MHz, DMSO -d$_6$) δ 9.92 (s, 1 H, OH), 8.34 (s, 1 H, H6), 7.77 (d, J=9.0 Hz, 1 H, H4), 7.19 (dd, J=9.0, 2.6 Hz, 1 H, H3), 7.12 (d, J=2.6 Hz, 1 H, H1), 2.88 (t, J=6.1 Hz, 2 H, H7 or H10),2.78 (t, J=6.1 H, 2 H, H7 or H10), 1.87-1.74 (m, 4 H, H8 and H9); $^{13}$C NMR (125 MHz, DMSO -d6) δ 155.5, 148.8, 141.1, 138.5, 130.9, 129.4, 128.4, 120.0, 104.0, 26.5, 24.3, 22.1, 21.9; MS (FAB+) m/e (rel intensity) 200 (M+H, 100), 124 (8), 107 (14); HRMS for C$_{13}$H$_{14}$NO (M+H), calcd 200.1075, found 200.1079.

EXAMPLE 101

2-[(2-Nitrobenzyl)oxy]-7,8,9,10-tetrahydrophenanthridine (Compound 276)

A mixture of Compound 275 (57.17 g, 287 mmol), 2-nitrobenzyl bromide (68.19 g, 316 mmol), powdered potassium carbonate (142.0 g, 1.03 mol) and tetra-n-butylammonium iodide (3.18 g, 8.61 mmol) in dry DMF (400 mL) was stirred at 25° C. for 3 hours and then poured into a mixture of ethyl ether (200 mL), dichloromethane (1500 mL), and water (200 mL) with stirring. After allowing this mixture to settle, the aqueous layer was discarded. The organic layer was washed with water (3×1500 mL), dried (MgSO$_4$), and filtered through a 8 cm×8 cm plug of silica with rinsing with ethyl ether (300 mL). The combined filtrates were evaporated in vacuo, and the residue was purified by recrystallization from chloroform-ethyl ether to give 90.41 g (94 percent) of Compound 276: off-white crystalline solid; mp 153°-154° C.; R$_f$=0.48 (silica, 40 percent ethyl acetate in dichloromethane); IR (CHCl$_3$) ν$_{max}$ 2939, 1619, 1526, 1508, 1433, 1342 cm$^{-1}$; $^1$H NMR (300 MHz, CDCl$_3$) δ 8.50 (s, 1 H, H6), 8.19 (dd, J=7.4, 1.0 Hz, 1 H, aromatic), 7.99 (d, J=9.1 Hz, 1 H, H4), 7.97 (dd, J=7.4, 1.0 Hz, 1 H, aromatic), 7.71 (td, J=7.4, 1.0 Hz, 1 H, aromatic), 7.52 (td, J=7.4, 1.0 Hz, 1 H, aromatic), 7.39 (dd, J=9.1, 2.8 Hz, 1 H, H3), 7.24 (d, J=2.8 Hz, 1 H, H1), 5.61 (s, 2 H, benzylic), 2.99 (t, J= 6.1 Hz, 2 H, H7 or H10), 2.88 (t, J=6.1 Hz, 2 H, H7 or H10), 2.01-1.84 (m, 4 H, 8 H and H9); —C NMR (125 MHz, CDCl$_3$) δ 156.0. 150.3, 146.9, 142.4, 140.0, 134.0, 133.9, 133.4, 131.5, 130.1, 128.5, 128.4, 124.9, 119.8, 102.7, 66.7, 27.1, 24.9, 22.3, 22.2; MS (FAB+) m/e (rel intensity) 335 (M+H, 100), 200 (13); HRMS for C$_{20}$H$_{19}$N$_2$O$_3$ (M+H), calcd 335.1396, found 335.1394.

EXAMPLE 102

2-[(Trifluoromethanesulfonyl)oxy]-7,8,9,10-tetrahydrophenanthridine (Compound 227)

To a solution of Compound 275 (23.6 g, 118.4 mmol) in dry pyridine (236 mL) was added trifluormethanesulfonic anhydride (24.0 mL, 142.1 mmol) at −30° C. over 15 minutes. After being stirred at zero degrees C for 24 hours, the mixture was diluted with dichloromethane (800 mL), washed with saturated aqueous sodium bicarbonate (400 mL×2), saturated aqueous copper sulfate (400 mL×3), and brine (400 mL). The organic layer was dried (Na$_2$SO$_4$) and evaporated in vacuo and the residue was purified by flash column chromatography (silica, 10 percent ethyl acetate in dichloromethane) to give 40.7 g (100 percent) of Compound 277: white crystalline solid; mp 80°-81° C. (from ethyl ether-petroleum ether); R$_f$=0.39 (10 percent ethyl acetate in dichloromethane); IR (film) ν$_{max}$ 2934, 2865, 1614, 1597, 1504, 1416, 1208, 1004, 928 cm$^{-1}$; $^1$H NMR (500 MHz, CDCl$_3$) δ 8.65 (s, 1 H, H6), 8.11 (d, J=9.2 Hz, 1 H, H4), 7.78 (d, J=2.7 Hz, 1 H, H1), 7.49 (dd, J=9.2, 2.7 Hz, 1 H, H3), 3.04 (t, J=6.2 Hz, 2 H, H10), 2.89 (t, J=6.2 Hz, 2 H, H7), 2.00-1.93 (m, 2 H, CH$_2$), 1.92-1.87 (m, 2 H, CH$_2$); —C NMR (125 MHz, CDCl$_3$) δ 153.7, 147.1, 145.1, 141.4, 132.6, 131.3, 128.0, 121.3, 117.5, 114.7, 27.0, 24.8, 22.0, 21.9; MS (FAB+) m/e (rel intensity) 332 (M+H, 100), 199 (13), 171 (8), 133 (7); HRMS for C$_{14}$H$_{13}$F$_2$NO$_3$S (M+H), calcd 332.0568, found 332.0568.

EXAMPLE 103

2-[3-[(tert-Butyldiphenylsilyl)oxy]propynyl]-7,8,9,10-tetrahydrophenanthridine (Compound 279)

To a mixture of Compound 277 (1.28 g, 3.86 mmol), 3-[(tert-butyldiphenylsilyl)oxy]propyne (Compound 278, 1.48 g, 5.02 mmol), and diethylamine (800 mL, 7.73 mmol) in dry degassed N,N-dimethylformamide (7.7 mL) was added copper (I) iodide (74 mg, 0.39 mmol) followed by bis(triphenylphosphine)palladium(II) chloride (135 mg, 0.19 mmol). After being stirred in the dark for 11 hours under argon, the mixture was diluted with ethyl acetate (50 mL) and washed with saturated aqueous sodium bicarbonate (20 mL×2) and brine (20 mL). The organic layer was dried (Na$_2$SO$_4$) and evaporated in vacuo, and the residue was purified by flash column chromatography (silica, 10 percent ethyl ether in dichloromethane) to give 1.78 g (97 percent) of Compound 279: R$_f$=0.39 (10 percent ethyl acetate in dichloromethane); IR (film) ν$_{max}$ 3048, 2932, 2857, 2227, 1589, 1568, 1502, 1428, 1370, 1112 cm$^{-1}$; $^1$H NMR (500 MHz, CDCl3) δ 8.59 (s, 1 H, H6), 7.95 (d, J=8.6 Hz, 1 H, H4), 7.92 (d, J=1.5 Hz, 1 H, H1), 7.84-7.78 (m, 4 H, aromatic), 7.53 (dd, J=8.6, 1.5 Hz, 1 H, H3), 7.48-7.39 (m, 6 H, aromatic), 4.62 (s, 2 H, C≡CCH$_2$O), 3.04 (t, J=5.8 Hz, 2 H, H10), 2.87 (t, J=5.8 Hz, 2 H, H7), 2.01-1.93 (m, 2 H, CH$_2$), 1.93-1.85 (m, 2 H, CH$_2$), 1.12 (s, 9 H, t-Bu); $^{13}$C NMR (125 MHz, CDCl$_3$) δ 152.8, 145.6, 141.0, 135.6, 133.1, 130.6, 130.2, 129.7, 129.6, 127.6, 127.5, 120.7, 88.4, 85.3, 53.2, 27.0, 26.7, 24.8, 22.2, 22.1, 19.2; MS (FAB+) m/e (rel intensity) 476 (M+H, 100), 418 (9), 388 (12), 220 (11), 197 (9); HRMS for C$_{32}$H$_{34}$NOSi (M+H), calcd 476.2410, found 476.2410.

EXAMPLE 104

2-Methoxy-7,8,9,10-tetrahydrophenanthridine N-Oxide (Compound 280a)

Representative Procedure

To a solution of Compound 273 (91.80 g, 430 mmol) in dichloromethane (500 mL) cooled at zero degrees C was added a solution of mCPBA (55 percent, 161.7 g, 516 mmol) in dichloromethane (900 mL), and the resulting mixture was stirred at 25° C. for 1 hour. Dimethyl sulfide (6.95 mL, 94.6 mmol) was added and stirring was continued for 15 minutes followed by addition of saturated aqueous sodium bicarbonate solution (1000 mL). The organic layer was separated and the aqueous layer was extracted with dichloromethane (500 mL). The combined organic layers were dried (MgSO4), filtered through a 3 cm×3 cm plug of silica, and evaporated in vacuo. The residue was purified by recrystallization from benzene-cyclohexane to give a total of 88.34 g (90 percent) of the N-oxide Compound 280a: off-white crystalline solid; mp 167°–169° C.; $R_f$=0.31 (silica, 20 percent methanol in ethyl acetate); IR (CHCl3) $\nu_{max}$ 2943, 1617, 1512, 1459, 1428, 1379, 1108 cm$^{-1}$; $^1$H NMR (500 MHz, CDCl3) δ 8.65 (d, J=9.5 Hz, 1 H, H4), 8.18 (s, 1 H, H6), 7.30 (dd, J=9.5, 2.6 Hz, 1 H, H3), 7.10 (d, J=2.6 Hz, 1 H, H1), 2.95 (t, J=6.2 Hz, 2 H, H 10), 2.77 (t, J=6.2 Hz, 2 H, H7), 1.99–1.94 and 1.89–1.85 (m, 2 H each, H8 and H9); $^{13}$C NMR (125 MHz, CDCl3) δ 159.1, 134.8, 134.3, 131.4, 130.8, 121.7, 120.3, 101.8, 55.5, 27.0, 24.7, 22.1, 21.8; MS (FAB+) m/e (rel intensity) 230 (M+H, 100), 213 (10); HRMS for C14H16NO2 (M+H), calcd 230.1181, found 230.1194.

EXAMPLE 105

2-[(2-Nitrobenzyl)oxy]-7,8,9,10-tetrahydrophenanthridine N-oxide (Compound 280b)

Prepared in 87 percent yield as described for Compound 280a. Compound 280b: off-white crystalline solid; mp 181°–181.5° C. (from chloroform-ethyl acetate-ethyl ether); IR (CHCl3) $\nu_{max}$ 2944, 1616, 1526, 1432, 1383 cm$^{-1}$; $^1$NMR (500 MHz, CDCl3) δ 8.70 (d, J=9.5 Hz, 1 H, H4), 8.19 (dd, J=7.7, 1.2 Hz, 1 H, aromatic), 8.19 (s, 1 H, H6), 7.93 (dd, J=7.7, 1.2 Hz, 1 H, aromatic), 77.2 (td, J=7.7, 1.2 Hz, 1 H, aromatic), 7.53 (td, J=7.7, 1.2 Hz, 1 H, aromatic), 7.41 (dd, J=9.5, 2.6 Hz, 1 H, H3), 7.23 (d, J=2.6 Hz, 1 H, H1), 5.59 (s, 2 H, benzylic), 2.92 (t, J=6.3 Hz, 2 H, H7 or H10), 2.77 (t, J=6.3 Hz, 2 H, H7 or H10), 1.99–1.85 (m, 4 H, H8 and H9); $^{13}$C NMR (125 MHz, CDCl3) δ 157.6, 146.8, 135.2, 134.7, 134.1, 132.7, 131.4, 131.1, 130.8, 128.6, 128.5, 125.0, 122.1, 120.3, 103.5, 66.9, 27.1, 24.7, 22.1, 21.8; MS (FAB+) m/e (rel intensity) 351 (M+H, 100), 335 (8), 216 (7), 124 (6), 107 (10); HRMS for C20H19N2O4 (M+H), calcd 351.1345, found 351.1345. Anal. Calcd for C20H18N2O4; C, 68.56; H, 5.18; N, 8.00. Found: C, 68.32; H, 5.13; N, 7.88.

EXAMPLE 106

2-[3-[(tert-Butyldiphenylsilyl)oxy]propynl]-7,8,9,10-tetrahydrophenanthridine N-oxide (Compound 280c)

Prepared in 91 percent yield as described for Compound 280a. Compound 280c: $R_f$=0.61 (15 percent methanol in ethyl acetate); IR (film) $\delta_{max}$ 3070, 2932, 2857, 2232, 1588, 1568, 1428, 1372, 1301, 1237, 1112 cm$^{-1}$; $^1$H NMR (500 MHz, CDCl3) δ 8.64 (d, J=8.9 Hz, 1 H H4), 8.27 (s, 1 H, H6), 7.87 (br s, 1 H, H1), 7.80–7.74 (m, 4 H, aromatic), 7.52 (br d, J=8.9 Hz, 1 H, H3), 7.46–7.38 (m, 6 H, aromatic) 4.59 (s, 2 H, C≡CC-H2O), 2.96 (t, J=6.2 Hz, 2 H, H10), 2.77 (t, J=6.2 Hz, 2 H, H7), 2.00–1.91 (m, 2 H, CH2), 1.91–1.84 (m, 2 H, CH2), 1.09 (s, 9 H, t-Bu); $-^C$ NMR (125 MHz, CDCl3) δ 138.6, 136.6, 135.6, 132.9, 132.2, 131.5, 131.0, 129.8, 129.2, 127.7, 126.5, 123.3, 120.2, 90.0, 84.3, 53.0, 27.0, 26.6, 24.6, 22.0, 21.9, 19.1; MS (FAB+) m/e (rel intensity) 492 (M+H, 100), 434 (12), 404 (21), 388 (11), 197 (13); HRMS for C32H34NO2Si (M+H), calcd 492.2359, found 492.2364.

EXAMPLE 107

10-Acetoxy-2-methoxy-7,8,9,10-tetrahydrophenanthridine (Compound 281a)

Representative Procedure

A mixture of the N-oxide Compound 280a (10.00 g, 43.3 mmol) and acetic anhydride (150 mL) was heated at 70° C. for 1 hour and then evaporated in vacuo to dryness. The residue was dissolved in dichloromethane (700 mL) and saturated aqueous sodium bicarbonate (400 mL) was added. After stirring for 15 minutes, the aqueous layer was separated and extracted with dichloromethane (2×200 mL). The combined organic extracts were washed with brine (400 mL), dried (MgSO4) and filtered through a 3 cm×3 cm plug of silica. The silica plug was rinsed with a 1:1 mixture of dichloromethane-ethyl acetate (400 mL). The combined filtrates were concentrated in vacuo and the residue was dissolved in methanol (50 mL). After standing in the refrigerator at zero degrees C for 15 hours, the crystalline precipitate was filtered and washed with ice-cooled methanol (30 mL) to give, after drying under vacuum (0.02 Torr, 20 hours), the acetate Compound 281a (6.73 g, 57 percent): white crystalline solid; mp 116.5°–117° C.; $R_f$=0.48 (silica, ethyl ether); IR (CHCl3) $\nu_{max}$ 2935, 1725, 1647, 1620, 1506 cm$^{-1}$; $^1$H NMR (500 MHz, CDCl3) δ 8.58 (s, 1 H, H6), 7.97 (d, J=9.1 Hz, 1 H, H4), 7.30 (dd, J=9.1, 2.7 Hz, 1 H, H3), 7.09 (d, J=2.7 Hz, 1 H, H1), 6.60 (br s, 1 H, H10), 3.88 (s, 3 H, OCH3), 3.04 (br d, J=17.6 Hz, 1 H, H7), 2.89–2.82 (m, 1 H, H7), 2.25 (br d, J=14.3 Hz, 1 H, H9), 2.09 (s, 3 H, COCH3), 2.01–1.95 (m, 3 H, H8 and H9); $^{13}$C NMR (125 MHz, CDCl3) δ 170.4, 158.3, 149.7, 142.9, 135.5, 131.4, 131.3, 127.6, 120.7, 100.6, 64.4, 55.4, 29.0, 26.7, 21.1, 17.2; MS (FAB+) m/e (rel intensity) 272 (M+H, 100), 230 (33), 212 (28); HRMS for C16H18NO3 (M+H), calcd 272.1287, found 272.1288. Anal. Calcd for C16H17NO3: C, 70.83; H, 6.32; N, 5.16. Found: C, 70.75; H, 6.39; N, 5.10.

EXAMPLE 108

10-Acetoxy-2-[(2-nitrobenzyl)oxy]-7,8,9,10-tetrahydrophenanthridine (Compound 281b)

Prepared in 74 percent yield as described for Compound 281a. Compound 281b: white crystalline solid; mp 125°–127° C. (from dichloromethane-ethyl ether); $R_f$=0.43 (silica, 4 percent methanol in dichloromethane); IR (CHCl3) $\nu_{max}$ 3019, 2948, 2870, 1728, 1619, 1527, 1507, 1438, 1367, 1341 cm$^{-1}$; $^1$H NMR (500 MHz, CDCl3) δ 8.56 (s, 1 H, H6), 8.24 (dd, J=7.7, 0.8 Hz, 1 H, aromatic), 8.00 (d, J=9.1 Hz, 1 H, H4), 7.81 (dd, J=7.7, 0.8 Hz, 1 H, aromatic), 7.64 (td, J=7.7, 0.8 Hz, 1 H, aromatic), 7.48 (td, J=7.7, 0.8 Hz, 1 H, aromatic), 7.40 (dd, J=9.1, 2.6 Hz, 1 H, H3), 7.09 (d, J=2.6 Hz, 1 H, H1), 6.43 (t, J=6.0 Hz, 1H, H10), 5.61 and 5.59 (ABq, J=15.8 Hz, 2 H, benzylic), 2.99 (m, 1 H, H7), 2.80 (m, 1H, H7), 2.15 (m, 1H, H9), 1.91 (s, 3 H, OCOCH$_3$), 1.93–1.79 (m, 3 H, H8 and H9); $^{13}$NMR (125 MHz, CDCl$_3$) δ 170.1, 156.7, 150.2, 147.0, 143.1, 135.8, 133.9, 133.4, 131.8, 131.6, 128.4, 128.3, 127.6, 125.2, 120.7, 102.5, 67.3, 64.1, 29.0, 26.7, 20.8, 17.2; MS (FAB+) m/e (rel intensity) 351 (M+H, 100), 333 (7), 216 (10), 165 (8) HRMS for C$_{26}$H$_{19}$N$_2$O$_4$ (M+H), calcd 351.1345, found 351.1345.

EXAMPLE 109

10-Acetoxy-2-[(3-[tert-butyldiphenylsilyl)oxy]-propynyl]-7,8,9,10-tetrahydrophenanthridine (Compound 281c)

Prepared in 91 percent yield as described for Compound 281a. Compound 281c: R$_f$=0.37 (silica, 30 percent ethyl acetate in petroleum ether); IR (film) δ$_{max}$ 2931, 2856, 2227, 1734, 1500, 1427, 1370, 1228, 1112, 702 cm$^{-1}$; $^1$H NMR (500 MHz, CDCl$_3$) δ 8.70 (s, 1H, H6), 7.99 (d, J=8.6 Hz, 1 H, H4), 7.81 (br s, 1 H, H1) 7.80–7.75 (m, 4 H, aromatic), 7.78 (br d, J=8.6 Hz, 1 H, H3), 7.48–7.39 (m, 6 H, aromatic), 6.49 (br s, 1 H, H10), 4.59 (s, 2 H, C≡CCH2O), 3.04 (br d, J=16.7 Hz, 1 H, H7), 2.86 (ddd, J=16.7, 9.8, 6.7 Hz, 1H, H7), 2.31 (br d, J=12.0 Hz, 1H, H9), 2.08 (s, 3 H, COCH3), 2.00–1.88 (m, 3 H, H9 and H8), 2.08 (s, 3 H, T-Bu); $^{13}$C NMR (125 MHz, CDCl3) δ 170.1, 152.9, 146.3, 136.5, 135.6, 133.1, 131.8, 131.2, 130.1, 129.8, 127.7, 126.3, 125.8, 121.9, 89.0, 84.9, 64.4, 53.2, 28.5, 26.8, 26.7, 21.2, 19.2, 17.1; MS (FAB+) m/e (rel intensity) 534 (M+H, 100), 474 (45), 218 (53), 197 (28), 154 (30); HRMS for C$_{34}$H$_{36}$NO$_3$Si (M+H), calcd 534.2464, found 534.2443.

EXAMPLE 110

10-Hydroxy-2-methoxy-7,8,9,10-tetrahydrophenanthridine (Compound 282a)

Representative Procedure

To a solution of Compound 281a (7.10 g, 26.2 mmol) in dry methanol (200 mL) was added Dowex 1×8-200 hydroxide form (1.00 g) and the resulting mixture was heated at 60° C. for 24 hours. The warm reaction mixture was filtered and the filtrate was distilled until 100 mL remained. Ethyl ether (100 mL) was added to the residue and the resulting solution was allowed to stand in the refrigerator at zero degrees C for 16 hours. The crystalline precipitate was filtered off, washed with ethyl ether (50 mL) to give 5.03 g (84 percent) of Compound 282a: white crystalline solid; mp 189.5°–190.5° C.; R$_f$=0.21 (silica, ethyl ether); IR (CHCl$_3$) ν$_{max}$ 3156, 2931, 1621, 1508 cm$^{-1}$; $^1$H NMR (300 Mz, CDCl$_3$) δ 8.45 (s, 1H, H6), 7.96 (d, J=9.2 Hz, 1 H, H4), 7.50 (d, J=2.6 Hz, 1 H, H3), 7.31 (dd, J=9.2, 2.6 Hz, 1 H, H1), 5.37 (br s, 1 H, H10), 3.97 (s, 3 H, OCH$_3$), 2.97–2.75 (m, 2 H, H7), 2.75–2.30 (br s, 1H, OH), 2.30 (br d, J=10.6 Hz, 1 H, H9), 2.07–1.96 (m, 3 H, H8 and H9); $^{13}$C NMR (125 Mz, DMSO-d$_6$) δ 157.1, 149.7, 142.5, 140.2, 130.2, 129.7, 128.1, 119.7, 103.0, 61.0, 55.3, 31.8, 26.6, 16.7; MS (FAB+) m/e (rel intensity) 230 (M+H, 100), 212 (10); HRMS for C$_{14}$H$_{16}$NO$_2$ (M+H), calcd 230.1181, found 230.1189. Anal. Calcd for C$_{14}$H$_{15}$NO$_2$: C, 73.34; H, 6.59; N, 6.11. Found: C, 73.16; H, 6.73; N, 6.08.

EXAMPLE 111

10-Hydroxy-2-[(2-nitrobenzyl)oxy]-7,8,9,10-tetrahydrophenanthridine (Compound 282b)

Prepared in 89 percent yield as described for Compound 282a. Compound 282b: white crystalline solid; mp 181°–183° C. (from methanol-ethyl ether); R$_f$=0.22 (silica, 40 percent ethyl acetate in dichloromethane); IR (CHCl$_3$) ν$_{max}$ 3018, 2943, 2866, 1619, 1508, 1335 cm$^{-1}$; $^1$H NMR (500 MHz, DCSO-d$_6$) δ 8.49 (s, 1 H, H6), 8.13 (dd, J=7.7, 1.0 Hz, 1 H, aromatic), 7.89 (d, J=9.1 Hz, 1 H, H4), 7.87 (dd, J=7.7, 1.0 Hz, 1 H, aromatic), 7.80 (td, J=7.7, 1.0 Hz, 1H, aromatic), 7.68 (d, J=2.7 Hz, 1 H, H1), 7.63 (td, J=7.7, 1.0 Hz, 1 H, aromatic), 7.38 (dd, J=9.1, 2.7 Hz, 1 H, H3), 5.60 and 5.57 (ABq, J=14.6 Hz, 2 H, benzylic), 5.39 (d, J=6.6 Hz, 1H, OH), 5.12 (br dt, J=6.32, 3.1 Hz, H10), 2.88 (m, 1 H, H7), 2.71 (ddd, J=17.2, 10.5, 5.5 Hz, 1H, H7), 2.06–1.90 (m, 2H, H9), 1.85–1.74 (m, 2H, H8); $^{13}$C NMR (125 MHz, DMSO-d$_6$) δ 155.8, 150.2, 147.6, 142.7, 140.3, 134.0, 132.1, 130.9, 129.9, 129.6, 129.3, 128.0, 124.8, 119.7, 104.8, 66.6, 61.0, 31.7, 26.6, 16.7; MS (FAB+) m/e (rel intensity) 351 (M+H, 100), 333 (7), 216 (10); HRMS for C$_{20}$H$_{19}$N$_2$O$_4$ (M+H), calcd 351.1345, found 351.1345. Anal. Calcd for C$_{20}$H$_{18}$N$_2$O$_4$: C, 68.56; H, 5.18; N, 8.00. Found: C, 68.27; H, 5.20; N, 7.93.

EXAMPLE 112

2-[3-[(tert-Butyldiphenylsilyl)oxy]propynyl]-10-hydroxy-7,8,9,10-tetrahydrophenathridine (Compound 282c)

Prepared in 69 percent yield as described for Compound 282a. compound 282c: white crystalline solid; mp 132°–133° C. (from ethyl ether-petroleum ether); R$_f$=0.17 (silica, 30 percent ethyl acetate in petroleum ether); IR (film) ν$_{max}$ 3398, 3070, 2932, 2857, 2232, 1588, 1568, 1428, 1372, 1196, 1112 cm$^{-1}$; $^1$H NMR (500 MNz, CDCl$_3$) δ 8.43 (s, 1H, H6), 8.23 (d, J=1.1 Hz, 1H, H1), 7.88 (d, J=8.6 Hz, 1H, H4), 7.81–7.78 (m, 4H, aromatic), 7.49 (dd, J=8.6, 1.1 Hz, 1H, H3), 7.48–7.39 (m, 6H, aromatic), 5.31 (br s, 1H, H10), 4.59 (s, 2H, C≡CCH$_2$O), 3.05 (br, 1H, OH), 2.83 (br d, J=11.5 Hz, 1H, H7), 2.72 (ddd, J=17.3, 11.5, 5.6 Hz, 1H, H7), 2.25 (br d, J=12.7, Hz, 1H, H9), 2.08–1.98 (m, 1H, H9), 1.93.1.84 (m, 2H, H8), 1.11 (s, 9H, t-Bu); $^{13}$C NMR (125 MHz, CDCl$_3$) δ 152.8, 146.1, 140.3, 135.6, 133.0, 130.9, 130.3, 129.8, 129.6, 127.7, 127.1, 126.5, 121.4, 88.8, 85.1, 62.3, 53.2, 31.3, 27.0, 26.7, 19.2, 16.7; MS (FAB+) m/e (rel intensity) 492 (M+H, 100), 434 (8), 236 (8), 199 (11), 154 (7); HRMS for C$_{32}$H$_{34}$NO$_2$Si (M+H), calcd 492.2359, found 492.2359.

EXAMPLE 113

10-[(tert)-butyldimethylsilyl)oxy]-2-methoxy-7,8,9,10-tetrahydrophenanthridine (Compound 310)

To a stirred suspension of Compound 282a (6.15 g, 26.8 mmol) and 2,6-lutidine (4.69 mL, 40.2 mmol) in dichloromethane (80 mL) at 10° C. was added tert-butyldimethylsilyl triflate (7.40 mL, 32.2 mmol). After stirring at 20° for one hour, methanol (5 mL) was added, stirring was continued for 5 minutes, and the reaction mixture was evaporated to dryness in vacuo. The residue was purified by flash column chromatography (silica, 10 percent ethyl acetate in dichloromethane) and the product was recrystallized from cyclohexane-hexanes to give 8.42 g (91 percent) of Compound 310: white crystalline solid; mp 127°–127.5° C.; R$_f$=0.53 (silica, 20 percent ethyl acetate in dichloromethane); IR (CHCl$_3$) ν$_{max}$ 2954, 2855, 1622, 1507 cm$^{-1}$; $^1$H NMR (300 MHz, CDCl$_3$) δ 8.53 (s, 1H, H6), 7.96 (d, J=8.8 Hz, 1H, H4), 7.29 (m, 2H, H1 and H3), 5.40 (t, J=2.8 Hz, 1H, H10), 3.95 (s, 3H, OCH$_3$), 3.00 (dd, J=17.5, 4.8 Hz, 1H, H7), 2.81 (ddd, J=17.5, 11.5, 5.9 Hz, 1H, H7), 2.27–2.13 (m, 2H, CH$_2$), 1.87-1.75 (m, 2H, CH$_2$), 0.86 (s, 9H, t-Bu), 0.23 (s, 6H, Si (CH$_3$)$_2$); $^{13}$C NMR (125 MHz, CDCl$_3$) δ 157.7, 150.3, 143.1, 140.0, 131.2, 129.7, 128.0, 120.0, 102.0, 63.5, 55.5, 31.6, 27.0, 25.9, 18.2, 16.3, −3.5, −4.3; MS (FAB+) m/e (rel intensity) 344 (M+H, 100), 286 (24), 212 (16); HRMS for C$_{20}$H$_{30}$NO$_2$Si (M+H), calcd 344.2046, found 344.2052. Anal. Calcd for C$_{20}$H$_{29}$NO$_2$Si: C, 69.92; H, 8.51; N, 4.08. Found: C, 70.02; H, 8.71; N, 3.98.

EXAMPLE 114

N-[(Phenyloxy)carbonyl]-10-[(tert-butyldimethylsilyl)oxy]-6-ethynyl-2-methoxy-5,6,7,8,9,10-hexahydrophenanthridine (Compound 311)

A solution of Compound 310 (7.84 g, 22.8 mmol) in dry THF (110 mL) was cooled at −78° C. and treated with ethynylmagnesium bromide (55.36 mL, 0.5M solution in THF, 27.7 mmol). The solution was briefly warmed to zero degrees C and cooled to −78° C. again, and phenyl chloroformate (4.36 mL, 27.7 mmol) was added. The reaction mixture was allowed to slowly warm to 25° C. over one hour, quenched with saturated aqueous ammonium chloride (100 mL), poured into saturated aqueous sodium bicarbonate (100 mL) and extracted with dichloromethane (2×100 mL). The combined organic layers were dried (MgSO$_4$) and evaporated in vacuo, and the residue was purified by flash column chromatography (silica, 10 percent ethyl ether in petroleum ether) to give 11.15 g (100 percent) of Compound 311: white foam (about 3:1 mixture of diastereomers as determined by $^1$H NMR); R$_f$=0.34 (silica, 20 percent ethyl ether in petroleum ether); IR (CHCl$_3$) ν$_{max}$ 3302, 2948, 2933, 2896, 2855, 1716, 1593, 1493, 1385, 1303 cm$^{-1}$; $^1$H NMR (500 MHz, CDCl$_3$) δ 7.90-7.10 (m, 6H, aromatic), 6.94 (br s, 1H, aromatic), 6.80 (dd, J=8.9, 2.9 Hz, 1H, aromatic), 5.64 and 5.60 (2 s, 1H, H6), 4.96 and 4.67 (2 br s, 1H, H10), 3.83 and 3.82 (2 s, 3H, OCH$_3$), 2.51-1.61 (m, 7H, H7, H8, H9, and C≡CH), 0.95 and 0.82 (2 s, 9H, t-Bu), 0.28, 0.20, and 0.08 (singlets, 6H, Si (CH$_3$)$_2$); $^{13}$C NMR (125 MHz, CDCl$_3$) δ 151.0, 129.7, 129.3, 125.7, 121.7, 111.8, 111.6, 109.8, 79.9, 71.6, 64.9, 64.0, 55.6, 55.5, 48.8, 32.6, 31.4, 28.2, 27.8, 26.0, 25.9, 18.4, 18.1, 18.0, −3.1, −3.6, −4.1, −4.3; MS (FAB +) m/e (rel intensity) 489 (M+, 47), 464 (29), 432 (100), 396 (15), 358 (62), 344 (10), 236 (29), 212 (16), 151 (15); HRMS for C$_{29}$H$_{35}$NO$_4$Si (M+), calcd 489,2335, found 489.2349.

EXAMPLE 115

N-[(Phenyloxy)carbonyl]-10-[(tert)-butyldimethylsilyl)oxy]-6a,10a-epoxy-6-ethynyl-2-methoxy-5,6,6a,7,8,9,10,10a-octahydrophenanthridine (Compound 312)

A solution of Compound 311 (9.26 g, 18.9 mmol) in dichloromethane (125 mL) was treated with mCPBA (97 percent, 6.53 g, 36.8 mmol) and stirred at 35° C. for 2 hours. After cooling to 20° C., dimethylsulfide (22.77 mL, 37.8 mmol) was added and stirring was continued for 20 minutes. The reaction mixture was poured into saturated aqueous sodium bicarbonate (200 mL) and extracted with ethyl ether (300 mL). The combined organic layers were washed with brine (100 mL), dried (MgSO$_4$), and evaporated in vacuo. The residue was purified by recrystallization from ethyl ether-petroleum ether to give 9.50 g (99 percent) of Compound 312: white crystalline solid (about 3:1 mixture of diastereomers as determined by $^1$H NMR); mp 116°-119° C.; R$_f$=0.29 (silica, 20 percent ethyl ether in petroleum ether); IR (CHCl$_3$) ν$_{max}$ 3303, 2950, 2932, 2883, 2855, 1722, 1585, 1503, 1384, 1300 cm$^{-1}$; $^1$H NMR (500 MHz, CDCl$_3$) δ 7.47-7.07 (m, 7H, aromatic), 6.86 and 6.83 (two sets of dd, J=8.8, 2.9 Hz, 1H, aromatic), 5.51 (m, 1H, H6), 4.88 (m, 1H, H10, minor isomer), 4.77 (dd, J=9.9, 5.6 Hz, 1H, H10, major isomer), 3.81 and 3.80 (2 s, 3H, OCH$_3$), 2.38 (dd, J=14.4, 7.2 Hz, 1H, CH$_2$, minor isomer), 2.31 (dd, J=14.4, 5.6 Hz, 1H, CH$_2$, major isomer), 2.07 (s, 1H, C≡CH) 1.91-1.61 (m, 5H, H7, H8 and H9) 0.88 and 0.80 (2 s, 9H, t-Bu) 0.27, 0.20, 0.15, 0.08, 0.03, and −0.02 (singlets, 6H, Si (CH$_3$)$_2$); $^{13}$C NMR (125 MHz, CDC$_3$) δ 153.8, 151.2, 129.2, 128.5, 128.1, 125.5, 121.8, 121.6, 115.3, 115.0, 113.3, 112.1 78.6, 73.4, 72.7, 70.0, 55.6, 55.5, 48.1, 29.4, 26.4, 26.0, 25.7, 24.0, 22.4, 20.4, 18.2, 18.1, 13.5, −2.8, −2.9, −3.4, −5.2; MS (FAB+) m/e (rel intensity) 638 (M+Cs, 100), 506 (14), 448 (43); HRMS for C$_{29}$H$_{35}$NO$_5$SiCs (M+Cs), calcd. 638.1339, found 638.1360. Anal. Calcd for C$_{29}$H$_{35}$NO$_5$Si: C, 68.88; H, 6.98; N, 2.77. Found: C, 68.88; H, 7.21; N, 2.66.

EXAMPLE 116

N-[(phenoxy)carbonyl]-6a10a-epoxy-6-ethynyl-10-hydroxy-2-methoxy-5,6,6a,7,8,9,10,10a-octahydrophenanthridine (Compound 313)

A solution of Compound 312 (9.56 g, 18.9 mmol) in THF (100 mL) was treated with tetra-n-butylammonium fluoride (TBA F) (23.6 mL, 1.0M in THF, 23.6 mmol) at zero degrees C for one hour and evaporated to dryness in vacuo. The residue was purified by flash column chromatography (silica, 7 percent ethyl acetate in dichloromethane) to give 7.35 g (99 percent) of Compound 313: white foam (about 3:1 mixture of diastereomers as determined by $^1$H NMR); R$_f$=0.40 (silica, 70 percent ethyl ether in petroleum ether); IR (CHCl$_3$) ν$_{max}$ 3600, 3300, 2950, 1720, 1590, 1500, 1490, 1385, 1300 cm$^{-1}$; $^1$H NMR (500 MHz, CDCl$_3$) δ7.47 (d, J=2.8 Hz, 1H, aromatic, major isomer), 7.44-7.09 (m, 6H, aromatic, major isomer; 7H, aromatic, minor isomer), 6.91 (dd, J=8.8, 2.8 Hz, 1H, aromatic, minor isomer), 6.90 (dd, J=2.0 Hz, 1H, aromatic, major isomer), 5.59 (d, J=2.0 Hz, 1H, H6, major isomer), 5.57 (d, J=2.0 Hz, 1H, H6, minor isomer), 4.87 (br s, 1H, H10, minor isomer), 4.67 (br dd, J=14.5, 6.0 Hz, 1H, H10, major isomer), 3.84 (s, 3H, OCH$_3$), 2.45 (dd, J=15.0, 7.5 Hz, 1H, CH$_2$, minor isomer), 2.34 (dt, J=14.7, 4.6 Hz, 1H, CH$_2$, major isomer), 2.11-1.40 (m, 7H, CH$_2$); MS (FAB+) m/e (rel intensity) 391 (M+, 100), 374 (18), 254 (13); HRMS for C$_{23}$H$_{21}$NO$_5$ (M+), calcd 391.1420, found 391.1450.

EXAMPLE 117

N-[(Phenyloxy)carbonyl]-6a,10a-epoxy-6-ethynyl-2-methoxy-10-oxo-5,6,6a,7,8,9,10,10a-octahydrophenanthridine (Compound 314)

A solution of Compound 314 (1.15 g, 2.93 mmol) in dichloromethane (25 mL) was treated with powdered, activated 4 Å molecular seives (1.0 g) and pyridinium chlorochromate (1.26 g, 5.85 mmol). The suspension was stirred at 25° C. for 2 hours, diluted with ethyl ether (25 mL), and filtered through a 3 cm×3 cm plug of silica. The silica plug was rinsed with ethyl ether (100 mL) and the combined filterates were concentrated in vacuo. The residue was purified by recrystallization from ethyl acetate-benzene-pentroleum ether to give 0.98 g (87 percent) of Compound 314: white crystalline solid; mp 186.5°–187.5° C.; $R_f$=0.48 (silica, 50 percent ethyl ether in petroleum ether); IR (CHCl$_3$) $\nu_{max}$ 3303, 2960, 1717, 1609, 1493, 1380, 1311, 1299 cm$^{-1}$; $^1$H NMR (500 MHz, CDCl$_3$) δ 7.97 (d, J=2.9 Hz, 1H, aromatic), 7.40–7.08 (m, 6H, aromatic), 6.93 (dd, J=8.8, 2.9 Hz, 1H, aromatic), 5.70 (d, J=2.3 Hz, 1H, H6), 3.84 (s, 3H, OCH$_3$), 2.76 (dt, J=15.5, 5.0, 1H, H9), 2.59 (ddd, J=15.5, 10.2, 6.0 Hz, 1H, H9), 2.36–2.28 (m, 2H, H7), 2.22 (s, 1H, C≡CH), 2.00–1.90 (m, 2H, H8); $^{13}$C NMR (125 MHz, CDCl$_3$) δ 201.3, 157.3, 154.1, 151.0, 129.3, 128.5, 127.6, 125.7, 124.0, 121.4, 114.9, 114.8, 77.7, 74.6, 74.3, 57.3, 55.5, 47.5, 38.8, 23.7, 18.3; MS (FAB+) m/e (rel intensity) 389 (M+, 88), 358 (21), 307 (88), 286 (100), 167 (30); HRMS for C$_{23}$H$_{19}$NO$_5$ (M+), calcd 389.1263, found 389.1266.

EXAMPLE 118

N-[(Phenyloxy)carbonyl]-6-[6-(trimethylsilyl)-3(Z)-hexene-1,5-diynyl]-6a,10a-epoxy-2-methoxy-10-oxo-5,6,6a,7,8,9,10,10a-octahydrophenanthridine (Compound 315)

A solution of Compound 314 (5.69 g, 14.6 mmol) in dry degassed benzene (120 mL) was added to copper (I) iodide (0.666 g, 3.51 mmol), and to the resulting mixture was added 1-chloro-4-(trimethylsilyl)-but-1-en-3-yne (3.69 g, 23.4 mmol) and tetrakis(triphenylphosphine) (2.89 mL, 29.2 mmol) and tetrakis(triphenylphosphine) palladium (0) (1.01 g, 0.877 mmol) in dry degassed benzene (60 mL). The reaction mixture was stirred at 25° C. for 2 hours, diluted with ethyl ether (200 mL), poured into saturated aqueous ammonium chloride (200 mL), and extracted with ethyl ether (2×70 mL). The combined organic layers were dried (MgSO$_4$) and evaporated in vacuo. The residue was purified by flash column chromatography (silica, 25 percent ethyl ether in petroleum ether) to give 5.43 g (73 percent) of Compound 315: white foam; $R_f$=0.29 (silica, 30 percent ethyl ether in petroleum ether); IR (CHCl$_3$) $\nu_{max}$ 2958, 2836, 1717, 1609, 1590, 1493, 1380, 1299, 1251 cm$^{-1}$; $^1$H NMR (300 MHz, CDCl$_3$) δ 7.94 (d, J=3.0 Hz, 1H, aromatic), 7.38–7.06 (m, 6H, aromatic), 6.89 (dd, J=8.9, 3.0 Hz, 1H, aromatic), 5.92 (d, J=1.6 Hz, 1H, H6), 5.86 (d, J=11.0 Hz, 1H, olefinic), 5.65 (br d, J=11.0 Hz, 1H, olefinic), 3.81 (s, 3H, OCH$_3$), 2.78–2.62 (m, 2H, H9), 2.37–2.25 (m, 2H, H7), 2.05–1.85 (m, 2H, H8), 0.20 (s, 9H, Si(CH$_3$)$_3$); $^{13}$C NMR (125 MHz, CDCl$_3$) δ 201.2, 157.2, 154.1, 151.0, 129.3, 128.6, 128.5, 125.7, 124.0, 121.4, 120.7, 118.9, 114.8, 114.8, 103.5, 101.5, 90.5, 83.0, 74.6, 57.4, 55.4, 48.4, 38.8, 23.8, 18.2, −0.17; MS (FAB+) m/e (rel intensity) 511 (M+, 100), 390 (8), 362 (9), 176 (11), 120 (10); HRMS for C$_{30}$H$_{29}$NO$_5$Si (M+), calcd 511.1815, found 511.1815.

EXAMPLE 119

N-[(Phenyloxy)carbonyl]-6-[3(Z)-hexene-1,5-diynyl]-6a,10a-epoxy-2-methoxy-10-oxo-5,6,6a,7,8,9,10,10a,-octahydrophenanthridine (Compound 316)

silver nitrate (1.43 g, 8.44 mmol) was added to a solution of Compound 315 (1.08 g, 2.11 mmol) in 48 mL of H$_2$O-EtOH-THF (1:1:1) at 25° C. followed by stirring for 15 minutes. Potassium cyanide (0.962 g, 14.8 mmol) was then added and the mixture was stirred for one hour, concentrated in vacuo to 20 mL, poured into saturated aqueous sodium bicarbonate (30 mL), and extracted with dichloromethane (3×40 mL). The combined organic layers were dried (MgSO$_4$) and evaporated in vacuo, and the residue was purified by flash column chromatography (silica, 35 percent ethyl ether in petroleum ether) to give 0.807 g (88 percent) of Compound 316: white foam $R_f$=0.22 (silica, 40 percent ethyl ether in petroleum ether); IR (CHCl$_3$) $\nu_{max}$ 3299, 2947, 1716, 1609, 1590, 1501, 1493, 1380, 1299, 1253 cm$^{-1}$; $^1$H NMR (500 MHz, CDCl$_3$) 7.96 (d, J=2.9 Hz, 1H, aromatic), 7.38–7.07 (m, 6H, aromatic), 6.89 (dd, J=8.9, 2.9 Hz, 1H, aromatic), 5.88 (s, 1H, H6), 5.77 and 5.74 (ABq, J=11.2 Hz, 2H, olefinic), 3.81 (s, 3H, OCH$_3$), 3.16 (d, J=1.5 Hz, 1H, C≡CH), 2.74 (dt, J=15.3, 5.0 Hz, 1H, H9), 2.67 (ddd, J=15.3, 10.1, 6.1 Hz, 1H, H9), 2.36–2.26 (m, 2H, H7), 1.99–1.89 (m, 2H, H8); $^{13}$C NMR (125 MHz, CDCl$_3$) δ 201.5, 157.2, 154.1, 151.0, 129.3, 128.7, 128.5, 125.7, 124.1, 121.4, 120.4, 120.3, 114.8, 114.7, 90.6, 85.1, 82.7, 80.3, 74.9, 57.4, 55.5, 48.3, 38.8, 23.8, 18.6; MS (FAB+) m/e (rel intensity) 439 (M+, 100), 364 (8), 176 (19), 120 (10); HRMS for C$_{27}$H$_{21}$NO$_5$ (M+), calcd 439.1420, found 439.1434.

EXAMPLE 120

Compound 317

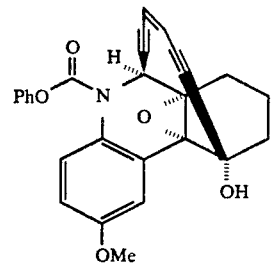

A solution of Compound 316 (575 mg, 1.31 mmol) in dry toluene (100 mL) was cooled to −78° C. and treated with lithium diisopropylamide (1.40 mL, 1.0M solution in THF) followed by stirring for one hour at −78° C. The reaction mixture was quenched with saturated aqueous ammonium chloride (30 mL). The reaction mixture was allowed to warm to room temperature, poured into saturated aqueous sodium bicarbonate (100 mL), and extracted with ethyl ether (50 mL). The combined organic layers were dried (MgSO$_4$) and evaporated in vacuo. The residue was purified by flash column chromatography (silica, 30→60 percent ethyl ether in petroleum ether) to give recovered 73 (79 mg, 14 percent) and 378 mg (66 percent) of Compound 317: white crystalline solid; mp 157°–159° C. (dec., ethyl ether); $R_f$=0.25 (silica, 50 percent ethyl ether in petroleum ether); IR (CHCl$_3$) $\nu_{max}$ 3444, 2954, 1717, 1610, 1592, 1505, 1493, 1383, 1321, 1301 cm$^{-1}$; $^1$H NMR (500 MHz, CDCl$_3$) δ 8.23 (d, J=2.9 Hz, 1H, aromatic), 7.34–7.12 (m, 6H, aromatic), 6.84 (dd, J=8.9, 2.9 Hz, 1H, aromatic), 5.83 (d, J=10.0 Hz, 1H, olefinic), 5.67 (dd, J=10.0, 1.4 Hz, 1H, olefinic), 5.50 (br s, 1H, NCHC≡C), 3.78 (s, 3H, OCH$_3$), 2.73 (br s, 1H, OH), 2.31 (dd, J=15.1, 8.3 Hz, 1H, CH$_2$), 2.18–2.13 (m, 2H, CH$_2$), 1.98 (m, 1H, CH$_2$), 1.88 (dt, J=12.0, 2.8 Hz, 1H, CH$_2$), 1.70 (m, 1H, CH$_2$); $^{13}$C NMR (125 MHz, CDCl$_3$) δ 156.6, 153.9, 151.1, 129.3, 128.9, 128.8, 127.1, 125.6, 124.1, 122.1, 121.5, 116.4, 113.8, 100.5, 94.1, 88.7, 73.7, 73.1, 65.8, 64.4, 55.4, 50.5, 35.2, 23.1, 19.2; MS (FAB+) m/e (rel intensity) 439 (M+, 100), 379 (25); HRMS for C$_{27}$H$_{21}$NO$_5$ (M+), calcd 439.1420, found 439.1419.

EXAMPLE 121

Compound 318

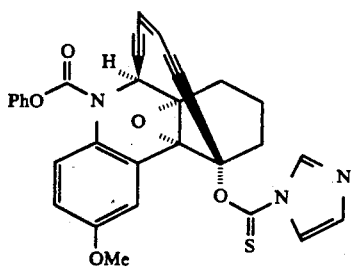

Thiocarbonyldiimidazole (1.26 g, 7.09 mmol) was added to a solution of Compound 317 (1.04 g, 2.36 mmol) and DMAP (0.188 g, 1.53 mmol) in dry dichloromethane (5 mL) at 25° C. After stirring at 25° C. for 72 hours, the solution was concentrated in vacuo and the residue was purified by flash column chromatography (silica, 6 percent ethyl ether in dichloromethane) to give 1.30 g (100 percent) of Compound 318: white foam; $R_f$=0.39 (silica, 10 percent ethyl ether in dichloromethane); IR (CHCl$_3$) $\nu_{max}$ 2932, 1722, 1610, 1587, 1502, 1463, 1383, 1321, 1244, 1198; 1H NMR (500 MHz, CDCl$_3$) δ 8.39 (s, 1H, aromatic and imidazole), 7.02 (d, J=0.9 Hz, 1H, 7H, aromatic and imidazole), 7.02 (d, J=0.9 Hz, 1H, aromatic), 6.85 (dd, J=8.9, 2.9 Hz, 1H, aromatic), 5.94 (d, J=10.0 Hz, 1H, olefinic), 5.73 (dd, J=10.0, 1.6 Hz, 1H, olefinic), 5.54 (d, J=1.6 Hz, 1H, NCHC≡C), 3.54 (s, 3H, OCH$_3$), 3.04 (dt, J=12.1, 3.2 Hz, 1H, CH$_2$), 2.41 (dt, J=15.2, 8.2 Hz, 1H, CH$_2$), 2.29–2.08 (m, 3H, CH$_2$), 1.82 (m, 1H, CH$_2$); 13C NMR (125 MHz, CDCl$_3$) δ 179.1, 153.7, 151.0, 137.2, 131.1, 129.4, 129.3, 129.1, 127.9, 125.8, 124.0, 123.4, 121.5, 117.7, 114.8, 113.9, 100.8, 94.3, 89.0, 85.6, 74.4, 63.7, 55.5, 55.1, 50.9, 50.5, 28.6, 22.6, 18.5; MS (FAB+) m/e (rel intensity) 550 (M+H, 40), 422 (100), 369 (39), 273 (52), 258(30), 243 (44), 219 (40), 178 (66); HRMS for C$_{31}$H$_{24}$N$_3$O$_5$S (M+H), calcd 550.1437, found 550.1437.

EXAMPLE 122

Compound 319

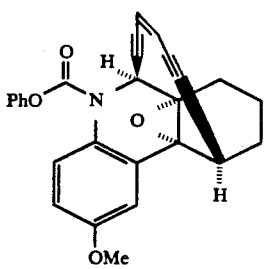

A solution of 318 (230 mg, 0.418 mmol) in dry benzene (8 mL) was treated with n-Bu$_3$SnH (250 mL, 0.929 mmol) and AIBN (15 mg, catalytic) at 75° C. for one four. The solution was concentrated in vacuo, and the residue was purified by flash column chromatography (silica, 10→30 percent ethyl ether in petroleum ether) to give 152 mg (86 percent) of Compound 319: white crystalline solid; mp 126°–128° C. (dec., from ethyl ether); $R_f$=0.31 (silica, 30 percent ethyl ether in petroleum ether); IR (CHCl$_3$) $\nu_{max}$ 2926, 1721, 1502, 1380, 1297, 1271, 1200 cm$^{-1}$; 1H NMR (500 NHz, CDCl$_3$) δ 7.33–7.10 (m, 7H, aromatic), 6.84 (dd, J=8.8, 2.8 Hz, 1H, aromatic), 5.77 (dd, J=9.9, 1.6 Hz, 1H, olefinic), 5.66 (dd, J=9.9, 1.6 Hz, 1H, olefinic), 5.47 (d, J=1.6 Hz, 1H, NCHC≡C), 3.81 (s, 3H, OCH$_3$), 3.72 (br s, 1H, C≡CCHC), 2.39 (dd, J=15.2, 8.1 Hz, 1H, CH$_2$), 2.23 (m, 1H, CH$_2$), 2.05–1.89 (m, 2H, CH$_2$), 1.58 (m, 1H, CH$_2$), 1.20 (m, 1H, CH$_2$); 13C NMR (125 MHz, CDCl$_3$) δ 156.9, 153.9, 151.1, 129.8, 129.3, 128.7, 127.4, 125.6, 125.0, 121.9, 121.5, 113.3, 113.0, 101.6, 94.1, 91.4, 88.9, 70.0, 61.0, 55.5, 50.0, 29.5, 23.3, 22.5, 15.6; MS (FAB+) m/e (rel intensity) 424 (M+H, 100), 341 (44); HRMS for C$_{27}$H$_{22}$NO$_4$ (M+H), calcd 424.1549, found 424.1532.

EXAMPLE 123

Compound 320

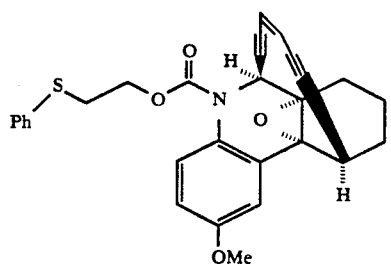

A mixture of Compound 319 (40 mg, 0.094 mmol), 2-(phenylthio)ethanol (29 mg, 0.19 mmol), cesium carbonate (153 mg, 0.47 mmol), and 18-crown-6 (25 mg, 0.094 mmol) in dry acetonitrile (8 mL) was stirred at 25° C. for 45 hours and evaporated in vacuo. The residue was dissolved in dichloromethane (10 mL), filtered through a 5 mm×5 mm plug of silica, and evaporated in vacuo. The residue was purified by flash column chromatography (silica, 20 percent ethyl ether in petroleum ether) to give 44 mg (91 percent) of Compound 320: white crystalline solid; mp 163°–165° C. (dec., from ethyl ether); $R_f$=0.43 (silica, 40 percent ethyl ether in petroleum ether); IR (CHCl$_3$) $\nu_{max}$ 2932, 1700, 1502, 1392, 1229, 1270; 1H NMR (500 MHz, CDCl$_3$) δ 7.40–7.18 (m, 6H, aromatic), 7.10 (d, J=2.7 Hz, 1H, aromatic), 6.82 (dd, J=8.8, 2.7 Hz, 1H, aromatic), 5.77 (dd, J=9.9, 1.5 Hz, 1H, olefinic), 5.65 (dd, J=9.9, 1.5 Hz, 1H, olefinic), 5.42 (br s, 1H, NCHC≡C), 4.38–4.21 (m, 2H, PhSCH$_2$CH$_2$O), 3.87 (s, 3H, OCH$_3$), 3.70 (s, 1H, C≡CCH), 3.18–3.12 (m, 2H, PhSCH$_2$CH$_2$O), 2.36 (m, 1H, CH$_2$), 2.24–1.57 (m, 5H, CH$_2$); MS (FAB+) m/e (rel intensity) 483 (M+, 100), 440 (21), 425 (28); HRMS for C$_{29}$H$_{25}$NO$_4$S (M+), calcd 483.1504, found 483.1511.

EXAMPLE 124

Compound 41b

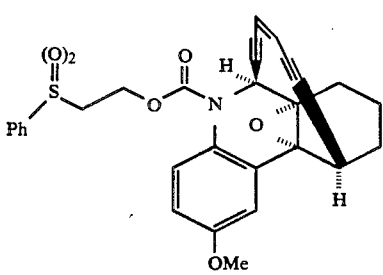

Similarly prepared from Compound 320 in 88 percent yield as described for Compound 45. Compound 41b: white foam; $R_f=0.40$ (silica, 5 percent ethyl ether in dichloromethane); IR (CHCl$_3$) $\nu_{max}$ 3056, 3017, 2933, 2190, 1708, 1503, 1446, 1397, 1321, 1144 cm$^{-1}$; $^1$H NMR (500 MHz, CDCl$_3$) δ 8.09–7.08 (m, 7H, aromatic), 6.80 (br s, 1H, aromatic), 5.76 (d, J=9.9 Hz, 1H, olefinic), 5.64 (d, J=9.9 Hz, 1H, olefinic), 5.36–4.98 (m, 1H, NCHC≡C), 4.53–4.34 (m, 2H, SO$_2$CH$_2$CH$_2$O), 3.82 (s, 3H, OCH$_3$), 3.68 (s, 1H, C≡CCH), 3.53–3.44 (m, 2H, SO$_2$CH$_2$CH$_2$O), 2.32 (br s, 1H, CH$_2$), 2.17 (dt, J=15.3, 9.3 Hz, 1H, CH$_2$), 2.00–1.86 (m, 2H, CH$_2$), 1.77 (m, 1H, CH$_2$), 1.57 (m, 1H, CH$_2$); $^{13}$C NMR (125 MHz, CDCl$_3$) δ 156.8, 134.0, 133.7, 130.2, 129.8, 129.4, 128.3, 128.0, 127.4, 124.9, 121.9, 113.2, 112.8, 101.5, 93.9, 91.4, 69.9, 65.8, 59.4, 55.5, 55.1, 49.8, 29.4, 23.2, 22.4, 15.6, 15.2; HRMS (FAB+) for C$_{29}$H$_{26}$NO$_6$S (M+H), calcd 516.1481, found 516.1499.

EXAMPLE 125

Compound 321

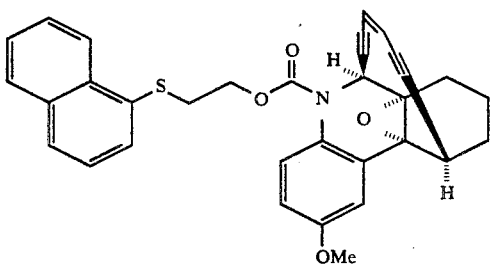

Similarly prepared from Compound 319 and 2-(1-naphthylthio)ethanol in 92 percent yield as described for Compound 320. Compound 321: white crystalline solid; mp 190°–192° C. (dec., from ethyl ether); $R_f=0.41$ (silica, 40 percent ethyl ether in petroleum ether); IR (CDCl$_3$) $\nu_{max}$ 3051, 2920, 2849, 1707, 1501, 1454, 1391, 1275, 1208 cm$^{-1}$; $^1$H NMR (500 MHz, CDCl$_3$) δ 8.43 (br d, J=6.3 Hz, 1H, aromatic), 7.85 (d, J=8.0 Hz, 1H, aromatic), 7.77 (d, J=8.0 Hz, 1H, aromatic), 7.68 (br s, 1H, aromatic), 7.57 (br t, J=6.3 Hz, 1H, aromatic), 7.52 (td, J=7.0, 1.1 Hz, 1H, aromatic), 7.41 (br t, J=7.5 Hz, 1H, aromatic), 7.30 (br s, 1H, aromatic), 7.09 (d, J=2.8 Hz, 1H, aromatic), 6.79 (br d, J=6.3 Hz, 1H, aromatic), 5.76 (dd, J=9.9, 1.6 Hz, 1H, olefinic), 5.65 (dd, J=9.9, 1.6 Hz, 1H, olefinic), 5.42–5.22 (br s, 1H, NCHC≡C), 4.35–4.17 (m, 2H, OCH$_2$(H$_2$S, 3.81 (s, 3H, OCH$_3$), 3.69 (br s, 1H, CH$_2$H, OCH$_2$CH$_2$S), 3.81 (s, 3H, OCH$_3$), 3.69 (br s, 1H, CH$_2$), 2.19 (m, 1H, CH$_2$), 2.04–1.87 (m, 2H, CH$_2$), 1.77 (m, 1H, CH$_2$), 1.61 (m, 1H, CH$_2$); HRMS (FAB+) for C$_{33}$H$_{27}$NO$_4$SCs (M+Cs), calcd 666.0715, found 666.0715.

EXAMPLE 126

Compound 41c

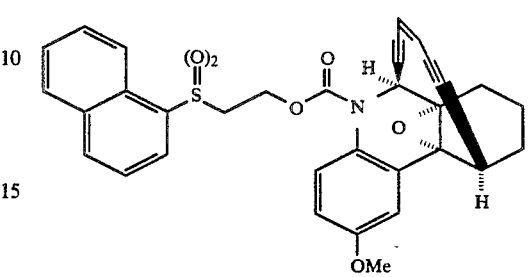

Similarly prepared from Compound 321 in 85 percent yield as described for Compound 45. Compound 41c: white foam; $R_f=0.39$ (silica, 5 percent ethyl ether in dichloromethane); IR (CDCl$_3$) $\nu_{max}$ 3055, 2919, 2849, 1708, 1503, 1455, 1398, 1292, 1212, 1152, 1125, 1026, 809, 771 cm$^{-1}$; $^1$H NMR (500 MHz, CDCl$_3$) δ 8.73–8.68 (m, 1H, aromatic), 8.66–8.29 (m, 1H, aromatic), 8.12 (m, 1H, aromatic), 7.97 (br d, J=7.7 Hz, 1H, aromatic), 7.70 (m, 1H, aromatic), 7.63 (br t, J=7.7 Hz, 1H, aromatic), 7.58 (m, 1H, aromatic), 7.17–6.96 (m, 1H, aromatic), 7.05 (br s, 1H, aromatic), 6.79–6.67 (m, 1H, aromatic), 5.76 (br d, J=9.6 Hz, 1H, olefinic), 5.64 (m, 1H, olefinic), 5.31–4.76 (br s, 1H NCHC≡C), 4.58–4.32 (m, 2H, OCH$_2$CH$_2$SO$_2$), 3.80 (s, 3H, OCH$_3$), 3.70–3.65 (m, 3H, OCH$_2$CH$_2$SO$_2$ and CH$_2$CHC≡C), 2.32 (m, 1H, CH$_2$), 2.13 (m, 1H, CH$_2$), 1.98–1.84 (m, 2H, CH$_2$), 1.75 (m, 1H, CH$_2$), 1.56 (m, 1H, CH$_2$); $^{13}$C NMR (125 MHz, CDCl$_3$) δ 156.7, 135.6, 134.2, 130.8, 129.4, 129.0, 128.7, 127.4, 127.1, 124.9, 124.5, 123.9, 123.8, 121.9, 113.2, 112.8, 101.5, 97.8, 94.0, 91.4, 88.6, 69.9, 65.8, 59.4, 55.5, 55.4, 54.7, 49.7, 29.4, 23.2, 22.3, 15.6, 15.2; HRMS (FAB+) for C$_{33}$H27NO6SCs (M+Cs), calcd 698.0613, found 698.0627.

EXAMPLE 127

Compound 322

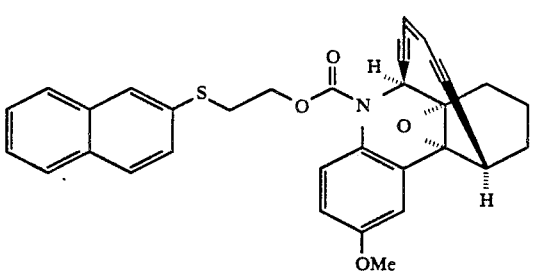

Similarly prepared from Compound 319 and 2-(2-naphthylthio)ethanol in 85 percent yield as described for Compound 320. Compound 322: white crystalline solid; mp 206°–208° C. (dec., from ethyl ether); $R_f=0.40$ (silica, 40 percent ethyl ether in petroleum ether); IR (CDCl$_3$) $\nu_{max}$ 3052, 2937, 1707, 1501, 1452, 1393, 1276, 1209 cm$^{-1}$; $^1$H NMR (500 MHz, CDCl$_3$) δ 7.83 (br s, 1H, aromatic), 7.79–7.75 (m, 3H, aromatic), 7.49–7.42 (m, 3H, aromatic), 7.26 (br s, 1H, aromatic), 7.08 (d, J=2.8 Hz, 1H, aromatic), 6.78 (br s, 1H, aromatic, 5.75 (dd, J=9.9, 1.7 Hz, 1H, olefinic), 5.64 (dd, J=9.9, 1.7 Hz, 1H, olefinic), 5.43–5.15 (br s, 1H, NCHC≡C), 4.43–4.27 (m, 2H, OCH$_2$CH$_2$S), 3.79 (s, 3H, OCH$_3$), 3.68 (br s, 1H, CH$_2$CHC≡C), 3.31–3.22 (m, 2H, OCH$_2$CH$_2$S), 2.35 (m, 1H, CH$_2$), 2.20 (m, 1H, CH$_2$), 2.04–1.87 (m, 2H, CH$_2$), 1.77 (m, 1H, CH$_2$), 1.58 (m, 1H, CH$_2$); HRMS (FAB+) for C$_{33}$H$_{27}$NO$_4$SCs (M+Cs), calcd 666.0715, found 666.0715.

EXAMPLE 128

Compound 41d

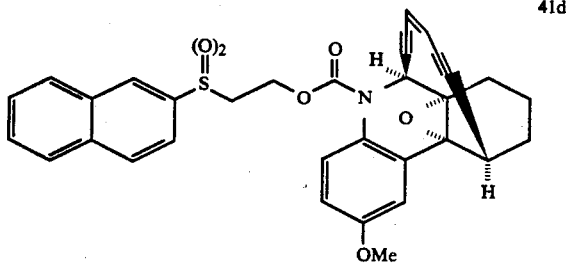

Similarly prepared from Compound 322 in 92 percent yield as described for Compound 45. Compound 41d: white foam; R$_f$=0.39 (silica, 5 percent ethyl ether in dichloromethane); IR (CDCl$_3$) ν$_{max}$ 3056, 2922, 2851, 1709, 1503, 1452, 1400, 1268, 1213, 1153, 1126 cm$^{-1}$; $^1$H NMR (500 MHz, CDCl$_3$) δ 8.55–8.44 (m, 1H, aromatic), 8.07–7.26 (m, 4H, aromatic), 7.67 (td, J=8.1, 1.2 Hz, 1H, aromatic), 7.62 (td, J=8.1, 1.2 Hz, 1H, aromatic), 7.05–6.60 (m, 3H, aromatic), 5.73 (d, J=9.7 Hz, 1H, olefinic), 5.61 (d, J=9.7 Hz, 1H, olefinic), 5.30–4.48 (br s, 1H, NCHC≡C), 4.55–4.44 (m, 2H, OCH$_2$CH$_2$SO$_2$), 3.78 (s, 3H, OCH$_3$), 3.61–3.53 (m, 3H, OCH$_2$CH$_2$SO$_2$, CH$_2$CHC≡C), 2.30 (m, 1H, CH$_2$), 2.10 (m, 1H, CH$_2$), 1.98–1.82 (m, 2H, CH$_2$), 1.73 (m, 1H, CH$_2$), 1.53 (m, 1H, CH$_2$); $^{13}$C NmR (125 MHz, CDCl$_3$) δ 156.6. 135.8, 135.3, 133.5, 132.1, 130.0, 129.9, 129.6, 129.3, 128.0, 127.5, 127.1, 124.9, 122.5, 121.8, 113.2, 112.4, 101.4, 93.9, 91.3, 88.7, 69.8, 65.8, 670.7, 59.7, 55.4, 55.3, 49.7, 29.4, 23.1, 22.2, 15.5, 15.2; HRMS (FAB+) for C$_{33}$H$_{27}$NO$_6$Cs (M+Cs), calcd 698.0613, found 698.0620.

EXAMPLE 129

2-[(2-Nitrobenzyl)oxy]-10-[(triethylsilyl)oxy]-7,8,9,10-tetrahydro-phenanthridine (Compound 323)

Similarly prepared in 95 percent yield as described for Compound 310. Compound 323: white crystalline solid; mp 110°–111° C. (from cyclohexane-hexanes); R$_f$=0.54 (silica, 40 percent ethyl acetate in dichloromethane); IR (CHCl$_3$) ν$_{max}$ 2953, 2908, 2875, 1619, 1526, 1506 cm$^{-1}$; $^1$H NMR (500 MHz, CDCl$_3$) δ 8.55 (s, 1H, H6), 8.22 (dd, J=7.7, 1.2 Hz, 1H, aromatic), 8.01 (d, J=9.1 Hz, 1H, H4), 7.99 (dd, J=7.7, 1.2 Hz, 1H, aromatic), 7.71 (td, J=7.7, 1.2 Hz, 1H, aromatic), 7.52 (td, J=7.7, 1.2 Hz, 1H, aromatic), 7.51 (d, J=2.7 Hz, 1H, H1), 7.40 (dd, J=9.1, 2.7 Hz, 1H, H3), 5.67 and 5.63 (ABq, J=15.3 Hz, 2H, benzylic), 5.40 (t, J=3.1 Hz, 1H, H10), 3.02–2.97 (m, 1H, H7), 2.81 (ddd, J=17.3, 11.5, 5.8 Hz, 1H, H7), 2.26–2.11 (m, 2H, H)9), 1.90–1.81 (m, 2H, H8), 0.98 (t, J=7.9 Hz, 9H, OSi(CH$_2$CH$_3$)$_3$), 0.73 (q, J=7.9 Hz, 6H, OSi(CH$_2$CH$_3$)$_3$); $^{13}$C NMR (125 MHz, CDCl$_3$) δ 156.2, 150.8, 146.8, 143.4, 140.1, 134.1, 133.7, 131.6, 130.0, 128.4, 128.3, 128.1, 125.0, 120.0, 103.7, 66.9, 63.7, 32.0, 27.2, 16.6, 7.1, 5.6; MS (FAB+) m/e (rel intensity) 465 (M+H, 100), 435 (8), 330 (11), 198 (10); HRMS for C$_{26}$H$_{33}$N$_2$O$_4$Si (M+H), calcd 465.2209, found 465.2209. Anal. Calcd for C$_{26}$H$_{32}$N$_2$O$_4$Si: C, 67.21; H, 6.98; N, 6.03. Found: C, 66.99; H, 7.00; N, 5.94.

EXAMPLE 130

N-[(Phenyloxy)carbonyl]-6-ethynyl-2-[(2-nitrobenzyl)oxy]-10-[(triethylsilyl)oxy]-5,6,7,8,9,10-hexahydrophenanthridine (Compound 324)

Similarly prepared in 100 percent yield as described for Compound 311. Compound 324: white foam (ca. 3:1 mixture of diastereomers as determined by $^1$H NMR); R$_f$=0.37 (silica, 20 percent ethyl ether-petroleum ether); IR (CDCl$_3$) ν$_{max}$ 3299, 3014, 2950, 2908, 2874, 1718, 1526, 1493, 1384, 1341, 1303 cm$^{-1}$; $^1$H NMR (500 MHz, CDCl$_3$) δ 8.19 (dd, J=7.7, 1.3 Hz, 1H, aromatic), 7.93 (dd, J=7.7, 1.3 Hz, 1H, aromatic), 7.70 (td, J=7.7, 1.3 Hz, 1H, aromatic), 7.50 (td, J=7.7, 1.3 Hz, 1H, aromatic), 7.38 (br t, J=7.2 Hz, 1H, aromatic), 7.24–7.17 (m, 6H, aromatic), 6.85 (dd, J=8.8, 2.8 Hz, 1H, H3), 5.66 (d, J=1.9 Hz, 1H, H6, major isomer), 5.61 (d, J=1.9 Hz, 1H, H6, minor isomer), 5.53 (s, 2H, benzylic), 4.98 (br s, 1H, H10, major isomer), 4.69 (br s, 1H, H10, minor isomer), 2.52–2.44 (m, 1H, CH$_2$), 2.30–2.19 (m, 1H, CH$_2$), 2.00–1.92 (m, 3H, CH$_2$), 1.75–1.64 (m, 1H, CH$_2$); $^{13}$C NMR (125 MHz, CDCl$_3$) δ 155.1, 150.9, 146.8, 136.7, 134.1, 134.0, 129.4, 129.3, 128.4, 128.2, 128.1, 125.7, 125.0, 121.7, 112.7, 112.4, 111.1, 110.9, 79.8, 71.8 and 71.7, 67.1 and 67.0, 65.1 and 64.2, 48.8, 32.7 and 31.9, 28.2, 27.9, 7.1 and 7.0, 5.7 and 5.5; MS (FAB+) m/e (rel intensity) 610 (M+, 100), 581 (25), 517 (13), 479 (86), 343 (7), 222 (18); HRMS for C$_{35}$H$_{38}$N$_2$O$_6$Si (M+), calcd 610.2499, found 610.2495.

EXAMPLE 131

N-[(Phenyloxy)carbonyl]-6a10a-epoxy-6-ethynyl-2-[(2-nitrobenzyl)oxy]-10-[(triethylsilyl)oxy]-5,6,6a,7,8,9,10,-10a-octahydrophenanthridine (Compound 325)

Similarly prepared in 95 percent yield as described for Compound 312. Compound 325: white crystalline solid (ca. 3:1 mixture of diastereomers as determined by $^1$H NMR); mp 135°–137° C. (from dichloromethane-cyclohexane-hexanes); R$_f$=0.44 (silica, 30 percent ethyl ether in petroleum ether); IR (CHCl$_3$) 3303, 2953, 2912, 2874, 2252, 1718, 1612, 1502, 1302 cm$^{-1}$; $^1$H NMR (500 MHz, CDCl$_3$) δ 8.18 (dd, J=7.7, 1.3 Hz, 1H, aromatic), 7.93–7.91 (m, 1H, aromatic), 7.69 (t, J=7.7 Hz, 1H, aromatic), 7.63–7.61 (m, 1H, aromatic), 7.50 (t, J=7.7 Hz, 1H, aromatic), 7.42–7.31 (m, 3H, aromatic), 7.19–7.10 (m, 3H, aromatic), 6.96 (dd, J=8.8, 2.7 Hz, 1H, H3, major isomer), 6.93 (dd, J=8.8, 2.7 Hz, 1H, H3, minor isomer), 5.55 (d, J=2.1 Hz, 1H, H6), 5.52 (s, 2H, benzylic), 4.93 (br s, 1H, H10, minor isomer), 4.80 (dd, J=9.9, 5.6 Hz, 1H, H10, major isomer), 2.43 (dd, J=13.9, 6.8 Hz, 1H, CH$_2$, minor isomer), 2.34 (dd, J=14.8, 5.7 Hz, 1H, CH$_2$, major isomer), 2.11 (d, J=2.0 Hz, 1H, C≡CH)m, 2.18–1.87 (m, 2H, CH$_2$), 1.76–1.65 (m, 2H, CH$_2$), 1.48–1.33 (m, 1H, CH$_2$), 1.00 (t, J=7.9 Hz, 9H, Si(CH$_2$CH$_3$)$_3$), 0.71 (q, J=7.9 Hz, 6H, Si(CH$_2$CH$_3$)$_3$); $^{13}$C NMR (125 MHz, CDCl$_3$) δ 155.8, 153.9, 151.1, 146.8, 134.0, 133.8, 129.4, 129.2, 128.3, 128.2, 125.5, 125.0, 121.5, 116.3, 116.0, 113.8, 113.2, 78.5 and 78.4, 73.3, 72.8, 70.3 and 69.9, 67.1 and 67.0, 60.4 and 58.8, 48.4 and 47.9, 29.4 and 27.2, 24.0 and 23.9, 20.4 and 20.2, 7.0 and 6.9, 5.8 and 5.5; MS (FAB+) m/e (rel intensity) 627 (M+H, 40), 626 (M+, 100), 597 (52), 581 (10), 490 (26); HRMS for C$_{35}$H$_{38}$N$_2$O$_7$Si (M+), calcd 626.2448, found 626.2450. Anal. Calcd for C$_{35}$H$_{38}$N$_2$O$_7$Si: C, 67.07; H, 6.11; N, 4.47. Found: C, 66.91; H, 6.14; N, 4.36.

EXAMPLE 132

N-[(Phenyloxy)carbonyl]-6a,10a-epoxy-6-ethynyl-10-hydroxy-2-[(2-nitrobenzyl)oxy]-5,6,6a,7,8,9,10,10a-octahydrophenanthridine (Compound 326)

A solution of Compound 325 (45.27 g, 72.3 mmol) and tert-butylthiol (5.70 mL, 50.6 mmol) in THF (250 mL) was treated at zero degrees C. with tetra-n-butylammonium fluoride (TBAF, 75.9 mL, 1.0M solution in THF, 75.9 mmol). The reaction mixture was stirred at 20° C. for 30 minutes, diluted with ethyl ether (750 mL), poured into water (1500 mL), and separated. The organic layer was washed with water (2×2000 mL), dried over anhydrous MgSO$_4$, and evaporated in vacuo. The residue was purified by suspending it in hot acetonitrile (500 mL), cooling to 10° C., and filtering. The white solid was washed with acetonitrile (100 mL) and ethyl ether (200 mL) to give 32.70 g (88 percent) of Compound 326: white crystalline solid (about 3:1 mixture of diastereomers as determined by $^1$H NMR); mp 207°–209° C. (acetonitrile); R$_f$=0.46 (silica, 10 percent ethyl acetate in dichloromethane); IR (CHCl$_3$) $\nu_{max}$ 3469, 3196, 2950, 2922, 1689, 1521, 1495, 1386 cm$^{-1}$; $^1$H NMR (500 MHz, DMSO-d$_6$) δ 8.13 (dd, J=7.8, 1.2 Hz, 1H, aromatic), 7.84 (br dd, J=7.8, 1.2 Hz, 1H, aromatic), 7.79 (td, J=7.8, 1.2 Hz, 1H, aromatic), 7.63 (td, J=7.8, 1.2 Hz, 1H, aromatic), 7.60 (d, J=2.7 Hz, 1H, H1, major isomer), 7.55 (d, J=2.7 Hz, 1H, H1, minor isomer), 7.49–7.13 (m, 6H, aromatic), 7.04 (dd, J=8.8, 2.7 Hz, 1H, H3, major isomer), 7.01 (dd, J=8.8, 2.7 Hz, 1H, H3, minor isomer), 5.65–5.44 (m, 2H, benzylic; 1H, OH; 1H, H6, minor isomer), 5.31 (m, 1H, H6, major isomer), 4.67 (br s, 1H, H10, minor isomer), 4.48 (dt, J=9.0, 6.5 Hz, 1H, H10, major isomer), 2.27 (dd, J=14.1, 6.7 Hz, 1H, CH$_2$, minor isomer), 2.22 (dd, J=14.8, 5.4 Hz, 1H, CH$_2$, major isomer), 1.80–1.20 (m, 5H, CH$_2$); $^{13}$C NMR (125 MHz, DMSO-d$_6$) δ 155.6, 153.3, 150.8, 147.6, 134.0, 132.2, 129.5, 129.4, 129.3, 128.5, 128.2, 125.8, 124.8, 121.7, 115.8, 115.4, 114.1, 78.5, 76.0, 72.8, 67.0 and 66.7,; 66.0, 62.4 and 60.2, 47.5, 29.1 and 27.3, 25.1 and 23.7, 22.4 and 19.8; MS (FAB+) m/e (rel intensity) 513 (M+H, 100), 391 (86); HRMS for C$_{27}$H$_{25}$N$_2$O$_7$ (M+H), calcd 513.1662, found 513.1662. Anal. Calcd for C$_{29}$H$_{24}$N$_2$O$_7$: C, 67.96; H, 4.72; N, 5.47. Found: C, 67.71; H, 4.84; N, 5.36.

EXAMPLE 133

N-[(Phenyloxy)carbonyl]-6a,10a-epoxy-6-ethynyl-2-[(2-nitrobenzyl)oxy]-10-oxo-5,6,6a,7,8,9,10,10a-octahydrophenanthridine (Compound 327)

Similarly prepared in 100 percent yield as described for Compound 314. Compound 327: white crystalline solid; mp 128°–130° C. (from dichloromethane-benzene-pentane); R$_f$=0.28 (silica, dichloromethane); IR (CHCl$_3$) $\nu_{max}$ 3300, 2945, 2252, 1717, 1526, 1493, 1380, 1342, 1308, 1252 cm$^{-1}$; $^1$H NMR (500 MHz, CDCl$_3$) δ 8.16 (dd, J=7.8, 1.2H, 1H, aromatic), 8.11 (d, J=2.7 Hz, 1H, H1), 7.91 (dd, J=7.8, 1.2 Hz, 1H, aromatic), 7.69 (td, J=7.8, 1.2 Hz, 1H, aromatic), 7.49 (td, J=7.8, 1.2 Hz, 1H, aromatic), 7.43–7.32 (m, 4H, aromatic), 7.20 (br t, J=7.2 Hz, 1H, aromatic), 7.09 (br d, J=7.2 Hz, 1H, aromatic), 7.00 (dd, J=8.9, 2.7 Hz, 1H, H3), 5.71 (d, J=2.4 Hz, 1H, H6), 5.50 (s, 2H, benzylic), 2.75 (dt, J=15.1, 5.1 Hz, 1H, H9), 2.59 (ddd, J=15.1, 10.0, 6.0 Hz, 1H, H9), 2.36–2.28 (m, 2H, H7), 2.23 (br s, 1H, C≡CH), 2.03–1.88 (m, 2H, H8); $^{13}$C NMR (125 MHz, CDCl$_3$) δ 201.1, 155.9, 154.0, 151.0, 146.9, 134.0, 133.4, 129.3, 129.3, 128.7, 128.6, 128.3, 125.8, 125.0, 124.4, 121.4, 116.9, 115.0, 77.5, 74.7, 74.4, 67.2, 57.2, 47.5, 38.7, 23.7, 18.3; MS (FAB+) m/e (rel intensity) 511 (M+H, 100), 375 (20); HRMS for C$_{29}$H$_{23}$N$_2$O$_7$ (M+H), calcd 511.1505, found 511.1525. Anal. Calcd for C$_{29}$H$_{23}$N$_2$O$_7$.½(C$_6$H$_6$): C, 69.94, H, 4.59; N, 5.10. Found: C, 69.81H, 4.53; N, 4.88.

EXAMPLE 134

N-[(Phenyloxy)carbonyl]-6-[6-(trimethylsilyl)-3(Z)-hexene-1,5-diynyl]-6a,10a-epoxy-2-[(2-nitrobenzyl)oxy]-10-oxo-5,6,6a,7,8,9,10,10a-octahydrophenanthridine (Compound 328)

Similarly prepared in 78 percent yield as described for Compound 315. Compound 328: white foam; R$_f$=0.40 (silica, dichloromethane); IR (CHCl$_3$) $\nu_{max}$ 2956, 1718, 1526, 1493, 1380, 1342, 1308, 1250, 1203, 844 cm$^{-1}$; $^1$H NMR (500 MHz, CDCl$_3$) δ 8.16 (dd, J=7.9, 1.2 Hz, 1H, aromatic), 8.09 (d, J=3.0 Hz, 1H, H1), 7.90 (br d, J=7.9 Hz, 1H, aromatic), 7.69 (td, J=7.9, 1.2 Hz, 1H, aromatic), 7.51–7.06 (m, 7H, aromatic), 6.97 (dd, J=8.8, 3.0 Hz, 1H, H3), 5.93 (d, J=1.6 Hz, H6), 5.82 (d, J=11.1 Hz, olefinic), 5.66 (br d, J=11.1 Hz, olefinic), 5.49 (s, 2H, benzylic), 2.77–2.62 (m, 2H, H9), 2.38–2.25 (m, 2H, H7), 2.01–1.90 (m, 2H, H8), 0.20 (s, 9H, SiC(CH$_3$)$_3$); $^{13}$C NMR (125 MHz, CDCl$_3$) δ 201.1, 155.8, 153.9, 151.0, 146.9, 134.0, 133.4, 129.3, 128.7, 128.6, 128.4, 125.7, 125.0, 124.3, 121.5, 121.4, 120.8, 118.9, 116.9, 115.0, 103.6, 101.5, 90.4, 83.1, 74.7, 67.2, 57.2, 48.3, 38.7, 23.8, 18.2, 0.16; MS (FAB+) m/e (rel intensity) 632 (M+, 100), 496 (14), 376 (10), 319 (7); HRMS for C$_{26}$H$_{32}$N$_3$O$_7$Si (M+), calcd 632.1979, found 632.1999.

EXAMPLE 135

N-[(Phenyloxy)carbonyl]-6-[3(Z)-hexene-1,5-diynyl]-6a,10a-epoxy-2-[(2-nitrobenzyl)oxy]-10-oxo-5,6,6a,7,8,9,10,10a-octahydrophenanthridine (Compound 329)

Similarly prepared in 96 percent yield as described for Compound 316. Compound 329: unstable white foam; R$_f$=0.52 (silica, 60 percent ethyl ether in petroleum ether); IR (CDCl$_3$) $\nu_{max}$ 3300, 2945, 1717, 1582, 1492, 1380, 1309 cm$^{-1}$; $^1$H NMR (300 MHz, CDCl$_3$) δ 8.05 (dd, J=7.8, 1.0 Hz, 1H, aromatic), 7.99 (d, J=2.8 Hz, 1H, H1), 7.78 (br d, J=7.8 Hz, 1H, aromatic), 7.58 (td, J=7.8, 1.0 Hz, 1H, aromatic), 7.41–6.97 (m, 7H, aromatic), 6.86 (dd, J=8.8, 2.8 Hz, 1H, H3), 5.78 (s, 1H, H6), 5.70 and 5.63 (ABq, J=11.0 Hz, 2H, olefinic), 5.38 (s, 2H, benzylic), 3.07 (d, J=0.8 Hz, C≡CH), 2.68–2.54 (m, 2H, H9), 2.27–2.21 (m, 2H, H7), 1.89–1.80 (m, 2H, H8); HRMS (FAB+) for C$_{33}$H$_{25}$N$_2$O$_7$ (M+H), calcd 561.1662, found 561.1641.

EXAMPLE 136

Compound 330

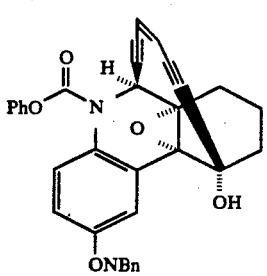

Similarly prepared in 86 percent yield as described for Compound 317. Compound 330: white crystalline solid; mp 196°-197° C. (from dichloromethane-ethylethyl ether-petroleum ether); $R_f=0.35$ (silica, 60 percent ethyl ether in petroleum ether); IR (CHCl$_3$) $v_{max}$ 3430, 2955, 2252, 1718, 1689, 1523, 1492, 1386, 1340, 1325, 1274 cm$^{-1}$; $^1$H NMR (500 MHz, CDCl$_3$) δ 8.26 (d, J=2.8 Hz, 1H, H1), 8.15 (dd, J=7.8, 1.2 Hz, 1H, aromatic), 7.88 (d, J=7.8, 1.2 Hz, 1H, aromatic), 7.64 (td, J=7.8, 1.2 Hz, 1H, aromatic), 7.46 (td, J=7.8, 1.2 Hz, 1H, aromatic), 7.36-7.12 (m, 6H, aromatic), 6.95 (dd, J=8.9, 2.8 Hz, 1H, H3), 5.81 (d, J=10.0 Hz, 1H, olefinic), 5.67 (dd, J=10.0, 1.4 Hz, 1H, olefinic), 5.51 (s, 2H, benzylic), 5.50 (br s, 1H, NCHC≡C), 2.31 (dd, J=15.1, 8.3 Hz, 1H, CH$_2$), 2.21 (s, 1H, OH), 2.20-2.14 (m, 2H, CH$_2$), 1.97 (m, 1H, CH$_2$), 1.88 (dt, J=12.1, 3.0 Hz, 1H, CH$_2$), 1.73 (m, 1H, CH$_2$); $^{13}$C NMR (125 MHz, CDCl$_3$) δ 155.0, 147.0, 134.0, 133.9, 129.6, 129.3, 129.2, 129.0, 128.7, 128.1, 127.3, 126.7, 124.9, 124.1, 124.0, 122.0, 121.5, 117.7, 114.7, 100.4, 94.0, 93.9, 88.7, 73.6, 73.0, 67.0, 64.2, 50.5, 35.1, 23.0, 19.1; HRMS (FAB+) for C$_{33}$H$_{24}$N$_2$O$_7$ (M+), calcd 560.1584, found 560.1584. Anal. Calcd for C$_{33}$H$_{24}$N$_2$O$_7$·½(H$_2$O): C, 69.59; H, 4.42; N, 4.92. Found: C, 69.57; H, 4.32; N, 4.72.

EXAMPLE 137

Compound 331

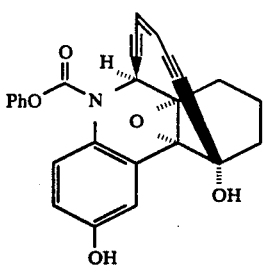

A solution of Compound 330 (809 mg, 1.44 mmol) in a mixture of dichloromethane (60 mL), methanol (240 mL), and triethylamine (0.02 mL) was distributed into 20 test tubes (16×20 mm, Fisher disposable borosilicate culture tubes) and exposed to sunlight at 28° C. for 4 hours. The combined solutions were evaporated in vacuo, and the residue was purified by flash column chromatography (silica, 15 percent ethyl acetate in dichloromethane) to give a tan crystalline solid which was further purified by recrystallization from ethyl acetate-dichloromethane-ethyl ether-petroleum ether to give 469 mg (76 percent) of Compound 331: white crystalline solid; mp 205°-206° C; $R_f=0.23$ (silica, 15 percent ethyl acetate in dichloromethane); IR (CHCl$_3$) $v_{max}$ 3412, 3209, 2945, 1690, 1500, 1385, 1328 cm$^{-1}$; $^1$H NMR (500 MHz, DMSO-d$_6$) δ 9.43 (s, 1H, ArOH), 8.13 (d, J=2.7 Hz, 1H, aromatic), 7.39 (br t, J=7.7 Hz, 2H, aromatic), 7.25-7.10 (m, 4Hm, aromatic), 6.62 (dd, J=8.7, 2.7 Hz, 1H, aromatic), 6.24 (s, 1H, OH), 6.10 (d, J=10.0 Hz, olefinic), 5.89 (dd, J=10.0, 1.6 hz, olefinic), 5.41 (br s, 1H, NCHC≡C), 2.23 (dd, J=15.3, 8.5 Hz, CH$_2$), 2.06-2.00 (m, 2H, CH$_2$), 1.83-1.74 (m, 2H, CH$_2$), 1.66-1.62 (m, 1H, CH$_2$); $^{13}$C NmR (125 MHz, DMSO-d$_6$) δ 154.2, 150.8, 129.4, 127.2, 127.1, 125.7, 125.1, 122.1, 121.6, 117.9, 114.7, 102.6, 94.3, 92.6, 88.9, 72.5, 71.8, 64.9, 63.8, 50.3, 34.2, 22.9, 18.7; MS (FAB+) m/e (rel intensity) 425 (M+, 100 ), 255 (86); HRMS for C$_{26}$H$_{19}$NO$_5$ (M+), calcd 425.1263, found 425.1281.

EXAMPLE 138

Compound 332

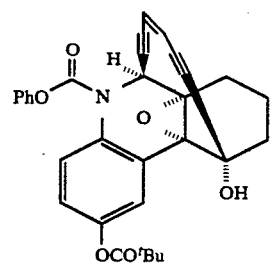

A suspension of Compound 331 (469 mg, 1.10 mmol) in dichloromethane (4.0 mL) was treated with triethylamine (184 mL, 1.32 mmol) and freshly distilled pivaloyl chloride (149 mL, 1.21 mmol) followed by stirring at 20° C. for 30 minutes to give a clear solution which was diluted with ethyl ether (15 mL), poured into water (30 mL) and extracted with ethyl ether (10 mL). The combined organic layers were washed with water (30 mL), saturated aqueous sodium bicarbonate (30 mL) and brine (30 mL), dried (MgSO$_4$), filtered through a 2cm×2 cm plug of silica with rinsing with ethyl ether (20 mL). The combined filtrates were evaporated in vacuo, the residue was purified by recrystallization from dichloromethane-ethyl ether-petroleum ether to give 505 mg (90 percent) of Compound 332: white crystalline solid; mp 245°-247° C. (dec.); $R_f=0.32$ (silica, 50 percent ethyl ether in petroleum ether); IR (CHCl$_3$) $v_{max}$ 3464, 2969, 2870, 1723, 1492, 1381, 1316, 1203, 1177, 1118 cm$^{-1}$; $^1$H NMR (500 MHz, CDCl$_3$) δ 8.36 (d, J=2.7 Hz, 1H, aromatic), 7.45-7.11 (m, 6H, aromatic), 7.02 (dd, J=8.7, 2.7 Hz, 1H, aromatic), 5.88 (d, J=10.0 Hz, 1H, olefinic), 5.53 (d, J=1.3 Hz, 1H, NCHC≡C), 2.61 olefinic), 5.53 (d, J=1.3 Hz, 1H, NCHC≡C), 2.61 (br s, 1H, OH), 2.32 (dd, J=14.7, 7.9 Hz, 1H, CH$_2$), 2.24-1.68 (m, 5H, CH$_2$), 1.35 (s, 9H, t-Bu); $^{13}$C NMR (125 MHz, CDCl$_3$) δ 177.2, 151.3, 148.0, 133.1, 129.3. 129.0, 127.1, 127.0, 125.8, 124.4, 124.3, 122.2, 121.5, 121.2, 100.1, 94.4, 93.6, 88.9, 73.9, 73.2, 64.1, 50.3, 39.1, 35.2, 27.1, 23.1, 19.2; HRMS (FAB+) for C$_{31}$H$_{27}$NO$_6$ (M+), calcd, 509.1838, found 509.1838.

EXAMPLE 139

Compound 333

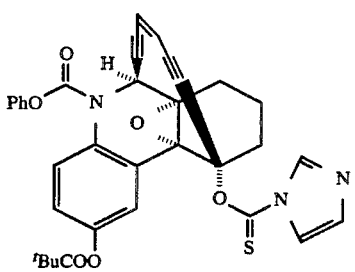

Similarly prepared in 100 percent yield as described for Compound 318. Compound 333: white crystalline solid; mp 108°–110° C. (dec., from dichloromethane-benzene-cyclohexane); $R_f$=0.20 (silica, 50 percent ethyl ether-petroleum ether); IR (CHCl$_3$) $\nu_{max}$ 2971, 2871, 1750, 1724, 1494, 1384, 1316, 1283, 1244, 1229, 1208, 1106 cm$^{-1}$; $^1$H NMR (500 MHz, CDCl$_3$) δ 8.41 (br s, 1H, aromatic), 7.61–7.16 (m, 9H, aromatic), 7.05 (dd, J=8.8, 2.6 Hz, 1H, aromatic), 6.00 (d, J=10.1 Hz, 1H, olefinic), 5.78 (dd, J=10.1, 1.5 Hz, 1H, olefinic), 5.61 (d, J=1.5 Hz, 1H, NCHC≡C), 3.08 (br d, J=12.2 Hz, 1H, CH$_2$), 2.48–1.81 (m, 5H, CH$_2$), 1.17 (s, 9H, t-Bu); $^{13}$C NMR (125 MHz, CDCl$_3$) δ 179.1, 176.6, 150.8, 148.1, 137.4, 133.2, 131.1, 129.4, 128.3, 127.8, 127.5, 125.9, 124.2, 123.4, 122.6, 121.6, 121.4, 117.4, 100.8, 93.9, 93.8, 89.2, 85.6, 74.6, 63.4, 50.2, 38.9, 28.6, 26.8, 22.5, 18.5; MS (FAB+) m/e (rel intensity) 620 (M+H, 9), 560 (12), 492 (32), 372 (6), 289 (17), 258 (9), 246 (12), 235 (29), 213 (10), 179 (100); HRMS for C$_{35}$H$_{30}$N$_3$O$_6$S (M+H), calcd 620.1855, found 620.1832.

EXAMPLE 140

Compound 334

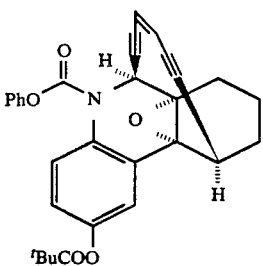

Similarly prepared in 95 percent yield as described for Compound 319. Compound 334: white crystalline solid; mp>300° C. (dec., from dichloromethane-ethyl ether-pentane); $R_f$=0.43 (silica, 30 percent ethyl ether in petroleum ether); IR (CHCl$_3$) $\nu_{max}$ 3052, 2966, 2934, 2870, 1748, 1723, 1494, 1377, 1315, 1284, 1264, 1204, 1116 cm$^{-1}$; $^1$H NMR (500 MHz, CDCl$_3$) δ 7.51–7.11 (m, 7H, aromatic), 7.03 (dd, J=8.8, 2.6 Hz, 1H, aromatic), 5.83 (dd, J=9.9, 1.5 Hz, 1H, olefinic), 5.69 (dd, J=9.9, 1.5 Hz, 1H, olefinic), 5.52 (d, J=1.5 Hz, 1H, NCHC≡C), 3.74 (s, 1H, C≡CHC), 2.42 (dd, J=15.2, 8.7 Hz, 1H, CH$_2$), 2.30–1.59 (m, 5H, CH$_2$), 1.20 (s, 9H, t-Bu); $^{13}$C NMR (125 MHz, CDCl$_3$) δ 176.8, 150.9, 148.2, 132.8, 129.9, 129.3, 127.3, 127.2, 125.7, 125.2, 122.0, 121.5, 121.2, 120.3, 101.3, 93.6, 91.5, 89.0, 70.2, 60.8, 49.8, 39.1, 29.5, 27.1, 23.2, 22.5, 15.6; MS (FAB+) m/e (rel intensity) 494 (M+H, 100), 409 (6), 288 (7), 272 (10), 260 (7), 246 (9), 233 (7); HRMS for C$_{31}$H$_{28}$NO$_5$ (M+H), calcd 494.1967, found 494.1967.

EXAMPLE 141

Compound 335

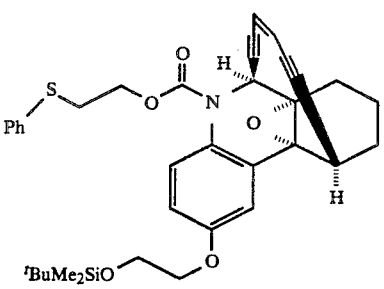

Cesium carbonate (9.00 g, 27.6 mmol) was flame dried under vacuum for 10 minutes and cooled. To the cesium carbonate was added 18-crown-6 (2.36 g, 8.93 mmol), 2-(phenylthio)ethanol (0.968 mL, 7.17 mmol), and dry acetonitrile (200 mL). After stirring for 10 minutes at 25° C., 91 (885 mg, 1.79 mmol) was added and stirring was continued for another 40 hours at 25° C. A solution of (tBuMe$_2$Si)OCH$_2$CH$_2$OTs (2.66 g, 7.17 mmol) in dry benzene (5 mL) was added followed by stirring at 25° C. for another 40 hours. The reaction mixture was filtered through a short pad of Celite and evaporated in vacuo. The residue was diluted with ethyl ether (120 mL), filtered from the precipitated 18-crown-6.CH$_3$CN complex, and evaporated in vacuo. The residue was purified by flash column chromatography (silica, 17:6:2 petroleum ether-benzene-ethyl ether) to give an off-white crystalline solid which was further purified by recrystallization from benzene-pentane to give 785 mg (70 percent) of Compound 335: white crystalline solid; mp 146°–147° C.; $R_f$=0.47 (silica, 20 percent ethyl ether in petroleum ether); IR (CDCl$_3$) $\nu_{max}$ 3053, 2949, 2928, 2853, 1706, 1503, 1392, 1271, 1132 cm$^{-1}$; $^1$H NMR (500 MHz, CDCl$_3$) δ 7.37–7.17 (m, 6H, aromatic), 7.07 (d, J=2.8 Hz, 1H, aromatic), 6.81 (dd, J=8.8, 2.8 Hz, 1H, aromatic), 5.74 (dd, J=9.9, 1.5 Hz, 1H, olefinic), 5.63 (dd, J=9.9, 1.5 Hz, 1H, olefinic), 5.41–5.18 (m, 1H, NCHC≡C), 4.36–4.16 (m, 2H, PhSCH$_2$CH$_2$O), 4.02 (t, J=5.0 Hz, 2H, ArOCH$_2$CH$_2$OTBS), 3.95 (t, J=5.0 Hz, 2H, ArOCH$_2$CH$_2$OTBS), 3.66 (br s, 1H, CHC≡C), 3.17–3.10 (m, 2H, PhSCH$_2$CH$_2$O), 2.34 (m, 1H, CH$_2$), 2.16 (dt, J=15.1, 9.3 Hz, 1H, CH$_2$), 2.03–1.84 (m, 2H, CH$_2$), 1.75 (m, 1H, CH$_2$), 1.53 (m, 1H, CH$_2$), 0.90 (s, 9H, t-Bu), 0.09 (s, 6H, Si(CH$_3$)$_2$); $^{13}$C NMR (125 MHz, CDCl$_3$) δ 156.0, 135.0, 129.9, 129.5, 129.1, 128.8, 127.4, 127.3, 126.6, 124.9, 121.9, 113.8, 113.6, 101.5, 94.3, 91.3, 88.6, 70.1, 69.5, 64.6, 61.9, 60.9, 49.7, 32.4, 29.5, 25.9, 23.2, 22.5, 18.4, 15.6, −5.2; HRMS (FAB+) for C$_{36}$H$_{41}$NO$_5$SSi (M+), calcd 627.2475, found 627.2485. Anal. Calcd for C$_{36}$H$_{41}$NO$_5$SSi: C, 68.87; H, 6.58; N, 2.23; S, 5.10; Si, 4.47. Found: C, 68.78; H, 6.59; N, 2.15; S, 5.14; Si, 4.34.

EXAMPLE 142

Compound 336

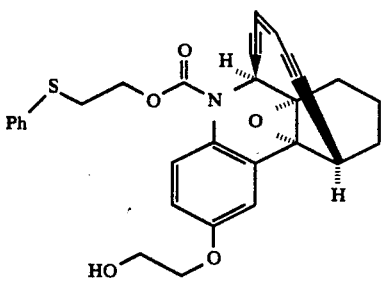

A solution of Compound 335 (758 mg, 121 mmol) in THF (20 mL) was treated with tetra-n-butylammonium fluoride (TBAF) (1.33 mL, 1.0M solution in THF, 1.33 mmol) and followed by stirring at 20° C. for 20 minutes. The reaction mixture was evaporated in vacuo, and the residue was purified by flash column chromatography (silica, 75 percent ethyl ether in petroleum ether) to give 617 mg (100 percent) of Compound 336 white foam; $R_f = 0.42$ (silica, 90 percent ethyl ether in petroleum ether); IR (CHCl$_3$) 3586, 2936, 1702, 1502, 1394, 1319, 1271, 1230, 1206 cm$^{-1}$; $^1$H NMR (500 MHz, CDCl$_3$) δ 7.38–7.19 (m, 6H, aromatic), 7.12 (d, J=2.8 Hz, 1H, aromatic), 7.84 (dd, J=8.8, 2.8 Hz, 1H, aromatic), 7.77 (dd, J=9.9, 1.4 Hz, 1H, olefinic), 7.65 (dd, J=9.9, 1.4 Hz, 1H, olefinic), 5.43–5.18 (m, 1H, NCHC≡C), 4.38–4.20 (m, 2H, PhSCH$_2$CH$_2$O), 4.09 (t, J=4.4 Hz, 2H, ArOCH$_2$CH$_2$OH), 3.97 (br t, J=4.4 Hz, 2H, PhSCH$_2$CH$_2$O), 2.36 (m, 1H, CHC≡C), 3.19–3.12 (m, 2H, PhSCH$_2$CH$_2$O), 2.36 (m, 1H, CH$_2$), 2.19 (dt, J=15.3, 9.4 Hz, 1H, CH$_2$), 2.08 (br s, 1H, OH), 2.02–1.85 (m, 2H, CH$_2$), 1.77 (m, 1H, CH$_2$), 1.58 (m, 1H, CH$_2$); $^{13}$C NMR (125 MHz, CDCl$_3$) δ 155.7, 135.0, 129.9, 129.7, 129.2, 129.1, 127.6, 127.5, 126.6, 124.9, 122.0, 113.8, 113.7, 101.5, 94.2, 91.4, 88.6, 70.2, 69.5, 64.6, 61.4, 60.9, 49.7, 32.4, 29.5, 23.2, 22.5, 15.6; HRMS (FAB+) for C$_{30}$H$_{27}$NO$_5$S (M+), calcd 513.1610, found 513.1619.

EXAMPLE 143

Compound 153

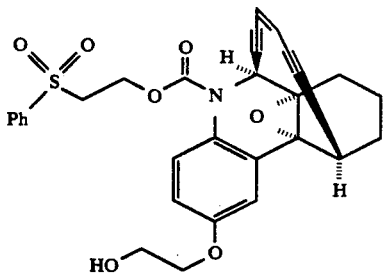

Similarly prepared in 99 percent yield as described for Compound 47. Compound 153: white foam; $R_f = 0.16$ (silica, ethyl ether); IR (CDCl$_3$) $\nu_{max}$ 3520, 2934, 2870, 1707, 1503, 1399, 1320, 1292, 1206 cm$^{-1}$; $^1$H NMR (500 MHz, CDCl$_3$) δ 7.88–7.10 (m, 7H, aromatic), 6.82 (br s, 1H, aromatic), 5.76 (br d, J=9.7 Hz, 1H, olefinic), 5.64 (br d, J=9.7 Hz, 1H, olefinic), 5.36–4.99 (m, 1H, NCHC≡C), 4.52–4.33 (m, 2H, SO$_2$CH$_2$CH$_2$O), 4.08 (br s, 2H, ArOCH$_2$CH$_2$OH), 3.96 (br s, 2H, ArOCH$_2$CH$_2$OH), 3.66 (s, 1H, CHC≡C), 3.50–3.42 (m, 2H, SO$_2$CH$_2$CH$_2$O), 2.33 (br s, 1H, CH$_2$), 2.20–2.13 (m, 2H, CH$_2$ and OH), 1.99–1.84 (m, 2H, CH$_2$), 1.77 (m, 1H, CH$_2$), 1.57 (m, 1H, CH$_2$); $^{13}$C NMR (125 MHz, CDCl$_3$) δ 155.9, 138.9, 134.0, 129.7, 129.4, 128.7, 128.0, 127.8, 127.6, 125.0, 121.9, 113.8, 101.4, 93.9, 91.4, 88.8, 70.0, 69.5, 61.4, 60.8, 59.3, 55.1, 49.7, 29.7, 29.4, 23.2, 22.4, 15.6; HRMS (FAB+) C$_{30}$H$_{28}$NO$_7$S (M+H), calcd 546.1586, found 546.1598.

EXAMPLE 144

2-[3-(tert-Butyldiphenylsilyl)oxy]-propynyl]-10-[(triethylsilyl)oxy]-7,8,9,10-tetrahydrophenanthridine (Compound 340)

Similarly prepared in 88 percent yield as described for Compound 310. Compound 340: $R_f = 0.66$ (silica, 30 percent ethyl acetate in petroleum ether); IR (film) $\nu_{max}$ 2953, 2875, 1499, 1427, 1370, 111, 1085, 702 cm$^{-1}$; $^1$H NMR (500 MHz, CDCl$_3$) δ 8.86 (s, 1H, H6), 8.22 (br s, 1H, H1), 7.97 (d, J=8.6 Hz, 1H, H4), 7.82–7.77 (m, 4H, aromatic), 7.56 (br d, J=8.6 Hz, 1H, H3), 7.48–7.39 (m, 6H, aromatic), 5.44 (br s, 1H, H10), 4.61 (s, 2H, C≡CH$_2$O), 2.98 (br d, J=17.0 Hz, 1 H, H7), 2.80 (ddd, J=17.0, 11.4, 5.7 Hz, 1H, H7), 2.21 (br d, J=12.7 Hz, 1H, H9), 2.17–2.09 (m, 1H, H9), 1.93–1.84 (s, 2H, H8), 1.12 (s, 9H, $^t$Bu), 1.01 (t, J=8.0 Hz, 9H, Si(CH$_2$CH$_3$)$_3$), 0.76 (q, J=8.0 Hz, 6 H, Si(CH$_2$CH$_3$)$_3$); $^{13}$C NMR (125 MHz, CDCl$_3$) δ 153.2, 146.4, 140.8, 135.6, 133.1, 130.6, 130.2, 129.8, 129.7, 127.7, 127.4, 126.6, 120.9, 88.4, 84.9, 63.5, 53.1, 32.0, 27.1, 26.7, 19.2, 16.8, 6.9, 5.4; MS (FAB+) m/e (rel intensity) 606 (M+H, 100), 474 (8), 220 (15), 197 (19), 181 (6); HRMS for C$_{38}$H$_{48}$NO$_2$Si$_2$ (M+H), calcd 606.3224, found 606.3230.

EXAMPLE 145

N-[(Phenyloxy)carbonyl]-2-[3-(tert-butyldiphenylsilyl)oxy]-propynyl]-6-ethynyl-10-[(triethylsilyl)oxy]-5,6,7,8,9,10-hexahydrophenanthridine (Compound 341)

Similarly prepared in 83 percent yield as described for Compound 311. Compound 341: $R_f = 0.55$ (silica, 50 percent ethyl ether in petroleum ether); IR (film) $\nu_{max}$ 3283, 2954, 2229, 2117, 1722, 1659, 1592, 1494, 1383, 1322 cm$^{-1}$; $^1$H NMR (500 MHz, CDCl$_3$) δ 7.84 and 7.50 (2br s, 1H, H1), 7.79–7.74 (m, 4H, aromatic), 7.48–7.37 (m, 8H, aromatic), 7.31–7.18 (m, 5H, aromatic), 5.68 and 5.62 (2br s, 1H, H6), 4.99 and 4.68 (2br, s, 1H, H10), 4.56 and 4.55 (2s, 2H, C≡CH$_2$O), 2.54–2.43 (m, 1H, H7), 2.32–2.19 (m, 1H, H7), 2.22 (br s, 1H, C≡CH), 2.08–1.87 (m, 3H, 1.78–1.62 (m, 1H), 1.11 (s, 9H, $^t$Bu), 1.06 and 0.95 (2t, J=7.9 Hz, 9H, Si(CH$_2$CH$_3$)$_3$), 0.78 and 0.67 (2q, J=7.9 Hz, 6H, Si(CH$_2$CH$_3$)$_3$); $^{13}$C NMR (125 MHz, CDCl$_3$) δ 150.8, 135.4, 133.1, 130.0, 129.7, 129.5, 129.4, 129.1, 127.8, 127.7, 127.5, 127.1, 126.3, 125.8, 121.6, 121.5, 120.9, 87.1, 84.6 and 84.5, 79.7 and 79.5, 72.0 and 71.9, 64.8 and 64.6, 53.2 and 53.1, 48.7 and 48.1, 32.7 and 31.9, 28.2 and 27.8, 26.7, 19.2, 18.2, 7.1 and 6.9, 5.6 and 5.3; MS (FAB+) m/e (rel intensity) 884 (M+Cs, 68), 694 (70), 620 (36), 197 (100); HRMS for C$_{47}$H$_{53}$NO$_4$Si$_2$Cs (M+Cs), calcd 884.2567, found 884.2567.

EXAMPLE 146

N-[(Phenyloxy)carbonyl]-2-[3-(tert-butyldiphenylsilyl)oxy]-propynyl]-6a,10a-epoxy-6-ethynyl-10-[(triethylsilyl)oxy]-5,6,6a,7,8,9,10,10a-octahydrophenanthridine (Compound 342)

Similarly prepared in 87 percent yield as described for Compound 312. Compound 342: Major Isomer: $R_f=0.41$ (silica, 10 percent ethyl acetate in petroleum ether); IR (film) $v_{max}$ 3282, 2954, 2226, 2122, 1727, 1590, 1494, 1372, 1315, 1202 cm$^{-1}$; $^1$H NMR (500 MHz, CDCl$_3$) δ 7.99 (br s, 1H, H1), 7.79–7.74 (m, 4H, aromatic), 7.48–7.39 (m, 7H, aromatic), 7.38–7.31 (m, 3 H, aromatic), 7.22 (br t, J=7.0 Hz, 1H, aromatic), 7.18–7.11 (m, 2H, aromatic, 5.58 (d, J=1.9 Hz, 1H, H6), 4.78 (dd, J=9.8, 5.67 Hz, 1H, H10), 4.55 (s, 2H, C≡CCH$_2$O), 2.34 (br dd, J=14.7, 5.5 Hz, 1H, CH$_2$), 212 (br s, 1H, C≡CH), 1.97–1.88 (m, 2H, CH$_2$), 1.79–1.72 (m, 1H, CH$_2$), 1.68 (br d, J=10.7 Hz, 1H, CH$_2$), 1.43–1.31 (m, 1H, CH$_2$), 1.10 (s, 9H, t-Bu), 1.01 (t, J=7.9 Hz, 9H, Si(CH$_2$CH$_3$)$_3$), 0.73 (q, J=7.9 Hz, 6H, Si(CH$_2$CH$_3$)$_3$); $^{13}$C NMR (125 MHz, CDCl$_3$) δ 150.9, 135.6, 135.3, 133.1, 132.5, 131.2, 129.8, 129.3, 127.7, 125.7, 121.5, 87.7, 84.2, 78.3, 73.6, 72.9, 69.6, 60.2, 53.1, 47.7, 29.3, 26.6, 23.8, 20.3, 19.2, 7.0, 5.7; MS (FAB+) m/e (rel intensity) 900 (M+Cs, 100), 710 (15), 197 (48); HRMS for C$_{47}$H$_{53}$NO$_5$Si$_2$Cs (M+Cs), calcd 900.2517, found 900.2526. Minor Isomer: $R_f=0.48$ (silica, 10 percent ethyl acetate in petroleum ether); IR (film) $v_{max}$ 3307, 2955, 2222, 2124, 1726, 1590, 1494, 1371, 1317, 1202 cm$^{-1}$; $^1$H NMR (500 MHz, CDCl$_3$) δ 7.79 (br s, 1H, H1), 7.78–7.74 (m, 4H, aromatic), 7.48–7.33 (m, 10 H, aromatic)), 7.21 (br t, J=7.0 Hz, 1H, aromatic), 7.18–7.08 (m, 2H, aromatic), 5.54 (d, J=2.2 Hz, 1H, H6), 4.94 (br s, 1H, H10), 4.55 (s, 2H, C≡CCH$_2$O), 2.42 (br dd, J=14.2, 6.1 Hz, 1H, CH$_2$), 2.16 (br s, 1H, C≡CH), 2.06–1.97 (m, 2H, CH$_2$), 1.97–1.86 (m, 2H, CH$_2$), 1.72–1.66 (m, 1H, CH$_2$), 1.50–1.42 (m, 1H, CH$_2$), 1.10 (s, 9H, Bu), 0.98 (t, J=8.0 Hz, 9H, Si(CH$_2$CH$_3$)$_3$), 0.72 (q, J=8.0 Hz, 6 H, Si(CH$_2$CH$_3$)$_3$); $^{13}$C NMR (125 MHz, CDCl$_3$) δ 150.9, 135.6, 134.8, 133.1, 131.6, 131.0, 129.8, 129.3, 127.7, 125.7, 121.5, 87.7, 84.1, 78.2, 73.0, 70.5, 65.3, 58.6, 53.1, 47.7, 29.7, 26.7, 25.6, 22.7, 19.2, 6.9, 5.4; MS (FAB+) m/e (rel intensity) 900 (M+Cs, 74), 710 (24), 197 (100); HRMS for C$_{47}$H$_{53}$NO$_5$Si$_2$Cs (M+Cs), calcd 900.2517, found 900.2526.

EXAMPLE 147

N-[(Phenyloxy)carbonyl]-2-[3-(tert-butyldiphenylsilyl)oxy]-propynyl]-6a,10a-epoxy-6-ethynyl-10-hydroxy-5,6,6a,7,8,9,10,10a-octahydrophenanthridine (Compound 343)

Similarly prepared in 92 percent yield as described for Compound 313. Compound 343: $R_f=0.23$ (major isomer) and 0.25 (minor isomer) (silica, 40 percent ethyl ether in petroleum ether); IR (film) $v_{max}$ 3484, 3289, 2931, 2222, 1723, 1590, 1494, 1372, 1319, 1202, 1111 cm$^{-1}$; $^1$H NMR (500 MHz, CDCl$_3$) δ 7.98 and 7.89 (d, J=1.5 Hz, and br s, 1H, H1), 7.80–7.76 (m, 4H, aromatic), 7.48–7.40 (m, 7H, aromatic), 7.40–7.32 (m, 3H, aromatic), 7.22 (br t, J=7.3 Hz, 1H, aromatic), 7.18–7.10 (m, 2H, aromatic), 5.63 and 5.59 (2 d, J=2.4 and 2.2 Hz, 1H, H6), 4.84 and 4.67 (2 br s, 1H, H10), 4.57 and 4.56 (2 s, 2H, C≡CCH$_2$O), 2.45 and 2.36 (dd and ddd, J=15.2, 7.6 Hz and J=14.7, 5.0, 5.0 Hz, 1H, CH$_2$), 2.23 and 2.17 (2 br s, 1H, C≡C—H), 2.14 (br s, 1H, OH), 2.08–1.88 (m, 2H, CH$_2$), 1.78–1.68 (m, 1H, CH$_2$), 1.64–1.51 (m, 1H, CH$_2$), 1.45–1.35 (m, 1H, CH$_2$), 1.11 (s, 9H, t-Bu); $^{13}$C NMR (125 MHz, CDCl$_3$) 150.8, 135.6, 135.3, 133.1 and 133.0, 132.0, 131.7, 129.7, 129.3, 127.7, 125.8, 121.4, 88.1 and 87.9, 84.4 and 84.3, 78.3 and 78.0, 74.6, 73.4 and 70.6, 66.3 and 64.1, 60.5 and 58.0, 53.1, 47.6, 29.9 and 29.6, 26.7, 24.1, 22.7 and 19.1, 18.8; MS (FAB+) m/e (rel intensity) 786 (M+Cs, 100), 596 (14), 566 (16), 199 (49); HRMS for C$_{41}$H$_{39}$NO$_5$SiCs (M+Cs), calcd 786.1652, found 786.1691.

EXAMPLE 148

N-[(Phenyloxy)carbonyl]-2-[3-(tert-butyldiphenylsilyl)oxy]propynyl]-6a,10a-epoxy-6-ethynyl-10-oxo-5,6,6a,7,8,9,10,10a-octahydrophenanthridine (Compound 344)

Similarly prepared in 90 percent yield as described for Compound 314. Compound 344: $R_f=0.54$ (silica, 50 percent ethyl ether in petroleum ether); IR (film) $v_{max}$ 3289, 2930, 2238, 2090, 1725, 1590, 1494, 1372, 1317, 1203, 1112 cm$^{-1}$; $^1$H NmR (500 MHz, CDCl$_3$) δ 8.43 (br s, 1H, H1), 7.79–7.73 (m, 4H, aromatic), 7.47–7.39 (m, 7H, aromatic), 7.39–7.32 (m, 3H, aromatic), 7.23 (br t, J=6.9 Hz, 1H, aromatic), 7.16–7.08 (m, 2H, aromatic), 5.73 (d, J=1.2 Hz, 1H, H6), 4.54 (s, 2H, C≡CCH$_2$O), 2.76 (ddd, J=15.5, 4.8, 4.8 Hz, 1H, H9), 2.60 (ddd, J=15.5, 10.0, 6.1 Hz, 1H, H9), 2.38–2.28 (m, 2H, CH$_2$), 2.24 (br s, 1H, C≡C—H), 2.06–1.89 (m, 2H, CH$_2$), 1.10 (s, 9H, $^t$Bu); $^{13}$C NMR (125 MHz, CDCl$_3$) δ 200.5, 150.8, 135.6, 135.4, 133.3, 133.1, 132.1, 129.8, 129.4, 127.7, 125.9, 121.4, 88.2, 84.2, 77.3, 74.9, 74.6, 57.0, 53.1, 47.3, 38.7, 26.7, 23.7, 19.2, 18.3; MS (FAB+) m/e (rel intensity) 784 (M+Cs, 100), 564 (50), 197 (46); HRMS for C$_{41}$H$_{37}$NO$_5$SiCs (M+Cs), calcd 784.1495, found 784.1495.

EXAMPLE 149

N-[(Phenyloxy)carbonyl]-2-[3-(tert-butyldiphenylsilyl)oxy]propynyl]-6-[6-(trimethylsilyl)-3(Z)-hexene-1,5-diynyl]-6a,10a-epoxy-10-oxo-5,6,6a,7,8,9,10,10a-octahydrophenanthridine (Compound 345)

Similarly prepared in 67 percent yield as described for Compound 315. Compound 345: $R_f=0.71$ (silica, 50 percent ethyl ether in petroleum ether); IR (film) $v_{max}$ 2927, 2143, 1725, 1593, 1493, 1374, 1314, 1252, 1202, 1111, 884 cm$^{-1}$; $^1$H NMR (500 MHz, CDCl$_3$) δ 8.42 (d, J=1.5 Hz, 1H, H1), 7.79–7.73 (m, 4H, aromatic), 7.48–7.38 (m, 7H, aromatic), 7.36 (br t, J=7.6 Hz, 2H, aromatic), 7.34 (dd, J=8.5, 1.5 Hz, 1H, H3), 7.22 (br t, J=7.6 Hz, 1H, aromatic), 7.16–7.08 (m, 2H, aromatic), 5.97 (d, J=1.6 Hz, 1H, H6), 5.84 (d, J=10.8 Hz, 1H, olefinic), 5.68 (d, J=10.8 Hz, 1H, olefinic), 4.54 (s, 2H, C≡CCH$_2$O), 2.76 (ddd, J=15.0, 5.1, 5.1 Hz, 1H, H9), 2.71 (ddd, J=150.0, 10.1, 6.1 Hz, 1H, H9), 2.40–2.29 (m, 2H, CH$_2$), 2.06–1.88 (m, 2H, CH$_2$), 1.11 (s, 9H, t-Bu), 0.23 (s, 9H, Si(CH$_3$)$_3$); $^{13}$C NMR (125 MHz, CDCl$_3$) δ 200.5, 150.9, 135.7, 135.6, 133.4, 133.1, 132.1, 129.8, 129.4, 127.7, 125.9, 121.4, 121.0, 118.7, 103.8, 101.5, 90.1, 88.2, 84.3, 83.2, 74.9, 57.2, 53.1, 48.2, 38.8, 26.7, 23.9, 19.2, 18.2, 0.1; MS (FAB+) m/e (rel intensity) 906 (M+Cs, 100), 197 (72); HRMS for C$_{48}$H$_{47}$NO$_5$Si$_2$Cs (M+Cs), calcd 906.2047, found 906.2049.

EXAMPLE 150

N-[(Phenyloxy)carbonyl]-2-[3-(tert-butyldiphenylsilyl)oxy]propynyl]-6-[3(Z)-hexene-1,5-diynyl]-6a,10a-epoxy-10-oxo-5,6,6a,7,8,9,10,10a-octahydrophenanthridine (Compound 346)

Similarly prepared in 90 percent yield as described for Compound 316. Compound 346: $R_f$=0.44 (silica, 50 percent ethyl ether in petroleum ether); IR (film) $v_{max}$ 3290, 2930, 2228, 2094, 1723, 1590, 1493, 1371, 1316, 1201, 1112 cm$^{-1}$; $^1$H NMR (500 MHz, CDCl$_3$) δ 8.44 (d, J=1.5 Hz, 1H, H1), 7.82-7.55 (m, 4H, aromatic), 7.48-7.41 (m, 7H, aromatic), 7.38 (br t, J=7.6 Hz, 2H, aromatic), 7.34 (dd, J=8.4, 1.5 Hz, 1H, H3), 7.23 (br t, J=7.6 Hz, 1H, aromatic), 7.18-7.10 (m, 2H, aromatic), 5.93 (d, J=1.8 Hz, 1H, H6), 5.81 (dd, J=11.1, 1.7 Hz, 1H, olefinic), 5.78 (br d, J=11.1 Hz, 1H, olefinic), 4.5 (s, 2H, C≡CCH2O), 3.17 (d, J=1.7 Hz, 1H, C≡CH), 2.77 (ddd, J=15.4, 4.9, 4.9 Hz, 1H, H9), 2.70 (ddd, J=15.4, 10.1, 67.0 Hz, 1H, H9), 2.41-2.38 (m, 2H, CH$_2$), 2.06-1.99 (m, 2H, CH$_2$), 1.11 (s, 9H, $^t$Bu); $^{13}$C NMR (125 MHz, CDCl$_3$) δ 200.7, 150.8, 135.6, 133.3, 133.0, 131.9, 129.7, 129.3, 127.7, 125.8, 121.4, 120.7, 90.1, 88.1, 85.3, 84.3, 82.9, 80.1, 75.1, 57.1, 53.1, 48.2, 38.7, 26.7, 23.8, 19.1, 18.3; MS (FAB+) m/e (rel intensity) 834 (M+Cs, 100), 197 (83); HRMS for C$_{45}$H$_{39}$NO$_5$SiCs (M+Cs), calcd 834.1652, found 834.1652.

EXAMPLE 151

Compound 347

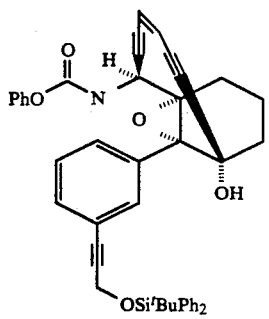

Similarly prepared in 90 percent yield as described for Compound 317. Compound 347: $R_f$=0.36 (silica, 50 percent ethyl ether in petroleum ether); IR (film) $v_{max}$ 3450, 2930, 2230, 1723, 1590, 1494, 1381, 1320, 1120, 1111, 703 cm$^{-1}$; $^1$H NMR (500 MHz, CDCl$_3$) δ 8.73 (d, J=1.7 Hz, 1H, aromatic), 7.80-7.74 (m, 4H, aromatic), 7.47-7.38 (m, 7H, aromatic), 7.36 (br t, J=7.8 Hz, 2H, aromatic), 7.28 (dd, J=8.4, 1.7 Hz, 1H, aromatic), 7.22 (br t, J=7.8 Hz, 1H, aromatic), 7.18-7.12 (m, 2H, aromatic), 5.87 (d, J=10.0 Hz, 1H, olefinic), 5.68 (dd, J=10.0, 1.6 Hz, 1H, olefinic), 5.64 (d, J=1.1 Hz, 1H, NCHC≡C), 4.53 (s, 2H, C≡CCH2O), 2.70 (br s, 1H, OH), 2.31 (dd, J=15.0, 8.2 Hz, 1H, CH$_2$), 2.24-2.11 (m, 2H, CH$_2$), 2.06-1.87 (m, 2H, CH$_2$), 1.78-1.68 (m, 1H, CH$_2$), 1.10 (s, 9H, t-Bu); $^{13}$C NMR (125 MHz, CDCl$_3$) δ 150.8, 135.6, 134.8, 133.1, 131.2, 129.7, 129.3, 127.9, 127.7, 125.8, 124.1, 122.0, 121.5, 119.9, 100.5, 94.2, 93.5, 88.8, 87.3, 85.0, 73.9, 73.0, 64.1, 53.2, 50.2, 35.1, 29.6, 26.7, 23.1, 19.1; MS (FAB+) m/e (rel intensity) 834 (M+Cs, 87), 197 (100); HRMS for C$_{45}$H$_{39}$NO$_5$SiCs (M+Cs), calcd 834.1652, found 834.1660.

EXAMPLE 152

Compound 348

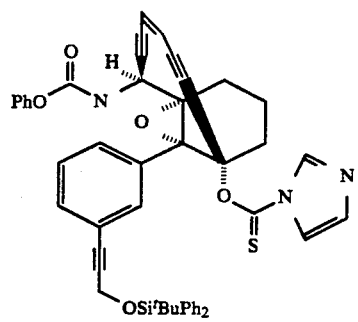

Similarly prepared in 76 percent yield as described for Compound 318. Compound 348: $R_f$=0.27 (silica, 50 percent ethyl ether in petroleum ether); IR (film) $v_{max}$ 2930, 2233, 1727, 1590, 1493, 1385, 1319, 1283, 1197, 1106, 703 cm$^{-1}$; $^1$H NMR (500 MHz, CDCl$_3$) δ 8.38 (s, 1H, imidazole), 7.73 (d, J=1.5 Hz, 1H, aromatic), 7.72-7.67 (m, 4H, aromatic), 7.59 (s, 1H, imidazole), 7.51-7.36 (m, 9H, aromatic), 7.32 (dd, J=8.4, 1.5 Hz, 1H, aromatic), 7.25 (br t, J=7.5 Hz, 1 H, aromatic), 7.18 (br d, J=7.5 Hz, 2H, aromatic), 6.98 (s, 1H, imidazole), 5.99 (d, J=10.0 Hz, 1H, olefinic), 5.78 (dd, J=10.0, 1.7 Hz, 1H, olefinic), 5.60 (d, J=1.5 Hz, 1H, NCHC≡C), 4.42 (s, 2H, C≡CCH2O), 3.20-3.11 (m, 1H, CH$_2$), 2.43 (dd, J=15.2, 8.0 Hz, 1H, CH$_2$), 2.37-2.18 (m, 2H, CH$_2$), 2.17-2.05 (m, 1H, CH$_2$), 1.90-1.80 (m, 1H, CH$_2$), 1.05 (s, 9H, t-Bu); $^{13}$C NMR (125 MHz, CDCl$_3$) δ 179.3, 150.8, 137.3, 135.9, 135.6, 133.1, 133.0, 132.8, 131.7, 131.1, 129.8, 129.5, 128.3, 127.7, 126.7, 126.0, 124.3, 123.4, 121.5, 120.4, 117.5, 100.6, 94.4, 93.7, 89.2, 88.1, 85.4, 84.0, 74.9, 63.6, 53.1, 50.3, 28.5, 26.7, 22.7, 19.2, 18.5; MS (FAB+) m/e (rel intensity) 944 (M+Cs, 95), 684 (38), 476 (46), 197 (100); HRMS for C$_{49}$H$_{41}$N$_3$O$_5$SSiCs (M+Cs), calcd 944.1591, found 944.1272.

EXAMPLE 153

Compound 349

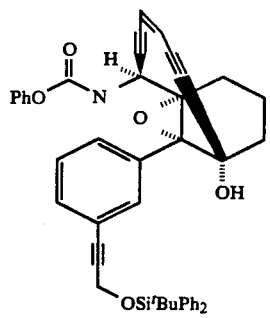

Similarly prepared in 77 percent yield as described for Compound 319. Compound 349: $R_f$=0.70 (silica, 50 percent ethyl ether in petroleum ether); IR (film) $v_{max}$ 2930, 2226, 2184, 1726, 1591, 1493, 1371, 1317, 1201, 1112, 702 cm$^{-1}$; $^1$H NMR (500 MHz, CDCl$_3$) δ 7.82-7.76 (m, 4H, aromatic), 7.59 (d, J=1.3 Hz, 1H, H1), 7.49-7.35 (m, 7H, aromatic), 7.29 (dd, J=8.4, 1.3 Hz, 1H, H3), 7.23 (br t, J=7.4 Hz, 1H, aromatic), 7.18-7.12 (m, 2H, aromatic), 5.83 (dd, J=9.8, 1.2 Hz, 1H, olefinic), 5.70 (dd, J=9.8, 1.5 Hz, 1H, olefinic), 5.54 (s, 1H, H6), 4.57 (s, 2H, C≡CCH2O), 3.74 (br s, 1H, H10), 2.42 (dd, J=15.5, 8.3 Hz, 1H, CH2), 2.26 (ddd, J=15.3, 9.5, 9.5 Hz, 1H, CH2), 2.09-1.90 (m, 2H, CH2), 1.89-1.80 (m, 1H, CH2), 1.68-1.58 (m, 1H, CH2), 1.11 (s, 9H, t-Bu); 13C NMR (125 MHz, CDCl3), δ 150.8, 135.7, 135.3, 133.1, 131.3, 130.6, 129.7, 129.3, 128.7, 127.7, 125.8, 125.2, 121.9, 121.5, 119.9, 101.5, 93.5, 91.5, 89.0, 87.7, 84.6, 70.2, 60.7, 53.2, 49.8, 29.4, 26.7, 23.2, 22.5, 19.2, 15.6; MS (FAB+) m/e (rel intensity) 818 (M+Cs, 100), 598 (48), 430 (22), 197 (51); HRMS for C45H39NO4SiCs (M+Cs), calcd 818.1703, found 818.1703.

EXAMPLE 154

Compound 350

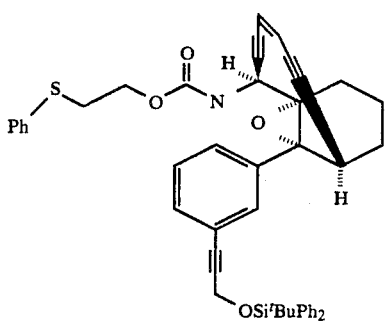

Similarly prepared in 92 percent yield as described for Compound 263. Compound 350: R$_f$=0.52 (silica, 40 percent ethyl ether in petroleum ether); IR (film) ν$_{max}$ 2931, 2246, 2193, 1713, 1587, 1496, 1391, 1318, 1269, 1111 cm$^{-1}$; 1H NMR (500 MHz, CDCl3) δ 7.81-7.76 (m, 4H, aromatic), 7.54 (d, J=1.1 Hz, 1H, aromatic), 7.48-7.38 (m, 8H, aromatic), 7.38-7.32 (br, 1H, aromatic), 7.31 (t, J=7.5 Hz, 2H, aromatic), 7.26 (dd, J=7.5, 1.1 Hz, 1H, aromatic), 7.22 (t, J=7.5 Hz, 1H, aromatic), 5.80 (dd, J=9.8, 1.1 Hz, 1H, olefinic), 5.67 (dd, J=9.8, 1.4 Hz, 1H, olefinic), 5.41 (br s, 1H, NCHC≡C), 4.57 (s, 2H, C≡CCH2O), 4.38 (dt, J=11.1, 7.1 Hz, 1H, PhSCH2CH2O), 4.32-4.21 (br s, 1H, PhSCH2CH2O), 3.69 (br s, 1H, C≡CCHC), 3.23-3.09 (m, 2H, PhSCH2CH2O), 2.37 (dd, J=15.3, 8.4 Hz, 1H, CH2), 2.20 (ddd, J=15.3, 9.6, 9.6 Hz, 1H, CH2), 2.04-1.87 (m, 2H, CH2), 1.84-1.78 (m, 1H, CH2), 1.63-1.56 (m, 1H, CH2), 1.11 (s, 9H, t-Bu); 13C NMR (125 MHz, CDCl3) δ 153.9, 135.6, 135.4, 134.8, 133.1, 131.2, 130.4, 130.0, 129.7, 129.1, 128.3, 127.6, 126.6, 125.1, 121.9, 119.4, 101.5, 93.7, 91.4, 88.7, 87.5, 84.7, 70.4, 64.8, 60.6, 53.2, 49.3, 32.4, 29.3, 26.7, 23.1, 22.5, 19.2, 15.6; MS (FAB+) m/e (rel intensity) 878 (M+Cs, 100), 197 (30); HRMS for C47H43NO4SSiCs (M+Cs), calcd 878.1736, found 878.1701.

EXAMPLE 155

Compound 351

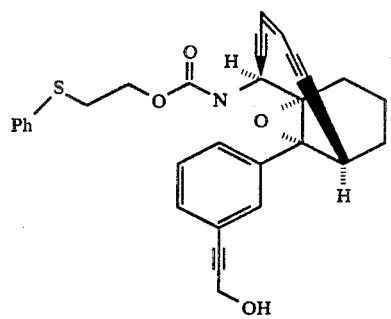

To a solution of Compound 350 (29 mg, 0.039 mmol) in THF (1 mL) was added tetra-n-butylammonium fluoride (58 mL, 1.0M solution in THF, 0.058 mmol) at zero degrees C. After being stirred for 15 minutes, the mixture was concentrated in vacuo and the residue was purified by flash column chromatography (silica, 70 percent ethyl ether in petroleum ether) to afford 16 mg (81 percent) of Compound 351: R$_f$=0.68 (silica, 80 percent ethyl ether in petroleum ether); IR (film) ν$_{max}$ 3398, 2933, 2226, 2194, 1713, 1609, 1583, 1496, 1391, 1319, 1237 cm$^{-1}$; 1H NMR (500 MHz, CDCl3) δ 7.64 (s, 1H, aromatic), 7.42-7.32 (m, 4H, aromatic), 7.29 (t, J=7.6 Hz, 2H, aromatic), 7.20 (t, J=7.6 Hz, 1H, aromatic), 5.77 (dd, J=9.8, 1.4 Hz, 1H, olefinic), 5.67 (dd, J=9.8, 1.6 Hz, 1H, olefinic), 5.39 (br s, 1 H, NCHC≡C), 4.48 (s, 2H, C≡CCH2O), 4.36 (dt, J=11.1, 6.9 Hz, 1H, PhSCH2CH2O), 4.30-4.19 (m, 1H, PhSCH2CH2O), 3.70 (br s, 1H, C≡CCHC), 3.22-3.08 (m, 2H, PhSCH2CH2O), 2.34 (dd, J=15.1, 8.3 Hz, 1H, CH2), 2.18 (ddd, J=15.1, 9.6, 9.6 Hz, 1H, CH2), 2.04 (br s, 1H, OH), 2.01-1.83 (m, 2H, CH2), 1.81-1.74 (m, 1H, CH2), 1.61-1.53 (m, 1H, CH2); 13C NMR (125 MHz CDCl3) δ 153.9, 135.6, 134.7, 131.2, 130.6, 129.9, 129.1, 128.5, 126.6, 125.1, 121.9, 119.0, 101.4, 93.6, 91.5, 88.7, 87.2, 85.2, 70.4, 64.8, 60.6, 51.5, 49.3, 32.4, 29.3, 23.1, 22.5, 15.5; MS (FAB+) m/e (rel intensity) 640 (M+Cs, 96), 186 (100); HRMS for C31H25NO4SCs (M+Cs), calcd 640.0559, found 640.0572.

EXAMPLE 156

Compound 300

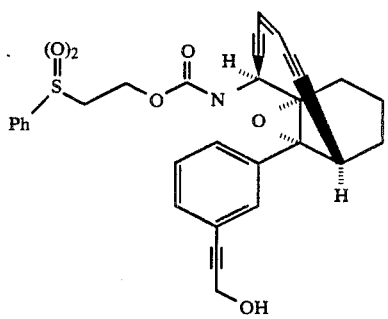

Similarly prepared in 82 percent yield as described for Compound 41b. Compound 300: R$_f$=0.37 (silica, ethyl ether); IR (film) ν$_{max}$ 3498, 2932, 2226, 2196, 1713, 1498, 1396, 1321, 1144, 734 cm$^{-1}$; 1H NMR (500 MHz, CDCl₃) δ 7.88 (br s, 2H, aromatic), 7.62 (br s, 2H, aromatic), 7.51 (br s, 2H aromatic), 7.27 (t, J=6.8 Hz, 1H, aromatic), 7.18 (br s, 1H, aromatic), 5.76 (d, J=9.8 Hz, 1H, olefinic), 5.63 (d, J=9.8 Hz, 1H, olefinic), 5.28 (br s, 1H, NCHC≡C), 4.62–4.32 (m, 2H, SO₂CH₂CH₂O), 4.47 (m, 2H, C≡CCH₂O), 3.67 (br s, 1H, C≡CCHC), 3.55–3.39 (m, 2H, SO₂CH₂CH₂O), 2.31 (dd, J=15.1, 7.8 Hz, 1H, CH₂), 2.22 (br s, 1H, OH), 2.16 (ddd, J=15.1, 9.5 9.5 Hz, 1H, CH₂), 1.99–1.73 (m, 3H, CH₂), 1.62–1.52 (m, 1H, CH₂); ¹³C NMR (125 MHz, CDCl₃) δ 153.5, 138.7, 135.2, 134.0, 131.3, 130.6, 129.4, 128.6, 127.9, 125.1, 121.8, 119.3, 101.3, 93.2, 91.5, 88.8, 87.4, 84.9, 70.2, 60.5, 59.5, 55.0, 51.4, 49.4, 29.2, 23.1, 22.4, 15.5; MS (FAB+) m/e (rel intensity) 672 (M+Cs, 100); HRMS for C₃₁H₂₅NO₆SCs (M+Cs), calcd 672.0457, found 672.0457.

EXAMPLE 157

Compound 360

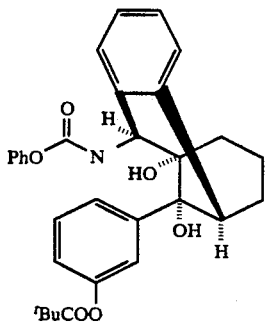

A solution of Compound 334 (54 mg, 0.109 mmol) in benzene (1.5 mL) and freshly distilled 1,4-cyclohexadiene (0.5 mL) was treated with p-toluenesulfonic acid (36 mg, 0.189 mmol) and water (36 mL, 2.0 mmol) followed by heating at 80° C. for 30 minutes. The reaction mixture was diluted with ethyl ether (5 mL), filtered through a 1 cm×1 cm plug of silica, and evaporated in vacuo. The residue was purified by preparative TLC (silica, 12 percent ethyl ether in dichloromethane) to give 43 mg (80 percent) of Compound 360: white foam; R$_f$=0.14 (silica, 30 percent ethyl ether in petroleum ether); IR (CDCl₃) ν$_{max}$ 3480, 2933, 2872, 1750, 1718, 1490, 1378, 1314, 1288, 1205, 1161, 1121 cm⁻¹; ¹H NMR (500 MHz, CDCl₃) δ 7.47–7.38 (m, 5H, aromatic), 7.23–7.13 (m, 5H, aromatic), 6.89 (d, J=7.3 Hz, 1H, aromatic), 6.79 (dd, J=9.0, 2.7 Hz, 1H, aromatic), 5.79 (s, 1H, NCHAr), 3.32 (s, 1H, CH₂CHAr), 3.14 (s, 1H, OH), 2.55 (s, 1H, OH), 2.28 (m, 1H, CH₂), 2.05 (m, 1H, CH₂), 1.75 (m, 1H, CH₂), 1.42–1.30 (m, 2H, CH₂), 1.32 (s, 9H, C(O)C(CH₃)₃), 0.84 (m, 1H, CH₂); ¹³C NMR (125 MHz, CDCl₃) δ 177.1, 151.1, 147.8, 138.9, 135.3, 131.9, 129.4, 128.7, 128.4, 127.5, 126.9, 125.7, 124.2, 121.7, 120.7, 119.2, 72.9, 69.3, 51.4, 39.0, 32.6, 27.1, 26.6, 18.3; MS (FAB+) m/e (rel intensity) 646 (M+Cs, 100), 584 (34); HRMS for C₃₁H₃₁NO₆Cs (M+Cs), calcd 646.1206, found 646.1219.

EXAMPLE 158

Compound 361

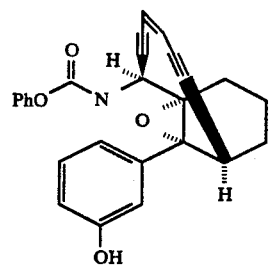

A solution of Compound 334 (123 mg, 0.25 mmol) and cesium carbonate (33 mg, 1.00 mmol) in dry methanol (5 mL) was stirred at 40° C. for 1 hour. Dry ice (1 g) was added and stirring was continued for 10 minutes. The solution was evaporated in vacuo, and the residue was dissolved in dichloromethane (10 mL) and ethyl ether (2 mL). The solution was filtered through a 1 cm×1 cm plug of silica and evaporated to give 95 mg (93 percent) of Compound 361: white foam; R$_f$=0.34 (silica, 50 percent ethyl ether in petroleum ether); IR (CDCl₃) n$_{max}$ 3394, 3055, 2941, 1707, 1593, 1499, 1382, 1314, 1289, 1199, 1024, 909 cm⁻¹; ¹H NMR (500 MHz, CDCl₃) δ 7.34–7.06 (m, 7H, aromatic), 6.73 (m, 1H, aromatic), 5,79 (dd, J=9.9, 1.7 Hz, 1H, olefinic), 5.67 (dd, J=9.9, 1.7 Hz, 1H, olefinic), 5.47 (d, J=1.7 Hz, NCHC≡C), 5.42 (br s, 1H, ArOH), 3.67 (s, 1H, CHC≡C), 2.39 (dd, J=15.7, 8.4 Hz, 1H, CH₂), 2.22 (m, 1H, CH₂), 2.04–1.89 (m, 2H, CH₂), 1.79 (m, 1H, CH₂), 1.59 (m, 1H, CH₂); ¹³C NMR (125 MHz, CDCl₃) δ 153.1, 129.9, 129.3, 128.5, 127.6, 125.7, 125.0, 121.9, 121.5, 115.3, 114.2, 112.2, 104.1, 101.6, 94.0, 91.4, 88.9, 70.0, 61.0, 50.0, 29.5, 23.2, 22.5, 15.6; HRMS (FAB+) for C₂₆H₁₉NO₄Cs (M+Cs), calcd 542.0368, found 542.0379.

EXAMPLE 159

Compound 362

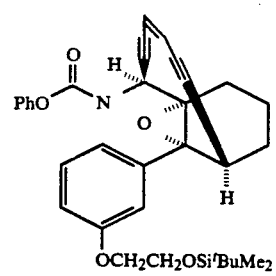

Cesium carbonate (203 mg, 0.623 mmol) was flame-dried under vacuum for 10 minutes and allowed to cool to ambient temperature. To the cesium carbonate was added 107 (85 mg, 0.208 mmol), 18-crown-6 (27 mg, 0.104 mmol), ᵗBuMe₂SiOCH₂CH₂OTs (152 mg, 0.415 mmol), and dry acetonitrile (10 mL). After stirring for 6 hours at 25° C., the reaction mixture was filtered through a cotton plug and evaporated in vacuo. The residue was diluted with ethyl ether (20 mL), filtered from the precipitated 18-crown-6 CH₃CN complex, and evaporated in vacuo. The residue was purified by preparative TLC (silica, 9:1:1 petroleum ether-ethyl ether-dichloromethane) to give 78 mg (66 percent) of Compound 362: white foam; R$_f$=0.42 (silica, 20 percent ethyl ether in petroleum ether); IR (CDCl$_3$) ν$_{max}$ 3054, 2951, 2929, 2881, 2855, 1723, 1504, 1494, 1378, 1273, 1200, 1131, 960 cm$^{-1}$; 1H NMR (500 MHz, CDCl$_3$) δ 7.36-7.33 (m, 3H, aromatic), 7.21-7.10 (m, 3H, aromatic), 7.14 (d, J=2.8 Hz, 1H, aromatic), 6.86 (dd, J=8.9, 2.8 Hz, 1H, aromatic), 5.78 (dd, J=9.9, 1.3 Hz, 1H, olefinic), 5.67 (dd, J=9.9, 1.3 Hz, 1H, olefinic), 5.48 (d, J=1.3 Hz, 1H, NCHC≡C), 4.05 (t, J=5.2 Hz, 2H, ArOCH$_2$CH$_2$OTBS), 3.97 (t, J=5.2 Hz, 2H, ArOCH$_2$CH$_2$OTBS), 3.73 (br s, 1H, CHC≡C), 2.40 (dd, J=15.2, 8.0 Hz, 1H, CH$_2$), 2.23 (dt, J=15.2, 9.5 Hz, 1H, CH$_2$), 2.06-1.90 (m, 2H, CH$_2$), 1.81 (m, 1H, CH$_2$), 1.61 (m, 1H, CH$_2$); 13C NMR (125 MHz, CDCl$_3$) δ 156.3, 153.7, 151.2, 129.8, 129.3, 128.7, 127.4, 125.6, 125.0, 121.9, 121.5, 113.9, 113.8, 101.6, 94.1, 91.4, 88.9, 70.0, 69.6, 61.9, 61.0, 50.0, 29.5, 25.9, 23.3, 22.5, 18.4, 15.6, −5.2; MS (FAB+) m/e (rel intensity) 700 (M+Cs, 100), 568 (50), 510 (11); HRMS for C$_{34}$H$_{37}$NO$_5$SiCs (M+Cs), calcd 700.1495, found 700.1488.

EXAMPLE 160

Compound 363

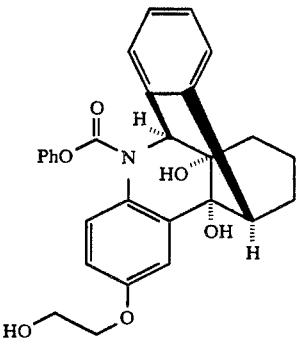

A solution of Compound 362 (62 mg, 0.109 mmol) in benzene (1.5 mL) and freshly distilled 1,4-cyclohexadiene (0.5 mL) was treated with p-toluenesulfonic acid (39 mg, 0.189 mmol) and water (36 mL, 2.0 mmol), followed by heating at 50° C. for 2 hours. The reaction mixture was diluted with ethyl acetate (5 mL), filtered through a 1 cm×1 cm plug of sodium bicarbonate, and evaporated in vacuo. The residue was purified by preparative TLC (silca, ethyl acetate) to give 35 mg (71 percent) of Compound 363: white foam; R$_f$=0.54 (silica, ethyl acetate); IR (CDCl$_3$) ν$_{max}$ 3453, 3065, 2932, 2872, 1703, 1611, 1493, 1456, 1381, 1301, 1203, 1062, 907 cm$^{-1}$; 1H NMR (500 MHz, CDCl$_3$) δ 7.43-7.05 (m, 10H, aromatic), 6.84 (d, J=7.4 Hz, 1H, aromatic), 6.61 (dd, J=9.1, 3.0 Hz, 1H, aromatic), 5.74 (s, 1H, NCHAr), 3.94 (dt, J=5.2, 4.3 Hz, 2H, ArOCH$_2$CH$_2$OH), 3.83 (t, J=4.3 Hz, 2H, ArOCH$_2$CH$_2$OH), 3.28 (s, 1H, CH$_2$CHAr), 3.27 (br s, 1H, OH), 2.90 (br s, 1H, OH), 2.26 (tt, J=13.0, 3.6 Hz, 1H, CH$_2$), 2.08 (td, J=13.5, 6.2 Hz, 1H,CH$_2$), 1.91 (br s, 1H, OH), 1.75 (dd, J=13.5, 4.7 Hz, 1H, CH$_2$), 1.40-1.33 (m, 2H, CH$_2$), 0.83 (m, 1H, CH$_2$); 13C NMR (125 MHz, CDCl$_3$) δ 155.6, 151.1, 139.0, 136.5, 135.5, 129.4, 128.5, 128.3, 127.8, 127.3, 126.8, 125.6, 123.9, 121.8, 114.3, 111.6, 72.9, 69.5, 69.3, 64.1, 61.2, 51.5, 32.7, 26.6, 18.3; HRMS (FAB+) for C$_{28}$H$_{27}$NO$_6$Cs (M+Cs), calcd 606.0893, found 606.0899.

Physical data for further selected compounds:

Compound 76

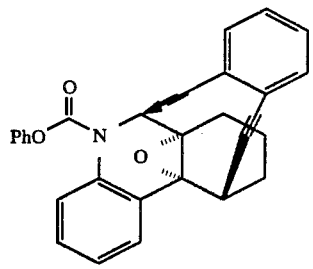

R$_f$=0.44 (33 percent ethyl ether in petroleum ether); 1H NMR (300 MHz, CDCl$_3$): δ 7.68 (dd, J=7.8, 1.1 Hz, 1H, aromatic), 7.52 (br s, 1H, aromatic), 7.37 (t, J=7.7 Hz, 2H, aromatic), 7.30 (dd, J=7.4, 1.1 Hz, 1H, aromatic), 7.26-7.13 (m, 8H, aromatic), 5.61 (s, 1H, CHN), 3.87 (t, J=2.8 Hz, 1H, CH$_2$CH—), 2.49 (dd, J=15.0, 7.8 Hz, 1H, CH$_2$), 2.32-2.19 (m, 1H, CH$_2$), 2.08-1.98 (m, 2H, CH$_2$), 1.90-1.82 (m, 1H, CH$_2$), 1.68-1.55 (m, 1H, CH$_2$); 13C NMR (125 MHz, CDCl$_3$) δ 150.9, 135.6, 130.0, 129.2, 129.2, 128.9, 128.8, 128.6, 128.3, 128.3, 128.1, 128.1, 127.7, 127.2, 126.8, 125.6, 125.2, 121.5, 121.5, 96.9, 90.7, 90.6, 88.8, 70.1, 60.7, 49.7, 28.9, 22.7, 22.6, 15.5; UV (EtOH) λ$_{max}$ (log ε) 282 (3.55), 260 (sh, 3.74), 237-210 (br, 4.36-4.32) nm; HRMS Calcd. for C$_{30}$H$_{21}$NO$_3$Cs: 576.0576 (M+Cs⊕), found 576.0611 (M+Cs⊕).

Compound 76a

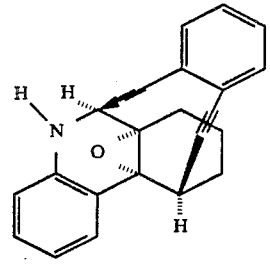

R$_f$=0.46 (silica gel, 20% ethyl ether in benzene containing 0.5% propylamine); 1H NMR (300 MHz, C$_6$D$_6$): δ 7.47 (dd, J=7.7, 0.9 Hz, 1H, aromatic), 7.03 (m, 2H, aromatic), 6.93 (td, J=7.7, 1.2 Hz, 1H, aromatic), 6.70 (td, J=7.3, 1.0 Hz, 1H, aromatic), 6.62 (m, 2H, aromatic), 67.19 (dd, J=7.9, 1.0 Hz, 1H, aromatic), 3.74 (d, J=2.5 Hz, 1H, CHN), 3.53 (t, J=3.0 Hz, 1H, CHCH$_2$), 3.31 (d, J=2.1 Hz, 1H, NH), 2.32-2.30 (m, 1H, CH$_2$), 2.05-1.90 (m, 3H, CH$_2$CH$_2$), 1.58-1.48 (m, 1H, CH$_2$), 1.37-1.24 (m, 1H, CH$_2$); 13C NMR (125 MHz, CD$_3$OD): δ 144.6, 135.4, 130.8, 130.7, 129.9, 129.8, 129.4, 128.9, 128.3, 123.4, 119.9, 119.0, 98.7, 95.5, 91.1, 87.6, 71.5, 62.7, 51.9, 43.6, 25.2, 24.2, 16.9; IR (CHCl$_3$) n$_{max}$ 3360, 2945, 2890, 1620, 1500, 1475, 1450, 1305, 1160, 925, 760 cm$^{-1}$; HRMS Calcd for C$_{23}$H$_{18}$NO: (M+H+), 324.1388, found 324.1388 (M+H+).

Compound 76b

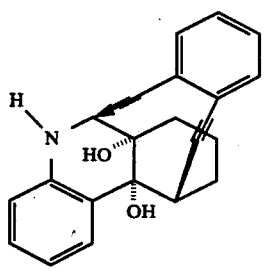

$R_f$=0.70 (silica gel, 66% ethyl ether in petroleum ether); ¹H NMR (300 MHz, CD₂Cl₂): δ 7.53 (dd, J=8.0, 1.3 Hz, 1H, aromatic), 7.40–7.18 (m, 4H, aromatic), 7.09 (td, J=7.6, 1.5 Hz, 1H, aromatic), 6.94 (td, J=7.8, 1.1 Hz, 1H, aromatic), 6.59 (dd, J=7.8, 0.8 Hz, 1H, aromatic), 4.21 (br, 1H, NH), 4.19 (s, 1H, OH), 4.07 (br s,, 1H, CHN), 3.68 (t, J=1.7 Hz, 1H, CHCH₂), 2.28–1.72 (m, 7H, OH, CH₂CH₂CH₂); HRMS Calcd for C₂₃H₁₉NO₂Cs (M+Cs⁺): 474.0470, found 474.0493 (M+Cs⁺).

Compound 87

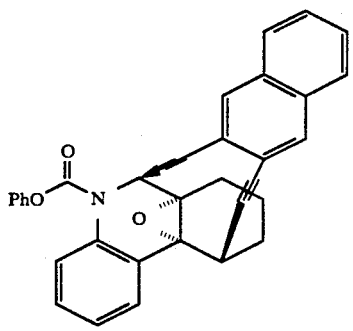

$R_f$=0.52 (33 percent ethyl ether in petroleum ether); ¹H NMR (300 MHz, CDCl₃): δ 7.75 (s, 1H, aromatic), 7.73 (s, 1H, aromatic), 7.72–7.66 (m, 3H, aromatic), 7.53 (br s, 1H, aromatic), 7.50–7.42 (m, 2H, aromatic), 7.38 (t, J=7.7 Hz, 2H, aromatic), 7.30–7.13 (m, 5H, aromatic), 5.64 (s, 1H, CHN), 3.92 (br s, 1H, CH₂CH), 2.53 (dd, J=15.4, 7.5 Hz, 1H, CH₂), 2.34–2.22 (m, 1H, CH₂), 2.12–2.00 (m, 2H, CH₂), 1.91–1.84 (m, 1H, CH₂), 1.70–1.60 (m, 1H, CH₂); ¹³C NMR (62.9 MHz, CDCl₃): δ150.9, 135.8, 132.3, 131.7, 130.3, 129.3, 129.3, 128.7, 128.4, 128.3, 128.1, 127.7, 127.6, 127.6, 127.3, 127.2, 127.2, 125.6, 125.2, 123.8, 122.7, 121.5, 121.5, 96.4, 90.7, 90.5, 88.8, 70.2, 60.8, 49.8, 28.9, 22.7, 22.6, 15.5; IR (CHCl₃) ν$_{max}$ 2931, 1719, 1602, 1493, 1380, 1323, 1299, 1286, 1274, 1147, 975, 920, 894 cm⁻¹; HRMS calcd. for C₃₄H₂₃NO₃Cs: 626.0732 (M+Cs⊕), found 626.0732 (M+Cs⊕).

Compound 87a

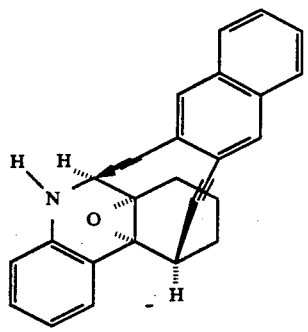

$R_f$=0.46 (silica gel, 20 percent ethyl ether in benzene containing 0.5% propylamine); ¹H NMR (300 MHz, C₆D₆): δ 7.53 (s, 1H, aromatic), 7.51 (s, 1H, aromatic), 7.22–7.00 (m, 5H, aromatic), 6.95 (td, J=8.0, 1.3 Hz, 1H, aromatic), 6.73 (td, J=7.4, 1.0 Hz, 1H, aromatic),. 6.23 (br d, J=7.8 Hz, 1H, aromatic), 3.80 (d, J=2.9 Hz, 1H, CHN), 3.61 (t, J=3.0 Hz, 1H, CHCH₂), 3.35 (br d, J=2.5 Hz, 1H, NH), 2.40–2.28 (m, 1H, CH₂), 2.15–1.95 (m, 3H, CH₂CH₂), 1.64–1.55 (m, 1H, CH₂), 1.40–1.28 (m, 1H, CH₂); HRMS Calcd for C₂₇H₂₀NO: (M+H⁺): 374.1545, found 374.1549 (M+H⁺).

Compound 87b

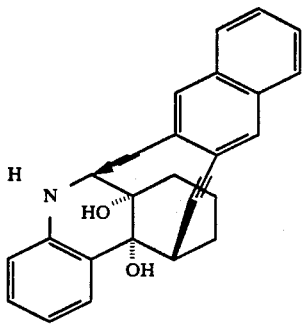

$R_f$=0.50 (silica gel, 75% ethyl ether in petroleum ether); ¹H NMR (300 MHz, THF-d₈): δ 7.71 (s, 1H, aromatic), 7.63 (m, 2H, aromatic), 7.54 (s, 1H, aromatic), 7.37–7.28 (m, 3H, aromatic), 6.80 (t, J=7.9 Hz, 1H, aromatic), 6.62 (t, J=7.1 Hz, 1H, aromatic), 6.38 (d, J=7.9 Hz, 1H, aromatic), 5.59 (s, 1H, NH), 4.64 (s, 1H, CHN), 4.18 (s,, 1H, OH), 4.01 (s, 1H, CHCH₂), 2.30–1.40 (m, 7H, OH, CH₂CH₂CH₂); ¹³C NMR (125 MHz, CD₃OD+CDCl₃): δ 141.9, 139.9, 138.9, 134.5, 130.1, 129.1, 128.6, 128.6, 128.3, 128.3, 128.2, 127.6, 127.3, 126.9, 121.0, 116.6, 104.1, 99.9, 86.5, 84.8, 73.6, 73.4, 55.2, 41.3, 34.5, 28.5, 20.2; IR (CHCl₃) ν$_{max}$ 3475, 3390, 2930, 1620, 1480, 1010, 975, 900, 750 cm⁻¹; UV (MeOH) λ$_{max}$ (log ε) 285 (3.81, sh), 259 (4.50) nm; HRMS Calcd for C₂₇H₂₁NO₂Cs (M+Cs⁺): 524.0627, found 524.0681 (M+Cs⁺).

Compound 89

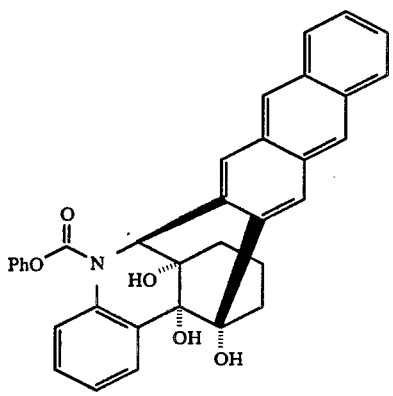

$R_f$=0.53 (50 percent ethyl ether in benzene); $^1$H NMR (300 MHz, CDCl$_3$): δ 8.40 (s, 1H, aromatic), 8.23 (s, 1H, aromatic), 8.22 (s, 1H, aromatic), 7.99–7.88 (m, 2H, aromatic), 7.75 (dd, J=7.7, 1.7 Hz, 1H, aromatic), 7.54 (s, 1H, aromatic), 7.50–7.40 (m, 5H, aromatic), 7.30 (d, J=7.4 Hz, 3H, aromatic), 7.14–7.00 (m, 2H, aromatic), 6.11 (s, 1H, CHN), 3.62 (br s, 1H, CH$_2$CH), 2.46 (dddd, J=10.8, 10.8, 3.3, 3.3 Hz 1H, CH$_2$), 2.30 (ddd, J=13.6, 13.6, 6.0 Hz, 1H, CH$_2$), 1.94 (dd, J=13.3, 4.6 Hz, 1H, CH$_2$) 1.60 (br, 2H, OH), 1.53 (br t, J=13.5 Hz, 2H, CH$_2$), 0.98 (ddddd, J=13.9, 13.9, 13.9, 4.3, 4.3 Hz, 1H, CH$_2$); IR (CHCl$_3$ $\nu_{max}$ 3694, 3567, 2952, 1688, 1604, 1488, 1379, 1319, 1296, 1287, 1269, 1060, 909 cm$^{-1}$.

Compound 115a

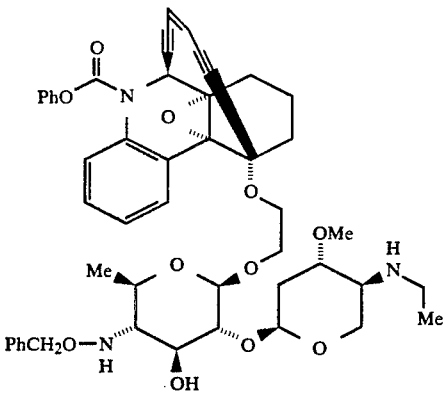

Pale yellow oil; $R_f$=0.39 (silica, 10 percent methanol in dichloromethane), $[α]_D^{25}$= −87.3° (c=0.48, CHCl$_3$), $^1$H NMR, (500 MHz, C$_6$D$_6$): δ=8.97 (dd, 1H, J=4.2, 0.7 Hz, Dyn-Ar), 7.52 (m, 1H, Dyn-Ar), 7.41–6.98 (m, 12H, 11 Ar, propargylic H), 6.98 (dd, 1H, J=7.1, 7.1 Hz, Dyn-Ar), 5.89 (bs, 1H, OH), 5.83 (bs, 1H, O-N—H), 5.78 (s, 1H, E-1), 5.28 (d, 1H, J=10.0 Hz, vinylic H), 5.10 (dd, 1H, J=10.0, 1.7 Hz, vinylic H), 4.58–4.51 (m, 2H, CH$_2$—Ph), 4.50 (d, 1H, J=7.4, A-1), 4.48–4.40 (m, 1H, E-5ax), 4.25–4.17 (m, 1H, E-5eq), 4.13–4.02 (m, 3H, A-3, OCH$_2$CH$_2$O), 4.01–3.94 (m, 1H, OCH$_2$CH$_2$O), 3.93–3.90 (m, 1H, E-3), 3.77 (dd, 1H, J=9.5, 7.3 Hz, A-2), 3.69–3.52 (m, 1H, A-5), 3.26 (s, 3H, OCH$_3$), 2.78–2.66 (m, 2H, E-4, N—CH$_2$), 2.65–2.57 (m, 1H, N—CH$_2$), 2.47 (dd, 1H, J=12.0, 2.2 Hz, E-2eq), 2.44 (dd, 1H, J=9.5, 9.5 Hz, A-4), 2.31 (dd, 1H, J=14.5, 6.5 Hz, Dyn-CH$_2$), 2.04 (d, 1H, J=6.7 Hz, Dyn-CH$_2$), 1.95–1.83 (m, 4H, CH$_2$), 1.43 (dd, 1H, J=14.5, 9.3 Hz, E-2ax), 1.33 (d, 3H, J=6.1 Hz, A-6), 1.04 (t, 3H, J=6.5 Hz, N—CH$_2$—CH$_3$); IR (CHCl$_3$) $\nu_{max}$=2965, 2931, 1733, 1380, 1323, 1146, 1098, 1071 cm$^{-1}$; HRMS calcd. for C$_{49}$H$_{55}$N$_3$O$_{11}$ (M+Cs⊕) 994.2891; found 994.2904.

Compound 115b

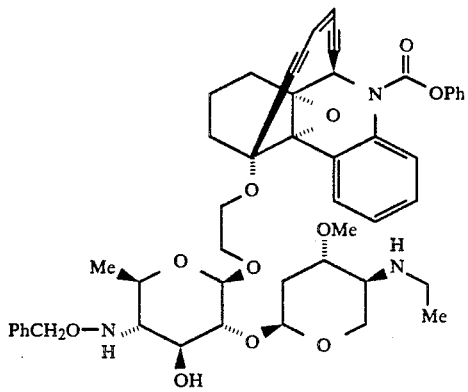

Pale yellow oil; $R_f$=0.38 (silica, 10 percent methanol in dichloromethane), $[α]_D^{25}$= +125.7° (c=0.68, CHCl$_3$), $^1$H NMR (500 MHz, C$_6$D$_6$): δ=8.93 (dd, 1H, J=4.2, 0.7 Hz, Dyn-Ar), 7.56 (dd, J=7.4, 1.4 Hz, Dyn-Ar), 7.32–7.02 (m, 12H, 11 Ar, propagylic H), 6.90 (dd, 1H, J=7.1, 7.1 Hz, Dyn-Ar), 5.90 (bs, 1H, O—N—H), 5.88 (bs, 1H, OH), 5.82 (s, 1H, E-1), 5.29 (d, 1H, J=10.2 Hz, vinylic H), 5.11 (dd, 1H, J=10.2, 1.7 Hz, vinylic H), 4.56–4.51 (m, 2H, CH$_2$Ph), 4.49 (dd, 1H, J=11.1, 9.0 Hz, E-5ax), 4.48 (d, 1H, J=7.4 Hz, A-1), 4.22–4.17 (m, 2H, OCH$_2$CH$_2$), 4.14 (dd, 1H, J=11.1, 4.7 Hz, E-5eq), 4.09 (dd, 1H, J=9.5, 9.5 Hz, A-3), 4.06–4.01 (m, 1H, OCH$_2$CH$_2$O), 3.93–3.88 (m, 1H, OCH$_2$CH$_2$O), 3.87–3.81 (m, 1H, E-3), 3.78 (dd, 1H, J=9.5, 7.1 Hz, A-2), 3.58 (dq, 1H, J=9.5, 6.1 Hz, A-5), 3.27 (s, 3H, OCH$_3$), 2.84 (ddd, 1H, J=9.0, 9.0, 4.7 Hz, E-4), 2.77 (m, 2H, N—CH$_2$), 2.54 (dd, 1H, J=12.2, 2.5 Hz, E-2eq), 2.42 (dd, 1H, J=9.5, 9.5 Hz, A-4), 2.30 (dd, 1H, J=14.6, 10.5 Hz, Dyn-CH$_2$), 2.06 (dd, 1H, J=14.6, 7.1 Hz, Dyn-CH$_2$), 1.97–1.83 (m, 4H, Dyn-CH$_2$H, 1.51 (dd, 1H, J=12.2, 9.2 Hz, E-2ax), 1.33 (d, 3H, J=6.1 Hz, A-6), 1.10 (t, 3H, J=6.5 Hz, N—CH$_2$—CH$_3$); IR (CHCl$_3$): $\nu_{max}$=2962, 2957, 2929, 1733, 1386, 1323, 1146, 1097, 1070 cm$^{-1}$; HRMS calcd. for C$_{49}$H$_{55}$N$_3$O$_{11}$ (M+Cs⊖) 994.2891: found 994.2904.

Compounds 127a and 127b

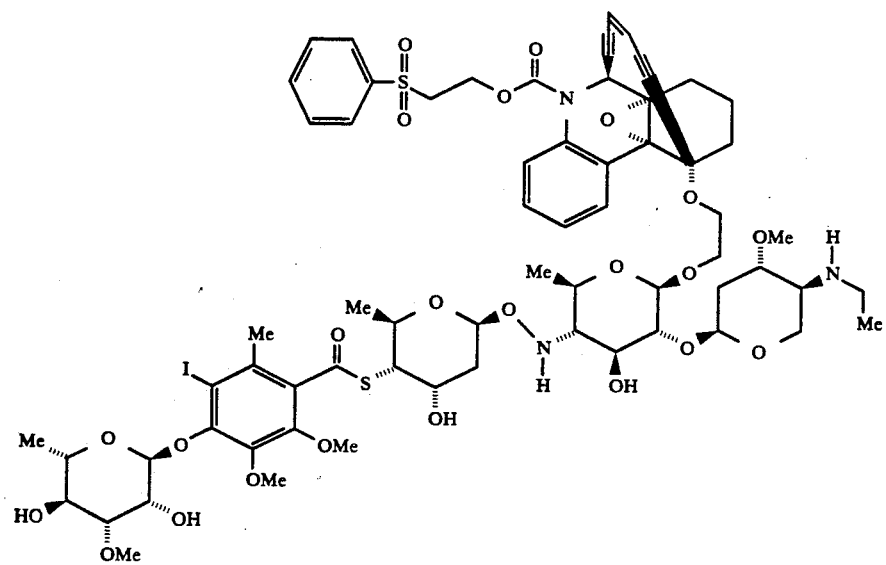

127a and 127b

Compound 127a: Colorless oil: $R_f$=0.24 (10 percent methanol in dichloromethane); $[\alpha]D^{25}$ (CH$_2$Cl$_2$, c=0.25)+113.6°; IR (neat) $\nu_{max}$ 2940, 1720, 1460, 1410, 1325, 1150, 1070 cm$^{-1}$; $^1$H NMR (500 MHZ, CDCl$_3$): δ=8.40–6.85 (series of multiplets, 9H, aromatic), 6.27 (bs, 1H, ON H), 5.77 (d, J=10.0, 1H, vinylic), 5.73 (d, J=2.1 Hz, 1H, D-1) 5.63 (d, J=10.0 Hz, 1H, vinylic), 5.50 (bs, 1H, E-1), 5.33 (bs, 2H, propargylic), 5.03 (dd, J=10.0, 2.1 Hz, 1H, B-1) 4.40 (m, 3H, D-2, C H$_2$O), 4.42 (d, J=7.9 Hz, 1H, A-1), 4.32 (m. 1H, B-3) 4.19 (dq, J=9.5, 6.0 Hz, 1H, D-5), 4.16 (m, 1H, E-5 $_{ax}$), 4.07 (dq, J=10.8, 6.0 Hz, 1H, b-5), 4.02 (dd, J=10.0, 10.0 Hz, 1H, A-3), 3.97 (m, 2H, E-3, E-3, E-5$_{eq}$), 3.87–3.97 (series of multiplets, 5H, A-2, D-3, C H$_2$O), 3.88 (s, 3H, CH$_3$O, aromatic), 3.83 (s, 3H, CH$_3$O, aromatic), 3.73 (dd, J=10.8, 2.6 Hz, 1H, B-4) 3.68–3.56 (series of multiplets, 3H, A-5, D-4, C H$_2$O), 3.58 (s, H, C H$_3$O, D-ring), 3.48 (bs, 2H, C H$_2$O), 3.37 (s, H, C H$_3$O, E-ring), 2.69 (m, 2H, E-4, CH$_2$N), 2.61 (m, 2H, E-4, C H$_2$N), 2.29 (s, 3H, C H$_3$, aromatic), 2.27 (dd, J=10.0, 10.0 Hz, 1H, A-4), 2,21–1.53 (series of multiplets, 9H B-2 $_{ax}$, B-2$_{eq}$. CH$_2$), 1.46 (m, 1H, E-2$_{ax}$), 1.41 (d, J=6.0 Hz, B-6), 1.30 (d, J=6.0 Hz, 6H, A-6, D-6), HRMS (FAB+) calcd. for C$_{67}$H$_{84}$IN$_3$O$_{23}$S$_2$Cs (M⊕+Cs): 1622.3036, found: 1622.3069.

Compound 127b: Colorless oil: $R_f$=0.24 (10% methanol in dichloromethane); $[\alpha]D^{25}$ (CH$_2$Cl$_2$, c=0.33)–119.2°; IR (neat); $\nu_{max}$ 2940, 1720, 1460, 1410, 1325, 1150, 1070 cm$^{-1}$; $^1$H NMR (500 MHz, CDCl$_3$): δ=8.45–7.01 (series of multiplets, 9H, aromatic), 6.30 (bs, 1H, ON H), 5.78 (d, J=10.0, 1H, vinylic), 5.72 (d, J=2.1 Hz, D-1), 5.62 (d, J=10.0 Hz, 1H, vinylic) 5.42 (bs, 1H, E-1), 5.34 (bs, H, propargylic), 5.02 (dd, J=10.0, 2.1 Hz, 1H, B-1), 4.48 (m, 2H, CH$_2$O), 4.46 (dd, J=3.2, 1.7 Hz, 1H, D-2) 4.38 (d, J-7.4 Hz, 1H, A-1), 4.30 (m, 1H, B-3), 4.18 (dq, J=9.5, 6.0 Hz, 1H, D-5), 4.06 (dq, J=10.8, 6.0 Hz, 1H, B-5) 3.99 (dd, J=10.0, 10.0 Hz, 1H, A-3), 3.98–3.78 (series of multiplets, 7H, D-#, E-3, E-5$_{ax}$, E-5$_{eq}$. CH$_2$O), 3.87 (s, H, CH$_3$), aromatic), 3.82 (s, 3H, CH$_3$O aromatic), 3.73 (dd, J+10.2, 2.2 Hz, 1H, B-4), 3.61 (m, 2H, D-4, C H$_2$O), 3.56 (s, 3H, CH$_3$O, D-ring, 3.51 (dd, J=7.4 Hz, 1H, A-2), 3.47 (dq. J=10.0, 6.0 Hz, 1H, A-5), 3.45 (bs, 2H, C H$_2$O), 3.33 (s, 3H, C H$_3$O E-ring), 2.65 (m, 3H, E-4, C H$_2$N), 2.29 (s, 3H, C H$_3$, aromatic), 2.27 (dd. J=10.0 Hz, 1H, A-4) 2.24–1.52 (series of multiplets, 9H, B-2$_{ax}$, B-2$_{eq}$.E-2$_{eq}$., CH$_2$), 1.47 (m, 1H, E-b 2$_{ax}$), 1.39 (d, J-6.0 Hz, 3H, B-6), 1.30 (d, J-6.0 Hz, 3H, D-6), 1.28 (d, J=6.0 Hz, 3H, A-6) 1.10 (t, J=7.0 Hz, 3H, C H$_3$CH$_2$N); MS: m/e (rel intensity) 1622 (M⊕+Cs, 30); HRMS (FAB+) calcd for C$_{67}$H$_{84}$IN$_3$O$_{23}$S$_2$C$_2$ (M⊕+Cs); 1622.3036.

Compound 160

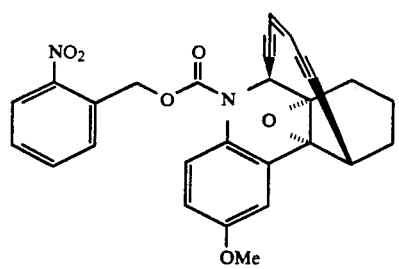

160

$^1$H NMR (300 MHz, CDCl$_3$): δ 8.08 (1H, d, J=8.8 Hz, aromatic), 7.60–7.40 (4H, m, aromatic), 7.11 (1H, d, J=2.8 Hz, aromatic), 5.76 (1H, dd, J=9.9, 1.6 Hz, olefinic), 5.65–5.40 (3H, m, olefinic, CH$_2$OCON), 3.81 (3H, s, OCH$_3$), 3.70 (1H, br s, CHC≡C), 2.40–1.75 (1H; m, CH$_2$CH$_2$CH$_2$); HRMS calcd. for C$_{28}$H$_{22}$N$_2$O$_6$Cs 615.0532 (M⊕ +Cs), found 615.0527 (M⊕+CS).

Compound 161

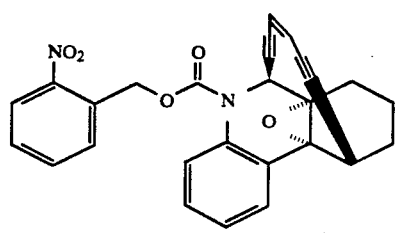

161

¹H NMR (300 MHz, CDCl₃): δ 8.10 (1H, d, J=8.3 Hz, aromatic), 7.62–7.20 (7H, m, aromatic), 5.77 (1H, dd, J=9.9, 1.7 Hz, olefinic), 5.72–5.45 (3H, m, olefinic, CH₂OCON), 3.78 (1H, br s, CHC≡C), 2.46–1.72 (6H, m, CH₂CH₂CH₂); HRMS calcd. for C₂₇H₂₀N₂O₅Cs 585.0427 (M⊕+Cs), found 585.0411 (M⊕+Cs).

Although the present invention has now been described in terms of certain preferred embodiments, and exemplified with respect thereto, one skilled in the art will readily appreciate that various modifications, changes, omissions and substitutions may be made without departing from the spirit thereof.

What is claimed is:

1. A compound corresponding to the structure

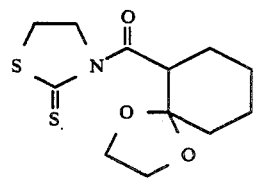

* * * * *